(12) United States Patent
Bock et al.

(10) Patent No.: US 8,263,635 B2
(45) Date of Patent: Sep. 11, 2012

(54) INHIBITORS OF CYP 17

(75) Inventors: Mark G. Bock, Cambridge, MA (US);
Christoph Gaul, Basel (CH);
Venkateshwar Rao Gummadi, Basel (CH); Saumitra Sengupta, Basel (CH)

(73) Assignee: Novartis AG, Basel (CH)

( * ) Notice: Subject to any disclaimer, the term of this patent is extended or adjusted under 35 U.S.C. 154(b) by 187 days.

(21) Appl. No.: 12/824,845

(22) Filed: Jun. 28, 2010

(65) Prior Publication Data

US 2010/0331326 A1 Dec. 30, 2010

(30) Foreign Application Priority Data

Jun. 26, 2009 (IN) .......................... 1500/CHE/2009
Oct. 21, 2009 (IN) .......................... 2181/DEL/2009

(51) Int. Cl.
*A61K 31/415* (2006.01)
*C07D 233/00* (2006.01)

(52) U.S. Cl. ..................... 514/399; 548/316.4

(58) Field of Classification Search .................. 514/399; 548/316.4
See application file for complete search history.

(56) References Cited

U.S. PATENT DOCUMENTS

| 3,832,352 | A | 8/1974 | Ilvespää |
| 5,145,845 | A | 9/1992 | Johnson et al. |
| 5,519,036 | A | 5/1996 | Himmelsbach et al. |
| 5,789,425 | A | 8/1998 | Takano et al. |
| 7,405,233 | B2 | 7/2008 | Wilde et al. |
| 2005/0154028 | A1* | 7/2005 | Bromidge et al. ............ 514/341 |
| 2006/0167065 | A1 | 7/2006 | Wilde et al. |
| 2009/0264650 | A1 | 10/2009 | Cho et al. |
| 2010/0222588 | A1 | 9/2010 | Peterson et al. |
| 2011/0039893 | A1* | 2/2011 | Kori et al. ..................... 514/333 |

FOREIGN PATENT DOCUMENTS

| EP | 0719773 B1 | 11/2001 |
| JP | 1996 176111 A1 | 7/1996 |
| WO | 9708150 A1 | 3/1997 |
| WO | 0154694 A1 | 8/2001 |
| WO | 0220493 A2 | 3/2002 |
| WO | 03057220 A1 | 7/2003 |
| WO | WO 2004/009558 A2 | 1/2004 |
| WO | 2006078698 A1 | 7/2006 |
| WO | 2007109330 A2 | 9/2007 |
| WO | 2008094556 A2 | 8/2008 |
| WO | 2009078992 A1 | 6/2009 |
| WO | 2009097567 A1 | 8/2009 |
| WO | 2009143039 A2 | 11/2009 |
| WO | 2009156484 A2 | 12/2009 |
| WO | 2009158473 A1 | 12/2009 |
| WO | 2010045303 A2 | 4/2010 |
| WO | 2011017534 A2 | 2/2011 |
| WO | 2011059969 A2 | 5/2011 |
| WO | 2011088160 A2 | 7/2011 |
| WO | 2011098776 A1 | 8/2011 |

OTHER PUBLICATIONS

Meth-Cohn O, Yan Z. Linear and macrocyclid ligands containing alternating pyridine and imidazolidin-2-one units. 1998, J. Chem. Soc. Perkin Trans 1, 423-436.*
King, F.D. (Ed.), "Bioisosteres, conformational restriction and pro-drugs—case history: an example of a conformational restriction approach," Medical Chemistry: Principles and Practice, 1994, Chapter 14, 206-209.*
Abad, A. et al., "Regioselective Preparation of Pyriclin-2-yl Ureas from 2-Chloropyriclines Catalyzed by Pd(0)", Synthesis, 2005, No. 6, pp. 0915-0924.
Anjaneyulu, B. et al., "Nitroirnidazoles: Part XXII-Synthesis of potential metabolites of satranidazole by non-nitroreductive and nitroreductive routes", Indian J. of Chem., 1991, vol. 30B, pp. 399-406.
Arya, V. P. et al., "Nitroimidazoles: Part XVI-Some 1-Methyl-3-nitro-5-substituted Imidazoles", Indian J. of Chem., 1982, vol. 21B., pp. 1115-1117.
Babczinski, P. et al., "Substituted Tetrahydropyrimidinones: A New Herbicidal Class of Compounds Inducing Chlorosis by Inhibition of Phytoene Desaturation", Pesticide Biochem. and Physiology, 1995. 52 pp. 45-59.
El-Metwally, S. et al., "Reactions of 1,3-Diphenyl-2-pyrazolin-5-one and 4-Amino-1,5-dimethyl-2-phenyl-1H-pyrazol-3(2H)-one. Synthesis of Some New Pyrazoles and Pyrazolones", Acta Chirri. Slov., 2010, vol. 57, No. 4, 941-947.
Ghandi, M. et al., "Synthesis of New Unsymmetrical 4,5-Dihydroxy-2-imidazolidinones", Molecules, 2006, 11, pp. 768-775.
Goodacre, C. J. et al., "A series of bisaryl imidazolidin-2-ones has shown to be selective and orally active 5-HT2c receptor antagonists", Bioorg. Med. Chem. Lett. 2005, 15 pp. 4989-4993.
Nagarajan, K. et al., "Nitroimidazoles: Part XIX-Structure-activity Relationships", Indian J. of Chem., 1984, vol. 23B, pp. 342-362.
Nagarajan, K. et al., "Nitroimidazoles, Part XXIII*-Activity of satranidazole series against anaerobic infections", Indian J. of Experimental Bio., 1992, vol. 30, pp. 193-200.
Njar, V. C. et al., "Inhibitors of 17alpha-hydroxylase/17,20-lyase (CYP17): potential agents for the treatment of prostate cancer", Curr Pharm Des. Mar. 1999;5(3),163-80. Abstract Only.
Saczewski, F., "2-Chloro-4,5-dihydroimidarole", Synthesis, 1984, pp. 170-172.

(Continued)

*Primary Examiner* — Paul Zarek
(74) *Attorney, Agent, or Firm* — Arlene K. Musser

(57) ABSTRACT

The present invention provides compounds of Formula (I) and (II), or a pharmaceutically acceptable salts thereof,

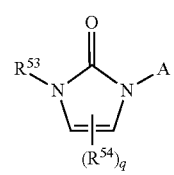
(I)

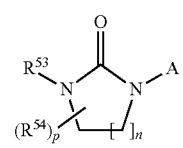

(II)

where $R^{53}$, $R^{54}$, p, q, and n are as defined herein. The compounds of the present invention have been found to be useful as 17α-hydroxylase/$C_{17,20}$-lyase inhibitors.

16 Claims, No Drawings

OTHER PUBLICATIONS

Saczewski F. et al., "2-Chloro-4,5-dihydroimidazole, Part X[1]", J. Heterocyclic Chem., 2002, vol. 39 pp. 911-915.

Hafner et al., "Synthesis of Symmetrically and Unsymmetrically Substituted N,N¢-Diarylimidazolin-2-ones by Copper-Catalyzed Arylamidation under Microwave-Assisted and Conventional Conditions", Synthesis, 2007 No. 9 pp. 1403-1411.

Johnson et al., "A New Synthesis of 2-Chloroalkyl Isocyanates", J. Org. Chem., 1967 vol. 32 pp. 1508-1510.

Shia et al., "Design, Synthesis, and Structure-Activity Relationship of Pyridyl Imidazolidinones: A Novel Class of Potent and Selective Human Enterovirus 71 Inhibitors", J. Med. Chem., 2002 vol. 45 pp. 1644-1655.

* cited by examiner

INHIBITORS OF CYP 17

RELATED APPLICATIONS

This application claims priority to IN Application Serial No. 01500/CHE/2009 filed 26 Jun. 2009 and IN Application Serial No. 2181/DEL/2009 filed 21 Oct. 2009, the contents of which are incorporated herein by reference in their entirety.

FIELD OF THE INVENTION

The present invention relates to cyclic urea derivatives and their use for the treatment of various disease conditions mediated by the regulation of 17α-hydroxylase/$C_{17,20}$-lyase.

BACKGROUND

The number of people diagnosed with cancer world wide has significantly increased and continues to rise at an alarming rate. Cancer is characterized by an increase in the number of abnormal cells derived from a given normal tissue, invasion of adjacent tissues by these abnormal cells, or lymphatic or blood-borne spread of malignant cells to regional lymph nodes and to distant sites (i.e., metastasis).

Of special interest are individuals diagnosed with androgen-dependent disorders, such as prostate cancer, and estrogen-dependent disorders, such as breast, uterine, and ovarian cancer.

Prostate cancer is currently the most common non-skin cancer and the second leading cause of cancer-related death in men after lung cancer. The primary course of treatment for patients diagnosed with organ-confined prostate cancer is usually prostatectomy or radiotherapy. These treatments for prostate and breast cancer are highly invasive and characterized by undesirable and serious side effects. Furthermore, a large percent of individuals who receive localized treatments such as surgery or radiotherapy may suffer from recurring cancer and widespread metastases. As with surgery and radiation therapies, there are several drawbacks to chemotherapy, including the fact that almost all chemotherapeutic agents are toxic, and chemotherapy causes significant, and often dangerous, side effects, such as severe nausea, bone marrow depression, and immunosuppression. Additionally, many tumor cells are resistant or become resistant to chemotherapeutic agents through multi-drug resistance.

Treatments such as hormone therapy are another option for individuals diagnosed with hormone-dependent, hormone-responsive, or hormone-sensitive cancers, such as prostate or breast cancer. However, some individuals who have been administered current hormone therapy treatments may not show a significant response to such treatments and some may suffer from relapsing of cancer.

Currently chemo-refractory and hormone-refractory cancer patients are left with very few treatment options and there remains an unmet need for more effective was to treat cancer such as, but not limited to, prostate cancer and breast cancer.

The demonstration by Huggins and Hodges C. V., (*Cancer Res.*, 1941, 1, 293) and Huggins et al in *Arch. Surg.*, 1941, 43, 209 lead to androgen ablation being considered as a possible approach to treatment. It has been demonstrated that testosterone levels are reduced by orchidectomy or by administration of GnRH analogs (gonadotropic releasing hormones). GnRH analogs can have side effects such as cardiovascular degeneration and osteoporosis, which are the two most potentially serious conditions induced by the continuous presence of GnRH. Moreover these treatment options only eliminate testosterone production from the testes and not that produced by the adrenal.

In the adrenal glands, the biosynthetic cascade also leads to the formation of gluco- and mineralcorticoids.

Since androgen and estrogen are hormones having various physiological activities such as differentiation and proliferation of cells and the like, it was thought that potent and specific compounds that inhibit androgen synthesis in the testes, adrenals, and other tissue may be more effective for the treatment of PCa (Njar, V. C. O.; Brodie, A. M. H., "Inhibitors of 17α-hydroxylase-$C_{17,20}$-lyase (CYP17): Potential agents for the treatment of prostate cancer", *Current Pharm. Design*, 1999, 5: 163-180).

In order to avoid unwanted side effects, androgen biosnthesis inhibitors have to be specific enough not to influence corticosteroid biosynthesis. A promising novel strategy for the treatment of prostrate cancer is the development of strong and selective inhibitors of CYP 17 as this would result in complete and exclusive elimination of androgen biosynthesis as suggested in Current Medicinal Chemistry, 2005, 12, 1623-1629.

Steroid-type compounds and non-steroid-type compounds are already known as steroid $C_{17,20}$-lyase inhibitors. The steroid-type compounds are disclosed in, for example, WO 92/15404, WO 93/20097, EP-A 288053, EP-A 413270 and the like. As non-steroid-type compounds, for example, in WO94/27989, WO96/14090 and WO97/00257 azole derivatives are described in WO95/09157 1H-benzimidazole derivatives are described in U.S. Pat. No. 5,491,161, dihydronaphthalene derivatives are described in WO99/18075, and naphthalene derivatives are shown in WO99/54309.

A variety of potent steroidal and non-steroidal inhibitors of CYP17 have been reported and some have been shown to be potent inhibitors of testosterone production in rodent models (Njar and Brodie, above). Jarman and colleagues have described the hormonal impact of their most potent CYP17 inhibitor, abiraterone in patients with prostate cancer (O'Donnell et al., "Hormonal impact of the 17α-hydroxylase/C17,20-lyase inhibitors abiraterone acetate (CB7630) in patients with prostate cancer", *Br. J. Cancer*, 2004, 90: 2317-2325). Abiraterone has been discussed in patents such as WO 200900132, WO 2008024485, WO 2006021776, WO 09509178, WO 09320097

Non-steroidal small molecule inhibitors have been described for example in *BMC* 2004,12, (4313), YM116, 2-(1H-imidazol-4-ylmethyl)-9H-carbazole, and their effects in decreasing adrenal androgen synthesis by inhibiting C17-20 lyase activity in NCI-H295 human adrenocortical carcinoma cells has been described by Ideyama Y, Kudoh M, Tanimoto K, Susaki Y, Nanya T, Nakahara T, Ishikawa H, Fujikura T, Akaza H, Shikama H in "*Jpn. J. Pharmacol.*, 1999, 79:No. 2(213-20)". Novel non-steroidal inhibitor of cytochrome P450 (17 alpha-hydroxylase/C17-20 lyase), YM116, and its role in decreased prostatic weights by reducing the serum concentrations of testosterone and adrenal androgens in rats has been reported by Ideyama Y, Kudoh M, Tanimoto K, Susaki Y, Nanya T, Nakahara T, Ishikawa H, Yoden T, Okada M, Fujikura T, Shikama H *Proc. Am. Assoc. Cancer Res.*, 1998, 39:89 Meet. (384)

Synthesis and biological evaluation of novel non-steroidal inhibitors of steroid 17,20 lyase has been described by-Yoden T, Okada Ni, Kawaminami E, Kinoyama I, Ideyama Y, Isomura Y in *Abstr. Pap. Am. Chem. Soc.*, 1997, 213 Meet.:Pt. 2(MEDI206)

Further illustrative of the background of the invention are patent applications such as US20080280864A1 or WO28154382A1.

SUMMARY

The compounds described herein have been shown to be inhibitors of 17α-hydroxylase/C$_{17,20}$-lyase.

One embodiment of the present invention provides compounds of Formula (I) or (II)

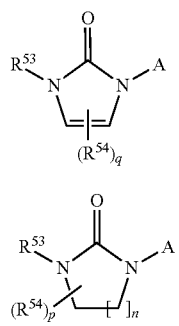

wherein
n is 1, 2, or 3;
R$^{53}$ is
(i) phenyl optionally substituted with 1 to 3 substituents selected from halo, -CN, -OH, (C$_1$-C$_6$)alkyl, halo-substituted (C$_1$-C$_6$)alkyl, (C$_1$-C$_6$)alkoxy, -NH$_2$, -NH(C$_1$-C$_4$)alkyl, -N((C$_1$-C$_4$)alkyl)$_2$, -NHC(O)-(C$_1$-C$_4$)alkyl, -C(O)NH$_2$, -C(O)-NH(C$_1$-C$_4$)alkyl, -C(O)—N((C$_1$-C$_4$)alkyl)$_2$, or a 5- to 6-membered heterocycle,
(ii) biphenyl optionally substituted with 1 to 3 substituents selected from (C$_1$-C$_4$)alkyl or halo,
(iii) phenyl fused to an additional phenyl, a 5- to 6-membered heteroaryl, a 5- to 6-membered partially or fully saturated cycloalkyl, or a 5- to 6-membered partially or fully saturated heterocycle, where said fused phenyl is optionally substituted with 1 to 4 substituents each independently selected from halo, -CN, (C$_1$-C$_6$)alkyl, (C$_1$-C$_6$)alkoxy, hydroxy-substituted (C$_1$-C$_4$)alkyl, halo-substituted (C$_1$-C$_4$)alkyl, cyclopropyl, oxo, -NH$_2$, -NH(C$_1$-C$_4$)alkyl, -N((C$_1$-C$_4$)alkyl)$_2$, -NHC(O)-(C$_1$-C$_4$)alkyl, or =N-OH,
(iv) 5- to 6-membered heteroaryl optionally substituted with 1 to 3 substituents selected from halo, -CN, -OH, (C$_1$-C$_6$)alkyl, halo-substituted (C$_1$-C$_6$)alkyl, (C$_1$-C$_6$)alkoxy, -NH$_2$, -NH(C$_1$-C$_4$)alkyl, -N((C$_1$-C$_4$)alkyl)$_2$, -NHC(O)-(C$_1$-C$_4$)alkyl, -C(O)NH$_2$, -C(O)—NH(C$_1$-C$_4$)alkyl, -C(O)-N((C$_1$-C$_4$)alkyl)$_2$, or a 5- to 6-membered heterocycle,
(v) 5- to 6-membered heteroaryl fused to another 5- to 6-membered heteroaryl, phenyl, 5- to 6-membered partially or fully saturated cycloalkyl, or a 5- to 6-membered partially or fully saturated heterocycle, where said fused heteroaryl is optionally substituted with 1 to 4 substituents each independently selected from halo, -CN, (C$_1$-C$_6$)alkyl, (C$_1$-C$_6$)alkoxy, hydroxy-substituted (C$_1$-C$_4$)alkyl, halo-substituted (C$_1$-C$_4$)alkyl, cyclopropyl, oxo, -NH$_2$, -NH(C$_1$-C$_4$)alkyl, -N((C$_1$-C$_4$)alkyl)$_2$, -NHC(O)-(C$_1$-C$_4$)alkyl, or =N-OH;
R$^{54}$ is (C$_1$-C$_4$)alkyl, halo-substituted (C$_1$-C$_4$)alkyl, or -CH$_2$OH, or two R$^{54}$ taken together with the carbon atom(s) to which they are attached form a 3- to 6-membered fully or partially saturated carbocyclic ring or two R$^{54}$ attached to adjacent carbons taken together with the carbons to which they are attached form a fused phenyl;
p is 0, 1, 2, or 3;
q is 0, 1 or 2;
A is a 5- to 10-membered heteroaryl containing one or more nitrogen atom(s), where said heteroaryl is optionally substituted with 1 to 3 substituents each independently selected from halo, -OH, -CN, (C$_1$-C$_4$)alkyl, halo-substituted (C$_1$-C$_4$)alkyl, hydroxy-substituted (C$_1$-C$_4$)alkyl, -(CH$_2$)$_r$O(C$_1$-C$_4$)alkyl, -(CH$_2$)$_r$CH(O(C$_1$-C$_4$)alkyl)$_2$, -NH(C$_1$-C$_4$)alkyl, -(CH$_2$)$_s$NH(C$_1$-C$_4$)alkyl, -(CH$_2$)$_r$N((C$_1$-C$_4$)alkyl)$_2$, -(CH$_2$)$_r$NH(C$_3$-C$_6$)cycloalkyl), -NH$_2$, -NHC(O)-(C$_1$-C$_4$)alkyl, -C(O)NH$_2$, -C(O)-NH(C$_1$-C$_4$)alkyl, -C(O)—N((C$_1$-C$_4$)alkyl)$_2$, or -C(O)-O(C$_1$-C$_4$)alkyl, where said (C$_1$-C$_4$)alkyl, said -(CH$_2$)$_r$O(C$_1$-C$_4$)alkyl, and said -(CH$_2$)$_s$NH(C$_1$-C$_4$)alkyl are optionally substituted with a 4- to 6-membered partially or fully saturated heterocycle or heteroaryl containing 1 to 3 heteroatoms each independently selected from O, S or N, where said heterocycle and said heteroaryl are optionally substituted with 1 to 3 (C$_1$-C$_4$)alkyl groups;
r is 0, 1 or 2; and
s is 1 or 2; or a pharmaceutically acceptable salt thereof with the proviso that (i) when A is an unsubstituted pyridine and R$^{53}$ is phenyl, R$^{53}$ is not unsubstituted or mono-substituted with halogen, CH$_3$, NH$_2$, -NHC(O)CH$_3$, or CF$_3$; (ii) A and R$^{53}$ are not both an unsubstituted pyridin-2-yl; and (iii) said compound is not 1-(3,4-dichloro-phenyl)-3[-6-(2-piperidin-1-yl-ethoxy)-pyridin-3-yl]imidazolidine-2-one, 1-(3,5-dichloropyridin-2-yl)-3-phenyltetrahydropyrimidin-2(1H)-one, 1,3-bis(6-chloropyridin-2-yl)tetrahydropyrimidin-2(1H)-one, 1,3-bis(4-methylpyridin-2-yl)imidazolidin-2-one, 1-(5-chloro-1H-benzo[d]imidazol-2-yl)-3-phenylimidazolidin-2-one, or 2-(2-oxo-3-phenylimidazolidin-1-yl)-1H-benzo[d]imidazole-5-carbonitrile.

In a particular embodiment, A is a 5-membered heteroaryl containing 1 to 2 nitrogen atom(s), where said heteroaryl is optionally substituted with (C$_1$-C$_4$)alkyl or halo-substituted (C$_1$-C$_4$)alkyl; or a pharmaceutically acceptable salt thereof.

In another particular embodiment, A is a 6-membered heteroaryl containing 1 to 2 nitrogen atom(s), where said heteroaryl is optionally substituted with (C$_1$-C$_4$)alkyl or halo-substituted (C$_1$-C$_4$)alkyl; or a pharmaceutically acceptable salt thereof.

In another particular embodiment, A is a pyridine, where said pyridine is optionally substituted with 1 to 3 substituents each independently selected from halo, -CN, (C$_1$-C$_4$)alkyl, halo-substituted (C$_1$-C$_4$)alkyl, hydroxy-substituted (C$_1$-C$_4$)alkyl, -(CH$_2$)$_r$O(C$_1$-C$_4$)alkyl, -(CH$_2$)$_r$CH(O(C$_1$-C$_4$)alkyl)$_2$, -(CH$_2$)$_r$NH(C$_1$-C$_4$)alkyl, -(CH$_2$)$_r$N((C$_1$-C$_4$)alkyl)$_2$, -(CH$_2$)$_r$NH(C$_3$-C$_6$)cycloalkyl), -NH$_2$, -NHC(O)-(C$_1$-C$_4$)alkyl, -C(O)NH$_2$, -C(O)-NH(C$_1$-C$_4$)alkyl, -C(O)-N((C$_1$-C$_4$)alkyl)$_2$, or -C(O)-O(C$_1$-C$_4$)alkyl, where said (C$_1$-C$_4$)alkyl, said -(CH$_2$)$_r$O(C$_1$-C$_4$)alkyl, and said -(CH$_2$)$_r$NH(C$_1$-C$_4$)alkyl are optionally substituted with a 5- to 6-membered partially or fully saturated heterocycle or heteroaryl containing 1 to 2 heteroatoms each independently selected from O, S or N, where said heterocycle and said heteroaryl are optionally substituted with 1 to 3 (C$_1$-C$_4$)alkyl groups; and r is 1 or 2; or a pharmaceutically acceptable salt thereof. Preferably, A is an optionally substituted pyridin-3-yl. In particular, a pyridin-3-yl substituted with trifluoromethyl or a (C$_1$-C$_4$)alkyl substituted with a 5- to 6-membered partially or fully saturated heterocycle (preferably, the heterocycle is attached to the alkyl group via a nitrogen ring atom, e.g. pyrrolidin-1-ylmethyl).

In yet another particular embodiment, the compound of Formula (I) or (II) is a compound of Formula (Ia) or (Ib)

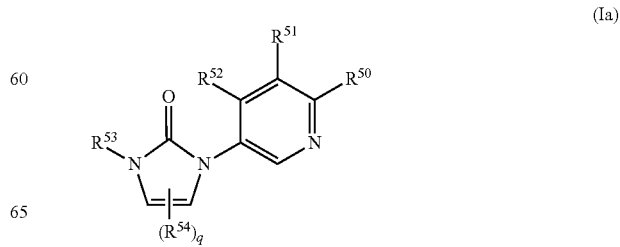

(Ia)

-continued

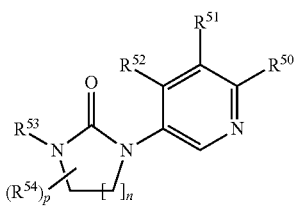
(Ib)

wherein n, $R^{50}$, $R^{51}$, $R^{52}$, $R^{53}$, $R^{54}$ and q are as defined above; or a pharmaceutically acceptable salt thereof. In a particular embodiment of the compound of Formula (Ib), $R^{52}$ is $CF_3$ or a $(C_1-C_4)$alkyl substituted with a 5- to 6-membered partially or fully saturated heterocycle (preferably, the heterocycle is attached to the alkyl group via a nitrogen ring atom, e.g. pyrrolidin-1-ylmethyl). In another particular embodiment of the compound of Formula (Ib), n is 1, and p is 0.

Another embodiment of the present invention provides compounds of Formula (Ia) or (Ib).

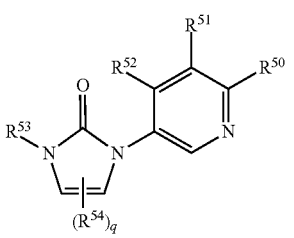
(Ia)

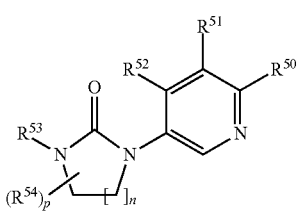
(Ib)

wherein:
n is 1, 2, or 3;
$R^{53}$ is
(i) phenyl optionally substituted with 1 to 3 substituents selected from halo, -CN, -OH, $(C_1-C_6)$alkyl, halo-substituted $(C_1-C_6)$alkyl, $(C_1-C_6)$alkoxy, $-NH_2$, $-NH(C_1-C_4)$alkyl, $-N((C_1-C_4)$alkyl$)_2$, $-NHC(O)-(C_1-C_4)$alkyl, $-C(O)NH_7$, $-C(O)-NH(C_1-C_4)$alkyl, $-C(O)-N((C_1-C_4)$alkyl$)_2$, or a 5- to 6-membered heterocycle,
(ii) biphenyl optionally substituted with 1 to 3 substituents selected from $(C_1-C_4)$alkyl or halo,
(iii) phenyl fused to an additional phenyl, a 5- to 6-membered heteroaryl, a 5- to 6-membered partially or fully saturated cycloalkyl, or a 5- to 6-membered partially or fully saturated heterocycle, where said fused phenyl is optionally substituted with 1 to 4 substituents each independently selected from halo, -CN, $(C_1-C_6)$alkyl, $(C_1-C_6)$alkoxy, hydroxy-substituted $(C_1-C_4)$alkyl, halo-substituted $(C_1-C_4)$alkyl, cyclopropyl, oxo, $-NH_2$, $-NH(C_1-C_4)$alkyl, $-N((C_1-C_4)$alkyl$)_2$, $-NHC(O)-(C_1-C_4)$alkyl, or $=N-OH$,
(iv) 5- to 6-membered heteroaryl optionally substituted with 1 to 3 substituents selected from halo, -CN, -OH, $(C_1-C_6)$alkyl, halo-substituted $(C_1-C_6)$alkyl, $(C_1-C_6)$alkoxy, $-NH_2$, $-NH(C_1-C_4)$alkyl, $-N((C_1-C_4)$alkyl$)_2$, $-NHC(O)-(C_1-C_4)$alkyl, $-C(O)NH_2$, $-C(O)-NH(C_1-C_4)$alkyl, $-C(O)-N((C_1-C_4)$alkyl$)_2$, or a 5- to 6-membered heterocycle,
(v) 5- to 6-membered heteroaryl fused to another 5- to 6-membered heteroaryl, phenyl, 5- to 6-membered partially or fully saturated cycloalkyl, or a 5- to 6-membered partially or fully saturated heterocycle, where said fused heteroaryl is optionally substituted with 1 to 4 substituents each independently selected from halo, -CN, $(C_1-C_6)$alkyl, $(C_1-C_6)$alkoxy, hydroxy-substituted $(C_1-C_4)$alkyl, halo-substituted $(C_1-C_4)$alkyl, cyclopropyl, oxo, $-NH_2$, $-NH(C_1-C_4)$alkyl, $-N((C_1-C_4)$alkyl$)_2$, $-NHC(O)-(C_1-C_4)$alkyl, or $=N-OH$;
$R^{54}$ is $(C_1-C_4)$alkyl (e.g., $-CH_3$), halo-substituted $(C_1-C_4)$alkyl (e.g., $-CF_3$), or $-CH_2OH$, or two $R^{54}$ taken together with the carbon atom(s) to which they are attached form a 3- to 6-membered fully or partially saturated carbocyclic ring (e.g., for a compound of Formula (Ia) when q is 2, the two $R^{54}$ on adjacent carbons may form a fused cycloalkenyl ring; and for compounds of Formula (Ib), when p is 2 or 3, two $R^{54}$ on adjacent carbons may form a fused fully or partially saturated cycloalkyl ring or two $R^{54}$ on the same carbon atom may form a spiral ring);
p is 0, 1, 2, or 3;
q is 0, 1 or 2;
$R^{50}$, $R^{51}$ and $R^{52}$ are each independently H, halo, -OH, -CN, $(C_1-C_4)$alkyl, halo-substituted $(C_1-C_4)$alkyl, hydroxy-substituted $(C_1-C_4)$alkyl, $-(CH_2)$, $-O(C_1-C_4)$alkyl, $=(CH_2)$, $-CH(O(C_1-C_4)$alkyl$)_2$, $-NH_2$, $-NH(C_1-C_4)$alkyl, $-N((C_1-C_4)$alkyl$)_2$, $-NHC(O)-(C_1-C_4)$alkyl, $-C(O)NH_2$, $-C(O)-NH(C_1-C_4)$alkyl, $-C(O)-N((C_1-C_4)$alkyl$)_2$, or $-C(O)-O(C_1-C_4)$alkyl;
r is 0, 1 or 2;
with the proviso that when $R^{50}$, $R^{51}$, and $R^{52}$ are H and $R^{53}$ is phenyl, $R^{53}$ is not unsubstituted or substituted with halogen or $CF_3$, or a pharmaceutically acceptable salt thereof.

In one embodiment, a compound of Formula (Ia) is provided having the definitions above.

In another embodiment, a compound of Formula (Ib) is provided having the definitions above.

In yet another embodiment, compounds of Formula (Ib) is provided where n is 1.

Preferably, $R^{50}$ is H or methyl (more preferably, $R^{50}$ is H); $R^{51}$ is H, halo, methyl, trifluoromethyl, methoxy, or $-C(O)OCH_3$; and $R^{52}$ is halo, -CN, methyl, ethyl, methoxy, hydroxymethyl, 1-hydroxyethyl, 2-hydroxypropan-2-yl, difluoromethyl, trifluoromethyl, dimethoxymethyl, $-NH_2$, or $-NHC(O)CH_3$.

Preferably (for compound of Formula (I), (II), (Ia) and (Ib)), $R^{53}$ is
(i) a phenyl optionally substituted with 1 of 2 substituents each independently selected form fluoro, chloro, cyano, methyl, difluoromethyl, trifluoromethyl, methoxy, or $-C(O)NHCH_3$;
(ii) a biphenyl optionally substituted with fluoro;
(iii) a fused phenyl selected from naphthalen-2-yl, naphthalen-1-yl, 1H-indol-5-yl, 1H-indol-6-yl, benzothiazol-5-yl, benzothiazol-6-yl, 1,2,3,4-tetrahydro-quinolin-6-yl, benzo[b]thiophen-5-yl, quinolin-6-yl, quinolin-7-yl, indan-5-yl, 1,2-dihydroquinolin-6-yl, 1H-indazol-5-yl, 1H-indazol-6-yl, benzofuran-5-yl, 2,3-dihydrobenzo[1,4]dioxin-6-yl, 2,3-dihydro-benzofuran-5-yl, benzo[1,3]dioxol-5-yl, 1,2,3,4-tetrahydro-quinolin-7-yl, quinoxalin-6-yl, benzooxazol-5-yl, benzo[d]isoxazol-5-yl, benzo[d]isoxazol-6-yl, 1H-benzoimidazol-5-yl, 2,3-dihydro-1H-indazol-5-yl, 2,3-dihydro-1H-indazol-6-yl, indolin-5-yl, or 1H-benzotriazol-5-yl, where said fused phenyl is optionally substituted with 1 to 3 substituents each independently selected from fluoro, chloro, methyl, ethyl, trifluoromethyl, methoxy, oxo, $-NH_2$, $=N-OH$ or cyclopropyl;
(iv) a 5- to 6-membered heteroaryl selected from thiophen-2-yl, thiophen-3-yl, pyridin-3-yl, pyridin-4-yl, pyrimidin-5-yl, 1H-pyrazol-4-yl, thiazol-2-yl, or isothiazol-4-yl, where said 5- to 6-membered heteroaryl is optionally substituted with 1 to 3 substituents each independently selected from fluoro, chloro, methyl, ethyl, isopropyl, hydroxy, difluoromethyl, trifluoromethyl, methoxy, -NH$_2$, -NHC(O)CH$_3$, -C(O)NHCH$_3$, or pyrrolidin-1-yl; or (v) a fused heteroaryl selected from benzo[b]thiophen-2-yl, benzo[b]thiophen-3-yl, quinolin-2-yl, quinolin-3-yl, benzooxazol-2-yl, benzothiazol-2-yl, 4,5,6,7-tetrahydro-thieno[2,3-c]pyridin-2-yl, imidazo[1,2-a]pyridin-3-yl, imidazo[1,2-a]pyridin-6-yl, imidazo[1,2-a]pyridin-7-yl, 3H-imidazo[4,5-b]pyridin-6-yl, thieno[3,2-c]pyridin-2-yl, thieno[3,2-c]pyridin-3-yl, or 1H-indol-3-yl, where said fused heteroaryl is optionally substituted with 1 to 4 substituents each independently selected from fluoro, chloro, cyano, methyl, or methoxy; or a pharmaceutically acceptable salt thereof.

More preferably, R$^{53}$ is
(i) a phenyl optionally substituted with 1 to 2 substituents each independently selected from fluoro, chloro, methyl, methoxy, trifluoromethyl, difluoromethyl, or cyano;
(ii) a biphenyl;
(iii) a fused phenyl selected from naphthalen-2-yl, quinolin-6-yl, 3,4-dihydro-2-oxo-quinolin-6-yl, benzo[b]thiophen-5-yl, benzo[d]isoxazol-5-yl, 1H-indazol-6-yl, 1H-indazol-5-yl, benzothiazol-6-yl, 1,2-dihydro-3-oxo-indazol-6-yl, indan-5-yl, 1H-benzotriazol-5-yl, benzofuran-5-yl, 2,3-dihydro-benzo[1,4]dioxin-6-yl, 2,3-dihydro-benzofuran-5-yl, or benzo[1,3]dioxol-5-yl where said fused phenyl is optionally substituted with 1 to 2 substituents each independently selected from chloro, fluoro, methyl, ethyl, difluoromethyl, trifluoromethyl, cyclopropyl, cyano, or amino;
(iv) a 5- to 6-membered heteroaryl selected from isothiazol-4-yl, thiophen-2-yl, thiophen-3-yl, or pyridin-4-yl, where said isothiazol-4-yl, said thiophen-2-yl, said thiophen-3-yl, and said pyridin-4-yl are optionally substituted with fluoro, chloro, methyl, trifluoromethyl, difluoromethyl, or methoxy; or
(v) a fused heteroaryl selected from thieno[3,2-c]pyridin-2-yl, thieno[3,2-c]pyridin-3-yl, thieno[3,2-c]pyridin-2-yl, imidazo[1,2-a]pyridin-7-yl, or benzo[b]thiophen-2-yl, where said fused heteroaryl is optionally substituted with 1 to 2 substituents each independently selected from fluoro, chloro, methyl, difluoromethyl, trifluoromethyl, cyclopropyl, or amino; or a pharmaceutically acceptable salt thereof.

In one preferred embodiment, R$^{53}$ is phenyl, 4-chloro-3-fluoro-phenyl, m-tolyl, 3-methoxy-phenyl, 3-chloro-4-fluoro-phenyl, 4-fluoro-3-methyl-phenyl, 3-trifluoromethyl-phenyl, 3-chloro-phenyl, 4-fluoro-3-trifluoromethyl-phenyl, 3-difluoromethyl-4-fluoro-phenyl, 3-cyano-4-fluorophenyl, 3-cyanophenyl, 3-chloro-4-cyanophenyl, 3,4-difluoro-phenyl, 4-trifluoromethyl-phenyl; or a pharmaceutically acceptable salt thereof.

In another preferred embodiment, R$^{53}$ is naphthalen-2-yl, benzo[b]thiophen-5-yl, 3-methyl-benzo[d]isoxazol-5-yl, 1H-indazol-5-yl, 1-methyl-1H-indazol-5-yl, 3-amino-1H-indazol-5-yl, 1H-indazol-6-yl, 3-amino-1H-indazol-6-yl, 3-methyl-1H-indazol-6-yl, 3-trifluoromethyl-1H-indazol-6-yl, benzothiazol-6-yl, 1,2-dihydro-3-oxo-indazol-6-yl, indan-5-yl, 1H-benzotriazol-5-yl, 3-methyl-benzofuran-5-yl, 2,3-dihydro-benzo[1,4]dioxin-6-yl, 2,3-dihydro-benzofuran-5-yl, or 2,2-difluoro-benzo[1,3]dioxol-5-yl; or a pharmaceutically acceptable salt thereof. More preferably, R$^{53}$ is benzothiazol-6-yl, 3-methyl-benzofuran-5-yl, 1H-indazol-6-yl, 3-methyl-1H-indazol-6-yl, or 3-trifluoromethyl-1H-indazol-6-yl; or a pharmaceutically acceptable salt thereof.

In yet another preferred embodiment, R$^{53}$ is 5-methyl-thiophen-2-yl, 5-chloro-thiophen-2-yl, 5-trifluoromethyl-thiophen-2-yl, 5-difluoromethyl-thiophen-3-yl, 5-methyl-thiophen-3-yl, 2-methyl-pyridin-4-yl, 2-trifluoromethyl-pyridin-4-yl, 2-chloro-pyridin-4-yl, or 2-methoxy-pyridin-4-yl; or a pharmaceutically acceptable salt thereof.

In yet another preferred embodiment, R$^{53}$ is 4-chloro-thieno[3,2-c]pyridin-2-yl, 4-chloro-thieno[3,2-c]pyridin-3-yl, thieno[3,2-c]pyridin-2-yl, 3-chloro-imidazo[1,2-a]pyridin-7-yl, benzo[b]thiophen-2-yl, or 4-methylthieno[3,2-c]pyridin-2-yl; or a pharmaceutically acceptable salt thereof.

In another embodiment of the compounds of Formula (I), (II), (Ia) or (Ib), R$^{54}$ is -CH$_3$ or CF$_3$.

Particular compounds include: 1-Benzothiazol-6-yl-3-(4-methyl-pyridin-3-yl)-imidazolidin-2-one; 1-(2-Chloro-pyridin-4-yl)-3-(4-methyl-pyridin-3-yl)-imidazolidin-2-one; 1-(4-Chloro-thieno[3,2-c]pyridin-2-yl)-3-(4-methyl-pyridin-3-yl)-imidazolidin-2-one; 1-(1H-Indazol-6-yl)-3-(4-methyl-pyridin-3-yl)-imidazolidin-2-one; 1-(3-Difluoromethyl-4-fluoro-phenyl)-3-(4-methyl-pyridin-3-yl)-1,3-dihydro-imidazol-2-one; 1-(4-Methyl-pyridin-3-yl)-3-(5-methyl-thiophen-3-yl)-1,3-dihydro-imidazol-2-one; 1-(3-Methyl-1H-indazol-6-yl)-3-(4-methyl-pyridin-3-yl)-imidazolidin-2-one; 1-Benzothiazol-6-yl-4-methyl-3-(4-methyl-pyridin-3-yl)-imidazolidin-2-one; 1-Benzo[b]thiophen-5-yl-3-(4-methyl-pyridin-3-yl)-1,3-dihydro-imidazol-2-one; and 1-Benzothiazol-6-yl-3-(4-methyl-pyridin-3-yl)-1,3-dihydro-imidazol-2-one; or a pharmaceutically acceptable salt thereof.

Other compounds include those described in the Example section below, in particular, those compounds having an IC$_{50}$ less than 1 μM (or 1,000 nM), preferably, less than 500 nM, more preferably, less than 100 nM.

In another aspect of the present invention a pharmaceutical composition is provided which comprises a compound of Formula (I), (II), (Ia) or (Ib) or a pharmaceutically acceptable salt thereof and a pharmaceutically acceptable carrier or excipient. The pharmaceutical composition optionally comprises at least one additional pharmaceutical agent (suitable pharmaceutical agents are described herein below).

In yet another aspect of the present invention, a method of treating a disease, disorder, or syndrome mediated by Cyp17 inhibition is provided, where the method comprises administering a compound according to Formula (I), (II), (Ia) or (Ib), or a pharmaceutical composition comprising the compound of Formula (I), (II), (Ia) or (Ib) and pharmaceutically acceptable excipients, to a subject in need thereof.

Another aspect of the present invention includes a compound according to Formula (I), (II), (Ia) or (Ib) for use in therapy (e.g., the use of a compound of Formula (Ia) or (Ib) for the treatment of a disease, disorder, or syndrome mediated by Cyp17 inhibition).

Yet another aspect of the present invention includes a method for treating a disease, disorder or syndrome mediated by Cyp17 inhibition comprising the step of administering
(i) a first composition comprising a compound of claim 1 through 21, or a pharmaceutically acceptable salt thereof, and a pharmaceutically acceptable carrier or excipient; and
(ii) a second composition comprising at least one additional pharmaceutical agent and a pharmaceutically acceptable carrier or excipient;
wherein said at least one additional pharmaceutical agent is an anticancer agent, chemotherapy agent, or antiproliferative compound. The first and second compositions may be administered either simultaneously or sequentially in any order.

In one particular embodiment for each of the methods and uses described above, the disease, disorder, or syndrome is selected from the group consisting of cancer (in particular, prostate cancer) and inflammation.

DEFINITIONS

As used herein, the terms "alkyl" refers to a hydrocarbon radical of the general formula C$_n$H$_{2n+1}$. The alkane radical may be straight or branched. For example, the term "(C$_1$-C$_6$)alkyl" refers to a monovalent, straight, or branched aliphatic group containing 1 to 6 carbon atoms (e.g., methyl, ethyl, n-propyl, i-propyl, n-butyl, i-butyl, s-butyl, t-butyl, n-pentyl, 1-methylbutyl, 2-methylbutyl, 3-methylbutyl, neopentyl, 3,3-dimethylpropyl, hexyl, 2-methylpentyl, and the like). Similarly, the alkyl portion (i.e., alkyl moiety) of an alkoxy, acyl (e.g., alkanoyl), alkylamino, dialkylamino, and alkylthio group have the same definition as above.

"Halo-substituted alkyl" refers to an alkyl group, as defined above, substituted with at least one halogen atom. For example, when the halogen atom is fluoro, common haloalkyl groups include fluoromethyl, difluoromethyl, trifluoromethyl, 2,2,2-trifluoroethyl, 2,2,2,1,1-pentafluoroethyl, and the like. Mixed halogen substitution are also included (e.g., chlorofluoromethyl).

The term "alkenyl" refers to a monovalent group derived from a hydrocarbon having at least one carbon-carbon double bond. The term "$C_2$-$C_6$-alkenyl" refers to a monovalent group derived from a hydrocarbon having two to six carbon atoms and comprising at least one carbon-carbon double bond. The alkenyl group can be unbranched or branched. Representative examples of alkenyl include vinyl, 1-propenyl, 2-propenyl, 1-methyl-1-propenyl, 1-methyl-2-propenyl, 2-methyl-1-propenyl, 2-methyl-2-propenyl, 1-butenyl, 2-butenyl, 3-butenyl, and so on.

The term "alkynyl" refers to a monovalent group derived from a hydrocarbon having at least one carbon-carbon triple bond. The term "$C_2$-$C_6$-alkynyl" refers to a monovalent group derived from a hydrocarbon having two to six carbon atoms and comprising at least one carbon-carbon triple bond. The alkynyl group can be unbranched or branched. Representative examples include ethynyl, propynyl, butyn-1-yl, butyn-2-yl, and so on.

The term "hydroxy-substituted alkyl" refers to an alkyl group, as defined above, substituted with one or more hydroxyl (-OH) groups (e.g., -CH$_2$OH, -CH(OH)$_2$, -CH(OH)-CH(OH, -CH(OH)-CH$_3$, and so on). Preferably, the alkyl group is substituted with 1 to 2 hydroxyl groups, more preferably one hydroxyl group.

"Halogen" or "halo" may be fluorine, chlorine, bromine or iodine (preferred halogens as substituents are fluorine and chlorine).

The term "oxo" or -C(O)- refers to a carbonyl group. For example, a ketone, aldehyde, or part of an acid, ester, amide, lactone, or lactam group.

The terms "partially or fully saturated carbocyclic ring" (also referred to as "partially or fully saturated cycloalkyl") refers to nonaromatic rings that are either partially or fully hydrogenated and may exist as a single ring, bicyclic ring or a spiral ring. Unless specified otherwise, the carbocyclic ring is generally a 3- to 8-membered ring. For example, partially or fully saturated carbocyclic rings (or cycloalkyl) include groups such as cyclopropyl, cyclopropenyl, cyclobutyl, cyclobutenyl, cyclopentyl, cyclopentenyl, cyclopentadienyl, cyclohexyl, cyclohexenyl, cyclohexadienyl, norbornyl (bicyclo[2.2.1]heptyl), norbornenyl, bicyclo[2.2.2]octyl, and the like.

The term "partially saturated or fully saturated heterocyclic ring" (also referred to as "partially saturated or fully saturated heterocycle") refers to nonaromatic rings that are either partially or fully hydrogenated and may exist as a single ring, bicyclic ring or a spiral ring. Unless specified otherwise, the heterocyclic ring is generally a 3- to 6-membered ring containing 1 to 3 heteroatoms (preferably 1 or 2 heteroatoms) each independently selected from sulfur, oxygen and/or nitrogen. Partially saturated or fully saturated heterocyclic rings include groups such as epoxy, aziridinyl, tetrahydrofuranyl, dihydrofuranyl, dihydropyridinyl, pyrolidinyl, N-methylpyrrolidinyl, imidazolidinyl, imidazolinyl, piperidinyl, piperazinyl, pyrazolidinyl, 2H-pyranyl, 4H-pyranyl, 2H-chromenyl, oxazinyl, morpholino, thiomorpholino, tetrahydrothienyl, tetrahydrothienyl 1,1-dioxide, and the like. Unless specified otherwise, the heterocyclic ring may be attached via any ring member.

The term "fused phenyl" refers to a phenyl group fused to another ring, such as another phenyl (i.e., naphthalene (e.g., naphthalen-2-yl, naphthalen-1-yl), a partially or fully saturated cycloalkyl (e.g., indan-5-yl, 2,3-dihydro-1H-indenyl, or tetrahydronaphthalenyl, etc.), a heteroaryl (e.g., 1H-indol-5-yl, 1H-indol-6-yl, benzothiazol-5-yl, benzothiazol-6-yl, benzo[b]thiophen-5-yl, quinolin-6-yl, quinolin-7-yl, isoquinolin-5-yl, isoquinolin-6-yl isoquinolin-7-yl, isoquinolin-8-yl, indazol-4-yl, indazol-5-yl, indazol-6-yl, indazol-7-yl, benzofuran-4-yl, benzofuran-5-yl, benzofuran-6-yl, benzofuran-7-yl, benzimidazol-4-yl, or quinoxalin-6-yl, benzooxazol-5-yl, benzo[d]isoxazol-5-yl, benzo[d]isoxazol-6-yl, 1H-benzoimidazol-4-yl, 1H-benzoimidazol-5-yl, 1H-benzoimidazol-6-yl, 1H-benzoimidazol-7-yl, 1H-benzotriazol-5-yl, etc.) or a partially saturated or fully saturated heterocycle (e.g., indolin-4-yl, indolin-5-yl, indolin-6-yl, indolin-7-yl, 1,2-dihydroquinolin-6-yl, 1,2,3,4-tetrahydro-quinolin-6-yl, 1,2,3,4-tetrahydro-quinolin-7-yl, 2,3-dihydro-1H-benzo[d]imidazolyl, 2,3-dihydro-1H-indazolyl, 2,3-dihydrobenzo[d]oxazolyl, 2,3-dihydrobenzo[1,4]dioxin-6-yl, 2,3-dihydro-benzofuran-5-yl, benzo[1,3]dioxol-5-yl, 2,3-dihydro-1H-indazol-5-yl, 2,3-dihydro-1H-indazol-6-yl, etc.), where the group is attached via one of the phenyl carbon atoms. When substituted, the fused phenyl can be substituted on any of the atoms within the fused system. For example, a benzofuranyl group may be substituted on the phenyl or furanyl portion of the benzofuranyl group.

The term "heteroaryl" or "heteroaromatic ring" refers to aromatic moieties containing at least one heteroatom (e.g., oxygen, sulfur, nitrogen or combinations thereof) within a 5- to 6-membered aromatic ring system (e.g., pyrrolyl, pyridyl, pyrazolyl, thienyl, furanyl, oxazolyl, imidazolyl, tetrazolyl, triazinyl, pyrimidyl, pyrazinyl, thiazolyl, isothiazolyl, etc.). A typical single heteroaryl ring is generally a 5- to 6-membered ring containing one to three heteroatoms each independently selected from oxygen, sulfur and nitrogen.

The term "fused heteroaryl" refers to a heteroaryl group fused to another ring, such as another heteroaryl (e.g. purinyl, thieno[3,2-c]pyridinyl (e.g., thieno[3,2-c]pyridin-2-yl and thieno[3,2-c]pyridin-3-yl), imidazo[1,2-a]pyridinyl (e.g., imidazo[1,2-a]pyridin-3-yl, imidazo[1,2-a]pyridin-6-yl, imidazo[1,2-a]pyridin-7-yl and 3H-imidazo[4,5-b]pyridin-6-yl), or benzo[b]thiophenyl, etc.), phenyl (e.g., benzo[b]thiophen-2-yl, benzo[b]thiophen-3-yl, quinolin-2-yl, quinolin-3-yl, benzooxazol-2-yl, benzothiazol-2-yl, 1H-indol-2-yl, 1H-indol-3-yl, isoquinolin-1-yl, isoquinolin-3-yl, isoquinolin-4-yl, benzofuran-2-yl, benzofuran-3-yl, indazol-3-yl, benzimidazol-2-yl, etc.), a partially or fully saturated cycloalkyl (e.g., 4,5,6,7-tetrahydrobenzo[d]oxazolyl, 4,5,6,7-tetrahydro-1H-indolyl, 5,6,7,8-tetrahydroquinolinyl, 5,6,7,8-tetrahydroisoquinolinyl, 4,5,6,7-tetrahydrobenzo[b]thiophenyl, 4,5,6,7-tetrahydrobenzofuranyl, 4,5,6,7-tetrahydro-1H-indazolyl, 4,5,6,7-tetrahydro-1H-benzo[d]imidazolyl, or 4,5,6,7-tetrahydrobenzo[d]oxazolyl, etc.), or a partially saturated or fully saturated heterocycle (e.g., 8,9-dihydro-7H-purinyl, 2,3-dihydrothieno[3,2-c]pyridinyl, 4,5,6,7-tetrahydro-thieno[2,3-c]pyridin-2-yl, 4,5,6,7-tetrahydrothieno[3,2-c]pyridinyl, or 5,6,7,8-tetrahydroimidazo[1,2-a]pyridinyl, etc.), where the heteroaryl group is attached via one of the heteroaryl ring atoms. When substituted, the fused heteroaryl can be substituted on any of the atoms within the fused system. For example, an imidazo[1,2-a]pyridinyl group may be substituted on the imidazole or pyridine portion of the fused system.

The phrase "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. The term "animal" refers to humans (male or female), companion animals (e.g., dogs, cats and horses), zoo animals, marine animals, birds and other similar animal species.

The phrase "pharmaceutically acceptable" indicates that the substance or composition must be compatible chemically and/or toxicologically, with the other ingredients comprising a formulation, and/or the mammal being treated therewith.

The terms "treating", "treat", or "treatment" embrace both preventative, i.e., prophylactic, and palliative treatment.

The term "compounds of the present invention" (unless specifically identified otherwise) refer to compounds of Formula (I), (II), (Ia) and (Ib), prodrugs thereof, pharmaceutically acceptable salts of the compounds, and/or prodrugs, and hydrates or solvates of the compounds, salts, and/or prodrugs, as well as, all stereoisomers (including diastereoisomers and enantiomers), tautomers and isotopically labeled compounds.

DETAILED DESCRIPTION

The present invention provides compounds and pharmaceutical formulations thereof that are useful in the treatment of diseases, conditions and/or disorders modulated by the inhibition of 17α-hydroxylase/$C_{17,20}$-lyase.

Compounds of the present invention may be synthesized by synthetic routes that include processes analogous to those well-known in the chemical arts, particularly in light of the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, Reagents for Organic Synthesis, v. 1-19, Wiley, New York (1967-1999 ed.), or Beilsteins Handbuch der organischen Chemie, 4, Aufl. ed. Springer-Verlag, Berlin, including supplements (also available via the Beilstein online database)).

For illustrative purposes, the reaction schemes depicted below provide potential routes for synthesizing the compounds of the present invention as well as key intermediates. For a more detailed description of the individual reaction steps, see the Examples section below. Those skilled in the art will appreciate that other synthetic routes may be used to synthesize the inventive compounds. Although specific starting materials and reagents are depicted in the schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

The schemes detailed below show general schemes for synthesizing compounds of the present invention (e.g., compounds of Formula (I), (II), (Ia) and (Ib)).

General Schemes

Scheme 1

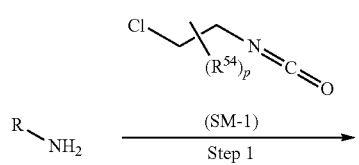

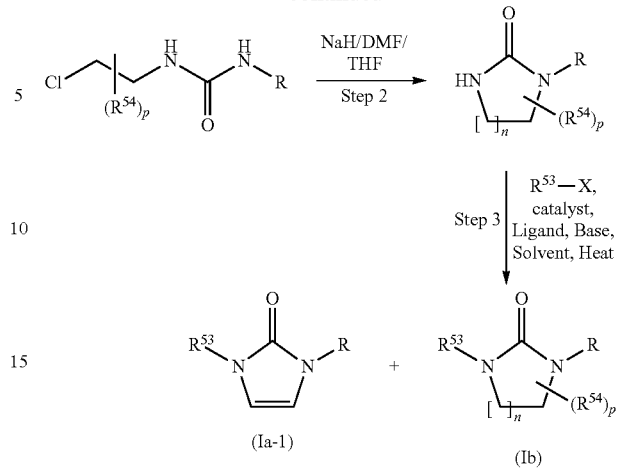

In Scheme I above, R is represented by -A or the following group

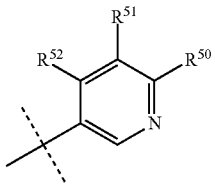

Step-1 & 2:

The intermediate products of Steps 1 and 2 may be synthesized using methods analogous to those described by Kak-Shan Shia, et al., in *J. Med. Chem.*, 2002, 45, 1644-1655 using the desired starting materials which are available commercially or synthesized using known procedures described in the art. For example, a variety of 2-chloroalkyl isocyanates can be prepared using the methods described by C K Johnson in *J Org Chem* (1967), 32(5), 1508-10. The reaction times in certain cases were prolonged to increase the % yield as compared to reported yields in the above mentioned J Med Chem reference.

Step-3:

The products of Step-2 obtained as described above may be converted into the desired products by reacting with the appropriate alkyl or aryl halides preferably chloro/bromo alkyl or an derivatives using conditions well know to those of skill in the art, e.g., the Buchwald-Hartwig C-N coupling conditions or NaH/DMF, and the like. Preferred conditions are those known as the 'Buchwald-Hartwig" reaction, e.g., in the presence of (a) a catalyst, such as copper iodide, (b) a base, such as potassium phosphate or cesium carbonate; and (c) a ligand, such as trans-1,2-diamino cyclohexane, in the presence of suitable solvents (e.g., 1,4-dioxane) at temperatures ranging from about room temperature to the refluxing temperature of the solvent. When p is zero, a compound of Formula (Ia-1) may also form. When a protection group is used, then the protecting group is removed using the conditions appropriate for the particular protecting group used to produce compounds of the present invention. For a more detailed description, see Examples 1 and 14 in the Example section below.

Alternatively, the substituents $R^{53}$ and R may be introduced in the reverse. For example, instead of starting with R-$NH_2$, $R^{53}$-$NH_2$ is used as the starting material. The R group is then introduced in step 3 by using R-X instead of $R^{53}$-X. See, e.g., Example 79 in the Example section below for a more detailed description.

Scheme 2 describes how one could make the starting material (SM-1) above where $R^{54}$ is other than hydrogen.

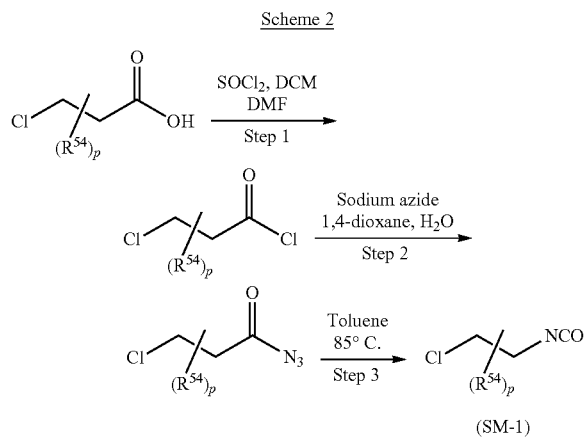

The desired chloro carboxylic acid is first converted to its corresponding acid chloride derivative using procedures well-known to those of skill in the art. For example, the carboxylic acid derivative may be treated with thionyl chloride in the presence of dimethylformamide (DMF) and a solvent (e.g., dichloromethane (DCM)). Other chlorinating agents may be used, e.g., phosphorous trichloride or phosphorous pentachloride. The acid chloride can then be converted to its corresponding azide by treatment with sodium azide. The azide is then converted to the desired isocyanate (SM-1) by the Curtius rearrangement, e.g., heating the azide at elevated temperatures.

Scheme 3 describes a synthesis for compounds of the present invention having an 1H-imidazol-2(3H)-one core (compounds of Formula (I) or (Ia).

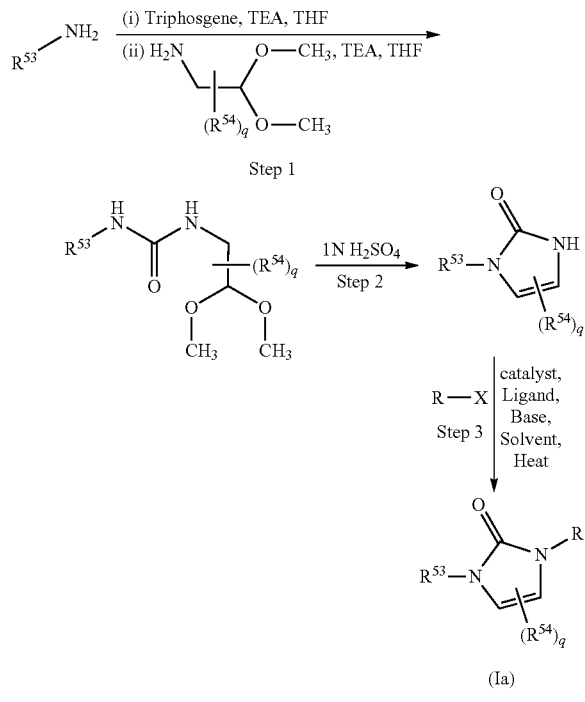

In Scheme 3 above, R is represented by -A or the following moiety

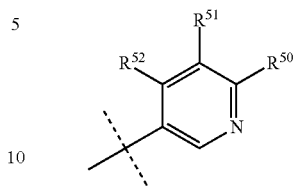

Step 1:

In Step-1, certain aromatic or heteroaromatic amines (in particular, 6-benzothiazolyl amine, 5-benzo[b]thiophenyl amine, 2-difluoromethyl-1-fluoro-phen-4-yl amine, 2-methyl-thiophene-4-yl amine, and the like) can undergo coupling with 2,2-dimethoxy-ethylamine via an isocyanate intermediate using reagents such as triphosgene, triethylamine (TEA) and suitable solvents (e.g., THF) to provide the corresponding 1-substituted 3-(2,2-dimethoxy-ethyl)-urea intermediate compounds.

Step 2:

In Step 2,1-substituted-1H-imidazol-2(3H)-one intermediates can be prepared by methods analagous to those known in art, such as the procedures described by T. Hafner, et al., in *Synthesis* (2007) 9, 1403-1411.

Step 3:

The products of Step 2 obtained as described above may be converted into the desired products by reacting with the desired aryl halides preferably iodo or bromo aryl derivatives using conditions such as the Buchwald-Hartwig C-N coupling conditions as described in Scheme 1 above. Alternatively, the product may be prepared via a copper-catalyzed N-arylation of the 1-substituted-1H-imidazol-2(3H)-one intermediate with conventional heating (e.g., $R^{53}$-X, $(CuOTf)_2$-$C_6H_6$, Cu:ligand:dibenzylideneacetone(dba)=1:5:1, in dioxane at about 150° C.). See, Hafner, et al., *Synthesis* (2007) 9, 1403-1411. For a more detailed description, see Examples 142 in the Example section below.

Scheme 4 provides an alternative synthesis for preparing compounds of Formula (II) or (Ib).

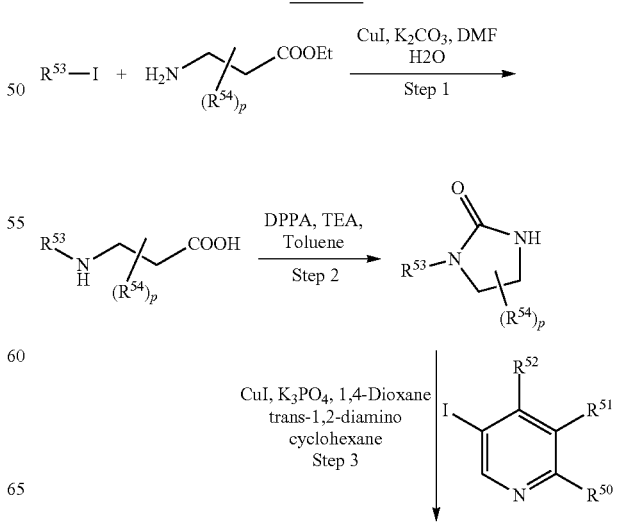

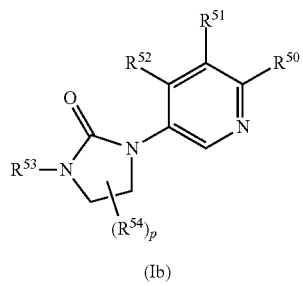

(Ib)

The desired $R^{53}$ group may be attached to the desired amino carboxylate compound via Buchwald-Hartwig C-N coupling conditions or NaH/DMF, and the like.

The cyclic urea is then formed using methods analogous to those described by Kak-Shan Shia, et al., in *J. Med. Chem.*, 2002, 45, 1644-1655. The pyridine derivative may then be coupled to the imidazoline via a Buchwald-Hartwig C-N coupling reaction described previously.

Alternatively, the unsymmetrical disubstituted-1H-imidazolin-2(31-1)-ones can be prepared by other methods discussed by T. Hafner, et al., in Synthesis (2007) 9, 1403-1411 (e.g., Brazier, S. A, et al., *J Chem. Soc.* (1912), 101, 2352 and Schonherr, H. J., et al, *Chem Ber* (1970), 103, 1037).

Scheme 5 provides another alternative synthesis for preparing compounds of Formula (II) or (Ib).

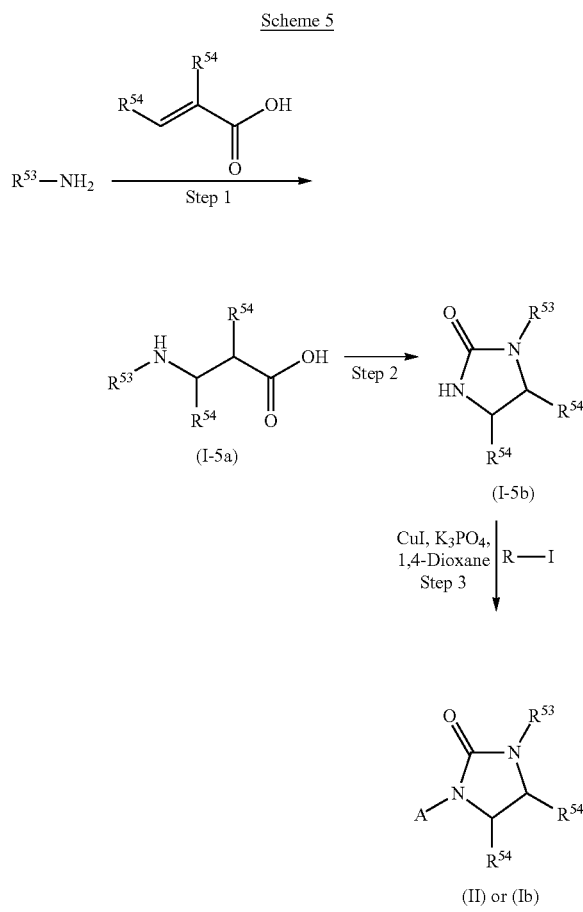

In Scheme 5 above, R is represented by -A or the following group

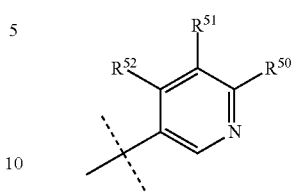

Intermediate (I-5a) may be formed via a Michael addition of the desired amine ($R^{53}$-NH$_2$) to the desired acrylic acid using procedures well-known to those of skill in the art. For example, the amine and acrylic acid in a suitable solvent (e.g., toluene) are heated at an elevated temperature (e.g., about 70° C. to about 100° C.) under an inert atmosphere. The amino acid intermediate (I-5a) may then be cyclized to form the cyclic urea intermediate (I-5b). For example, the cyclic urea intermediate (I-5b) may be formed by treating the amino acid intermediate (I-5a) with an activating agent (e.g., diphenyl phosphoryl azide (DPPA)) in the presence of an amine (e.g., triethylamine) and appropropriate solvent (e.g., toluene) at elevated temperatures. The desired A group may be coupled to the cyclic urea intermediate (I-5b) using standard coupling conditions described above to form the a compound of the Formula (II) or (Ib).

The Example section below provides a more detailed description of the synthetic schemes as well as other alternative processes for making compounds of the present invention which could be easily modified (e.g., substituting different starting materials) by those of skill in the art.

The compounds and intermediates described herein may be isolated and used as the compound per se or its salt. Many of the compounds represented by Formula (I), (II), (Ia), and (Ib) are capable of forming acid addition salts, particularly pharmaceutically acceptable acid addition salts. Pharmaceutically acceptable acid addition salts of the compound of Formula (I), (II), (Ia) and (Ib) include those of inorganic acids, for example, hydrohalic acids such as hydrochloric acid, hydrobromic acid or hydroiodic acid, nitric acid, sulfuric acid, phosphoric acid; and organic acids, for example aliphatic monocarboxylic acids such as formic acid, acetic acid, propionic acid and butyric acid, aliphatic hydroxy acids such as lactic acid, citric acid, tartaric acid or malic acid, dicarboxylic acids such as maleic acid or succinic acid, aromatic carboxylic acids such as benzoic acid, p-chlorobenzoic acid, diphenylacetic acid or triphenylacetic acid, aromatic hydroxy acids such as o-hydroxybenzoic acid, p-hydroxybenzoic acid, 1-hydroxynaphthalene-2-carboxylic acid or 3-hydroxynaphthalene-2-carboxylic acid, and sulfonic acids such as methanesulfonic acid or benzenesulfonic acid. These salts may be prepared from compounds of Formula (I), (II), (Ia) or (Ib) by known salt-forming procedures.

Compounds of the present invention which contain acidic, e.g. carboxyl, groups, are also capable of forming salts with bases, in particular pharmaceutically acceptable bases such as those well known in the art; suitable such salts include metal salts, particularly alkali metal or alkaline earth metal salts such as sodium, potassium, magnesium or calcium salts, or salts with ammonia or pharmaceutically acceptable organic amines or heterocyclic bases such as ethanolamines, benzylamines or pyridine. These salts may be prepared from compounds of Formula (I), (II), (Ia) and (Ib) by known salt-forming procedures.

In those compounds where there is an asymmetric carbon atom the compounds exist in individual optically active isomeric forms or as mixtures thereof, e.g. as racemic or diastereomeric mixtures. The present invention embraces both individual optically active R and S isomers as well as mixtures, e.g. racemic or diastereomeric mixtures, thereof.

The present invention includes all pharmaceutically acceptable isotopically-labeled compounds of the present invention wherein one or more atoms are replaced by atoms having the same atomic number, but an atomic mass or mass number different from the atomic mass or mass number usually found in nature.

Examples of isotopes suitable for inclusion in the compounds of the invention comprises isotopes of hydrogen, such as $^2$H and $^3$H, carbon, such as $^{11}$C, $^{13}$C and $^{14}$C, chlorine, such as $^{36}$Cl fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Isotopically-labeled compounds of the present invention can generally be prepared by conventional techniques known to those skilled in the art or by processes analogous to those described in the accompanying Examples and Preparations Sections using an appropriate isotopically-labeled reagent in place of the non-labeled reagent previously employed.

The compounds of the present invention may exist in unsolvated as well as solvated forms with pharmaceutically acceptable solvents such as water, ethanol, and the like, and it is intended that the invention embrace both solvated and unsolvated forms. For purposes of the present invention, solvates (including hydrates) are considered pharmaceutical compositions, e.g., a compound of Formula (I), (II), (Ia) or (Ib) (or pharmaceutically acceptable salt thereof) in combination with all excipient, wherein the excipient is a solvent.

Compounds of the present invention are useful for treating diseases, conditions and disorders mediated by the regulation of 17α-hydroxylase/$C_{17,20}$-lyase (e.g., cancer (in particular, prostate cancer) or inflammation); consequently, the compounds of the present invention (including the compositions and processes used therein) may be used in the manufacture of a medicament for the therapeutic applications described herein. Hence, another embodiment of the present invention is a pharmaceutical composition comprising a therapeutically effective amount of a compound of the present invention and a pharmaceutically acceptable excipient, diluent or carrier.

A typical formulation is prepared by mixing a compound of the present invention and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water, and the like. The particular carrier, diluent or excipient used will depend upon the means and purpose for which the compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG400, PEG300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

The formulations may be prepared using conventional dissolution and mixing procedures. For example, the bulk drug substance (i.e., compound of the present invention or stabilized form of the compound (e.g., complex with a cyclodextrin derivative or other known complexation agent)) is dissolved in a suitable solvent in the presence of one or more of the excipients. The compound of the present invention is typically formulated into pharmaceutical dosage forms to provide an easily controllable dosage of the drug and to give the patient an elegant and easily handleable product.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

A Cyp17 inhibitor of the present invention may be usefully combined with at least one additional pharmacologically active compound, particularly in the treatment of cancer. For example, a compound of the present invention, as defined above, may be administered simultaneously, sequentially or separately in combination with one or more agents selected from chemotherapy agents, e.g. mitotic inhibitors such as a taxane (e.g., paclitaxel or docetaxel), a vinca alkaloid (e.g., vincristine, vinblastine, vinorelbine or vinflunine) or other anticancer agents, e.g. cisplatin, 5-fluorouracil or 5-fluoro-2-4(1H,3H)-pyrimidinedione (5FU), flutamide or gemcitabine. Such combinations may offer significant advantages, including synergistic activity, in therapy.

A compound of the present invention may also be used in combination with other antiproliferative compounds. Such antiproliferative compounds include, but are not limited to aromatase inhibitors; antiestrogens; topoisomerase I inhibitors; topoisomerase II inhibitors; microtubule active compounds; alkylating compounds; compounds which induce cell differentiation processes; cyclooxygenase inhibitors; MMP inhibitors; mTOR inhibitors; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; methionine aminopeptidase inhibitors; bisphosphonates; biological response modifiers; antiproliferative antibodies; heparanase inhibitors; inhibitors of Ras oncogenic isoforms; telomerase inhibitors; proteasome inhibitors; compounds used in the treatment of hematologic malignancies; compounds which target, decrease or inhibit the activity of Flt-3; Hsp90 inhibitors such as 17-AAG (17-allylamino-gelda-namycin, NSC330507), 17-DMAG (17-dimethylaminoethylamino-17-demethoxy-geldana-mycin, NSC707545), IPI-504, CNF1010, CNF2024, CNF1010 from Conforma Therapeutics; temozolomide (TEMODAL); kinesin spindle protein inhibitors, such as SB715992 or SB743921 from GlaxoSmithKline, or pentamidine/chlorpromazine from CombinatoRx; PI3K inhibitors; RAF inhibitors; EDG binders, antileukemia compounds, ribonucleotide reductase inhibitors, S-adenosylmethionine decarboxylase inhibitors, antiproliferative anti-bodies or other chemotherapeutic compounds. Further, alternatively or in addition they may be used in combination with other tumor treatment approaches, including surgery, ionizing radiation, photodynamic therapy, implants, e.g. with corticosteroids, hormones, or they may be used as radiosensitizers. Also, in anti-inflammatory and/or antiproliferative treatment, combination with anti-inflammatory drugs is included. Combination is also possible with antihistamine drug substances, bronchodilatatory drugs, NSAID or antagonists of chemokine receptors.

The term "aromatase inhibitor" as used herein relates to a compound which inhibits the estrogen production, i.e. the conversion of the substrates androstenedione and testosterone to estrone and estradiol, respectively. The term includes, but is not limited to steroids, especially atame-stane, exemestane and formestane and, in paricular, non-steroids, especially aminoglutethimide, roglethimide, pyridoglutethimide, trilostane, testolactone, ketokonazole, vorozole, fadrozole, anastrozole and letrozole. Exemestane can be administered, e.g., in the form as it is marketed, e.g. under the trademark AROMASIN. Formestane can be administered, e.g., in the form as it is marketed, e.g. under the trademark LENTARON. Fadrozole can be administered, e.g., in the form as it is marketed, e.g. un-der the trademark AFEMA. Anastrozole can be administered, e.g., in the form as it is marketed, e.g. under the trademark ARIMIDEX. Letrozole can be administered, e.g., in the form as it is marketed, e.g. under the trademark FEMARA or FEMAR. Amino glutethimide can be administered, e.g., in the form as it is marketed, e.g. under the trademark, ORIMETEN. A combination of the invention comprising a chemo-therapeutic agent which is an aromatase inhibitor is particularly useful for the treatment of hormone receptor positive tumors, e.g., breast tumors.

The term "anti-estrogen" as used herein relates to a compound which antagonizes the effect of estrogens at the estrogen receptor level. The term includes, but is not limited to tamoxifen, fulvestrant, raloxifene and raloxifene hydrochloride. Tamoxifen can be administered, e.g., in the form as it is marketed, e.g. under the trademark NOLVADEX. Raloxifene hydrochloride can be administered, e.g., in the form as it is marketed, e.g. under the trademark EVISTA. Fulvestrant can be formulated as disclosed in U.S. Pat. No. 4,659,516 or it can be administered, e.g., in the form as it is marketed, e.g. under the trademark FASLODEX. A combination of the invention comprising a chemotherapeutic agent which is an anti-estrogen is particularly useful for the treatment of estrogen receptor positive tumors, e.g. breast tumors.

The term "anti-androgen" as used herein relates to any substance which is capable of inhibiting the biological effects of androgenic hormones and includes, but is not limited to, bicalutamide (CASODEX), which can be formulated, e.g. as disclosed in U.S. Pat. No. 4,636,505.

The term "gonadorelin agonist" as used herein includes, but is not limited to abarelix, goserelin and goserelin acetate. Goserelin is disclosed in U.S. Pat. No. 4,100,274 and can be administered, e.g., in the form as it is marketed, e.g. under the trademark ZOLADEX. Abarelix can be formulated, e.g. as disclosed in U.S. Pat. No. 5,843,901.

The term "topoisomerase I inhibitor" as used herein includes, but is not limited to topotecan, gimatecan, irinotecan, camptothecin and its analogues, 9-nitrocamptothecin and the macromolecular camptothecin conjugate PNU-166148 (compound A1 in WO99/17804). Irinotecan can be administered, e.g. in the form as it is marketed, e.g. under the trademark CAMPTOSAR. Topotecan can be administered, e.g., in the form as it is marketed, e.g. under the trademark HYCAMTIN.

The term "topoisomerase II inhibitor" as used herein includes, but is not limited to the anthracyclines such as doxorubicin (including liposomal formulation, e.g. CAELYX), daunorubicin, epirubicin, idarubicin and nemorubicin, the anthraquinones mitoxantrone and losoxantrone, and the podophillotoxines etoposide and teniposide. Etoposide can be administered, e.g. in the form as it is marketed, e.g. under the trademark ETOPOPHOS. Teniposide can be administered, e.g. in the form as it is marketed, e.g. under the trademark VM 26-BRISTOL. Doxorubicin can be administered, e.g. in the form as it is marketed, e.g. under the trademark ADRIBLASTIN or ADRIAMYCIN. Epirubicin can be administered, e.g. in the form as it is marketed, e.g. under the trademark FARMORUBICIN. Idarubicin can be administered, e.g. in the form as it is marketed, e.g. under the trademark ZAVEDOS. Mitoxantrone can be administered, e.g. in the form as it is marketed, e.g. under the trademark NOVANTRON.

The term "microtubule active compound" relates to microtubule stabilizing, microtubule destabilizing compounds and microtublin polymerization inhibitors including, but not limited to taxanes, e.g. paclitaxel and docetaxel, vinca alkaloids, e.g., vinblastine, especially vinblastine sulfate, vincristine especially vincristine sulfate, and vinorelbine, discodermolides, cochicine and epothilones and derivatives thereof, e.g. epothilone B or D or derivatives thereof. Paclitaxel may be administered e.g. in the form as it is marketed, e.g. TAXOL. Docetaxel can be administered, e.g., in the form as it is marketed, e.g. under the trademark TAXOTERE. Vinblastine sulfate can be administered, e.g., in the form as it is marketed, e.g. under the trademark VINBLASTIN R.P. Vincristine sulfate can be administered, e.g., in the form as it is marketed, e.g. under the trademark FARMISTIN. Discodermolide can be obtained, e.g., as disclosed in U.S. Pat. No. 5,010,099. Also included are Epothilone derivatives which are disclosed in WO 98/10121, U.S. Pat. No. 6,194,181, WO 98/25929, WO 98/08849, WO 99/43653, WO 98/22461 and WO 00/31247. Especially preferred are Epothilone A and/or B.

The term "alkylating compound" as used herein includes, but is not limited to, cyclophosphamide, ifosfamide, melphalan or nitrosourea (BCNU or Gliadel). Cyclophosphamide can be administered, e.g., in the form as it is marketed, e.g. under the trademark CYCLOSTIN. Ifosfamide can be administered, e.g., in the form as it is marketed, e.g., under the trademark HOLOXAN.

The term "antineoplastic antimetabolite" includes, but is not limited to, 5-Fluorouracil or 5-FU, capecitabine, gemcitabine, DNA demethylating compounds, such as 5-azacy-tidine and decitabine, methotrexate and edatrexate, and folic acid antagonists such as pemetrexed. Capecitabine can be administe-red, e.g., in the form as it is marketed, e.g. under the trademark XELODA. Gemcitabine can be administered, e.g., in the form as it is marketed, e.g. under the trademark GEMZAR. The term "platin compound" as used herein includes, but is not limited to, carboplatin, cis-platin, cisplatinum and oxaliplatin. Carboplatin can be administered, e.g., in the form as it is marketed, e.g. under the trademark CARBOPLAT. Oxaliplatin can be administered, e.g., in the form as it is marketed, e.g. under the trademark ELOXATIN.

The term "compounds targeting/decreasing a protein or lipid kinase activity"; or a "protein or lipid phosphatase activity"; or "further anti-angiogenic compounds" as used herein includes, but is not limited to, protein tyrosine kinase and/or serine and/or threonine kinase inhibitors or lipid kinase inhibitors, e.g., a) compounds targeting, decreasing or inhibiting the activity of the platelet-derived growth factor-receptors (PDGFR), such as compounds which target, decrease or inhibit the activity of PDGFR, especially compounds which inhibit the PDGF receptor, e.g. a N-phenyl-2-pyrimidineamine derivative, e.g. imatinib, SU101, SU6668 and GFB-111; b) compounds targeting, decreasing or inhibiting the activity of the fibroblast growth factor-receptors (FGFR); c) compounds targeting, decreasing or inhibiting the activity of the insulin-like growth factor receptor I (IGF-IR), such as compounds which target, decrease or inhibit the activity of IGF-IR, especially compounds which inhibit the kinase activity of IGF-I receptor, such as those compounds disclosed in WO 02/092599, or antibodies that target the extracellular domain of IGF-I receptor or its growth factors; d) compounds targeting, decreasing or inhibiting the activity of the Trk receptor tyrosine kinase family, or ephrin B4 inhibitors; e) compounds targeting, decreasing or inhibiting the activity of the Axl receptor tyrosine kinase family; f) compounds targeting, decreasing or inhibiting the activity of the Ret receptor tyrosine kinase; g) compounds targeting, decreasing or inhibiting the activity of the Kit/SCFR receptor tyrosine kinase, i.e C-kit receptor tyrosine kinases-(part of the PDGFR family), such as compounds which target, decrease or inhibit the activity of the c-Kit receptor tyrosine kinase family, especially compounds which inhibit the c-Kit receptor, e.g. imatinib; h) compounds targeting, decreasing or inhibiting the activity of members of the c-Abl family, their gene-fusion products (e.g. BCR-Abl kinase) and mutants, such as com-pounds which target decrease or inhibit the activity of c-AbI family members and their gene fusion products, e.g. a N-phenyl-2-pyrimidine-amine derivative, e.g. imatinib or nilotinib (AMN$_{107}$); PD180970; AG957; NSC 680410; PD173955 from ParkeDavis; or dasatinib (BMS-354825); i) compounds targeting, decreasing or inhibiting the activity of members of the protein kinase C (PKC) and Raf family of serine/threonine kinases, members of the MEK, SRC, JAK, FAK, PDK1, PKB/Akt, and Ras/MAPK family members, and/or members of the cyclin-dependent kinase family (CDK) and are especially those staurosporine derivatives disclosed in U.S. Pat. No. 5,093,330, e.g. midostaurin; examples of further compounds include e.g. UCN-01, safingol, BAY 43-9006, Bryostatin 1, Perifosine; Ilmofosine; RO 318220 and RO 320432; GO 6976; Isis 3521; LY333531/LY379196; isochinoline compounds such as those disclosed in WO 00/09495; FTIs; BEZ235 (a PI3K inhibitor) or AT7519 (CDK inhibitor); j) compounds targeting, decreasing or inhibiting the activity of protein-tyrosine kinase inhibitors, such as compounds which target, decrease or inhibit the activity of protein-tyrosine kinase inhibitors include imatinib mesylate (GLEEVEC) or tyrphostin. A tyrphostin is preferably a low molecular weight (mw<1500) compound, or a pharmaceutically acceptable salt thereof, especially a compound selected from the benzylidenemalonitrile class or the S-arylbenzenemalonirile or bisubstrate quinoline class of compounds, more especially any compound selected from the group consisting of Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin); k) compounds targeting, decreasing or inhibiting the activity of the epidermal growth factor family of receptor tyrosine kinases (EGFR, ErbB2, ErbB3, ErbB4 as homo- or heterodimers) and their mutants, such as compounds which target, decrease or inhibit the activity of the epidermal growth factor receptor family are especially compounds, proteins or antibodies which inhibit members of the EGF receptor tyrosine kinase family, e.g. EGF receptor, ErbB2, ErbB3 and ErbB4 or bind to EGF or EGF related ligands, and are in particular those compounds, proteins or monoclonal antibodies generically and specifically disclosed in WO 97/02266, e.g. the compound of ex. 39, or in EP 0 564 409, WO 99/03854, EP 0520722, EP 0 566 226, EP 0 787 722, EP 0 837 063, U.S. Pat. No. 5,747,498, WO 98/10767, WO 97/30034, WO 97/49688, WO 97/38983 and, especially, WO 96/30347 (e.g. compound known as CP 358774), WO 96/33980 (e.g. compound ZD 1839) and WO 95/03283 (e.g. compound ZM105180); e.g. trastuzumab (Herceptin), cetuximab (Erbitux), Iressa, Tarceva, OSI-774, CI-1033, EKB-569, OW-2016, E1.1, E2.4, E2.5, E6.2, E6.4, E2.11, E6.3 or E7.6.3, and 7H-pyrrolo-[2,3-d]pyrimidine derivatives which are disclosed in WO 03/013541; and 1) compounds targeting, decreasing or inhibiting the activity of the c-Met receptor, such as compounds which target, decrease or inhibit the activity of c-Met, especially compounds which inhibit the kinase activity of c-Met receptor, or antibodies that target the extracellular domain of c-Met or bind to HGF.

Further anti-angiogenic compounds include compounds having another mechanism for their activity, e.g. unrelated to protein or lipid kinase inhibition e.g. thalidomide (THALOMID) and TNP-470.

Compounds which target, decrease or inhibit the activity of a protein or lipid phosphatase are e.g., inhibitors of phosphatase 1, phosphatase 2A, or CDC25, e.g. okadaic acid or a derivative thereof.

Compounds which induce cell differentiation processes are e.g. retinoic acid, or tocopherol or tocotrienol.

The term cyclooxygenase inhibitor as used herein includes, but is not limited to, e.g. Cox-2 inhibitors, 5-alkyl substituted 2-arylaminophenylacetic acid and derivatives, such as celecoxib (CELEBREX), rofecoxib (VIOXX), etoricoxib, valdecoxib or a 5-alkyl-2-arylaminophenylacetic acid, e.g. 5-methyl-2-(2'-chloro-6'-fluoroanilino)phenyl acetic acid, lumiracoxib.

The term "bisphosphonates" as used herein includes, but is not limited to, etridonic, clodronic, tiludronic, pamidronic, alendronic, ibandronic, risedronic and zoledronic acid. "Etridonic acid" can be administered, e.g., in the form as it is marketed, e.g. under the trademark DIDRONEL. "Clodronic acid" can be administered, e.g., in the form as it is marketed, e.g. under the trademark BONEFOS. "Tiludronic acid" can be administered, e.g., in the form as it is marketed, e.g. under the trademark SKELID. "Pamidronic acid" can be administered, e.g. in the form as it is marketed, e.g. under the trademark AREDIA. "Alendronic acid" can be administered, e.g., in the form as it is marketed, e.g. under the trademark FOSAMAX. "Ibandronic acid" can be administered, e.g., in the form as it is marketed, e.g. under the trademark BONDRANAT. "Risedronic acid" can be administered, e.g., in the form as it is marketed, e.g. under the trademark ACTONEL. "Zoledronic acid" can be administered, e.g. in the form as it is marketed, e.g. under the trademark ZOMETA.

The term "mTOR inhibitors" relates to compounds which inhibit the mammalian target of rapamycin (mTOR) and which possess antiproliferative activity such as sirolimus (Rapamune), everolimus (CerticanO), CCI-779 and ABT578.

The term "heparanase inhibitor" as used herein refers to compounds which target, decrease or inhibit heparin sulfate degradation. The term includes, but is not limited to, PI-88.

The term "biological response modifier" as used herein refers to a lymphokine or interferons, e.g. interferon.

The term "inhibitor of Ras oncogenic isoforms", e.g. H-Ras, K-Ras, or N-Ras, as used herein refers to compounds which target, decrease or inhibit the oncogenic activity of Ras e.g. a "farnesyl transferase inhibitor" e.g. L-744832, DK8G557 or R115777 (Zarnestra).

The term "telomerase inhibitor" as used herein refers to compounds which target, decrease or inhibit the activity of telomerase. Compounds which target, decrease or inhibit the activity of telomerase are especially compounds which inhibit the telomerase receptor, e.g. telomestatin.

The term "methionine aminopeptidase inhibitor" as used herein refers to compounds which target, decrease or inhibit the activity of methionine aminopeptidase. Compounds which target, decrease or inhibit the activity of methionine aminopeptidase are e.g. bengamide or a derivative thereof.

The term "proteasome inhibitor" as used herein refers to compounds which target, decrease or inhibit the activity of the proteasome. Compounds which target, decrease or inhibit the activity of the proteasome include e.g. Bortezomid (Velcade) and MLN 341. The term "matrix metalloproteinase inhibitor" or ("MMP" inhibitor) as used herein includes, but is not limited to, collagen peptidomimetic and nonpeptidomimetic inhibitors, tetracycline derivatives, e.g. hydroxamate peptidomimetic inhibitor batimastat and its orally bioavailable analogue marimastat (BB-2516), prinomastat (AG3340), metastat (NSC 683551) BMS-279251, BAY 12-9566, TAA211, MMI270B or AAJ996. The term "compounds used in the treatment of hematologic malignancies" as used herein includes, but is not limited to, FMS-like tyrosine kinase inhibitors e.g. compounds targeting, decreasing or inhibiting the activity of FMS-like tyrosine kinase receptors (Flt-3R); interferon, 1-b-D-arabinofuransylcytosine (ara-c) and bisulfan; and ALK inhibitors e.g. compounds which target, decrease or inhibit anaplastic lymphoma kinase. Compounds which target, decrease or inhibit the activity of FMS-like tyrosine kinase receptors (Flt-3R) are especially compounds, proteins or antibodies which inhibit members of the Flt-3R receptor kinase family, e.g. PKC412, TKI258, midostaurin, a staurosporine derivative, SU11248 and MLN518.

The term "HSP90 inhibitors" as used herein includes, but is not limited to, compounds targeting, decreasing or inhibiting the intrinsic ATPase activity of HSP90; degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90 e.g., 17-allylamino,17-demethoxygeldanamycin (17AAG), a geldanamycin derivative; other geldanamycin related compounds; radicicol and HDAC inhibitors. An example HSP90 inhibitor is AUY922.

The term "antiproliferative antibodies" as used herein includes, but is not limited to, trastuzumab (Herceptin), Trastuzumab-DM1,erbitux, bevacizumab (Avastin), rituximab (Rituxan), PRO64553 (anti-CD40) and 2C4 Antibody. By antibodies is meant e.g. intact monoclonal antibodies, polyclonal antibodies, multispe-cific antibodies formed from at least 2 intact antibodies, and antibodies fragments so long as they exhibit the desired biological activity.

For the treatment of acute myeloid leukemia (AML), compounds of formula (I) can be used in combination with standard leukemia therapies, especially in combination with therapies used for the treatment of AML. In particular, compounds of formula (I) can be administered in combination with, e.g., farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412.

The term "antileukemic compounds" includes, for example, Ara-C, a pyrimidine analog, which is the 2-alphahydroxy ribose (arabinoside) derivative of deoxycytidine. Also included is the purine analog of hypoxanthine, 6-mercaptopurine (6-MP) and fludarabine phosphate.

Somatostatin receptor antagonists as used herein refers to compounds which target, treat or inhibit the somatostatin receptor such as octreotide, and SOM230 (pasireotide).

Tumor cell damaging approaches refer to approaches such as ionizing radiation. The term "ionizing radiation" referred to above and hereinafter means ionizing radiation that occurs as either electromagnetic rays (such as X-rays and gamma rays) or particles (such as alpha and beta particles). Ionizing radiation is provided in, but not limited to, radiation therapy and is known in the art. See Hellman, Principles of Radiation Therapy, Cancer, in *Principles and Practice of Oncology*, Devita et al., Eds., 4$^{th}$ Edition, Vol. 1, pp. 248-275 (1993).

The term "EDG binders" as used herein refers a class of immunosuppressants that modulates lymphocyte recirculation, such as FTY720.

The term "ribonucleotide reductase inhibitors" refers to pyrimidine or purine nucleoside analogs including, but not limited to, fludarabine and/or cytosine arabinoside (ara-C), 6-thioguanine, 5-fluorouracil, cladribine, 6-mercaptopurine (especially in combination with ara-C against ALL) and/or pentostatin. Ribonucleotide reductase inhibitors are especially hydroxyurea or 2-hydroxy-1H-isoindole-1,3-dione derivatives, such as PL-1, PL-2, PL-3, PL-4, PL-5, PL-6, PL-7 or PL-8 mentioned in Nandy et al., *Acta Oncologica*, Vol. 33, No. 8, pp. 953-961 (1994).

The term "S-adenosylmethionine decarboxylase inhibitors" as used herein includes, but is not limited to the compounds disclosed in U.S. Pat. No. 5,461,076.

Also included are in particular those compounds, proteins or monoclonal antibodies of VEGF disclosed in WO 98/35958, e.g. 1-(4-chloroanilino)-4-(4-pyridylmethyl)phthalazine or a pharmaceutically acceptable salt thereof, e.g. the succinate, or in WO 00/09495, WO 00/27820, WO 00/59509, WO 98/11223, WO 00/27819 and EP 0 769 947; those as described by Prewett et al, *Cancer Res*, Vol. 59, pp. 5209-5218 (1999); Yuan et al., *Proc Natl Acad Sci USA*, Vol. 93, pp. 14765-14770 (1996); Zhu et al., *Cancer Res*, Vol. 58, pp. 3209-3214 (1998); and Mordenti et al., *Toxicol Pathol*, Vol. 27, No. 1, pp. 14-21 (1999); in WO 00/37502 and WO 94/10202; ANGIOSTATIN, described by O'Reilly et al., *Cell*, Vol. 79, pp. 315-328 (1994); ENDOSTATIN, described by O'Reilly et al., *Cell*, Vol. 88, pp. 277-285 (1997); anthranilic acid amides; ZD4190; ZD6474; SU5416; SU6668; bevacizumab; or anti-VEGF antibodies or anti-VEGF receptor antibodies, e.g. rhuMAb and RHUFab, VEGF aptamer e.g. Macugon; FLT-4 inhibitors, FLT-3 inhibitors, VEGFR-2 IgG1 antibody, Angiozyme (RPI 4610) and Bevacizumab (Avastin).

Photodynamic therapy as used herein refers to therapy which uses certain chemicals known as photosensitizing compounds to treat or prevent cancers. Examples of photodynamic therapy includes treatment with compounds, such as e.g. VISUDYNE and porfimer sodium.

Angiostatic steroids as used herein refers to compounds which block or inhibit angiogenesis, such as, e.g., anecortave, triamcinolone, hydrocortisone, 11-epihydrocotisol, cortexolone, 17-hydroxyprogesterone, corticosterone, desoxycorticosterone, testosterone, estrone and dexamethasone.

Implants containing corticosteroids refers to compounds, such as e.g. fluocinolone, dexamethasone.

"Other chemotherapeutic compounds" include, but are not limited to, plant alkaloids, hormonal compounds and antagonists; biological response modifiers, preferably lymphokines or interferons; antisense oligonucleotides or oligonucleotide derivatives; shRNA or siRNA; or miscellaneous compounds or compounds with other or unknown mechanism of action.

The structure of the active compounds identified by code nos., generic or trade names may be taken from the actual edition of the standard compendium "The Merck Index" or from databases, e.g. Patents International (e.g. IMS World Publications).

EXAMPLES

The following abbreviations used in the examples below have the corresponding meanings:

| | |
|---|---|
| DIPA: | Diisopropylamine |
| DPPA: | Diphenylphosphoryl Azide |
| DCM: | Dichloromethane |
| DCE: | Dichloroethane |
| DMF: | N,N-Dimethylformamide |
| DMSO: | Dimethylsulfoxide |
| TEA: | Triethylamine |
| THF: | Tetrahydrofuran |
| NaBH(OAc)$_3$: | Sodium triacetoxy borohydride |
| PTSA: | Para toluene sulphonic acid |
| TES: | Triethyl silane |
| LiHMDS: | Lithium bis(trimethylsilyl)amide |
| TEA: | Triethyl amine |
| Pd$_2$(dba)$_3$: | Tris(dibenzylideneacetone)dipalladium(0) |
| TLC: | Thin Layer Chromatography |
| NMR: | Nuclear Magnetic Resonance |
| LCMS: | Liquid chromatography Mass spectrometry |
| HPLC: | High Performance Liquid Chromatography |

Example 1

Preparation of 1-Naphthalen-2-yl-3-pyridin-3-yl-imidazolidin-2-one (1A)

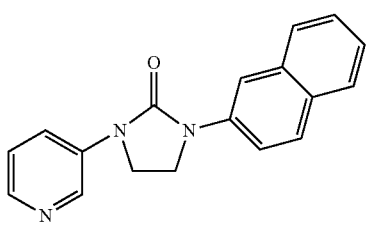

(1A)

Step 1: Preparation of Intermediate 1-(2-Chloro-ethyl)-3-pyridin-3-yl-urea (I-1a)

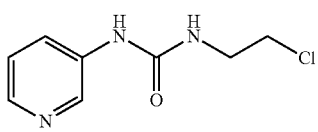

(I-1a)

1-Chloro-2-isocyanato-ethane (560 mg, 5.31 mmol) was added dropwise to a stirred solution of pyridin-3-ylamine (500 mg, 5.31 mmol) in toluene (10 mL) over a period of 30 minutes at 0° C. The reaction temperature was maintained at room temperature for 5 hours. The reaction was monitored by TLC (100% ethyl acetate). The reaction mixture was filtered, washed with toluene and dried under reduced pressure to afford 1.0 g (98% yield) of 1-(2-Chloro-ethyl)-3-pyridin-3-yl-urea.

$^1$H NMR (DMSO-D$_6$, 300 MHz): δ 8.9 (br s, 1H), 8.55 (br s, 1H), 8.1 (d, 1H), 7.9 (m, 1H), 7.3 (m, 1H), 6.5 (t, 1H), 3.65 (t, 2H), 3.45 (q, 2H)

LCMS purity: 99.75%, m/z=200.2(M+1)

Step 2: Preparation of Intermediate 1-Pyridin 3-yl-imidazolidin 2 one (I-1b)

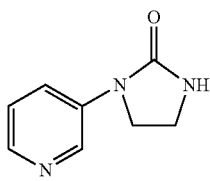

(I-1b)

1-(2-Chloro-ethyl)-3-pyridin-3-yl-urea (I-1a: 1000 mg, 5.0 mmol) in dry DMF (10 mL) was added to a stirred solution of sodium hydride (216 mg, 9.0 mmol) in THF (10 mL) at 0° C. The reaction temperature was maintained at room temperature for 30 minutes. The reaction was monitored by TLC (100% ethyl acetate). The reaction mixture was quenched with MeOH (5 mL) at 0° C. The reaction mixture was concentrated under reduced pressure and partitioned between ice water and chloroform. The organic layer was dried over Na$_2$SO$_4$, and concentrated under reduced pressure to afford 800 mg (97% yield) of 1-pyridin-3-yl-imidazolidin-2-one.

$^1$H NMR (CDCl$_3$, 300 MHz): δ 8.75 (d, 1H), 8.2 (dd, 1H), 8.0 (m, 1H), 7.35 (m, 1H), 7.15 (br s, 1H), 3.9 (m, 2H), 3.45 (m, 2H)

LCMS purity: m/z=164.2(M+1)

Final Step: Preparation of 1-Naphthalen-2-yl-3-pyridin-3-yl-imidazolidin-2-one (1A)

Copper iodide (10.0 mg, 0.113 mmol), trans-1,2-diamino cyclohexane (10.0 mg, 0.091 mmol) and potassium carbonate (169 mg, 1.22 mmol) were added to a solution of 1,4-dioxane (5 mL) previously purged with argon (10 minutes). The reaction mixture was purged with argon for 10 minutes, followed by the addition of 1-pyridin-3-yl-imidazolidin-2-one (I-1b: 100 mg, 0.61 mmol) and 2-bromo naphthalene (126 mg, 0.61 mmol). The reaction mixture was heated to reflux at 110° C. for 15 hours. The reaction was monitored by TLC (10% MeOH in chloroform). The reaction mixture was filtered through a celite bed and the bed was washed with chloroform. The organic layer was concentrated and purification by column chromatography (using silica gel of mesh size of 60-120, 20% ethyl acetate in hexane as eluent) afforded 48 mg (28% yield) of 1-naphthalen-2-yl-3-pyridin-3-yl-imidazolidin-2-one.

$^1$H NMR (DMSO-D$_6$, 300 MHz): δ 8.9 (d, 1H), 8.3 (d, 1H), 8.15-8.05 (m, 2H), 7.95-7.85 (m, 4H), 7.55-7.4 (m, 3H), 4.2-4.0 (m, 4H)

LCMS purity: 98.57%; m/z=290.0(M+1)

HPLC: 96.05%

Example 2

Preparation of 1-(1-Ethyl-1H-indol-5-yl)-3-pyridin-3-yl-imidazolidin-2-one (2A)

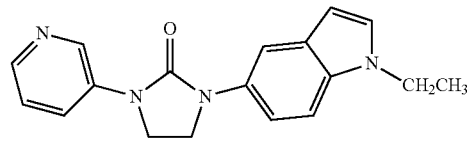

(2A)

Using the same reaction conditions as in Example 1, 1-pyridin-3-yl-imidazolidin-2-one (I-1b: 200 mg, 1.226 mmol) was reacted with 5-bromo-1-ethyl-1H-indole (274 mg, 1.226 mmol), 1,4-dioxane (10 mL), copper iodide (23.3 mg, 0.1226 mmol), trans-1,2-diamino cyclohexane (20.99 mg, 1.839 mmol) and potassium carbonate (338 mg, 2.452 mmol) to afford the crude product. Purification by column chromatography on silica gel (30% ethylacetate in hexane), afforded 185 mg of the product (49.33% yield).

$^1$H NMR (DMSO-D$_6$, 300 MHz): δ 8.85-8.8 (br s, 1H), 8.2 (d, 1H), 8.1-8.05 (m, 1H), 7.65 (s, 1H), 7.5 (s, 2H), 7.4-7.35 (m, 2H), 6.4 (d, 1H), 4.5 (q, 2H), 4.1-4.0 (m, 4H), 1.4 (t, 3H)

LCMS purity: 96.97%, m/z=307.0 (M+1)

HPLC: 98.74%

Example 3

Preparation of 1-(6-Methoxy-naphthalen-2-yl)-3-pyridin-3-O-imidazolidin-2-one (3A)

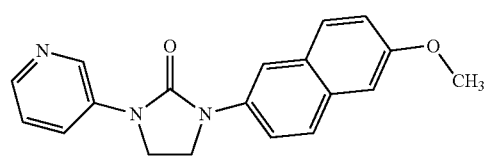

(3A)

Using the same reaction conditions as in Example 1, 1-pyridin-3-yl-imidazolidin-2-one (I-1b: 68.7 mg, 0.4217 mmol) was reacted with 2-bromo-6-methoxy-naphthalene (100 mg, 0.4217 mmol), 1,4-dioxane (5 mL), copper iodide (8.0 mg, 0.04217 mmol), trans-1,2-diamino cyclohexane (7 mg, 0.0632 mmol) and potassium carbonate (116 mg, 0.8432 mmol) to afford the crude product. Purification by column chromatography on silica gel (50% ethylacetate in hexane), afforded 72 mg of the product (55.22% yield).

$^1$H NMR (DMSO-D$_6$, 300 MHz): δ 8.9 (d, 1H), 8.3 (dd, 1H), 8.0-8.1 (m, 2H), 7.8 (m, 3H), 7.4 (m, 1H), 7.3 (d, 1H), 7.15 (dd, 1H), 4.2-4.0 (m, 4H), 3.85 (s, 3H)

LCMS purity: 96.72%, m/z=320.0 (M+1)
HPLC: 97.84%

Example 4

Preparation of 1-Benzothiazol-6-yl-3-pyridin-3-yl-imidazolidin-2-one (4A)

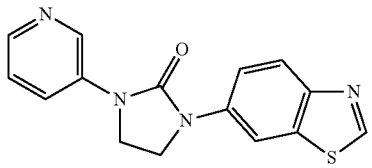

(4A)

Using the same reaction conditions as in Example 1, 1-pyridin-3-yl-imidazolidin-2-one (I-1b: 62 mg, 0.3831 mmol) was reacted with 6-iodo-benzothiazole (100 mg, 0.3831 mmol), 1,4-dioxane (10 mL), copper iodide (7 mg, 0.03831 mmol), trans-1,2-diamino cyclohexane (6 mg, 0.5747 mmol) and potassium carbonate (105 mg, 0.7662 mmol) to afford the crude product. Purification by column chromatography on silica gel (1% MeOH in chloroform), afforded 52 mg of the product (46.01% yield).

$^1$H NMR (DMSO-D$_6$, 300 MHz): δ 9.3 (s, 1H), 8.9 (d, 1H), 8.35-8.25 (m, 2H), 8.1-8.0 (m, 2H), 7.95 (dd, 1H), 7.45-7.4 (m, 1H), 4.2-4.0 (m, 4H)

LCMS purity: 93.45%, m/z=297.3 (M+1)
HPLC: 95.65%

Example 5

Preparation of 1-Ethyl-6-(2-oxo-3-pyridin-3-yl-imidazolidin-1-yl)-3,4-dihydro-1H-quinolin-2-one (5A)

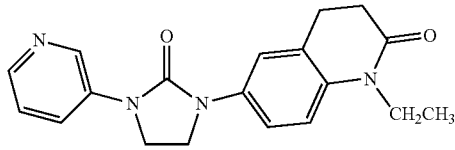

(5A)

Using the same reaction conditions as in Example 1, 1-pyridin-3-yl-imidazolidin-2-one (I-1b: 95 mg, 0.5882 mmol) was reacted with 6-bromo-1-ethyl-3,4-dihydro-1H-quinolin-2-one (150 mg, 0.5882 mmol), 1,4-dioxane (5 mL), copper iodide (11 mg, 0.05882 mmol), trans-1,2-diamino cyclohexane (10 mg, 0.08823 mmol) and potassium carbonate (162 mg, 1.1764 mmol) to afford the crude product. Purification by column chromatography on silica gel (1% MeOH in chloroform), afforded 94 mg of the product (47.71% yield).

$^1$H NMR (DMSO-D$_6$, 300 MHz): δ 8.85 (d, 1H), 8.3 (dd, 1H), 8.1-8.0 (m, 1H), 7.55-7.45 (m, 2H), 7.45-7.35 (m, 1H), 7.15 (d, 1H), 4.0 (s, 4H), 3.9 (q, 2H), 2.85 (t, 2H), 2.55-2.5 (m, 2H), 1.1 (t, 3H)

LCMS purity: 99.16%, m/z=337.3 (M+1)
HPLC: 95.77%

Example 6

Preparation of 1-(5-Fluoro-3-methyl-benzo[b]thiophen-2-yl)-3-pyridin-3-yl-imidazolidin-2-one (6A)

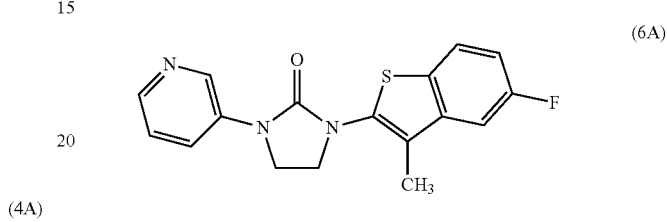

(6A)

Using the same reaction conditions as in Example 1, 1-pyridin-3-yl-imidazolidin-2-one (I-1b: 73 mg, 0.45 mmol) was reacted with 2-bromo-5-fluoro-3-methyl-benzo[b]thiophene (110 mg, 0.45 mmol), 1,4-dioxane (5 mL), copper iodide (8 mg, 0.045 mmol), trans-1,2-diamino cyclohexane (7 mg, 0.0675 mmol) and potassium carbonate (124 mg, 0.9 mmol) to afford the crude product. Purification by column chromatography on silica gel (1% MeOH in chloroform), afforded 90 mg of the product (61.64% yield).

$^1$H NMR (DMSO-D$_6$, 300 MHz): δ 8.9 (d, 1H), 8.3 (dd, 1H), 8.15-8.05 (m, 1H), 7.95-7.7 (m, 1H), 7.6 (dd, 1H), 7.45-7.4 (m, 1H), 7.3-7.2 (m, 1H), 4.15-4.0 (m, 4H), 2.3 (s, 3H)

LCMS purity: 98.04%, m/z =327.9 (M+1)
HPLC: 95.05%

Example 7

Preparation of 1-Benzo[b]thiophen-5-yl-3-pyridin-3-yl-imidazolidin-2-one (7A)

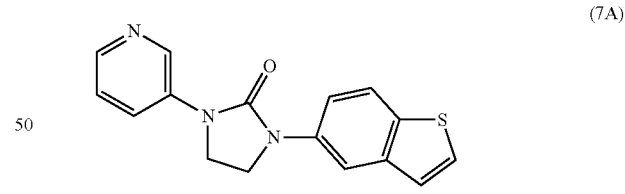

(7A)

Using the same reaction conditions as in Example 1, 1-pyridin-3-yl-imidazolidin-2-one (I-1b: 93.6 mg, 0.5747 mmol) was reacted with 5-iodo-benzo[b]thiophene (150 mg, 0.5747 mmol), 1,4-dioxane (5 mL), copper iodide (10 mg, 0.05747 mmol), trans-1,2-diamino cyclohexane (9 mg, 0.0862 mmol) and potassium carbonate (158.9 mg, 1.149 mmol) to afford the crude product. Purification by column chromatography on silica gel (1% MeOH in chloroform), afforded 70 mg of the product (41.42% yield).

$^1$H NMR (DMSO-D$_6$, 300 MHz): δ 8.9 (d, 1H), 8.3 (dd, 1H), 8.1-8.0 (m, 3H), 7.8-7.75 (m, 2H), 7.45-7.4 (m, 2H), 4.1-4.0 (m, 4H)

LCMS purity: 97.11%, m/z =296.3 (M+1)
HPLC: 97.46%

Example 8

Preparation of 1-Pyridin-3-yl-3-quinolin-6-yl-imidazolidin-2-one (8A)

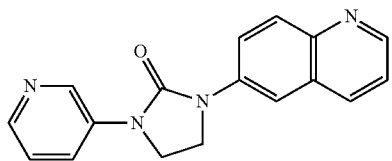

(8A)

Using the same reaction conditions as in Example 1, 1-pyridin-3-yl-imidazolidin-2-one (I-1b: 117 mg, 0.7215 mmol) was reacted with 6-bromo-quinoline (150 mg, 0.7215 mmol), 1,4-dioxane (5 mL), copper iodide (13 mg, 0.07215 mmol), trans-1,2-diamino cyclohexane (24.78 mg, 0.21645 mmol) and potassium carbonate (199.49 mg, 1.1443 mmol) to afford the crude product. Purification by column chromatography on silica gel (1% MeOH in chloroform), afforded 125 mg of the product (60.09% yield).

$^1$H NMR (DMSO-$D_6$, 300 MHz): δ 8.9 (d, 1H), 8.8 (dd, 1H), 8.4-8.25 (m, 3H), 8.15-8.0 (m, 2H), 7.9 (d, 1H), 7.55-7.4 (m, 2H), 4.2-4.0 (m, 4H)

LCMS purity: 98.99%, m/z =291.1 (M+1)

HPLC: 98.55%

Example 9

Preparation of 1-Benzothiazol-5-yl-3-pyridin-3-yl-imidazolidin-2-one (9A)

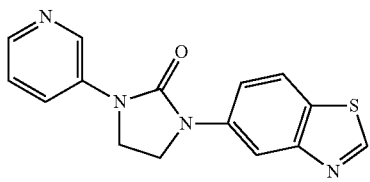

(9A)

Using the same reaction conditions as in Example 1, 1-pyridin-3-yl-imidazolidin-2-one (I-1b: 93.67 mg, 0.5747 mmol) was reacted with 5-iodo-benzothiazole (150 mg, 0.5747 mmol), 1,4-dioxane (5 mL), copper iodide (10.9 mg, 0.05747 mmol), trans-1,2-diamino cyclohexane (19.65 mg, 0.1724 mmol) and potassium carbonate (159 mg, 1.1494 mmol) to afford the crude product. Purification by column chromatography on silica gel (1% MeOH in chloroform) afforded 105 mg of the product (61.76% yield).

$^1$H NMR (DMSO-$D_6$, 300 MHz): δ 9.4 (s, 1H), 8.9 (d, 1H), 8.35-8.25 (m, 2H), 8.2-8.05 (m, 2H), 8.0-7.9 (dd, 1H), 7.45-7.4 (m, 1H), 4.2-4.0 (m, 4H)

LCMS purity: 98.09%, m/z =296.9 (M+1)

HPLC: 95.27%

Example 10

Preparation of 1-Naphthalen-2-yl-3-pyridin-3-yl-tetrahydro-pyrimidin-2-one (10A)

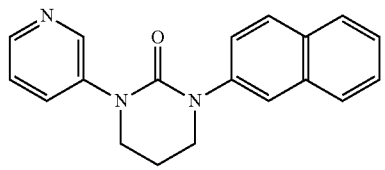

(10A)

Step 1: Preparation of Intermediate 1-(3-Chloro-propyl)-3-pyridin-3-yl-urea (I-10a)

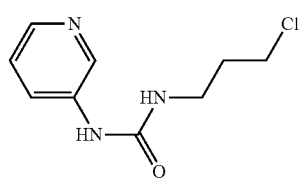

(I-10a)

1-Chloro-3-isocyanato-propane (1.897 g, 15.873 mmol) was added dropwise to a stirred solution of pyridin-3-ylamine (1 g, 10.582 mmol) in toluene (15 mL) over a period of 30 minutes at 0° C. The reaction temperature was maintained at room temperature for 6 hours. The reaction was monitored by TLC (100% ethyl acetate). The reaction mixture was filtered, washed with toluene and dried under reduced pressure to afford 2.1 g (95.45% yield) of 1-(3-chloro-propyl)-3-pyridin-3-yl-urea.

$^1$H NMR (DMSO-$D_6$, 300 MHz): 6; 8.65(brS, 1H), 8.5 (d, 1H), 8.15 (dd, 1H), 7.9 (m, 1H), 7.35 (m, 1H), 6.4 (t, 1H), 3.65 (t, 2H), 3.2 (q, 2H), 1.9 (m, 2H)

Step 2: 1-Pyridin-3-yl-tetrahydro-pyrimidin-2-one (I-10b)

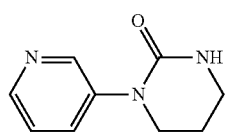

(I-10b)

1-(3-Chloro-propyl)-3-pyridin-3-yl-urea (I-10a: 2.1 g, 9.859 mmol) in dry DMF (10 mL) was added to a solution of sodium hydride (487 mg, 10.154 mmol) in THF (2 mL) at 0° C. The reaction temperature was maintained at room temperature for 30 minutes. The reaction was monitored by TLC (100% ethyl acetate). The reaction mixture was quenched with MeOH (5 mL) at 0° C., concentrated under reduced pressure and partitioned between ice cold water and chloroform. The organic layer was dried over $Na_2SO_4$, and concentrated under reduced pressure to afford 1.7 g (97.14% yield) of 1-pyridin-3-yl-tetrahydro-pyrimidin-2-one.

¹H NMR (DMSO-D₆, 300 MHz): δ 8.59(d, 1H), 8.3 (dd, 1H), 7.7 (m, 1H), 7.35 (m, 1H), 6.75 (brS, 1H), 3.7 (t, 2H), 3.35 (m, 2H), 1.9 (m, 2H)

Final Step: Preparation of 1-Naphthalen-2-yl-3-pyridin-3-yl-tetrahydro-pyrimidin-2-one (10A)

Using the same reaction conditions as in Example 1, 1-pyridin-3-yl-tetrahydro-pyrimidin-2-one (I-10b: 118 mg, 0.724 mmol) was reacted with 2-bromo-naphthalene (150 mg, 0.724 mmol), 1,4-dioxane (5 mL), copper iodide (13.79 mg, 0.0724 mmol), trans-1,2-diamino cyclohexane (24.865 mg, 0.2172 mmol) and potassium carbonate (200 mg, 1.448 mmol) to afford the crude product. Purification by column chromatography on silica gel (1% MeOH in chloroform) afforded 75 mg of the product (35.71% yield).

¹H NMR (DMSO-D₆, 300 MHz): δ 8.65 (d, 1H), 8.35-8.3 (m, 1H), 7.95-7.75 (m, 5H), 7.6-7.4 (m, 4H), 3.95-3.8 (m, 4H), 2.3-2.2 (m, 2H)

LCMS purity: 98.98%, m/z =304.0 (M+1)
HPLC: 99.14%

Example 11

Preparation of 1-(2-Chloro-4-methyl-quinolin-6-yl)-3-pyridin-3-yl-imidazolidin-2-one (11A)

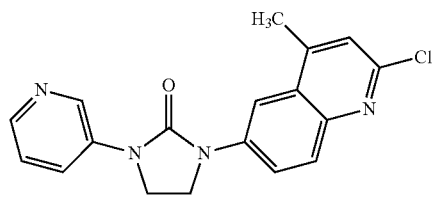

(11A)

Using the same reaction conditions as in Example 1, 1-pyridin-3-yl-imidazolidin-2-one (I-1b: 95.8 mg, 0.5882 mmol) was reacted with 6-bromo-2-chloro-4-methyl-quinoline (150 mg, 0.5882 mmol), 1,4-dioxane (5 mL), copper iodide (11.2 mg, 0.05882 mmol), trans-1,2-diamino cyclohexane (20.20 mg, 0.1764 mmol) and potassium carbonate (162.6 mg, 1.1764 mmol) to afford the crude product. Purification by column chromatography on silica gel (1% MeOH in chloroform) afforded 70 mg of the product (35.17% yield).

¹H NMR (DMSO-D₆, 300 MHz): δ 8.85 (d, 1H), 8.4-8.3 (m, 2H), 8.15-7.95 (m, 3H), 7.5-7.4 (m, 2H), 4.3-4.0 (m, 4H), 2.6 (s, 3H)

LCMS purity: 89.47%, m/z=339.0 (M+1)
HPLC: 97.08%

Example 12

Preparation of 1-(I-1-Hydroxyimino-indan-5-O-3-pyridin-3-yl-imidazolidin-2-one (12A)

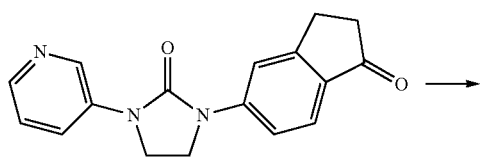 →

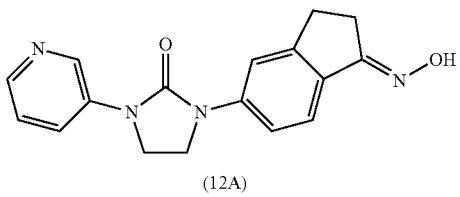

(12A)

Using the same reaction conditions as in Example 1, 1-pyridin-3-yl-imidazolidin-2-one (I-1b: 270 mg, 1.6587 mmol) was reacted with 5-bromo-indan-1-one (350 mg, 1.6587 mmol), 1,4-dioxane (10 mL), copper iodide (31.59 mg, 0.165879 mmol), trans-1,2-diamino cyclohexane (56.976 mg, 0.4976 mmol) and potassium carbonate (458.63 mg, 3.3174 mmol) to afford the crude product. Purification by column chromatography on silica gel (1% MeOH in chloroform) afforded 300 mg of 1-(1-oxo-indan-5-yl)-3-pyridin-3-yl-imidazolidin-2-one (61.72% yield). Hydroxylamine hydrochloride (141 mg, 2.044 mmol) and sodium acetate (167.6 mg, 2.044 mmol) in 5 mL of water were added to a solution of 1-(3-oxo-indan-5-yl)-3-pyridin-3-yl-imidazolidin-2-one (200 mg, 0.6814 mmol) in ethanol (7 mL). The reaction mixture was heated to 90° C. and maintained for 6 hours. The reaction mixture was then cooled to room temperature and the solvent was distilled from the reaction mixture. The precipitate formed was collected, washed with chloroform and dried under reduced pressure to afford 200 mg of the product (90% yield).

¹H NMR (DMSO-D₆, 300 MHz): δ 10.5 (s, 1H), 8.9 (s, 1H), 8.35-8.25 (br s, 1H), 8.1 (d, 1H), 7.7-7.4 (m, 4H), 4.0 (s, 4H), 3.05-3.0 (m, 2H), 2.85-2.7 (m, 2H)

LCMS purity: 98.13%, m/z=309.2 (M+1)
HPLC: 83.39%

Example 13

Preparation of 1-Benzo[b]thiophen-5-yl-3-pyridin-3-yl-tetrahydro-pyrimidin-2-one (13A)

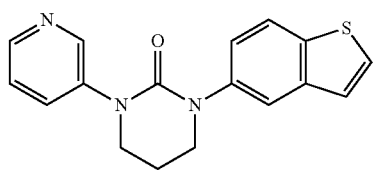

(13A)

Using the same reaction conditions as in Example 1, 1-pyridin-3-yl-tetrahydro-pyrimidin-2-one (I-10b: 67.8 mg, 0.3831 mmol) was reacted with 5-iodo-benzo[b]thiophene (100 mg, 0.3831 mmol), 1,4-dioxane (5 mL), copper iodide (7.29 mg, 0.03831 mmol), trans-1,2-diamino cyclohexane (13.15 mg, 0.1149 mmol) and potassium carbonate (106.1 mg, 0.7662 mmol) to afford 15 mg of the product (17.5% yield).

¹H NMR (DMSO-D₆, 300 MHz): δ 8.7-8.5 (br s, 1H), 8.4-8.3 (br s, 1H), 7.95 (d, 1H), 7.85-7.75 (m, 3H), 7.45-7.35 (m, 3H), 3.9 (q, 4H), 2.35-2.25 (m, 2H)

LCMS purity: 99.84%, m/z=309.9 (M+1)
HPLC: 94.28%

Example 14

Preparation of 1-(4-Methyl-pyridin-3-yl)-3-naphthalen-2-yl-imidazolidin-2-one (14A)

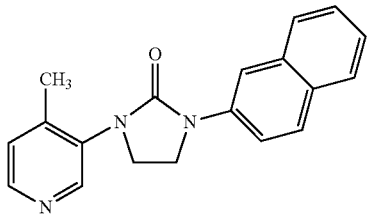

(14A)

Step 1: Preparation of Intermediate 1-(2-Chloroethyl)-3-(4-methyl-pyridin-3-yl)-urea (I-14a)

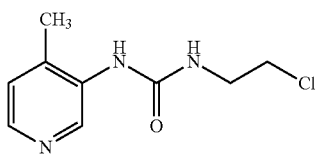

(I-14a)

1-Chloro-2-isocyanato-ethane (5.91 ml, 69.35 mmol) was added dropwise to a stirred solution of 4-methyl-pyridin-3-ylamine (5 g, 46.23 mmol) in toluene (180 mL) at 0° C. The reaction temperature was maintained at room temperature for 5 hours. The reaction was monitored by TLC (5% MeOH in chloroform). The reaction mixture was filtered, washed with toluene and dried under reduced pressure to afford 8.5 g (86% yield) of 1-(2-chloro-ethyl)-3-(4-methyl-pyridin-3-yl)-urea.

$^1$H NMR (DMSO-D$_6$, 300 MHz): δ 8.95 (s, 1H), 8.1 (m, 2H), 7.25 (d, 1H), 6.95 (t, 1H), 3.7 (t, 2H), 3.45 (q, 2H), 2.2 (s, 3H)

LCMS: m/z=214.1 (M+1)

Step 2: Preparation of Intermediate 1-(4-Methyl-pyridin-3-yl)-imidazolidin-2-one (I-14b)

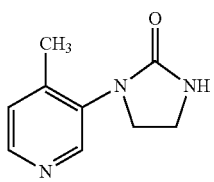

(I-14b)

1-(2-Chloro-ethyl)-3-(4-methyl-pyridin-3-yl)-urea (I-14a: 8.5 g, 39.96 mmol) in dry DMF (150 mL) was added to a stirred mixture of sodium hydride (2.87 g, 59.94 mmol) in THF (150 mL) at 0° C. The reaction temperature was maintained at room temperature for 30 minutes. The reaction was monitored by TLC. The reaction mixture was quenched with MeOH at 0° C., concentrated under reduced pressure and partitioned between ice water and chloroform. The organic layer was dried over Na$_2$SO$_4$, and concentrated under reduced pressure to afford 6.5 g (91% yield) of 1-(4-methyl-pyridin-3-yl)-imidazolidin-2-one.

$^1$H NMR (DMSO-D$_6$, 300 MHz): δ 8.4 (s, 1H), 8.3 (m, 1H), 7.3 (d, 1H), 6.85 (br s, 1H), 3.8 (t, 2H), 3.45 (t, 2H), 2.25 (s, 3H)

LCMS purity: 100%, m/z=178.3 (M+1)

Final Step: Preparation of 1-(4-Methyl-pyridin-3-yl)-3-naphthalen-2-yl-imidazolidin-2-one (14A)

Copper iodide (21.5 mg, 0.113 mmol), trans-1,2-diamino cyclohexane (0.041 mL, 0.339 mmol) and potassium carbonate (313 mg, 2.26 mmol) were added to 1,4-Dioxane (15 mL) previously sparged with argon (10 minutes). The reaction mixture was sparged with argon for a further 10 minutes, followed by the addition of 1-(4-methyl-pyridin-3-yl)-imidazolidin-2-one (I-14b: 200 mg, 1.13 mmol) and 2-bromo naphthalene (234 mg, 1.13 mmol). The resulting mixture was heated to reflux at 110° C. for 15 hours. The reaction was monitored by TLC (10% MeOH in chloroform). The reaction mixture was filtered through a celite and the bed was washed with chloroform. The organic layer was dried over Na$_2$SO$_4$ and concentrated. Purification by column chromatography (using silica gel of mesh size of 60-120, 1% MeOH in chloroform as eluent) afforded 250 mg (73% yield) of 1-(4-methyl-pyridin-3-yl)-3-naphthalen-2-yl-imidazolidin-2-one.

$^1$H NMR (DMSO-D$_6$, 300 MHz): δ 8.62 (s, 1H), 8.48-8.42 (m, 1H), 8.2 (dd, 1H), 8.0-7.85 (m, 4H), 7.55-7.4 (m, 3H), 4.4-4.25 (m, 2H), 3.95-4.1 (m, 2H), 2.35 (s, 3H)

LCMS purity: 98.31%, m/z=304.1 (M+1)

HPLC: 97.55%

Example 15

Preparation of 1-(4-Methyl-pyridin-3-yl)-3-(5-methyl-thiophen-2-yl)-imidazolidin-2-one (15A)

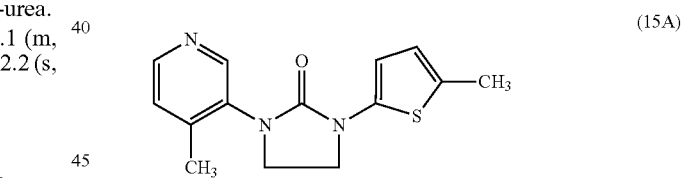

(15A)

Copper iodide (16 mg, 0.084 mmol), trans-1,2-diamino cyclohexane (28.8 mg, 0.25 mmol) and potassium phosphate (445 mg, 2.1 mmol) were added to 1,4-Dioxane (10 mL) previously degassed with argon (10 minutes). The reaction mixture was purged with argon for a further 10 minutes, followed by the addition of 1-(4-methyl-pyridin-3-yl)-imidazolidin-2-one (I-14b: 150 mg, 0.84 mmol) and 2-bromo-5-methylthiophene (150 mg, 0.84 mmol). The resulting mixture was heated to reflux at 110° C. for 4 hours. The reaction was monitored by TLC (10% MeOH in chloroform). The reaction mixture was filtered through celite and the celitebed was washed with chloroform. The organic layer was dried over Na$_2$SO$_4$ and concentrated. The concentrate was quenched with ice, the precipitate formed was collected and dried to afford 170 mg (74% yield) of 1-(4-methyl-pyridin-3-yl)-3-(5-methyl-thiophen-2-yl)-imidazolidin-2-one.

$^1$H NMR (DMSO-D$_6$, 300 MHz): δ 8.5 (s, 1H), 8.4 (d, 1H), 7.35 (d, 1H), 6.55 (d, 1H), 6.25 (d, 1H), 4.0 (s, 4H), 2.35 (s, 3H), 2.25 (s, 3H)

LCMS purity: 98.84%, m/z=274.0 (M+1)

HPLC: 97.43%

Example 16

Preparation of 1-Benzothiazol-6-yl-3-(4-methyl-pyridin-3-yl)-imidazolidin-2-one (16A)

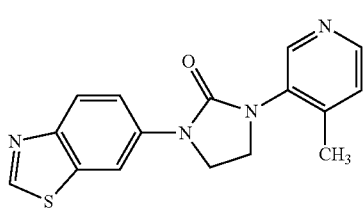

(16A)

Using the same reaction conditions as in Example 14, 1-(4-methyl-pyridin-3-yl)-imidazolidin-2-one (I-14b: 150 mg, 0.847 mmol) was reacted with 6-iodo-benzothiazole (200.93 mg, 0.847 mmol), 1,4-dioxane (20 mL), copper iodide (16.135 mg, 0.0847 mmol), trans-1,2-diamino cyclohexane (0.03 mL, 0.254 mmol) and potassium carbonate (233.97 mg, 1.694 mmol) to afford the crude product. Purification by column chromatography on silica gel (1% MeOH in chloroform) afforded 130 mg of the product (49.6% yield).

$^1$H NMR (DMSO-$D_6$, 300 MHz): δ 9.26 (s, 1H), 8.56 (s, 1H), 8.4 (d, 1H), 8.3 (d, 1H), 8.1-8.06 (m, 1H), 7.96 (dd, 1H), 7.38 (d, 1H), 4.2-4.1 (m, 2H), 4.0-3.92 (m, 2H), 2.3 (s, 3H)

LCMS purity: 97.79%, m/z =310.9 (M+1)

HPLC: 96.64%

Example 17

Preparation of 1-Ethyl-6-[3-(4-methyl-pyridin-3-yl)-2-oxo-imidazolidin-1-yl]-3,4-dihydro-1H-quinolin-2-one (17A)

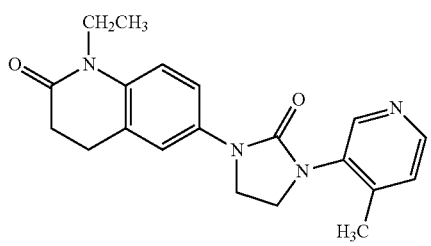

(17A)

Using the same reaction conditions as in Example 14, 1-(4-methyl-pyridin-3-yl)-imidazolidin-2-one (I-14b: 150 mg, 0.847 mmol) was reacted with 6-bromo-1-ethyl-3,4-dihydro-1H-quinolin-2-one (215.15 mg, 0.847 mmol), 1,4-dioxane (0.03 mL, 0.254 mmol), copper iodide (16.13 mg, 0.0847 mmol), trans-1,2-diamino cyclohexane (0.03 mL, 0.254 mmol) and potassium carbonate (233.97 mg, 1.694 mmol) to afford the crude product. Purification by column chromatography on silica gel (1% MeOH in chloroform) afforded 95 mg of the product (31.99%) yield.

$^1$H NMR (DMSO-$D_6$, 300 MHz): δ 8.56-8.5 (br s, 1H), 8.42-8.38 (br s, 1H), 7.52-7.46 (m, 2H), 7.35 (d, 1H), 7.13 (d, 1H), 4.1-3.85 (m, 6H), 3.35-3.25 (m, 2H), 2.85 (t, 2H), 2.25 (s, 3H), 1.1 (t, 3H)

LCMS purity: 96.43%, m/z=351.0 (M+1)

HPLC: 96.26%

Example 18

Preparation of 1-(4-Fluoro-phenyl)-3-(4-methyl-pyridin-3-yl)-imidazolidin-2-one (18A)

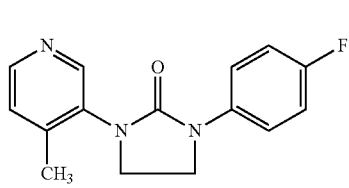

(18A)

Using the same reaction conditions as in Example 14, 1-(4-methyl-pyridin-3-yl)-imidazolidin-2-one (I-14b: 150 mg, 0.8465 mmol) was reacted with 1-bromo-4-fluoro-benzene (148.1 mg, 0.8465 mmol), 1,4-dioxane (25 mL), copper iodide (16 mg, 0.08465 mmol), trans-1,2-diamino cyclohexane (29 mg, 0.2539 mmol) and potassium carbonate (468 mg, 3.3860 mmol) to afford the crude product. Purification by column chromatography on silica gel (2% MeOH in chloroform) afforded 100 mg of the product (43% yield).

$^1$H NMR (DMSO-$D_6$, 300 MHz): δ 8.7-8.3 (m, 2H), 7.7-7.6 (m, 2H), 7.4-7.3 (br s, 1H), 7.2 (t, 2H), 4.1-3.9 (m, 4H), 2.3 (s, 3H)

LCMS purity: 99.85%, m/z =272.0 (M+1)

HPLC: 96.49%

Example 19

Preparation of 1-Biphenyl-4-O-3-(4-methyl-pyridin-3-yl)-imidazolidin-2-one (19A)

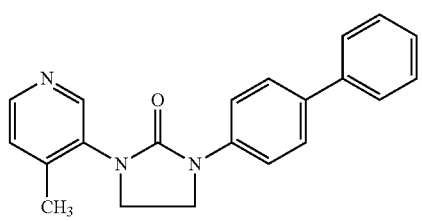

(19A)

Using the same reaction conditions as in Example 14, 1-(4-methyl-pyridin-3-yl)-imidazolidin-2-one (I-14b: 150 mg, 0.8465 mmol) was reacted with 4-bromo-biphenyl (197.3 mg, 0.8465 mmol), 1,4-dioxane (25 mL), copper iodide (16 mg, 0.08465 mmol), trans-1,2-diamino cyclohexane (29 mg, 0.2539 mmol) and potassium carbonate (468 mg, 3.3860 mmol) to afford the crude product. Purification by column chromatography on silica gel (2% MeOH in chloroform) afforded 147 mg of the product (52% yield).

$^1$H NMR (DMSO-$D_6$, 300 MHz): δ 8.6 (s, 1H), 8.4 (d, 1H), 7.8-7.6 (m, 6H), 7.45 (t, 2H), 7.35 (t, 2H), 4.1 (t, 2H), 4.0 (t, 2H), 2.3 (s, 3H)

LCMS purity: 85.37%, m/z =330.1 (M+1)

HPLC: 96.0%

Example 20

Preparation of 1-Ethyl-4-methyl-6-[3-(4-methyl-pyridin-3-yl)-2-oxo-imidazolidin-1-yl]-1H-quinolin-2-one (20A)

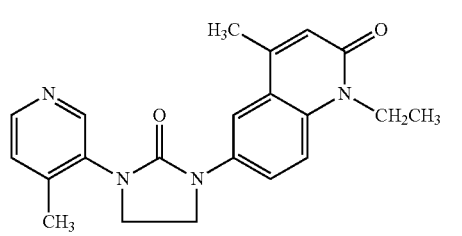

(20A)

Using the same reaction conditions as in Example 14, 1-(4-methyl-pyridin-3-yl)-imidazolidin-2-one (I-14b: 99 mg, 0.5597 mmol) was reacted with 6-bromo-1-ethyl-4-methyl-1H-quinolin-2-one (150 mg, 0.5597 mmol), 1,4-dioxane (5 mL), copper iodide (10.66 mg, 0.05597 mmol), trans-1,2-diamino cyclohexane (19.22 mg, 0.1679 mmol) and potassium carbonate (77.37 mg, 1.1194 mmol) to afford the crude product. Purification by column chromatography on silica gel (1% MeOH in chloroform) afforded 56 mg of the product (28.1% yield).

$^1$H NMR (DMSO-D$_6$, 300 MHz): δ 8.55 (s, 1H), 8.4 (d, 1H), 8.0-7.85 (m, 2H), 7.6 (d, 1H), 7.35 (d, 1H), 6.55 (s, 1H), 4.25 (q, 2H), 4.2-4.1 (m, 2H), 4.0-3.9 (m, 2H), 2.4 (s, 3H), 2.3 (s, 3H), 1.15 (t, 3H)

LCMS purity: 99.36%, m/z =362.9 (M+1)
HPLC: 97.77%

Example 21

Preparation of 1-(2-Chloro-4-methyl-quinolin-6-yl)-3-(4-methyl-pyridin-3-yl)-imidazolidin-2-one (21A)

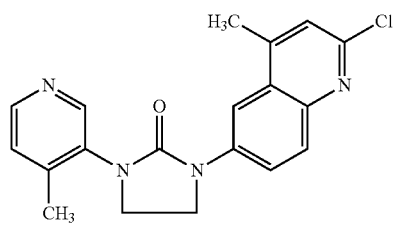

(21A)

Using the same reaction conditions as in Example 14, 1-(4-methyl-pyridin-3-yl)-imidazolidin-2-one (I-14b: 275.4 mg, 1.5564 mmol) was reacted with 6-bromo-2-chloro-4-methyl-quinoline (400 mg, 1.5564 mmol), 1,4-dioxane (10 mL), copper iodide (29.649 mg, 0.15564 mmol), trans-1,2-diamino cyclohexane (53.448 mg, 0.4668 mmol) and potassium carbonate (430 mg, 3.112 mmol) to afford the crude product. Purification by column chromatography on silica gel (1% MeOH in chloroform) afforded 256 mg of the product (46.54% yield).

$^1$H NMR (DMSO-D$_6$, 300 MHz): δ 8.55 (s, 1H), 8.45-8.3 (m, 2H), 8.0-7.9 (m, 2H), 7.5-7.45 (br s, 1H), 7.35 (d, 1H), 4.25-4.15 (m, 2H), 4.05-3.95 (m, 2H), 2.65 (s, 3H), 2.3 (s, 3H)

LCMS purity: 96.22%, m/z =352.9 (M+1)
HPLC: 98.78%

Example 22

Preparation of 4-Methyl-6-[3-(4-methyl-pyridin-3-yl)-2-oxo-imidazolodin-1yl]1H-quinolin-2-one (22A)

(21A)

(22A)

1N HCl (5 mL) was added to 1-(2-chloro-4-methyl-quinolin-6-yl)-3-(4-methyl-pyridin-3-yl)-imidazolidin-2-one (21A: 50 mg, 0.1418 mmol). The reaction mixture was stirred at 120° C. overnight. The reaction mass was cooled to 0° C., aqueous NaHCO$_3$ was added till a pH of about 8 was attained. The reaction mixture was extracted with chloroform. The organic layer was dried over Na$_2$SO$_4$ and concentrated to afford 38 mg of the product (80.85% yield).

$^1$H NMR (DMSO-D$_6$, 300 MHz): δ 11.5 (s, 1H), 8.55 (s, 1H), 8.4 (d, 1H), 7.85-7.8 (m, 2H), 7.4-7.3 (m, 2H), 6.5-6.4 (br s, 1H), 4.15-4.05 (m, 2H), 4.0-3.9 (m, 2H), 2.4 (s, 3H), 2.3 (s, 3H)

LCMS purity: 98.45%, m/z =334.9 (M+1)
HPLC: 93.73%

Example 23

Preparation of 1-(4-Methyl-pyridin-3-yl)-3-quinolin-2-yl-imidazolidin-2-one (23A)

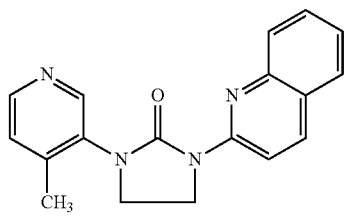

(23A)

Using the same reaction conditions as in Example 14, 1-(4-methyl-pyridin-3-yl)-imidazolidin-2-one (I-14b: 150 mg, 0.84650 mmol) was reacted with 2-chloro-quinoline (138.4 mg, 0.84650 mmol), 1,4-dioxane (30 mL), copper iodide (16 mg, 0.08465 mmol), trans-1,2-diamino cyclohexane (29 mg, 0.2539 mmol) and potassium carbonate (468 mg, 3.3860 mmol) to afford the crude product. Purification by column chromatography on silica gel (2% MeOH in DCM) afforded 105 mg of the product (40.8% yield).

$^1$H NMR (DMSO-D$_6$, 300 MHz): δ 8.6 (s, 1H), 8.5 (d, 1H), 8.4 (d, 1H), 8.3 (d, 1H), 7.9-7.8 (m, 2H), 7.75-7.65 (m, 1H), 7.5-7.45 (m, 1H), 7.4 (d, 1H), 4.3 (t, 2H), 4.0 (t, 2H), 2.3 (s, 3H)

LCMS purity: 97.22%, m/z =305.1 (M+1)
HPLC: 96.07%

Example 24

Preparation of 1-(4-Methyl-pyridin-3-yl)-3-quinolin-3-yl-imidazolidin-2-one (24A)

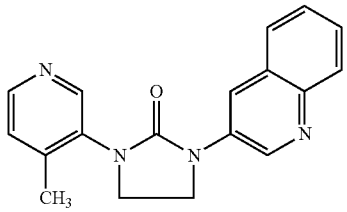

(24A)

Using the same reaction conditions as in Example 14, 1-(4-methyl-pyridin-3-yl)-imidazolidin-2-one (I-14b: 150 mg, 0.847 mmol) was reacted with 3-bromo-quinoline (176.13 mg, 0.847 mmol), 1,4-dioxane (15 mL), copper iodide (16.13 mg, 0.0847 mmol), trans-1,2-diamino cyclohexane (0.03 mL, 0.254 mmol) and potassium carbonate (233.97 mg, 1.694 mmol) to afford the crude product. Purification by column chromatography on silica gel (1% MeOH in chloroform) afforded 190 mg of the product (73.76% yield).

$^1$H NMR (DMSO-D$_6$, 300 MHz): δ 9.5 (d, 1H), 8.6 (s, 1H), 8.42 (d, 1H), 8.35 (d, 1H), 8.02-7.92 (m, 2H), 7.7-7.58 (m, 2H), 7.4 (d, 1H), 4.25-4.15 (m, 2H), 4.05-3.9 (m, 2H), 2.35 (s, 3H)

LCMS purity: 98.34%, m/z=305.2 (M+1)
HPLC: 95.64%

Example 25

Preparation of 1-(6-Methoxy-naphthalen-2-yl)-3-(4-methyl-pyridin-3-yl)-imidazolidin-2-one (25A)

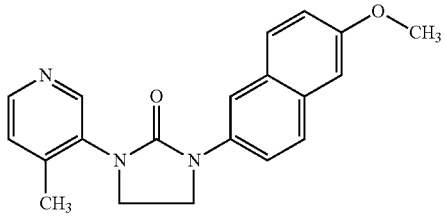

(25A)

Using the same reaction conditions as in Example 14, 1-(4-methyl-pyridin-3-yl)-imidazolidin-2-one (I-14b: 150 mg, 0.847 mmol) was reacted with 2-bromo-6-methoxy-naphthalene (200.74 mg, 0.847 mmol), 1,4-dioxane (15 mL), copper iodide (16.13 mg, 0.0847 mmol), trans-1,2-diamino cyclohexane (0.03 mL, 0.254 mmol) and potassium carbonate (233.97 mg, 1.694 mmol) to afford the crude product. Purification by column chromatography on silica gel (1% MeOH in chloroform) afforded 85 mg of the product (30.08% yield).

$^1$H NMR (DMSO-D$_6$, 300 MHz): δ 8.62-8.58 (br s, 1H), 8.44-8.4 (br s, 1H), 8.28 (dd, 1H), 7.86-7.76 (m, 3H), 7.4 (d, 1H), 7.28 (d, 1H), 7.16 (dd, 1H), 4.18-4.1 (m, 2H), 4.02-3.96 (m, 2H), 3.86 (s, 3H), 2.33 (s, 3H)

LCMS purity: 95.49%, m/z =334.1 (M+1)
HPLC: 93.56%

Example 26

Preparation of 1-Benzo[b]thiophen-2-yl-3-(4-methyl-pyridin-3-yl)-imidazolidin-2-one (26A)

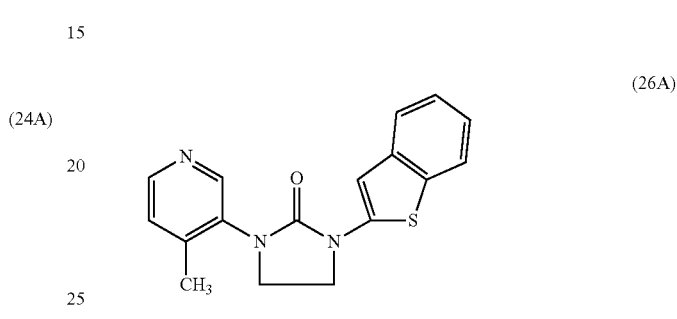

(26A)

Using the same reaction conditions as in Example 14, 1-(4-methyl-pyridin-3-yl)-imidazolidin-2-one (I-14b: 109.25 mg, 0.6171 mmol) was reacted with 2-bromo-benzo[b]thiophene (150 mg, 0.6171 mmol), 1,4-dioxane (5 mL), copper iodide (11.75 mg, 0.06171 mmol), trans-1,2-diamino cyclohexane (21.19 mg, 0.1851 mmol) and potassium carbonate (170.62 mg, 1.2342 mmol) to afford the crude product. Purification by column chromatography on silica gel (1% MeOH in chloroform) afforded 75 mg of the product (62.5% yield).

$^1$H NMR (DMSO-D$_6$, 300 MHz): δ 8.5 (s, 1H), 8.4 (d, 1H), 7.8 (d, 1H), 7.75 (d, 1H), 7.4 (d, 1H), 7.35-7.25 (m, 1H), 7.2 (t, 1H), 6.75 (s, 1H), 4.25-4.1 (m, 2H), 4.1-4.0 (m, 2H), 2.3 (s, 3H)

LCMS purity: 97.09%, m/z =310.1 (M+1)
HPLC: 92.27%

Example 27

Preparation of 1-Benzo[b]thiophen-5-yl-3-(4-methyl-pyridin-3-yl)-imidazolidin-2-one (27A)

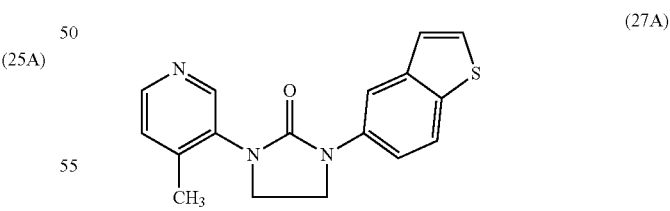

(27A)

Using the same reaction conditions as in Example 14, 1-(4-methyl-pyridin-3-yl)-imidazolidin-2-one (I-14b: 150 mg, 0.847 mmol) was reacted with 5-bromo-benzo[b]thiophene (180.5 mg, 0.847 mmol), 1,4-dioxane (15 mL), copper iodide (16.13 mg, 0.0847 mmol), trans-1,2-diamino cyclohexane (0.03 mL, 0.254 mmol) and potassium carbonate (233.97 mg, 1.694 mmol) to afford the crude product. Purification by column chromatography on silica gel (1% MeOH in chloroform) afforded 28 mg of the product in (10.69% yield).

¹H NMR (DMSO-D₆, 300 MHz): δ 8.75 (s, 1H), 8.55 (d, 1H), 8.04-7.98 (m, 2H), 7.84-7.76 (m, 2H), 7.63 (d, 1H), 7.45 (d, 1H), 4.2-4.1 (m, 2H), 4.05-3.95 (m, 2H), 2.4 (s, 3H)
LCMS purity: 91.88%, m/z =309.9 (M+1)
HPLC: 97.97%

Example 28

Preparation of 1-(1H-Indazol-5-yl)-3-(4-methyl-pyridin-3-yl)-imidazolidin-2-one (28A)

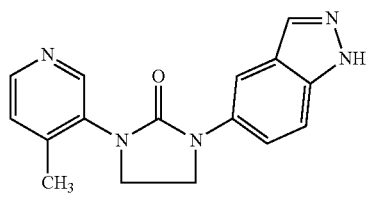

(28A)

Using the same reaction conditions as in Example 14, 1-(4-methyl-pyridin-3-yl)-imidazolidin-2-one (I-14b: 0.095 g, 0.00058 mol) was reacted with 5-bromo-1-(2-trimethylsilanyl-ethoxymethyl)-1H-indazole (0.170 g, 0.00058 mmol), 1,4-dioxane (10 mL), copper iodide (0.011 g, 0.000051 mol), trans-1,2-diamino cyclohexane (0.018 g, 0.00016 mol) and potassium carbonate (0.134 g, 0.00106 mmol) to afford the crude product. Purification by column chromatography on silica gel (1% MeOH in chloroform) afforded 0.24 g of 1-(4-Methyl-pyridin-3-yl)-3-[1-(2-trimethylsilanyl-ethoxymethyl)-1H-indazol-5-yl]-imidazolidin-2-one (97.5% yield).

TFA (0.096 g, 0.00084 mol) was added to solution of 1-(4-methyl-pyridin-3-yl)-3-[1-(2-trimethylsilanyl-ethoxymethyl)-1H-indazol-5-yl]-imidazolidin-2-one (0.24 g, 0.00056 mol) in DCM (10 mL) at 0° C. The reaction mixture was stirred at room temperature overnight. The reaction was monitored by TLC (10% MeOH in CHCl₃). The reaction mixture was concentrated and the concentrate was purified by preparative HPLC to afford 42 mg of the product (19.47% yield).

¹H NMR (CD₃OD, 300 MHz): δ 8.52 (s, 1H), 8.35 (d, 1H), 8.06-8.0 (br s, 1H), 7.86-7.76 (m, 2H), 7.6-7.5 (m, 1H), 7.45-7.4 (m, 1H), 4.2-4.1 (m, 2H), 4.05-3.95 (m, 2H), 2.4 (s, 3H)
LCMS purity: m/z=294.1 (M+1)
HPLC: 98.89%

Example 29

Preparation of 1-(3-Methyl-benzofuran-5-yl)-3-(4-methyl-pyridin-3-yl)-imidazolidin-2-one (29A)

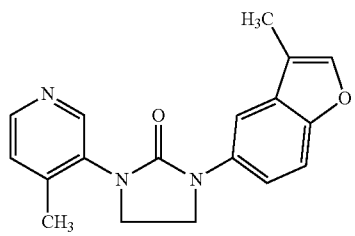

(29A)

Using the same reaction conditions as in Example 14, 1-(4-methyl-pyridin-3-yl)-imidazolidin-2-one (I-14b: 105 mg, 0.8465 mol) was reacted with 5-bromo-3-methyl-benzofuran (197 mg, 0.9311 mmol), 1,4-dioxane (10 mL), copper iodide (20 mg), trans-1,2-diamino cyclohexane (40 mg) and potassium carbonate (359 mg, 1.6930 mmol) to afford the crude product. Purification by column chromatography on silica gel (2% MeOH in chloroform) afforded 80 mg of the product (30.76% yield).

¹H NMR (CDCl₃, 300 MHz): δ 8.54 (s, 1H), 8.4 (d, 1H), 7.76-7.73 (m, 1H), 7.46-7.39 (m, 3H), 7.22 (d, 1H), 4.19-4.1 (m, 2H), 4.0-3.9 (m, 2H), 2.38 (s, 3H), 2.24 (s, 3H)
LCMS purity: 96.84%, m/z =307.9 (M+1)
HPLC: 96.37%

Example 30

Preparation of 1-(6-Fluoro-pyridin-3-O-3-(4-methyl-pyridin-3-yl)-imidazolidin-2-one (30A)

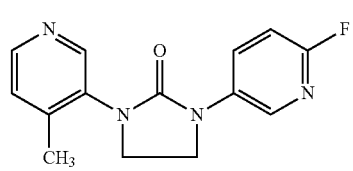

(30A)

Using the same reaction conditions as in Example 14, 1-(4-methyl-pyridin-3-yl)-imidazolidin-2-one (I-14b: 150 mg, 0.8474 mmol) was reacted with 5-bromo-2-fluoro-pyridine (87.7 mL, 0.8474 mmol), 1,4-dioxane (10 mL), copper iodide (16.13 mg, 0.084 mmol), trans-1,2-diamino cyclohexane (30.5 mL, 0.254 mmol) and potassium carbonate (234 mg, 1.695 mmol) to afford the crude product. Purification by column chromatography on silica gel (2% MeOH in chloroform), followed by preparative HPLC afforded 165 mg of the product (71.5% yield).

¹H NMR (CDCl₃, 300 MHz): δ 8.6-8.4 (m, 3H), 8.2 (s, 1H), 7.3-7.2 (m, 1H), 7.0-6.9 (m, 1H), 4.2-4.0 (m, 4H), 2.4 (s, 3H)
LCMS purity: 97.96%, m/z=273.1 (M+1)
HPLC: 95.26%

Example 31

Preparation of 1-(4-Methyl-pyridin-3-yl)-3-thiophen-3-yl-imidazolidin-2-one (31A)

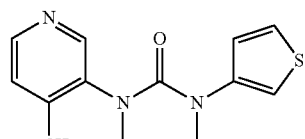

(31A)

Using the same reaction conditions as in Example 14, 1-(4-methyl-pyridin-3-yl)-imidazolidin-2-one (I-14b: 150 mg, 0.8474 mmol) was reacted with 3-bromo-thiophene (79.4 mL, 0.8474 mmol), 1,4-dioxane (10 mL), copper iodide (16.13 mg, 0.084 mmol), trans-1,2-diamino cyclohexane (30.5 mL, 0.254 mmol) and potassium carbonate (234 mg, 1.695 mmol) to afford the crude product. Purification by column chromatography on silica gel (2% MeOH in chloroform), followed by preparative HPLC afforded 22 mg of the product (10% yield).

¹H NMR (DMSO-D₆, 300 MHz): δ 8.5 (s, 1H), 8.4 (d, 1H), 7.6 (d, 2H), 7.4 (d, 1H), 7.1 (t, 1H), 4.1-3.9 (m, 4H), 2.3 (s, 3H)
LCMS purity: 97.96%, m/z =260.0 (M+1)
HPLC: 97.4%

Example 32

Preparation of 1-(5-Methoxy-pyridin-3-yl)-3-(4-methyl-pyridin-3-yl)-imidazolidin-2-one (32A)

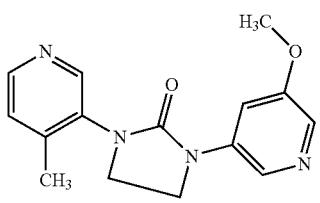

(32A)

Using the same reaction conditions as in Example 14, 1-(4-methyl-pyridin-3-yl)-imidazolidin-2-one (I-14b: 150 mg, 0.847 mmol) was reacted with 3-bromo-5-methoxy-pyridine (159.24 mg, 0.847 mmol), 1,4-dioxane (15 mL), copper iodide (16.13 mg, 0.0847 mmol), trans-1,2-diamino cyclohexane (0.03 mL, 0.254 mmol) and potassium carbonate (233.97 mg, 1.694 mmol) to afford the crude product. Purification by column chromatography on silica gel (1% MeOH in chloroform), followed by preparative HPLC afforded 23 mg of the product (9.55% yield).
¹H NMR (DMSO-D₆, 300 MHz): δ 8.8 (s, 1H), 8.55 (d, 2H), 8.2 (s, 1H), 7.8 (s, 1H), 7.7 (d, 1H), 4.2-3.9 (m, 4H), 3.9 (s, 3H), 2.4 (s, 3H)
LCMS purity: 96.22%, m/z=285.0 (M+1)
HPLC: 99.27%

Example 33

Preparation of 1-(5-Fluoro-3-methyl-benzo[b]thiophen-2-yl)-3-(4-methyl-pyridin-3-yl)-imidazolidin-2-one (33A)

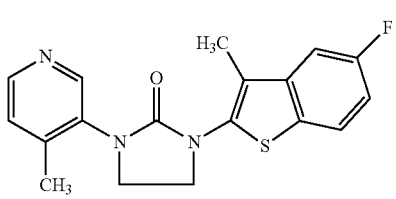

(33A)

Using the same reaction conditions as in Example 14, 1-(4-methyl-pyridin-3-yl)-imidazolidin-2-one (I-14b: 79.79 mg, 0.4508 mmol) was reacted with 2-bromo-5-fluoro-3-methyl-benzo[b]thiophene (110 mg, 0.4508 mmol), 1,4-dioxane (5 mL), copper iodide (8.58 mg, 0.04508 mmol), trans-1,2-diamino cyclohexane (15.48 mg, 0.1352 mmol) and potassium carbonate (124.6 mg, 0.9016 mmol) to afford the crude product. Purification by column chromatography on silica gel (1% MeOH in chloroform) afforded 84 mg of the product (60.45% yield).
¹H NMR (DMSO-D₆, 300 MHz): δ 8.55 (s, 1H), 8.4 (d, 1H), 7.95-7.85 (m, 1H), 7.62-7.55 (dd, 1H), 7.35 (d, 1H), 7.3-7.2 (m, 1H), 4.15-3.95 (m, 4H), 2.25 (d, 6H)
LCMS purity: 97.84%, m/z =342.0 (M+1)
HPLC: 97.83%

Example 34

Preparation of 1-(2-Chloro-pyrimidin-5-yl)-3-(4-methyl-pyridin-3-yl)-imidazolidin-2-one (34A)

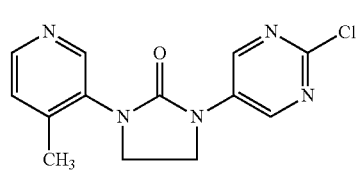

(34A)

Using the same reaction conditions as in Example 14, 1-(4-methyl-pyridin-3-yl)-imidazolidin-2-one (I-14b: 150 mg, 0.8465 mmol) was reacted with 5-bromo-2-chloro-pyrimidine (163.7 mg, 0.8465 mmol), 1,4-dioxane (30 mL), copper iodide (16 mg, 0.08465 mmol), trans-1,2-diamino cyclohexane (29 mg, 0.2539 mmol) and potassium carbonate (468 mg, 3.3860 mmol) to afford the crude product. Purification by column chromatography on silica gel (2% MeOH in chloroform), followed by preparative HPLC afforded 65 mg of the product (26.5% yield).
¹H NMR (DMSO-D₆, 300 MHz): δ 9.0 (s, 2H), 8.6 (s, 1H), 8.5 (s, 1H), 7.4 (s, 1H), 4.15-3.95 (m, 4H), 2.35 (s, 3H)
LCMS purity: 97.13%, m/z =290.0 (M+1)
HPLC: 96.83%

Example 35

Preparation of 1-(4-Methyl-pyridin-3-yl)-3-(1H-pyrazol-4-yl)-imidazolidin-2-one (35A)

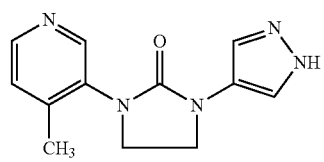

(35A)

Using the same reaction conditions as in Example 14, 1-(4-methyl-pyridin-3-yl)-imidazolidin-2-one (I-14b: 150 mg, 0.8465 mmol) was reacted with 4-bromo-1-trityl-1H-pyrazole (369.3 mg, 0.8465 mmol), 1,4-dioxane (50 mL), copper iodide (16 mg, 0.08465 mmol), trans-1,2-diamino cyclohexane (29 mg, 0.2539 mmol) and potassium carbonate (468 mg, 3.3860 mmol) to afford the crude product. Purification by column chromatography on silica gel (2% MeOH in chloroform) afforded 250 mg of 1-(4-Methyl-pyridin-3-yl)-3-(1-trityl-1H-pyrazol-4-yl)-imidazolidin-2-one (60% yield). Dioxane hydrochloride (10 mL) was added to a stirred solution of 1-(4-methyl-pyridin-3-yl)-3-(1-trityl-1H-pyrazol-4-yl)-imidazolidin-2-one (250 mg, 0.51484 mmol) in dioxane under nitrogen atmosphere at 0° C. The reaction mixture was stirred at room temperature for 2 hours with TLC monitoring (10% MeOH in DCM). The solvent was distilled from the reaction mixture and washed with ether. The precipitate was collected and dried under reduced pressure to afford 80 mg of the product (55% yield).
¹H NMR (DMSO-D₆, 300 MHz): δ 8.95 (s, 1H), 8.7 (d, 1H), 8.0 (d, 1H), 7.8 (s, 2H), 4.1-4.0 (m, 2H), 4.0-3.95 (m, 2H), 2.5 (s, 3H)
LCMS purity: 98.04%, m/z =244.1 (M+1)
HPLC: 94.48%

Example 36

Preparation of 1-(4-Methyl-pyridin-3-yl)-3-thiazol-2-yl-imidazolidin-2-one (36A)

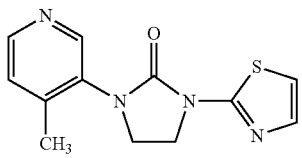
(36A)

Using the same reaction conditions as in Example 14, 1-(4-methyl-pyridin-3-yl)-imidazolidin-2-one (I-14b: 150 mg, 0.8465 mmol) was reacted with 2-bromo-thiazole (138.8 mg, 0.846 mmol), 1,4-dioxane (50 mL), copper iodide (16 mg, 0.08465 mmol), trans-1,2-diamino cyclohexane (29 mg, 0.2539 mmol) and potassium carbonate (468 mg, 3.3860 mmol) to afford the crude product. Purification by column chromatography on silica gel (2% MeOH in chloroform) afforded 125 mg of the product (56.8% yield). $^1$H NMR (DMSO-D$_6$, 300 MHz): δ 8.6 (s, 1H), 8.4 (s, 1H), 7.45-7.35 (m, 2H), 7.2 (d, 1H), 4.4 (t, 2H), 4.2 (t, 2H), 2.3 (s, 3H)

LCMS purity: 96.14%, m/z =261.0 (M+1)

HPLC: 97.87%

Example 37

Preparation of 1-(4-Methoxy-phenyl)-3-(4-methyl-pyridin-3-yl)-imidazolidin-2-one (37A)

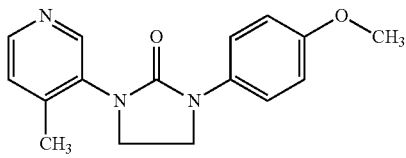
(37A)

Using the same reaction conditions as in Example 14, 1-(4-methyl-pyridin-3-yl)-imidazolidin-2-one (I-14b: 150 mg, 0.8474 mmol) was reacted with 1-bromo-4-methoxy-benzene (158 mg, 0.8474 mmol), 1,4-dioxane (5 mL), copper iodide (16.142 mg, 0.08474 mmol), trans-1,2-diamino cyclohexane (29.108 mg, 0.2542 mmol) and potassium carbonate (234.3 mg, 1.6948 mmol) to afford the crude product. Purification by column chromatography on silica gel (1% MeOH in chloroform) afforded 172 mg of the product (72.26% yield).

$^1$H NMR (DMSO-D$_6$, 300 MHz): δ 8.5 (s, 1H), 8.4 (d, 1H), 7.55-7.45 (m, 2H), 7.39-7.3 (d, 1H), 7.0-6.9 (m, 2H), 4.1-4.0 (m, 2H), 3.95-3.85 (m, 2H), 3.75 (s, 3H), 2.25 (s, 3H)

LCMS purity: 95.51%, m/z=284.1 (M+1)

HPLC: 96.79%

Example 38

Preparation of 1-(4-Chloro-phenyl)-3-(4-methyl-pyridin-3-yl)-imidazolidin-2-one (38A)

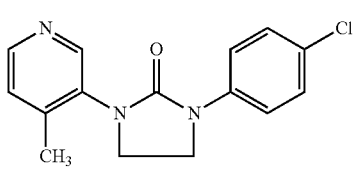
(38A)

Using the same reaction conditions as in Example 14, 1-(4-methyl-pyridin-3-yl)-imidazolidin-2-one (I-14b: 150 mg, 0.8474 mmol) was reacted with 1-bromo-4-chloro-benzene (162 mg, 0.8474 mmol), 1,4-dioxane (5 mL), copper iodide (16.142 mg, 0.08474 mmol), trans-1,2-diamino cyclohexane (29.108 mg, 0.2542 mmol) and potassium carbonate (234.3 mg, 1.6948 mmol) to afford the crude product. Purification by column chromatography on silica gel (1% MeOH in chloroform) afforded 155 mg of the product (63.78% yield).

$^1$H NMR (DMSO-D$_6$, 300 MHz): δ 8.55 (s, 1H), 8.4 (d, 1H), 7.7-7.6 (m, 2H), 7.5-7.3 (m, 3H), 4.05-3.9 (m, 2H), 3.9-3.8 (m, 2H), 2.25 (s, 3H)

LCMS purity: 98.81%, m/z=287.9 (M+1)

HPLC: 96.55%

Example 39

Preparation of 4-[3-(4-Methyl-pyridin-3-yl)-2-oxo-imidazolidin-1-yl]-benzonitrile (39A)

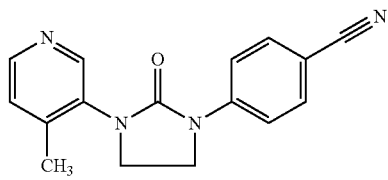
(39A)

Using the same reaction conditions as in Example 14, 1-(4-methyl-pyridin-3-yl)-imidazolidin-2-one (I-14b: 150 mg, 0.8465 mmol) was reacted with 4-bromo-benzonitrile (154 mg, 0.84650 mmol), 1,4-dioxane (50 mL), copper iodide (16 mg, 0.084650 mmol), trans-1,2-diamino cyclohexane (29 mg, 0.2539 mmol) and potassium carbonate (468 mg, 3.3860 mmol) to afford the crude product. Purification by column chromatography on silica gel (5% MeOH in DCM) afforded 151 mg of the product (64.2% yield).

$^1$H NMR (DMSO-D$_6$, 300 MHz): δ 8.55 (s, 1H), 8.4 (d, 1H), 7.8 (s, 4H), 7.3 (d, 1H), 4.2-4.15 (m, 2H), 4.0-3.95 (m, 2H), 2.3 (s, 3H)

LCMS purity: 100.00%, m/z=278.9 (M+1)

HPLC: 98.45%

Example 40

Preparation of 1-Benzooxazol-2-yl-3-(4-methyl-pyridin-3-yl)-imidazolidin-2-one (40A)

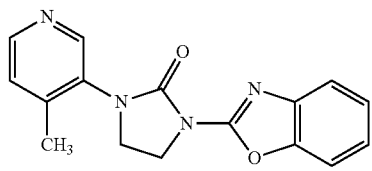
(40A)

Using the same reaction conditions as in Example 14, 1-(4-methyl-pyridin-3-yl)-imidazolidin-2-one (I-14b: 150 mg, 0.84650 mmol) was reacted with 2-chloro-benzooxazole (96 mL, 0.84650 mmol), 1,4-dioxane (50 mL), copper iodide (16 mg, 0.084650 mmol), trans-1,2-diamino cyclohexane (29 mg, 0.2539 mmol) and potassium carbonate (468 mg, 3.3860 mmol) to afford the crude product. Purification by column chromatography on silica gel (2% MeOH in DCM) afforded 40 mg of the product (16% yield).

$^1$H NMR (DMSO-D$_6$, 300 MHz): δ 8.7-8.6 (br s, 1H), 8.5-8.45 (br s, 1H), 7.75-7.6 (m, 2H), 7.5 (d, 1H), 7.4-7.25 (m, 2H), 4.35-4.25 (m, 2H), 4.15-4.05 (m, 2H), 2.3 (s, 3H)

LCMS purity: 96.56%, m/z=295.1 (M+1)
HPLC: 95.79%

Example 41

Preparation of 1-(5-Chloro-thiophen-2-yl)-3-(4-methyl-pyridin-3-yl)-imidazolidin-2-one (41A)

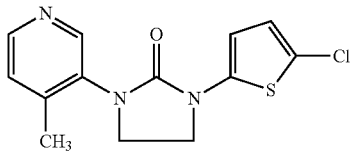

(41A)

Using the same reaction conditions as in Example 14, 1-(4-methyl-pyridin-3-yl)-imidazolidin-2-one (I-14b: 300 mg, 1.6949 mmol) was reacted with 2-bromo-5-chloro-thiophene (0.185 mL, 1.6949 mmol), 1,4-dioxane (10 mL), copper iodide (32 mg, 0.169 mmol), trans-1,2-diamino cyclohexane (58 mg, 0.5084 mmol) and potassium carbonate (467 mg, 3.3898 mmol) to afford the crude product. Purification by column chromatography on silica gel (1% MeOH in DCM) afforded 240 mg of the product (48.4% yield).

$^1$H NMR (DMSO-D$_6$, 300 MHz): δ 8.59 (s, 1H), 8.45 (d, 1H), 7.4 (d, 1H), 6.97 (d, 1H), 6.38 (d, 1H), 4.05 (s, 4H), 2.3 (s, 3H)

LCMS purity: 93.37%, m/z =293.8 (M+1)
HPLC: 99.32%

Example 42

Preparation of 1-(4-Methyl-pyridin-3-yl)-3-thiophen-2-yl-imidazolidin-2-one (42A)

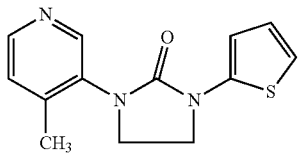

(42A)

Using the same reaction conditions as in Example 14, 1-(4-methyl-pyridin-3-yl)-imidazolidin-2-one (I-14b: 150 mg, 0.847 mmol) was reacted with 2-bromo-thiophene (0.08 mL, 0.847 mmol), 1,4-dioxane (10 mL), copper iodide (16.13 mg, 0.0847 mmol), trans-1,2-diamino cyclohexane (0.03 mL) and potassium carbonate (233 mg, 1.694 mmol) to afford the crude product. Purification by column chromatography on silica gel (1% MeOH in DCM) afforded 240 mg of the product (48.4% yield).

$^1$H NMR (DMSO-D$_6$, 300 MHz): δ 8.5 (s, 1H), 8.4 (d, 1H), 7.36 (d, 1H), 6.98 (dd, 1H), 6.92-6.86 (m, 1H), 6.5 (dd, 1H), 4.1-3.96 (m, 4H), 2.26 (s, 3H)

LCMS purity: 96.18%, m/z =260.0 (M+1)
HPLC: 98.53%

Example 43

Preparation of 1-(6-Hydroxy-pyridin-3-yl)-3-(4-methyl-pyridin-3-yl)-imidazolidin-2-one (43A)

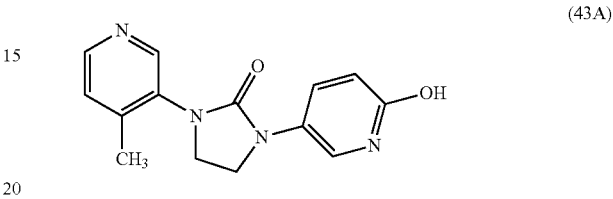

(43A)

1-(6-Fluoro-pyridin-3-yl)-3-(4-methyl-pyridin-3-yl)-imidazolidin-2-one (30A: 0.1 g, 0.00036 mmol) in 5% HCl (10 mL) was added into the reaction flask and the flask was heated to reflux at 100° C. overnight. The reaction was monitored by TLC (10% MeOH in chloroform. The reaction mixture was basified with NaHCO$_3$ solution and extracted with chloroform. The organic layer was washed with water, brine solution, dried and concentrated to afford 72 mg of the product (98.96% yield).

$^1$H NMR (DMSO-D$_6$, 300 MHz): δ 8.5 (s, 1H), 8.35 (d, 1H), 7.75 (dd, 1H), 7.6-7.5 (m, 1H), 7.35 (d, 1H), 6.3 (d, 1H), 3.85 (s, 4H), 2.25 (s, 3H)

LCMS purity: 96.74%, m/z=270.9 (M+1)
HPLC: 98.42%

Example 44

Preparation of N-Methyl-4-[3-(4-methyl-pyridin-3-yl)-2-oxo-imidazolidin-1-yl]-benzamide (44A)

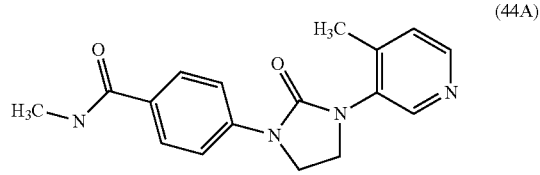

(44A)

Using the same reaction conditions as in Example 14, 1-(4-methyl-pyridin-3-yl)-imidazolidin-2-one (I-14b: 150 mg, 0.84650 mmol) was reacted with 4-bromo-benzoic acid methyl ester (182 mg, 0.84650 mmol), 1,4-dioxane (50 mL), copper iodide (16 mg, 0.084650 mmol), trans-1,2-diamino cyclohexane (29 mg, 0.2539 mmol) and potassium carbonate (468 mg, 3.3860 mmol) to afford the crude product. Purification by column chromatography on silica gel (5% MeOH in DCM) afforded 230 mg of 4-[3-(4-Methyl-pyridin-3-yl)-2-oxo-imidazolidin-1-yl]-benzoic acid methyl ester (91.6% yield).

LiOH (46.4 mg, 3.782 mmol) was added to a stirred solution of 4-[3-(4-methyl-pyridin-3-yl)-2-oxo-imidazolidin-1-yl]-benzoic acid methyl ester (230 mg, 0.7387 mmol) in (3:2:1) THF (10 mL, water (6 mL) and MeOH (3 mL). The reaction mixture was stirred at room temperature for 4 hours. The reaction was monitored by TLC (10% MeOH in DCM). The reaction mixture was concentrated under reduced pressure, followed by the addition of ice water and neutralized with 1N HCl till a pH of about 2 was attained. The precipitate was collected and dried under reduced pressure to afford 210 mg of 4-[3-(4-Methyl-pyridin-3-yl)-2-oxo-imidazolidin-1-yl]-benzoic acid (95% yield).

EDCI (176.4 mg, 0.9205 mmol), HOBt (5.8 mg, 0.2525 mmol), DIPEA (0.3 mL, 2.3006 mmol) and methylamine hydrochloride (62 mg, 0.9205 mmol) were added to a stirred solution of 4-[3-(4-methyl-pyridin-3-yl)-2-oxo-imidazolidin-1-yl]-benzoic acid (228 mg, 0.7668 mmol) in dry DMF (10 mL) at 0° C. under nitrogen atmosphere. The reaction mixture was stirred at room temperature for 12 hours. The reaction mixture was partitioned between water and ethylacetate. The organic layer was washed with water, brine solution, dried over $Na_2SO_4$ and concentrated under reduced pressure. Purification by column chromatography on silica gel (5% MeOH in DCM) afforded 155 mg of the product (65.4% yield).

$^1$H NMR (DMSO-$D_6$, 300 MHz): δ 8.65-8.55 (br s, 1H), 8.45-8.4 (br s, 1H), 8.35 (d, 1H), 7.9 (d, 2H), 7.7 (d, 2H), 7.4 (d, 1H), 4.15-4.05 (m, 2H), 4.0-3.85 (m, 2H), 2.8 (d, 3H), 2.3 (s, 3H)

LCMS purity: 87.61%, m/z=311.1 (M+1)
HPLC: 98.28%

Example 45

Preparation of 1-(3,4-Difluoro-phenyl)-3-(4-methyl-pyridin-3-yl)-imidazolidin-2-one (45A)

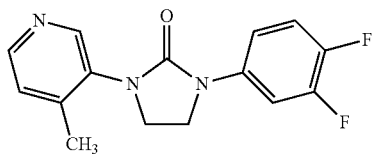

(45A)

Using the same reaction conditions as in Example 14, 1-(4-methyl-pyridin-3-yl)-imidazolidin-2-one (I-14b: 150 mg, 0.8474 mmol) was reacted with 4-bromo-1,2-difluoro-benzene (163.5 mg, 0.8474 mmol), 1,4-dioxane (5 mL), copper iodide (16.14 mg, 0.08474 mmol), trans-1,2-diamino cyclohexane (29.10 mg, 0.253942 mmol) and potassium carbonate (234.3 mg, 1.6948 mmol) to afford the crude product. Purification by column chromatography on silica gel (1% MeOH in $CHCl_3$) afforded 205 mg of the product (84.01% yield).

$^1$H NMR (DMSO-$D_6$, 300 MHz): δ 8.55 (s, 1H), 8.39 (d, 1H), 7.85-7.75 (m, 1H), 7.5-7.35 (m, 3H), 4.1-3.9 (m, 4H), 2.26 (s, 3H)

LCMS purity: 98.17%, m/z =290.0 (M+1)
HPLC: 98.83%

Example 46

Preparation of 1-(3-Chloro-4-fluoro-phenyl)-3-(4-methyl-pyridin-3-yl)-imidazolidin-2-one (46A)

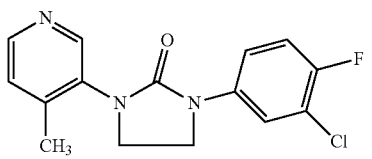

(46A)

Using the same reaction conditions as in Example 14, 1-(4-methyl-pyridin-3-yl)-imidazolidin-2-one (I-14b: 150 mg, 0.8465 mmol) was reacted with 4-bromo-2-chloro-1-fluoro-benzene (102 mL, 0.8465 mmol), 1,4-dioxane (20 mL), copper iodide (16 mg, 0.08465 mmol), trans-1,2-diamino cyclohexane (29 mg, 0.2539 mmol) and potassium carbonate (468 mg, 3.3860 mmol) to afford the crude product. Purification by column chromatography on silica gel (5% MeOH in DCM) afforded 220 mg of the product (84.2% yield).

$^1$H NMR (DMSO-$D_6$, 300 MHz): δ 8.55 (s, 1H), 8.4 (d, 1H), 7.9 (dd, 1H), 7.6-7.55 (m, 1H), 7.45-7.35 (m, 2H), 4.15-4.0 (m, 2H), 4.0-3.9 (m, 2H), 2.3 (s, 3H)

LCMS purity: 96.91%, m/z =306.0 (M+1)
HPLC: 98.62%

Example 47

Preparation of 1-Benzothiazol-2-yl-3-(4-methyl-pyridin-3-yl)-imidazolidin-2-one (47A)

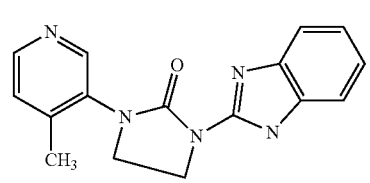

(47A)

Using the same reaction conditions as in Example 14, 1-(4-methyl-pyridin-3-yl)-imidazolidin-2-one (I-14b: 150 mg, 0.84 mmol) was reacted with 2-bromo-benzothiazole (179 mg, 0.847 mmol), 1,4-dioxane (10 mL), copper iodide (16 mg, 0.084 mmol), trans-1,2-diamino cyclohexane (28.8 mg, 0.25 mmol) and potassium carbonate (231 mg, 1.68 mmol) to afford the crude product. Purification by column chromatography on silica gel (1.5% MeOH in $CHCl_3$) afforded 95 mg of the product (36.5% yield).

$^1$H NMR (DMSO-$D_6$, 300 MHz): δ 8.6 (s, 1H), 8.45 (d, 1H), 8.3 (s, 1H), 7.95 (d, 1H), 7.75 (d, 1H), 7.45-7.35 (m, 1H), 7.3-7.25 (m, 1H), 4.35 (t, 2H), 4.05 (t, 2H), 2.3 (s, 3H)

LCMS purity: 98.81%, m/z=310.9 (M+1)
HPLC: 97.25%

Example 48

Preparation of 1-(1H-Indol-5-O-3-(4-methyl-pyridin-3-yl)-imidazolidin-2-one (48A)

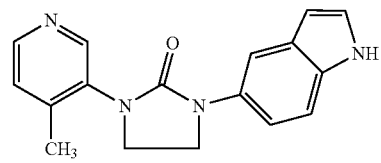

(48A)

Using the same reaction conditions as in Example 14, 1-(4-methyl-pyridin-3-yl)-imidazolidin-2-one (I-14b: 250 mg, 1.412 mmol) was reacted with 5-bromo-indole-1-carboxylic acid tert-butyl ester (0.499 g, 1.691 mmol), 1,4-dioxane (15 mL), copper iodide (0.0080 g), trans-1,2-diamino cyclohexane (0.0241 g, 0.2110 mmol) and potassium carbonate (0.389 g, 2.818 mmol) to afford the crude product. Purification by column chromatography on silica gel (10%

MeOH in CHCl$_3$) afforded 125 mg of 5-[3-(4-Methyl-pyridin-3-yl)-2-oxo-imidazolidin-1-yl]-indole-1-carboxylic acid tert-butyl ester (24% yield).

2N HCl (6 mL) was added to a solution of 5-[3-(4-methyl-pyridin-3-yl)-2-oxo-imidazolidin-1-yl]-indole-1-carboxylic acid tert-butyl ester (120 mg, 0.0306 mmol) in MeOH (3 mL) at 0° C. The reaction mixture was stirred at room temperature for 19 hours. The reaction was monitored by TLC (10% MeOH in CHCl$_3$). The resulting mixture was neutralized with NaHCO$_3$, filtered and dried to afford the crude product. Purification by preparative HPLC afforded 17 mg of the product (19.1% yield).

$^1$H NMR (DMSO-D$_6$, 300 MHz): δ 10.8 (s, 1H), 8.6 (s, 1H), 8.55 (s, 1H), 8.45-8.4 (m, 1H), 7.6 (s, 1H), 7.55-7.45 (m, 2H), 7.35-7.25 (m, 2H), 3.6-3.5 (m, 4H), 2.35 (s, 3H)

LCMS purity: 98.00%, m/z =293.0 (M+1)
HPLC: 92.87%

Example 49

Preparation of 1-(2,3-Dihydro-benzo[1,4]dioxin-6-yl)-3-(4-methyl-pyridin-3-yl)-imidazolidin-2-one (49A)

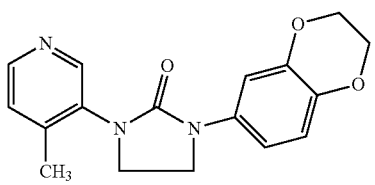

(49A)

Using the same reaction conditions as in Example 14, 1-(4-methyl-pyridin-3-yl)-imidazolidin-2-one (I-14b: 150 mg, 0.84 mmol) was reacted with 6-bromo-2,3-dihydro-benzo[1,4]dioxine (180 mg, 0.84 mmol), 1,4-dioxane (10 mL), copper iodide (16 mg, 0.084 mmol), trans-1,2-diamino cyclohexane (28.8 mg, 0.25 mmol) and potassium carbonate (231 mg, 1.68 mmol) to afford the crude product. Purification by column chromatography on silica gel (1% MeOH in CHCl$_3$) afforded 110 mg of the product (42.1% yield).

$^1$H NMR (DMSO-D$_6$, 300 MHz): δ 8.55 (s, 1H), 8.4 (d, 1H), 7.4 (d, 1H), 7.2 (d, 1H), 7.0 (dd, 1H), 6.85 (d, 1H), 4.3-4.2 (m, 4H), 4.0-3.9 (m, 4H), 2.3 (s, 3H)

LCMS purity: 99.67%, m/z =311.9 (M+1)
HPLC: 98.00%

Example 50

Preparation of 1-(4-Methyl-pyridin-3-O-3-(4-trifluoromethyl-phenyl)-imidazolidin-2-one (50A)

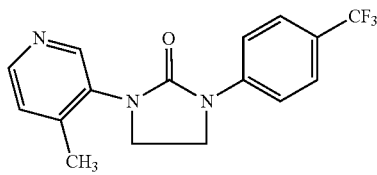

(50A)

Using the same reaction conditions as in Example 14, 1-(4-methyl-pyridin-3-yl)-imidazolidin-2-one (I-14b: 150 mg, 0.8474 mmol) was reacted with 1-bromo-4-trifluoromethyl-benzene (92 mL, 1.0168 mmol), 1,4-dioxane (20 mL), copper iodide (16 mg, 0.08484 mmol), trans-1,2-diamino cyclohexane (20 mL, 0.254 mmol) and potassium phosphate (355 mg, 212.27 mmol) to afford the crude product. Purification by column chromatography on silica gel (2% MeOH in CHCl$_3$) afforded 180 mg of the product (66% yield).

$^1$H NMR (DMSO-D$_6$, 300 MHz): δ 8.6 (s, 1H), 8.4 (d, 1H), 7.9-7.5 (m, 4H), 7.4 (d, 1H), 4.15-4.05 (m, 2H), 4.0-3.9 (m, 2H), 2.3 (s, 3H)

LCMS purity: 99.63%, m/z =321.8 (M+1)
HPLC: 99.1%

Example 51

Preparation of 1-(2,3-Dihydro-benzofuran-5-yl)-3-(4-methyl-pyridin-3-yl)-imidazolidin-2-one (51A)

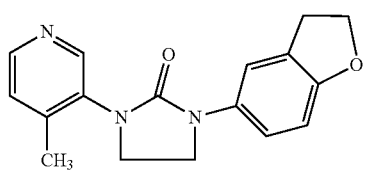

(51A)

Using the same reaction conditions as in Example 14, 1-(4-methyl-pyridin-3-yl)-imidazolidin-2-one (I-14b: 150 mg, 0.84 mmol) was reacted with 5-bromo-2,3-dihydro-benzofuran (167 mg, 0.84 mmol), 1,4-dioxane (10 mL), copper iodide (16 mg, 0.084 mmol), trans-1,2-diamino cyclohexane (28.8 mg, 0.25 mmol) and potassium phosphate (445 mg, 2.1 mmol) to afford the crude product. Purification by column chromatography on silica gel (1% MeOH in CHCl$_3$) afforded 200 mg of the product (80.9% yield).

$^1$H NMR (DMSO-D$_6$, 300 MHz): δ 8.5 (s, 1H), 8.35 (d, 1H), 7.5 (s, 1H), 7.3 (d, 1H), 7.2 (d, 1H), 6.8 (d, 1H), 4.5 (t, 2H), 4.0-3.85 (m, 4H), 3.2 (t, 2H), 2.3 (s, 3H)

LCMS purity: 90.40%, m/z=296.1 (M+1)
HPLC: 98.45%

Example 52

Preparation of 1-(4-Methyl-pyridin-3-yl)-3-quinolin-6-yl-imidazolidin-2-one (52A)

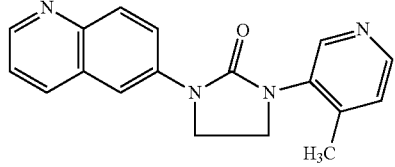

(52A)

Using the same reaction conditions as in Example 14, 1-(4-methyl-pyridin-3-yl)-imidazolidin-2-one (I-14b: 200 mg, 1.13 mmol) was reacted with 6-bromo-quinoline (233.9 mg, 1.13 mmol), 1,4-dioxane (15 mL), copper iodide (16.53 mg, 0.113 mmol), trans-1,2-diamino cyclohexane (0.04 mL, 0.339 mmol) and potassium carbonate (312 mg, 2.26 mmol) to afford the crude product. Purification by column chromatography on silica gel (0.5% MeOH in CHCl$_3$) afforded 150 mg of the product (43.668% yield).

$^1$H NMR (DMSO-D$_6$, 300 MHz): δ 8.8 (dd, 1H), 8.58 (s, 1H), 8.45-8.35 (m, 2H), 8.3 (d, 1H), 8.0 (d, 1H), 7.86 (d, 1H), 7.52-7.48 (m, 1H), 7.37 (d, 1H), 4.24-4.16 (m, 2H), 4.02-3.98 (m, 2H), 2.31 (s, 3H)

LCMS purity: 99.55%, m/z =305.2 (M+1)
HPLC: 95.53%

Example 53

Preparation of 1-(3-Fluoro-4-methoxy-phenyl)-3-(4-methyl-pyridin-3-yl)-imidazolidin-2-one (53A)

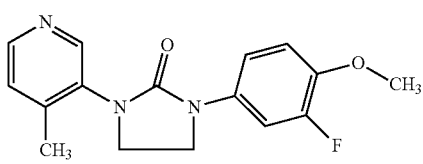
(53A)

Using the same reaction conditions as in Example 14, 1-(4-methyl-pyridin-3-yl)-imidazolidin-2-one (I-14b: 150 mg, 0.8474 mmol) was reacted with 4-bromo-2-fluoro-1-methoxy-benzene (191 mg, 0.932 mmol), 1,4-dioxane (20 mL), copper iodide (16 mg, 0.08474 mmol), trans-1,2-diamino cyclohexane (29.4 mg, 0.2542 mmol) and potassium phosphate (449 mg, 2.11 mmol) to afford 220 mg of the product (86% yield).

$^1$H NMR (DMSO-D$_6$, 300 MHz): δ 8.5 (s, 1H), 8.4 (d, 1H), 7.7-7.6 (dd, 1H), 7.35 (d, 1H), 7.3-7.1 (m, 2H), 4.0-3.8 (m, 7H), 2.3 (s, 3H)

LCMS purity: 99.59%, m/z=301.9 (M+1)
HPLC: 98.6%

Example 54

Preparation of 1-(4-Chloro-3-fluoro-phenyl)-3-(4-methyl-pyridin-3-yl)-imidazolidin-2-one (54A)

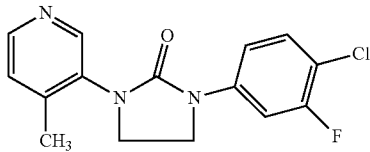
(54A)

Using the same reaction conditions as in Example 14, 1-(4-methyl-pyridin-3-yl)-imidazolidin-2-one (I-14b: 150 mg, 0.8474 mmol) was reacted with 4-bromo-1-chloro-2-fluoro-benzene (213 mg, 1.0168 mmol), 1,4-dioxane (20 mL), copper iodide (16 mg, 0.08474 mmol), trans-1,2-diamino cyclohexane (29.4 mg, 0.2542 mmol) and potassium phosphate (449.7 mg, 2.1185 mmol) to afford 190 mg of the product (73% yield).

$^1$H NMR (CDCl$_3$, 300 MHz): δ 8.5 (s, 1H), 8.4 (d, 1H), 7.6 (dd, 1H), 7.4-7.3 (m, 2H), 7.25-7.2 (m, 1H), 4.1-3.9 (m, 4H), 2.35 (s, 3H)

LCMS purity: 96.94%, m/z =306.1 (M+1)
HPLC: 96.4%

Example 55

Preparation of 1-(4-Methyl-pyridin-3-yl)-3-m-tolyl-imidazolidin-2-one (55A)

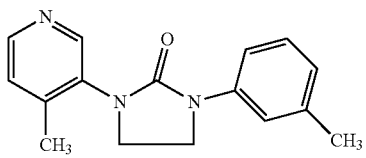
(55A)

Using the same reaction conditions as in Example 14, 1-(4-methyl-pyridin-3-yl)-imidazolidin-2-one (I-14b: 150 mg, 0.847 mmol) was reacted with 1-bromo-3-methyl-benzene (172.8 mg, 1.017 mmol), 1,4-dioxane (20 mL), copper iodide (16.13 mg, 0.0847 mmol), trans-1,2-diamino cyclohexane (0.03 mL, 0.254 mmol) and potassium phosphate (539.3 mg, 2.541 mmol) to afford the crude product. Purification by column chromatography on silica gel (1.2% MeOH in CHCl$_3$) afforded 153 mg of the product (67.69% yield).

$^1$H NMR (DMSO-D$_6$, 300 MHz): δ 8.54 (s, 1H), 8.38 (d, 1H), 7.48-7.38 (m, 2H), 7.35 (d, 1H), 7.23 (t, 1H), 6.86 (d, 1H), 4.08-3.98 (m, 2H), 3.96-3.88 (m, 2H), 2.28 (s, 3H), 2.32 (s, 3H)

LCMS purity: 93.74%, m/z =268.1 (M+1)
HPLC: 96.86%

Example 56

Preparation of 1-(3-Methoxy-phenyl)-3-(4-methyl-pyridin-3-yl)-imidazolidin-2-one (56A)

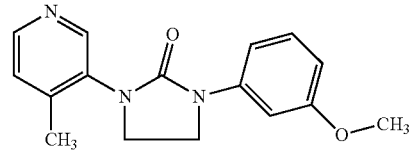
(56A)

Using the same reaction conditions as in Example 14, 1-(4-methyl-pyridin-3-yl)-imidazolidin-2-one (I-14b: 150 mg, 0.84650 mmol) was reacted with 1-bromo-3-methoxy-benzene (107 mg, 0.84650 mmol), 1,4-dioxane (50 mL), copper iodide (16 mg, 0.08465 mmol), trans-1,2-diamino cyclohexane (0.03 mL, 0.2539 mmol) and potassium phosphate (538 mg, 2.539 mmol) to afford the crude product. Purification by column chromatography on silica gel (2% MeOH in CHCl$_3$) afforded 180 mg of the product (75% yield).

$^1$H NMR (DMSO-D$_6$, 300 MHz): δ 8.55 (s, 1H), 8.4 (d, 1H), 7.4 (d, 1H), 7.35-7.25 (m, 2H), 7.2 (d, 1H), 6.65 (dd, 1H), 4.15-4.0 (m, 2H), 4.0-3.95 (m, 2H), 3.75 (s, 3H), 2.3 (s, 3H)

LCMS purity: 95.82%, m/z =283.9 (M+1)
HPLC: 97.25%

Example 57

Preparation of 1-(4-Methyl-pyridin-3-yl)-3-(4,5,6,7-tetrahydro-thieno[2,3-c]pyridin-2-yl)-imidazolidin-2-one, hydrochloride (57A)

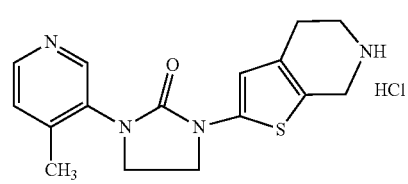
(57A)

Using the same reaction conditions as in Example 14, 1-(4-methyl-pyridin-3-yl)-imidazolidin-2-one (I-14b: 50 mg, 0.28216 mmol) was reacted with 2-bromo-4,7-dihydro-5H-thieno[2,3-c]pyridine-6-carboxylic acid tert-butyl ester (90 mg, 0.28216 mmol), 1,4-dioxane (20 mL), copper iodide (5.3 mg, 0.0282 mmol), trans-1,2-diamino cyclohexane (9.69 mg, 0.08464 mmol) and potassium phosphate (179.6 mg, 0.84650 mmol) to afford the crude product. Purification by column chromatography on silica gel (2% MeOH in DCM) afforded 70 mg of 2[3-(4-Methyl-pyridin-3-yl)-2-oxo-imidazolidin-1-yl]-4,7-dihydro-5H-thieno[2,3-c]pyridine-6-carboxylic acid tert-butyl ester (60% yield).

6N HCl (5 mL) was added dropwise to stirred solution of 2-[3-(4-methyl-pyridin-3-yl)-2-oxo-imidazolidin-1-yl]-4,7-dihydro-5H-thieno[2,3-c]pyridine-6-carboxylic acid tert-butyl ester (70 mg, 0.16887 mmol) in methanol (2 mL) at 0° C. The reaction mixture was stirred at room temperature for 12 hours. The reaction was monitored by TLC (5% MeOH in DCM). The solvent was distilled from the reaction mixture under reduced pressure, followed by the addition of diethyl-ether. The precipitate was washed with ether and dried under reduced pressure to afford 36 mg of the product (61% yield).

$^1$H NMR (DMSO-D$_6$, 300 MHz): δ 9.55 (s, 2H), 8.8 (s, 1H), 8.7-8.5 (m, 2H), 7.8 (d, 1H), 6.35 (s, 1H), 4.2 (s, 2H), 4.0 (s, 4H), 3.4 (t, 2H), 2.8 (t, 2H), 2.4 (s, 3H)

LCMS purity: 90.09%, m/z=315.1 (M+1)
HPLC: 84.27%

Example 58

Preparation of 1-(2-Chloro-pyridin-4-yl)-3-(4-methyl-pyridin-3-yl)-imidazolidin-2-one (58A)

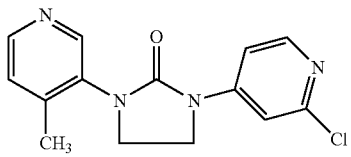

(58A)

Using the same reaction conditions as in Example 14, 1-(4-methyl-pyridin-3-yl)-imidazolidin-2-one (I-14b: 600 mg, 3.3898 mmol) was reacted with 2-chloro-4-iodo-pyridine (974 mg, 4.067 mmol), 1,4-dioxane (60 mL), copper iodide (65 mg, 0.3398 mmol), trans-1,2-diamino cyclohexane (0.12 mL, 1.0169 mmol) and potassium phosphate (2.15 g, 10.1694 mmol) to afford 810 mg of the product (83% yield).

$^1$H NMR (CDCl$_3$, 300 MHz): δ 8.5-8.4 (m, 2H), 8.3 (d, 1H), 7.6-7.5 (m, 2H), 7.2 (s, 1H), 4.1-3.9 (m, 4H), 2.35 (s, 3H)
LCMS purity: 90.8%, m/z=289.1 (M+1)
HPLC: 97.14%

Example 59

Preparation of 1-(4-Fluoro-3-methyl-phenyl)-3-(4-methyl-pyridin-3-yl)-imidazolidin-2-one (59A)

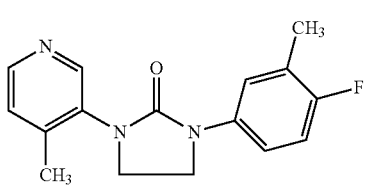

(59A)

Using the same reaction conditions as in Example 14, 1-(4-methyl-pyridin-3-yl)-imidazolidin-2-one (I-14b: 160 mg, 0.9039 mmol) was reacted with 4-bromo-1-fluoro-2-methyl-benzene (0.135 mL, 0.7142 mmol), 1,4-dioxane (15 mL), copper iodide (0.005 g, 0.0263 mmol), trans-1,2-diamino cyclohexane (0.015 g, 0.1315 mmol) and potassium phosphate (0.575 g, 2.7094 mmol) to afford the crude product. Purification by column chromatography on silica gel (1% MeOH in chloroform) afforded 26 mg of the product (30% yield).

$^1$H NMR (CDCl$_3$, 300 MHz): δ 8.6-8.4 (m, 2H), 7.5-7.4 (m, 1H), 7.35-7.25 (m, 2H), 7.0 (t, 1H), 4.1-3.9 (m, 4H), 2.4 (s, 3H), 2.3 (s, 3H)

LCMS purity: 95.40%, m/z=286.0 (M+1)
HPLC: 94.03%

Example 60

Preparation 1-(5-Chloro-2-fluoro-phenyl)-3-(4-methyl-pyridin-3-yl)-imidazolidin-2-one (60A)

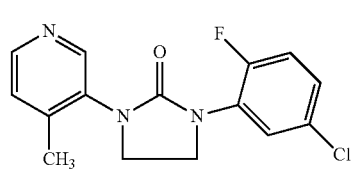

(60A)

Using the same reaction conditions as in Example 14, 1-(4-methyl-pyridin-3-yl)-imidazolidin-2-one (I-14b: 150 mg, 0.84650 mmol) was reacted with 2-bromo-4-chloro-1-fluoro-benzene (177 mg, 0.84650 mmol), 1,4-dioxane (10 mL), copper iodide (16 mg, 0.084650 mmol), trans-1,2-diamino cyclohexane (29 mg, 0.2539 mmol) and potassium phosphate (538 mg, 2.539 mmol) to afford the crude product. Purification by column chromatography on silica gel (2% MeOH in DCM) afforded 180 mg of the product (69.7% yield).

$^1$H NMR (DMSO-D$_6$, 300 MHz): δ 8.6-8.5 (br s, 1H), 8.4 (d, 1H), 7.7 (d, 1H), 7.4-7.3 (m, 3H), 4.1-3.85 (m, 4H), 2.15 (s, 3H)

LCMS purity: 98.67%, m/z=305.8 (M+1)
HPLC: 92.0%

Example 61

Preparation of 1-(2,4-Difluoro-phenyl)-3-(4-methyl-pyridin-3-yl)-imidazolidin-2-one (61A)

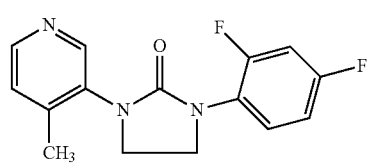

(61A)

Using the same reaction conditions as in Example 14, 1-(4-methyl-pyridin-3-yl)-imidazolidin-2-one (I-14b: 150 mg, 0.8474 mmol) was reacted with 1-bromo-2,4-difluorobenzene (0.114 mL, 1.0169 mmol), 1,4-dioxane (20 mL), copper iodide (16 mg, 0.08474 mmol), trans-1,2-diamino cyclohexane (29.4 mg, 0.254 mmol) and potassium phosphate (449.7 mg, 2.118 mmol) to afford the crude product. Purification by column chromatography on silica gel (2% MeOH in CHCl$_3$) afforded 150 mg of the product (61% yield).

$^1$H NMR (DMSO-D$_6$, 300 MHz): δ 8.52 (s, 1H), 8.39 (d, 1H), 7.65-7.55 (m, 1H), 7.45-7.30 (m, 2H), 7.2-7.1 (m, 1H), 3.9 (s, 4H), 2.3 (s, 3H)

LCMS purity: 99.49%, m/z=290.2 (M+1)
HPLC: 95.04%

Example 62

Preparation of 1-Benzothiazol-5-yl-3-(4-methylpyridin-3-yl)-imidazolidin-2-one (62A)

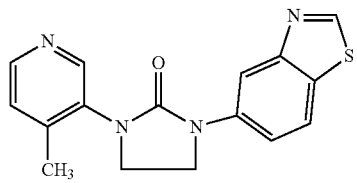

(62A)

Using the same reaction conditions as in Example 14, 1-(4-methyl-pyridin-3-yl)-imidazolidin-2-one (I-14b: 150 mg, 0.84650 mmol) was reacted with 5-iodo-benzothiazole (221 mg, 0.84650 mmol), 1,4-dioxane (25 mL), copper iodide (16 mg, 0.084650 mmol), trans-1,2-diamino cyclohexane (29 mg, 0.2539 mmol) and potassium phosphate (538 mg, 2.539 mmol) to afford the crude product. Purification by column chromatography on silica gel (2% MeOH in DCM) afforded 185 mg of the product (70.6% yield).

$^1$H NMR (DMSO-D$_6$, 300 MHz): δ 9.4 (s, 1H), 8.59 (s, 1H), 8.4 (d, 1H), 8.24-8.22 (m, 1H), 8.15-8.1 (m, 1H), 8.0-7.9 (m, 1H), 7.39 (d, 1H), 4.2-4.1 (m, 2H), 4.0-3.9 (m, 2H), 2.3 (s, 3H)

LCMS purity: 93.36%, m/z =311 (M+1)
HPLC: 95.21%

Example 63

Preparation of 6-[3-(4-Methyl-pyridin-3-yl)-2-oxo-imidazolidin-1-yl]-3,4-dihydro-1H-quinolin-2-one (63A)

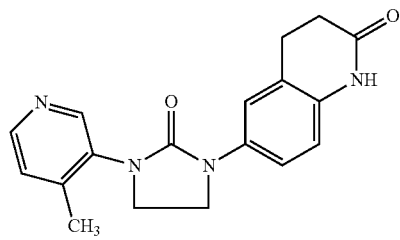

(63A)

Using the same reaction conditions as in Example 14, 1-(4-methyl-pyridin-3-yl)-imidazolidin-2-one (I-14b: 150 mg, 0.8474 mmol) was reacted with 6-bromo-2-oxo-3,4-dihydro-2H-quinoline-1-carboxylic acid tert-butyl ester (276 mg, 0.8474 mmol), 1,4-dioxane (5 mL), copper iodide (16.14 mg, 0.08474 mmol), trans-1,2-diamino cyclohexane (29.1 mg, 0.2542 mmol) and potassium carbonate (234.3 mg, 1.6948 mmol) to afford the crude product. Purification by preparative HPLC afforded 86 mg of the product (31.5% yield).

$^1$H NMR (DMSO-D$_6$, 300 MHz): δ 10.0 (s, 1H), 8.5 (s, 1H), 8.4 (d, 1H), 7.5-7.3 (m, 3H), 6.9-6.75 (d, 1H), 4.0-3.85 (m, 4H), 2.85 (t, 2H), 2.45-2.4 (m, 2H), 2.3 (s, 3H)

LCMS purity: 96.55%, m/z=322.9 (M+1)
HPLC: 97.13%

Example 64

Preparation of 1-(2,2-Difluoro-benzo[1,3]dioxol-5-yl)-3-(4-methyl-pyridin-3-yl)-imidazolidin-2-one (64A)

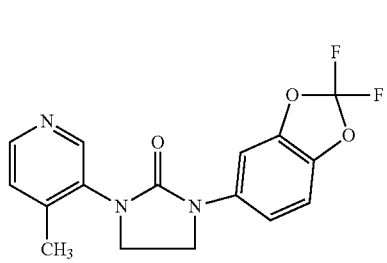

(64A)

Using the same reaction conditions as in Example 14, 1-(4-methyl-pyridin-3-yl)-imidazolidin-2-one (I-14b: 150 mg, 0.84650 mmol) was reacted with 5-bromo-2,2-difluoro-benzo[1,3]dioxole (200.6 mg, 0.84650 mmol), 1,4-dioxane (50 mL), copper iodide (16 mg, 0.084650 mmol), trans-1,2-diamino cyclohexane (29 mg, 0.2539 mmol) and potassium phosphate (538 mg, 2.539 mmol) to afford the crude product. Purification by column chromatography on silica gel (2% MeOH in DCM) afforded 260 mg of the product (92% yield).

$^1$H NMR (DMSO-D$_6$, 300 MHz): δ 8.6-8.4 (m, 2H), 7.7-7.69 (m, 1H), 7.25-7.2 (m, 1H), 7.06-6.9 (m, 2H), 4.1-3.9 (m, 4H), 2.35 (s, 3H)

LCMS purity: 95.12%, m/z=333.6 (M+1)
HPLC: 92.82%

Example 65

Preparation of 7-[3-(4-Methyl-pyridin-3-yl)-2-oxo-imidazolidin-1-yl]-3,4-dihydro-1H-quinolin-2-one (65A)

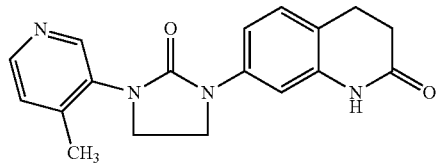

(65A)

Using the same reaction conditions as in Example 14, 1-(4-methyl-pyridin-3-yl)-imidazolidin-2-one (I-14b: 0.15 g, 0.00084 mol) was reacted with 7-bromo-2-oxo-3,4-dihydro-2H-quinoline-1-carboxylic acid tert-butyl ester (0.276 g, 0.00084 mol), 1,4-dioxane (20 mL), copper iodide (0.0158 g, 0.000084 mol), trans-1,2-diamino cyclohexane (0.28 g, 0.00025 mol) and potassium phosphate (0.356 g, 0.00168 mol) to afford the crude product. Purification by column chromatography on silica gel (5% MeOH in CHCl$_3$) afforded 0.145 g of 7-[3-(4-Methyl-pyridin-3-yl)-2-oxo-imidazolidin-1-yl]-2-oxo-3,4-dihydro-2H-quinoline-1-carboxylic acid tert-butyl ester (67.48% yield).

$^1$H NMR (DMSO-D$_6$, 300 MHz): δ 8.1-8.02 (br s, 1H), 7.15-7.0 (m, 2H), 6.99-6.92 (m, 1H), 2.95 (t, 2H), 2.65 (t, 2H), 2.1-2.0 (m, 2H), 1.8-1.7 (m, 1H), 1.45-1.40 (m, 5H), 1.25 (s, 11H)

Dioxane hydrochloride (3 mL) was added to 7-[3-(4-methyl-pyridin-3-yl)-2-oxo-imidazolidin-1-yl]-2-oxo-3,4-dihydro-2H-quinoline-1-carboxylic acid tert-butyl ester (0.145 g, 0.00034 mol) at 0° C. The resulting reaction mixture was stirred at room temperature for 2 hours. The reaction was monitored by TLC (40% ethylacetate in hexane). Purification by preparative HPLC, followed by column chromatography on silica gel (5% MeOH in CHCl$_3$) afforded 48 mg of the product (35.47% yield).

$^1$H NMR (DMSO-D$_6$, 300 MHz): δ 10.09 (s, 1H), 8.52 (s, 1H), 8.35 (d, 1H), 7.35 (d, 1H), 7.3-7.22 (m, 1H), 7.19-7.0 (m, 2H), 4.0-3.84 (m, 4H), 2.82 (t, 2H), 2.45-2.40 (m, 2H), 2.27 (s, 3H)

LCMS purity: 99.47%, m/z =322.8 (M+1)

Example 66

Preparation of N-{3-[3-(4-Methyl-pyridin-3-yl)-2-oxo-imidazolidin-1-yl]-phenyl}-acetamide (66A)

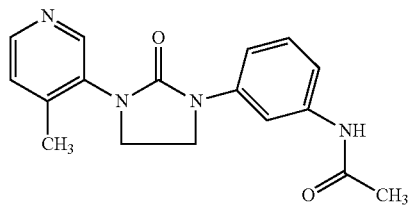
(66A)

Using the same reaction conditions as in Example 14, 1-(4-methyl-pyridin-3-yl)-imidazolidin-2-one (I-14b: 150 mg, 0.8474 mmol) was reacted with N-(3-bromo-phenyl)-acetamide (217.6 mg, 1.0169 mmol), 1,4-dioxane (20 mL), copper iodide (16 mg, 0.08474 mmol), trans-1,2-diamino cyclohexane (449.7 mg, 0.2542 mmol) and potassium phosphate (29.4 mg, 2.1185 mmol) to afford the crude product. Purification by column chromatography on silica gel (5% MeOH in CHCl$_3$), followed by preparative HPLC afforded 60 mg of the product (23% yield).

$^1$H NMR (DMSO-D$_6$, 300 MHz): δ 9.95 (s, 1H), 8.52 (s, 1H), 8.37 (d, 1H), 7.85 (s, 1H), 7.4-7.2 (m, 4H), 4.02-3.82 (m, 4H), 2.28 (s, 3H), 2.02 (s, 3H)

LCMS purity: 99.02%, m/z=310.9 (M+1)
HPLC: 99.6%

Example 67

Preparation of 1-(4-Methyl-pyridin-3-yl)-3-(3-methyl-thiophen-2-yl)-imidazolidin-2-one (67A)

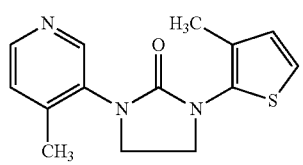
(67A)

Using the same reaction conditions as in Example 14, 1-(4-methyl-pyridin-3-yl)-imidazolidin-2-one (I-14b: 150 mg, 0.84 mmol) was reacted with 2-bromo-3-methyl-thiophene (150 mg, 0.84 mmol), 1,4-dioxane (10 mL), copper iodide (16 mg, 0.084 mmol), trans-1,2-diamino cyclohexane (28.8 mg, 0.25 mmol) and potassium phosphate (445 mg, 2.1 mmol) to afford the crude product. Purification by column chromatography on silica gel (2% MeOH in DCM) afforded 130 mg of the product (56.7% yield).

$^1$H NMR (DMSO-D$_6$, 300 MHz): δ 8.52 (s, 1H), 8.39 (d, 1H), 7.39-7.25 (dd, 2H), 6.85 (d, 1H), 4.0-3.82 (m, 4H), 2.29 (s, 3H), 2.12 (s, 3H)

LCMS purity: 98.05%, m/z=274.0 (M+1)
HPLC: 98.08%

Example 68

Preparation of 1-(4-Methyl-pyridin-3-yl)-3-(2-methyl-quinolin-6-yl)-imidazolidin-2-one (68A)

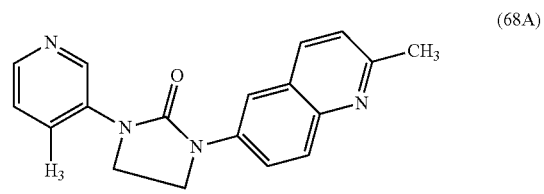
(68A)

Using the same reaction conditions as in Example 14, 1-(4-methyl-pyridin-3-yl)-imidazolidin-2-one (I-14b: 0.150 g, 0.847 mmol) was reacted with 6-bromo-2-methyl-quinoline (0.225 g, 1.016 mmol), 1,4-dioxane (20 mL), copper iodide (0.016 g, 0.084 mmol), trans-1,2-diamino cyclohexane (0.029 g, 0.254 mmol) and potassium phosphate (0.449 g, 2.1 mmol) to afford the crude product. Purification by column chromatography on silica gel (5% MeOH in CHCl$_3$) afforded 115 mg of the product (43% yield).

$^1$H NMR (CDCl$_3$, 300 MHz): δ 8.55 (s, 1H), 8.45 (d, 1H), 8.12 (dd, 1H), 8.05-8.0 (m, 2H), 7.85 (d, 1H), 7.3-7.2 (m, 2H), 4.24-4.15 (m, 2H), 4.05-3.95 (m, 2H), 2.75 (s, 3H), 2.39 (s, 3H)

LCMS purity: 99.63%, m/z=318.9 (M+1)
HPLC: 98.15%

Example 69

Preparation of 1-(4-Methyl-pyridin-3-yl)-3-phenyl-imidazolidin-2-one (69A)

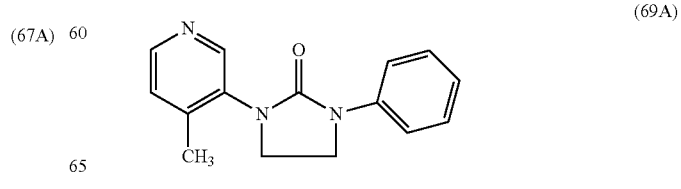
(69A)

Using the same reaction conditions as in Example 14, 1-(4-methyl-pyridin-3-yl)-imidazolidin-2-one (I-14b: 100 mg, 0.5643 mmol) was reacted with bromo-benzene (89 mg, 0.5643 mmol), 1,4-dioxane (20 mL), copper iodide (10 mg), trans-1,2-diamino cyclohexane (20 mg) and potassium phosphate (359 mg, 1.693 mmol) to afford the crude product. Purification by column chromatography on silica gel (1.2-1.4% MeOH in CHCl$_3$) afforded 132 mg of the product (92.30% yield).

$^1$H NMR (DMSO-D$_6$, 300 MHz): δ 8.6-8.3 (m, 2H), 7.65-7.6 (m, 2H), 7.42-7.3 (m, 3H), 7.05 (t, 1H), 4.1-3.85 (m, 4H), 2.28 (s, 3H)

LCMS purity: 95.32%, m/z =254.1 (M+1)
HPLC: 95.86%

Example 70

Preparation of 1-(4-Methyl-pyridin-3-yl)-3-(3-trifluoromethyl-phenyl)-imidazolidin-2-One (70A)

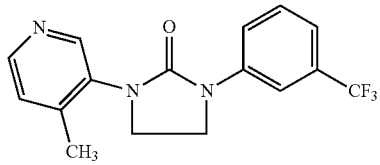

(70A)

Using the same reaction conditions as in Example 14, 1-(4-methyl-pyridin-3-yl)-imidazolidin-2-one (I-14b: 150 mg, 0.847 mmol) was reacted with 1-bromo-3-trifluoromethyl-benzene (0.14 mL, 1.016 mmol), 1,4-dioxane (10 mL), copper iodide (16.13 mg, 0.0847 mmol), trans-1,2-diamino cyclohexane (0.03 mL, 0.254 mmol) and potassium phosphate (539 mg, 2.54 mmol) to afford the crude product. Purification by column chromatography on silica gel (1.2% MeOH in CHCl$_3$) afforded 190 mg of the product (70.11% yield).

$^1$H NMR (DMSO-D$_6$, 300 MHz): δ 8.55 (s, 1H), 8.4 (d, 1H), 8.18-8.12 (br s, 1H), 7.8-7.77 (d, 1H), 7.6 (t, 1H), 7.42-7.32 (m, 2H), 4.15-4.05 (m, 2H), 4.0-3.9 (m, 2H), 2.29 (s, 3H)

LCMS purity: 95.74%, m/z =322.1 (M+1)
HPLC: 97.15%

Example 71

Preparation of 1-(1-Isopropyl-1H-pyrazol-4-yl)-3-(4-methyl-pyridin-3-O-imidazolidin-2-one (71A)

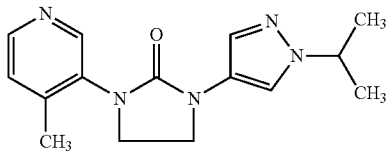

(71A)

Using the same reaction conditions as in Example 14, 1-(4-methyl-pyridin-3-yl)-imidazolidin-2-one (I-14b: 150 mg, 0.84650 mmol) was reacted with 4-iodo-1-isopropyl-1H-pyrazole (199.8 mg, 0.84650 mmol), 1,4-dioxane (50 mL), copper iodide (16 mg, 0.084650 mmol), trans-1,2-diamino cyclohexane (29 mg, 0.2539 mmol) and potassium phosphate (538 mg, 2.539 mmol) to afford the crude product. Purification by column chromatography on silica gel (2% MeOH in DCM) afforded 175 mg of the product (72.6% yield).

$^1$H NMR (DMSO-D$_6$, 300 MHz): δ 8.55-8.25 (m, 2H), 7.82 (s, 1H), 7.54 (s, 1H), 7.36-7.3 (m, 1H), 4.45 (quin, 1H), 4.0-3.8 (m, 4H), 2.25 (s, 3H), 1.4 (d, 6H)

LCMS purity: 99.86%, m/z =286.1 (M+1)
HPLC: 96.85%

Example 72

Preparation of 1-(2-Methoxy-pyridin-4-yl)-3-(4-methyl-pyridin-3-yl)-imidazolidin-2-one (72A)

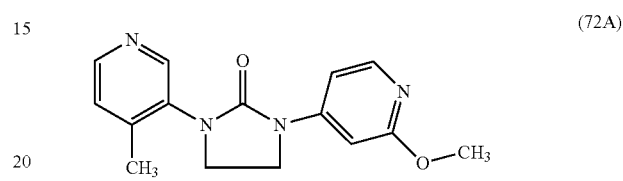

(72A)

Sodium methoxide (225 mg, 4.165 mmol) was added dropwise to a stirred solution of 1-(2-chloro-pyridin-4-yl)-3-(4-methyl-pyridin-3-yl)-imidazolidin-2-one (58A: 100 mg, 0.374 mmol) in 1,4-dioxane (20 mL) over a period of 10 minutes. The resulting mixture was heated to 110° C. and maintained at the same temperature for 4 days. The reaction was monitored by TLC (10% MeOH in CHCl$_3$). The solvent was distilled from the reaction mixture and the concentrate was partitioned between water and ethylacetate. The organic layer was dried over Na$_2$SO$_4$ to afford the crude product. Purification by column preparative HPLC afforded 30 mg of the product (30.61% yield).

$^1$H NMR (CDCl$_3$, 300 MHz): δ 8.5 (s, 1H), 8.45 (d, 1H), 8.08 (d, 1H), 7.44 (dd, 1H), 7.25-7.2 (d, 1H), 6.75 (d, 1H), 4.09-3.9 (m, 7H), 2.35 (s, 3H)

LCMS purity: 96.29%, m/z=285.1 (M+1)
HPLC: 98.13%

Example 73

Preparation of 1-imidazolidin-2-one (73A)

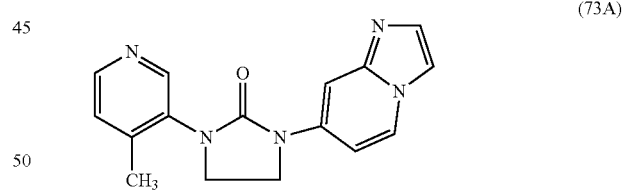

(73A)

Using the same reaction conditions as in Example 14, 1-(4-methyl-pyridin-3-yl)-imidazolidin-2-one (I-14b: 150 mg, 0.8474 mmol) was reacted with 7-bromo-imidazo[1,2-a]pyridine (166.94 mg, 0.8474 mmol), 1,4-dioxane (5 mL), copper iodide (16.1 mg, 0.08474 mmol), trans-1,2-diamino cyclohexane (29.1 mg, 0.2542 mmol) and potassium phosphate (539.63 mg, 2.542 mmol) to afford the crude product. Purification by column chromatography on silica gel (3% MeOH in CHCl$_3$) afforded 69 mg of the product (29.15% yield).

$^1$H NMR (DMSO-D$_6$, 300 MHz): δ 8.8-8.7 (br s, 1H), 8.6-8.5 (br s, 1H), 8.45-8.35 (br s, 1H), 8.1-7.9 (br s, 1H), 7.85-7.7 (m, 1H), 7.65-7.5 (br s, 2H), 7.4-7.3 (d, 1H), 4.1-3.9 (m, 4H), 2.3 (s, 3H)

LCMS purity: 98.45%, m/z=294.1 (M+1)
HPLC: 98.56%

Example 74

Preparation of 1-(4-Fluoro-3-methoxy-phenyl)-3-(4-methyl-pyridin-3-yl)-imidazolidin-2-one (74A)

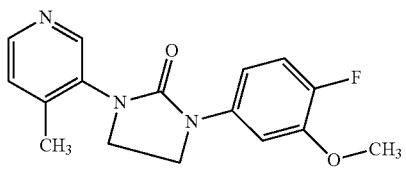
(74A)

Using the same reaction conditions as in Example 14, 1-(4-methyl-pyridin-3-yl)-imidazolidin-2-one (I-14b: 150 mg, 0.8474 mmol) was reacted with 4-bromo-1-fluoro-2-methoxy-benzene (191 mg, 0.9315 mmol), 1,4-dioxane (20 mL), copper iodide (16 mg, 0.08474 mmol), trans-1,2-diamino cyclohexane (29.4 mg, 0.254 mmol) and potassium phosphate (449.7 mg, 2.118 mmol) to afford the crude product. Purification by column chromatography on silica gel (5% MeOH in CHCl$_3$) afforded 170 mg of the product (66.7% yield).

$^1$H NMR (CDCl$_3$, 300 MHz): δ 8.52 (s, 1H), 8.42 (d, 1H), 7.8 (dd, 1H), 7.22 (d, 1H), 7.1-7.0 (m, 1H), 6.7-6.6 (m, 1H), 4.1-3.85 (m, 7H), 2.35 (s, 3H)

LCMS purity: 98.3%, m/z =301.8 (M+1)

HPLC: 96.74%

Example 75

Preparation of N-{5-[3-(4-Methyl-pyridin-3-yl)-2-oxo-imidazolidin-1-yl]-pyridin-2-yl}-acetamide (75A)

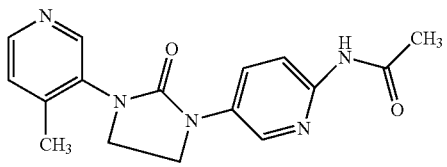
(75A)

Using the same reaction conditions as in Example 14, 1-(4-methyl-pyridin-3-yl)-imidazolidin-2-one (I-14b: 150 mg, 0.8465 mmol) was reacted with N-(5-bromo-pyridin-2-yl)-acetamide (217.4 mg, 1.016 mmol), 1,4-dioxane (20 mL), copper iodide (16 mg, 0.08474 mmol), trans-1,2-diamino cyclohexane (29.4 mg, 0.254 mmol) and potassium phosphate (449.7 mg, 2.118 mmol) to afford the crude product. Purification by column chromatography on silica gel (2% MeOH in CHCl$_3$) afforded 105 mg of the product (40% yield).

$^1$H NMR (CDCl$_3$, 300 MHz): δ 8.6-8.4 (m, 3H), 8.22 (d, 1H), 8.1-8.0 (br s, 1H), 8.0-7.9 (m, 1H), 7.25-7.2 (m, 1H), 4.15-3.95 (m, 4H), 2.35 (s, 3H), 2.2 (s, 3H)

LCMS purity: 97.86%, m/z =311.9 (M+1)

HPLC: 90.08%

Example 76

Preparation of 1-(2-Amino-pyridin-4-yl)-3-(4-methyl-pyridin-3-O-imidazolidin-2-one (76A)

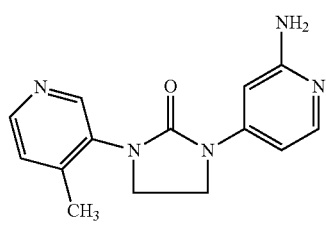
(76A)

6N HCl (4 mL) was added to a solution of N-{3-[3-(4-methyl-pyridin-3-yl)-2-oxo-imidazolidin-1-yl]-phenyl}-acetamide (75A: 100 mg, 0.3212 mmol) in ethanol (4 mL). The resulting reaction mixture was heated to 65° C. and maintained at 65° C. for 3 hours. The reaction was monitored by TLC (5% MeOH in CHCl$_3$). The reaction mixture was concentrated, followed by the addition of ice, NaHCO$_3$ and extracted with DCM. The organic layer was dried over Na$_2$SO$_4$ and concentrated. The concentrate was dissolved in DCM, followed by the addition of hexane to afford the precipitate which was collected and dried under reduced pressure to afford 55 mg of the product (63.5% yield).

$^1$H NMR (DMSO-D$_6$, 300 MHz): δ 8.52 (s, 1H), 8.39 (d, 1H), 7.78 (d, 1H), 7.35 (d, 1H), 6.88-6.8 (m, 1H), 6.63 (s, 1H), 5.8 (s, 2H), 4.0-3.8 (m, 4H), 2.25 (s, 3H)

LCMS purity: 99.73%, m/z =270.0 (M+1)

HPLC: 95.60%

Example 77

Preparation of 1-(4-Methyl-pyridin-3-yl)-3-quinoxalin-6-yl-imidazolidin-2-one (77A)

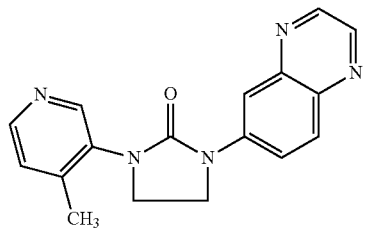
(77A)

Using the same reaction conditions as in Example 14, 1-(4-methyl-pyridin-3-yl)-imidazolidin-2-one (I-14b: 150 mg, 0.84650 mmol) was reacted with 6-bromo-quinoxaline (176.9 mg, 0.84650 mmol), 1,4-dioxane (20 mL), copper iodide (16 mg, 0.084650 mmol), trans-1,2-diamino cyclohexane (29 mg, 0.2539 mmol) and potassium phosphate (538 mg, 2.539 mmol) to afford the crude product. Purification by column chromatography on silica gel (2% MeOH in DCM) afforded 175 mg of the product (67.8% yield).

$^1$H NMR (DMSO-D$_6$, 300 MHz): δ 8.9 (d, 1H), 8.8 (d, 1H), 8.55 (dd, 2H), 8.48-8.39 (brS, 1H), 8.1 (d, 1H), 7.95 (d, 1H), 7.42-7.36 (m, 1H), 4.3-4.2 (m, 2H), 4.05-3.95 (m, 2H), 2.3 (s, 3H)

LCMS purity: 91.95%, m/z =306.1 (M+1)

HPLC: 96.82%

Example 78

Preparation of 1-(5-Difluoromethyl-thiophen-3-yl)-3-(4-methyl-pyridin-3-yl)-imidazolidin-2-one (78A)

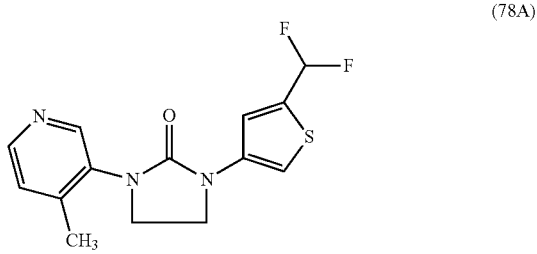

(78A)

Using the same reaction conditions as in Example 14, 1-(4-methyl-pyridin-3-yl)-imidazolidin-2-one (I-14b: 150 mg, 0.8474 mmol) was reacted with 4-bromo-2-difluoromethyl-thiophene (179.6 mg, 0.8474 mmol), 1,4-dioxane (5 mL), copper iodide (16.14 mg, 0.08474 mmol), trans-1,2-diamino cyclohexane (29.1 mg, 0.2542 mmol) and potassium phosphate (539.59 mg, 2.542 mmol) to afford the crude product. Purification by column chromatography on silica gel (2% MeOH in CHCl$_3$) afforded 22 mg of the product (8.5% yield).

$^1$H NMR (CDCl$_3$, 300 MHz): δ 8.9 (s, 1H), 8.55 (d, 1H), 7.9-7.6 (m, 2H), 7.06 (s, 1H), 6.5-7.0 (m, 1H), 4.1 (s, 4H), 2.68-(s, 3H)

LCMS purity: 95.24%, m/z =309.8 (M+1)
HPLC: 96.51%

Example 79

Preparation of 1-Naphthalen-2-yl-3-(5-trifluoromethyl-pyridin-3-yl)-imidazolidin-2-one (79A)

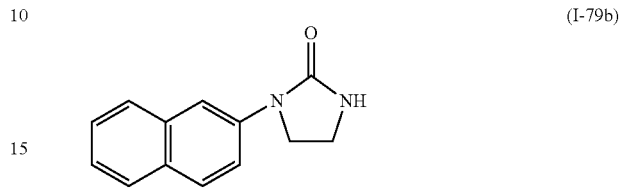

(79A)

Step 1: Preparation of Intermediate 1-(2-Chloro-ethyl)-3-naphthalen-2-yl-urea (I-79a)

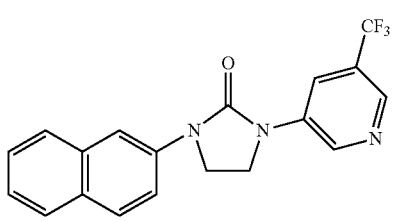

(I-79a)

1-Chloro-2-isocyanato-ethane (0.81 mL, 9.42 mmol) was added dropwise to a stirred solution of naphthalen-2-ylamine (900 mg, 6.28 mmol) in toluene (50 mL) over a period of 30 minutes at 0° C. The reaction temperature was maintained at room temperature for 5 hours. The reaction was monitored by TLC (5% MeOH in chloroform). The reaction mixture was filtered, washed with toluene and dried under reduced pressure to afford 1.3 g (83% yield) of 1-(2-chloro-ethyl)-3-naphthalen-2-yl-urea.

$^1$H NMR (DMSO-D$_6$, 300 MHz): δ 8.85 (s, 1H), 8.05 (d, 1H), 7.75 (m, 3H), 7.4 (m, 3H), 6.5 (t, 1H), 3.7 (t, 2H), 3.5 (q, 2H)

LCMS purity: 91.47%, m/z=249.1(M+1)

Step 2: Preparation of Intermediate 1-Naphthalen-2-yl-imidazolidin-2-one (I-79b)

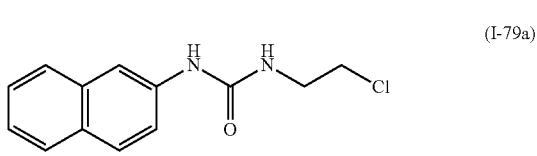

(I-79b)

1-(2-Chloro-ethyl)-3-naphthalen-2-yl-urea (I-79a: 750 mg, 3.01 mmol) in dry DMF (10 mL) was added to a stirred solution of sodium hydride (150 mg, 3.1 mmol) in THF (10 mL) at 0° C. The reaction temperature was maintained at room temperature for 30 minutes. The reaction was monitored by TLC (5% MeOH in chloroform, double run). The reaction mixture was quenched with MeOH at 0° C., concentrated under reduced pressure and partitioned between ice water and chloroform. The organic layer was dried over Na$_2$SO$_4$, and concentrated under reduced pressure to afford 600 mg (94% yield) of 1-naphthalen-2-yl-imidazolidin-2-one.

$^1$H NMR (DMSO-D$_6$, 300 MHz): δ 8.15 (dd, 1H), 7.85 (m, 3H), 7.7 (d, 1H), 7.5-7.3 (m, 2H), 7.05 (br s, 1H), 3.95 (t, 2H), 3.45 (t, 2H)

LCMS purity: 100%, m/z=213.1 (M+1)

Step 3: Preparation of 1-Naphthalen-2-yl-3-(5-trifluoromethyl-pyridin-3-β-imidazolidin-2-one (79A)

Copper iodide (12.6 mg, 0.066 mmol), trans-1,2-diamino cyclohexane (22.79 mg, 0.199 mmol) and potassium carbonate (183.5 mg, 1.32 mmol) were added to 1,4-dioxane (5 mL) and 3-bromo-5-trifluoromethyl-pyridine (150 mg, 0.66 mmol) previously degassed with argon (10 minutes). The reaction was purged with argon for a further 10 minutes, followed by the addition of 1-naphthalen-2-yl-imidazolidin-2-one (I-79b: 140 mg, 0.66 mmol) and the resulting mixture was heated to reflux at 110° C. for 15 hours. The reaction was monitored by TLC (50% ethyl acetate in hexane). The reaction mixture was filtered through celite and the bed was washed with chloroform. The organic layer was dried over Na$_2$O$_4$ and concentrated. Purification by column chromatography (using silica gel of mesh size of 60-120, 30% EtOAc in hexane as eluant) afforded 120 mg (52% yield) of 1-naphthalen-2-yl-3-(5-trifluoromethyl-pyridin-3-yl)-imidazolidin-2-one.

$^1$H NMR (DMSO-D$_6$, 300 MHz): δ 9.2 (d, 1H), 8.6 (d, 2H), 8.1 (dd, 1H), 8-7.86 (m, 4H), 7.56-7.4 (m, 2H), 4.1 (s, 4H)

LCMS purity: 94.5%, m/z=357.9 (M+1)
HPLC: 97.34%

Example 80

Preparation of 1-(5-Chloro-pyridin-3-O-3-naphthalen-2-yl-imidazolidin-2-one (80A)

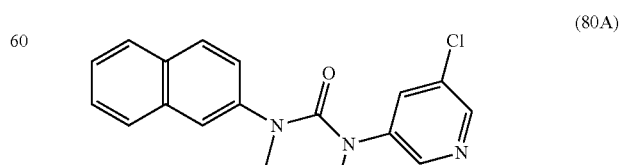

(80A)

Using the same reaction conditions as in Example 79, 1-naphthalen-2-yl-imidazolidin-2-one (I-79b: 110 mg, 0.5196 mmol) was reacted with 3-bromo-5-chloro-pyridine (100 mg, 0.5196 mmol), 1,4-dioxane (5 mL), copper iodide (9.89 mg, 0.05196 mmol), trans-1,2-diamino cyclohexane (17.84 mg, 0.1558 mmol) and potassium carbonate (143.5 mg, 1.039 mmol) to afford the crude product. Purification by column chromatography on silica gel (30% EtOAc in hexane) afforded 35 mg of the product (21.45% yield).

$^1$H NMR (DMSO-D$_6$, 300 MHz): δ 8.83 (d, 1H), 8.35-8.25 (m, 2H), 8.15-8.05 (m, 1H), 7.95-7.85 (m, 4H), 7.55-7.4 (m, 2H), 4.25-4.1 (m, 2H), 4.05-4.0 (m, 2H)

LCMS purity: 97.21%, m/z=323.9 (M+1)
HPLC: 96.37%

Example 81

Preparation of 1-(5-Fluoro-pyridin-3-yl)-3-naphthalen-2-yl-imidazolidin-2-one (81A)

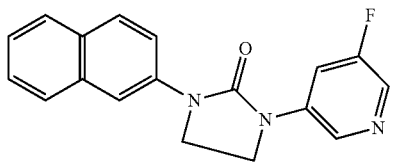

(81A)

Using the same reaction conditions as in Example 79, 1-naphthalen-2-yl-imidazolidin-2-one (I-79b: 120 mg, 0.5681 mmol) was reacted with 3-bromo-5-fluoro-pyridine (100 mg, 0.5681 mmol), 1,4-dioxane (5 mL), copper iodide (10.82 mg, 0.05681 mmol), trans-1,2-diamino cyclohexane (19.51 mg, 0.1704 mmol) and potassium carbonate (157.07 mg, 1.1362 mmol) to afford the crude product. Purification by column chromatography on silica gel (30% EtOAc in hexane) afforded 100 mg of the product (57.15% yield).

$^1$H NMR (DMSO-D$_6$, 300 MHz): δ 8.76 (t, 1H), 8.3 (d, 1H), 8.2-8.15 (m, 2H), 8.0-7.8 (m, 4H), 7.55-7.4 (m, 2H), 4.25-4.1 (m, 2H), 4.05-4.0 (m, 2H)

LCMS purity: 97.34%, m/z=308.2 (M+1)
HPLC: 97.51%

Example 82

Preparation of 1-(5-Methoxy-pyridin-3-yl)-3-naphthalen-2-yl-imidazolidin-2-one (82A)

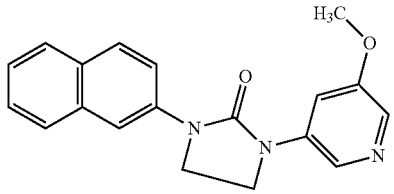

(82A)

Using the same reaction conditions as in Example 79, 1-naphthalen-2-yl-imidazolidin-2-one (I-79b: 112.7 mg, 0.5319 mmol) was reacted with 3-bromo-5-methoxy-pyridine (100 mg, 0.5319 mmol), 1,4-dioxane (5 mL), copper iodide (10.13 mg, 0.05319 mmol), trans-1,2-diamino cyclohexane (18.27 mg, 0.1595 mmol) and potassium carbonate (147.07 mg, 1.0638 mmol) to afford the crude product. Purification by column chromatography on silica gel (30% EtOAc in hexane) afforded 48 mg of the product (30.3% yield).

$^1$H NMR (DMSO-D$_6$, 300 MHz): δ 8.5-8.45 (br s, 1H), 8.2-8.1 (m, 1H), 8.1-8.0 (d, 1H), 8.0-7.8 (m, 5H), 7.55-7.4 (m, 2H), 4.2-4.0 (m, 4H), 3.9 (s, 3H)

LCMS purity: 95.38%, m/z=320.2 (M+1)
HPLC: 97.64%

Example 83

Preparation of 5-(3-Naphthalen-2-yl-2-oxo-imidazolidin-1-yl)-nicotinic Acid Methyl Ester (83A)

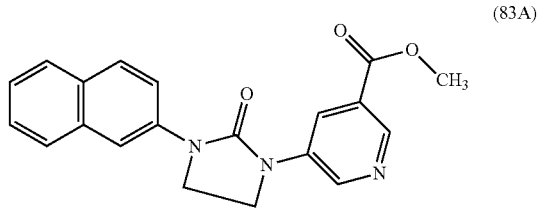

(83A)

Using the same reaction conditions as in Example 79, 1-naphthalen-2-yl-imidazolidin-2-one (I-79b: 100 mg, 0.4711 mmol) was reacted with 5-bromo-nicotinic acid methyl ester (112 mg, 0.5182 mmol), 1,4-dioxane (10 mL), copper iodide (11 mg), trans-1,2-diamino cyclohexane (22 mg) and potassium phosphate (200 mg, 0.9422 mmol) to afford the crude product. Purification by column chromatography on silica gel (80% EtOAc in hexane) afforded 44 mg of the product (26.99% yield).

$^1$H NMR (CDCl$_3$, 300 MHz): δ 9.1 (d, 1H), 8.99-8.92 (m, 1H), 8.58 (t, 1H), 8.05 (dd, 1H), 7.9-7.7 (m, 4H), 7.5-7.4 (m, 2H), 4.22-4.14 (m, 2H), 4.12-4.04 (m, 2H), 3.98 (s, 3H)

LCMS purity: 93.43%, m/z =348.0 (M+1)
HPLC: 92.04%

Example 84

Preparation of 1-benzothiazol-6-yl-3-(4-chloro-pyridin-3-O-imidazolidin-2-one (84A)

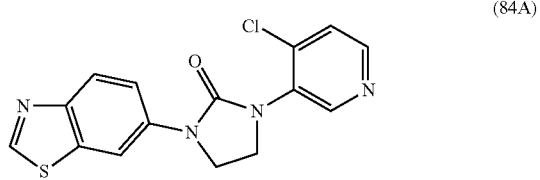

(84A)

Step 1: Preparation of Intermediate 1-benzothiazol-6-yl-3-(2-chloro-ethyl)-urea (I-84a)

1-Chloro-2-isocyanato-ethane (2.1 g, 19.99 mmol) was added drop wise to a stirred solution of benzothiazol-6-ylamine (2 g, 13.33 mmol) in toluene (80 mL) over a period of 15 minutes at 0° C. The reaction mixture was stirred at room temperature for 18 hours. The reaction was monitored by TLC (50% ethyl acetate in hexane). The reaction mixture was filtered, washed with toluene and dried under reduced pressure to afford 2.73 g (80.2% yield) of 1-benzothiazol-6-yl-3-(2-chloro-ethyl)-urea.

$^1$H NMR (DMSO-D$_6$, 300 MHz): δ 9.19 (s, 1H), 8.96 (s, 1H), 8.26 (d, 1H), 7.94 (d, 1H), 7.4 (dd, 1H), 6.55 (t, 1H), 3.72-3.64 (t, 2H), 3.5-3.42 (m, 2H)
LCMS purity: 85.64%, m/z=256.0 (M+1)

Step 2: Preparation of 1-benzothiazol-6-yl-imidazolidin-2-one (I-84b)

1-Benzothiazol-6-yl-3-(2-chloro-ethyl)-urea (I-84a: 2.7 g, 10.58 mmol) in dry DMF (80 mL) was added dropwise to a stirred mixture of sodium hydride (0.76 g, 31.74 mmol) in THF (100 mL) over a period of 20 minutes at 0° C. under nitrogen atmosphere. The reaction mixture was stirred at room temperature for 2 hours. The reaction was monitored by TLC (100% ethyl acetate). The reaction mixture was quenched with MeOH (6 mL), concentrated under reduced pressure, followed by the addition of ice. The precipitate was collected and dried under reduced pressure to afford 2.3 g (85.18% yield) of 1-benzothiazol-6-yl-imidazolidin-2-one as the required product.
$^1$H NMR (DMSO-D$_6$, 300 MHz): δ 9.24-9.2 (m, 1H), 8.24-8.19 (m, 1H), 8.04-7.84 (m, 2H), 7.1 (s, 1H), 3.95 (t, 2H), 3.45 (t, 2H)
CMS purity: 92.37%, m/z=220.0 (M+1)

Final Step: Preparation of 1-Benzothiazol-6-yl-3-(4-chloro-pyridin-3-yl)-imidazolidin-2-one (84A)

Using the same reaction conditions as in Example 14, 1-benzothiazol-6-yl-imidazolidin-2-one (I-84b: 0.150 g, 0.684 mmol) was reacted with 3-bromo-4-chloro-pyridine (0.157 g, 0.820 mmol), 1,4-dioxane (20 mL), copper iodide (0.012 g, 0.0684 mmol), trans-1,2-diamino cyclohexane (0.022 g, 0.20 mmol) and potassium phosphate (0.362 g, 1.71 mmol) to afford the crude product. Purification by column chromatography on silica gel (2% MeOH in CHCl$_3$) afforded 85 mg of the product (37.7% yield).
$^1$H NMR (DMSO-D$_6$, 300 MHz): δ 9.23 (s, 1H), 8.79 (s, 1H), 8.56 (d, 1H), 8.30 (d, 1H), 8.13 (d, 1H), 7.99 (d, 1H), 7.75 (d, 1H), 4.2-4.1 (m, 2H), 4.02-3.94 (m, 2H)
LCMS purity: 95.81%, m/z=331.0 (M+1)
HPLC: 95.36%

Example 85

Preparation of 1-(4-Methyl-pyridin-3-yl)-3-(2-pyrrolidin-1-yl-pyridin-4-yl)-imidazolidin-2-one (85A)

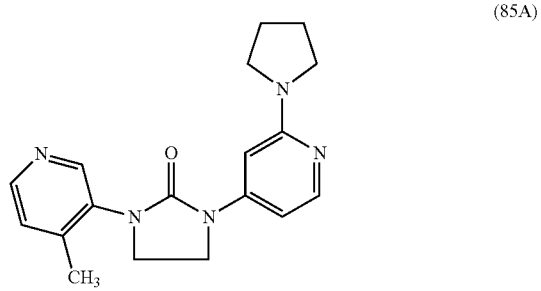

1-(2-Chloro-pyridin-4-yl)-3-(4-methyl-pyridin-3-yl)-imidazolidin-2-one (58A: 100 mg, 0.3463 mmol) and pyrrolidine (0.145 mL, 1.7317 mmol) were added to toluene previously degassed for 10 minutes. The resulting mixture was stirred for 5 minutes. This was followed by the addition of Pd(OAc)$_2$ (4 mg, 0.01732 mmol), diphenyl-phosphino-propane (14.3 mg, 0.03463 mmol) and potassium tertiary butoxide (66 mg, 0.6926 mmol) and stirring was continued for a further 10 minutes. The reaction mixture was heated to reflux for 16 hours. The reaction was monitored by TLC (10% MeOH in CHCl$_3$). The reaction mixture was cooled to room temperature, filtered and the filtrate was concentrated. Purification by column chromatography on silica gel (8% MeOH in chloroform) afforded 45 mg of the product (40% yield).
$^1$H NMR (CDCl$_3$, 300 MHz): δ 8.5 (s, 1H), 8.4 (d, 1H), 8.1 (d, 1H), 7.25-7.2 (m, 1H), 6.98-6.94 (br s, 1H), 6.6 (dd, 1H), 4.1-3.9 (m, 4H), 3.5 (t, 4H), 2.35 (s, 3H), 2.05-1.95 (m, 4H)
LCMS purity: 99.8%, m/z=324.2 (M+1)
HPLC: 84.5%

Example 86

Preparation of 1-(3-Chloro-2-fluoro-phenyl)-3-(4-methyl-pyridin-3-yl)-imidazolidin-2-one (86A)

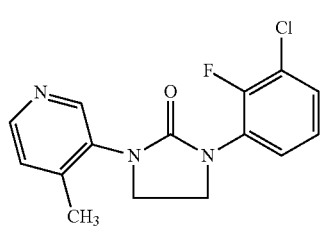

Using the same reaction conditions as described in Example 14, 1-(4-methyl-pyridin-3-yl)-imidazolidin-2-one (I-14b: 0.15 g, 0.847 mmol) was reacted with 1-bromo-3-chloro-2-fluoro-benzene (0.211 g, 1.016 mmol), 1,4-dioxane (20 mL), copper iodide (0.015 g, 0.084 mmol), trans-1,2-diamino cyclohexane (0.028 g, 0.254 mmol) and potassium phosphate (0.445 g, 2.1 mmol) to afford 8 mg of the product (0.03% yield).
$^1$H NMR (DMSO-D$_6$, 300 MHz): δ 8.68 (s, 1H), 8.49 (d, 1H), 7.6-7.45 (m, 3H), 7.3-7.22 (m, 1H), 4.09-3.95 (m, 4H), 2.36 (s, 3H)
LCMS purity: 96.83%, m/z=306.0 (M+1)
HPLC: 98.93%

Example 87

Preparation of 1-(4'-Fluoro-biphenyl-4-yl)-3-(4-methyl-pyridin-3-yl)-imidazolidin-2-one (87A)

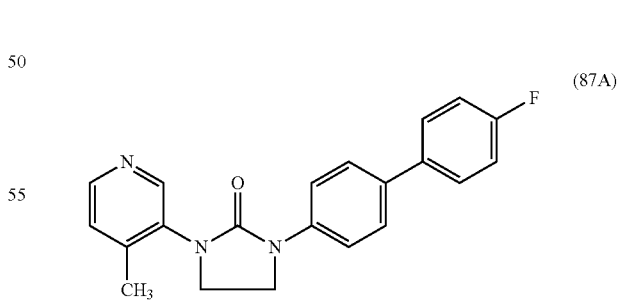

Using the same reaction conditions as in Example 14, 1-(4-methyl-pyridin-3-yl)-imidazolidin-2-one (I-14b: 100 mg, 0.5649 mmol) was reacted with 4'-fluoro-4-iodo-biphenyl (198 mg, 0.675 mmol), 1,4-dioxane (15 mL), copper iodide (0.0096 g, 0.0504 mmol), trans-1,2-diamino cyclohexane (0.0032 g, 0.0280 mmol) and potassium phosphate (0.359 g, 1.691 mmol) to afford the crude product. Purification by column chromatography on silica gel (1% MeOH in CHCl₃), followed by preparative HPLC afforded 12 mg of the product (12.35% yield).

¹H NMR (CDCl₃, 300 MHz): δ 8.55 (s, 1H), 8.42 (d, 1H), 7.7-7.64 (m, 2H), 7.6-7.5 (m, 3H), 7.24-7.2 (m, 2H), 7.15-7.05 (m, 2H), 4.15-4.05 (m, 2H), 4.0-3.9 (m, 2H), 2.38 (s, 3H)

LCMS purity: 98.86%, m/z =348.1 (M+1)
HPLC: 96.84%

Example 88

Preparation of 1-(3-Chloro-phenyl)-3-(4-methyl-pyridin-3-yl)-imidazolidin-2-one (88A)

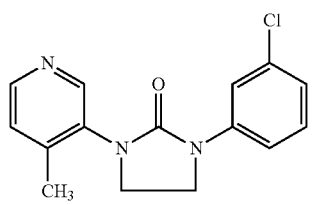

(88A)

Using the same reaction conditions as in Example 14, 1-(4-methyl-pyridin-3-yl)-imidazolidin-2-one (I-14b: 200 mg, 1.129 mmol) was reacted with 1-bromo-3-chloro-benzene (0.281 g, 1.471 mmol), 1,4-dioxane (20 mL), copper iodide (0.021 g, 0.110 mmol), trans-1,2-diamino cyclohexane (0.038 g, 0.333 mmol) and potassium phosphate (0.718 g, 3.386 mmol) to afford 192 mg of the product (59.25% yield).

¹H NMR (CDCl₃, 300 MHz): δ 8.52 (s, 1H), 8.42 (d, 1H), 7.7-7.6 (m, 1H), 7.55-7.41 (m, 1H), 7.32-7.19 (m, 2H), 7.1-7.0 (m, 1H), 4.1-3.9 (m, 4H), 2.38 (s, 3H)

LCMS purity: 99.41%, m/z =288.1 (M+1)
HPLC: 91.65%

Example 89

Preparation of 1-(4-Chloro-2-methyl-phenyl)-3-(4-methyl-pyridin-3-yl)-imidazolidin-2-one (89A)

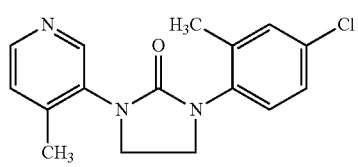

(89A)

Using the same reaction conditions as in Example 14, 1-(4-methyl-pyridin-3-yl)-imidazolidin-2-one (I-14b: 150 mg, 0.8474 mmol) was reacted with 1-bromo-4-chloro-2-methyl-benzene (174 mg, 0.8474 mmol), 1,4-dioxane (5 mL), copper iodide (16.19 mg, 0.08474 mmol), trans-1,2-diamino cyclohexane (29.1 mg, 0.2542 mmol) and potassium phosphate (539.63 g, 2.542 mmol) to afford 200 mg of the product (78.43% yield).

¹H NMR (DMSO-D₆, 300 MHz): δ 8.52 (s, 1H), 8.36 (d, 1H), 7.42-7.3 (m, 4H), 3.99-3.85 (m, 4H), 2.29 (d, 6H)

LCMS purity: 99.27%, m/z=301.8 (M+1)
HPLC: 96.77%

Example 90

Preparation of 1-(4-Fluoro-3-trifluoromethyl-phenyl)-3-(4-methyl-pyridin-3-yl)-imidazolidin-2-one (90A)

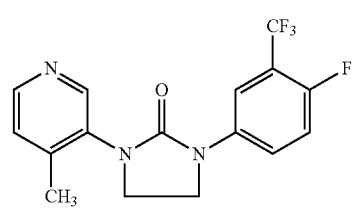

(90A)

Using the same reaction conditions as in Example 14, 1-(4-methyl-pyridin-3-yl)-imidazolidin-2-one (I-14b: 150 mg, 0.847 mmol) was reacted with 4-bromo-1-fluoro-2-trifluoromethyl-benzene (247 mg, 1.016 mmol), 1,4-dioxane (15 mL), copper iodide (16 mg, 0.0842 mmol), trans-1,2-diamino cyclohexane (0.0289 g, 0.2456 mmol) and potassium phosphate (0.538 g, 2.537 mmol) to afford the crude product. Purification by column chromatography on silica gel (1% MeOH in CHCl₃) afforded 173 mg of the product (60.27% yield).

¹H NMR (CDCl₃, 300 MHz): δ 8.52 (s, 1H), 8.44 (d, 1H), 7.9-7.75 (m, 2H), 7.3-7.19 (m, 2H), 4.12-3.9 (m, 4H), 2.39 (s, 3H)

LCMS purity: 92.1%, m/z=340.1 (M+1)
HPLC: 94.55%

Example 91

Preparation of 1-(3-Difluoromethyl-4-fluoro-phenyl)-3-(4-methyl-pyridin-3-yl)-imidazolidin-2-one (91A) and 1-(3-Difluoromethyl-4-fluoro-phenyl)-3-(4-methyl-pyridin-3-yl)-1,3-dihydro-imidazol-2-one (91B)

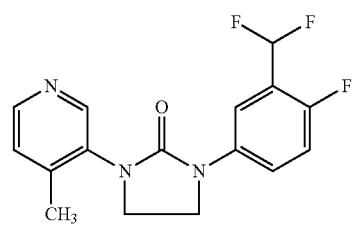

(91A)

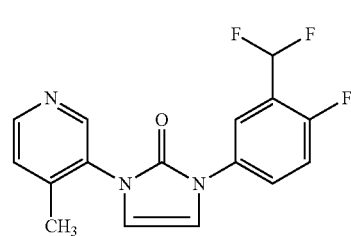

(91B)

Using the same reaction conditions as in Example 14, 1-(4-methyl-pyridin-3-yl)-imidazolidin-2-one (I-14b: 150 mg, 0.847 mmol) was reacted with 4-bromo-2-difluoromethyl-1-fluoro-benzene (228 mg, 1.016 mmol), 1,4-dioxane (10 mL), copper iodide (16.13 mg, 0.0847 mmol), trans-1,2-diamino cyclohexane (0.030 mL, 0.254 mmol) and potassium phosphate (539 mg, 2.54 mmol) to afford the crude product. Purification by column chromatography on silica gel (1% MeOH in CHCl$_3$), followed by preparative HPLC afforded 23 mg of compound 91A (8.45% yield) and 8 mg of compound 91B (2.94% yield).

Compound (91A):
$^1$H NMR (DMSO-D$_6$, 300 MHz): δ 8.55 (s, 1H), 8.4 (d, 1H), 8.0-7.9 (m, 1H), 7.8-7.69 (m, 1H), 7.49-7.32 (m, 2H), 7.22 (s, 1H), 4.14-3.89 (m, 4H), 2.28 (s, 3H)

LCMS purity: 95.56%, m/z=322.1 (M+1)

HPLC: 99.42%

Compound (91B):
$^1$H NMR (DMSO-D$_6$, 300 MHz): δ 8.59-8.45 (br s, 2H), 8.15-7.9 (m, 2H), 7.59-7.36 (m, 3H), 7.3-7.22 (br s, 1H), 7.15-7.02 (br s, 1H), 2.3 (s, 3H)

LCMS purity: 98.54%, m/z=320.1 (M+1)

HPLC: 98.02%

Example 92

Preparation of 1-(4-Methylpyridin-3-yl)-3-(5-methylthiophen-3-yl)-1H-imidazol-2(3H)-one (92A) and 1-(4-Methyl-pyridin-3-yl)-3-(5-methyl-thiophen-3-yl)-imidazolidin-2-one (92B)

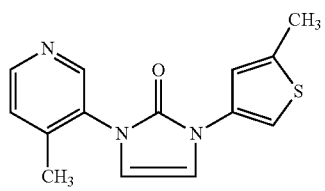

(92A)

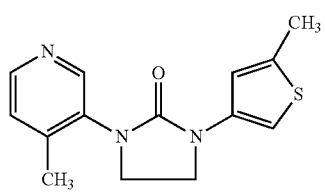

(92B)

Using the same reaction conditions as in Example 14, 1-(4-methyl-pyridin-3-yl)-imidazolidin-2-one (I-14b: 0.150 g, 0.847 mmol) was reacted with 4-bromo-2-methyl-thiophene (0.179 g, 1.016 mmol), 1,4-dioxane (20 mL), copper iodide (0.015 g, 0.084 mmol), trans-1,2-diamino cyclohexane (0.028 g, 0.254 mmol) and potassium phosphate (0.445 g, 2.1 mmol) to afford the crude product. Purification by column chromatography on silica gel (1% MeOH in CHCl$_3$), followed by preparative HPLC afforded 10 mg of the Compound 92A (4.3% yield) and 17 mg of Compound 92B (7.3% yield) was obtained.

Compound (92A):
$^1$H NMR (CDCl$_3$, 300 MHz): δ 8.5 (m, 2H), 7.26 (s, 2H), 7.1 (s, 1H), 6.75 (d, 1H), 6.44 (d, 1H), 2.5 (s, 3H), 2.35 (s, 3H)

LCMS purity: 98.71%, m/z=271.9 (M+1)

HPLC: 99.56%

Compound (92B):
$^1$H NMR (CDCl$_3$, 300 MHz): δ 8.52 (s, 1H), 8.4 (d, 1H), 7.35-7.19 (m, 2H), 6.6 (s, 1H), 4.05-3.89 (m, 4H), 2.5 (s, 3H), 2.35 (s, 3H)

LCMS purity: 99.44%, m/z =273.8 (M+1)

HPLC: 98.76%

Example 93

Preparation of 1-(2-Methyl-benzooxazol-5-yl)-3-(4-methyl-pyridin-3-yl)-imidazolidin-2-one (93A)

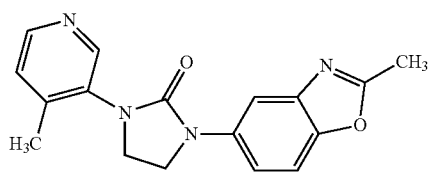

(93A)

Using the same reaction conditions as in Example 14, 1-(4-methyl-pyridin-3-yl)-imidazolidin-2-one (I-14b: 0.1 g, 0.00057 mol) was reacted with 5-bromo-2-methyl-benzooxazole (0.119 g, 0.000597 mol), 1,4-dioxane (20 mL), copper iodide (0.01 g, 0.000057 mol), trans-1,2-diamino cyclohexane (0.019 g, 0.00017 mol) and potassium phosphate (0.242 g, 0.00114 mol) to afford the crude product. Purification by column chromatography on silica gel (2% MeOH in CHCl$_3$), followed by preparative HPLC afforded 29 mg of the product (16% yield).

$^1$H NMR (CD$_3$OD, 300 MHz): δ 8.52 (s, 1H), 8.36 (d, 1H), 7.84 (d, 1H), 7.66-7.52 (m, 2H), 7.4 (d, 1H), 4.2-4.1 (m, 2H), 4.05-3.95 (m, 2H), 2.65 (s, 3H), 2.4 (s, 3H)

LCMS purity: 93.74%, m/z=309.1 (M+1)

HPLC: 99.08%

Example 94

Preparation of 1-Imidazo[1,2-a]pyridin-6-yl-3-(4-methyl-pyridin-3-yl)-imidazolidin-2-one (94A)

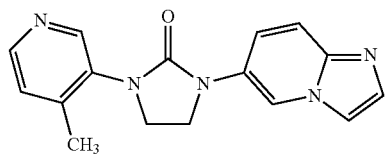

(94A)

Using the same reaction conditions as in Example 14, 1-(4-methyl-pyridin-3-yl)-imidazolidin-2-one (I-14b: 150 mg, 0.847 mmol) was reacted with 6-bromo-imidazo[1,2-a] pyridine (249.5 mg, 1.27 mmol), 1,4-dioxane (10 mL), copper iodide (16.13 mg, 0.0847 mmol), trans-1,2-diamino cyclohexane (0.03 mL, 0.254 mmol) and potassium phosphate (539 mg, 2.54 mmol) to afford the crude product. Purification by column chromatography on silica gel (5% MeOH in CHCl$_3$) afforded 110 mg of the product (44.35% yield).

$^1$H NMR (DMSO-D$_6$, 300 MHz): δ 8.75-8.7 (m, 1H), 8.55 (s, 1H), 8.4 (d, 1H), 7.98 (s, 1H), 7.8 (dd, 1H), 7.65-7.55 (m, 2H), 7.36 (d, 1H), 4.12-3.9 (m, 4H), 2.3 (s, 3H)

LCMS purity: 94.08%, m/z=294.1 (M+1)

HPLC: 92.22%

Example 95

Preparation of 1-(3-Methyl-1H-indazol-5-yl)-3-(4-methyl-pyridin-3-yl)-imidazolidin-2-one (95A)

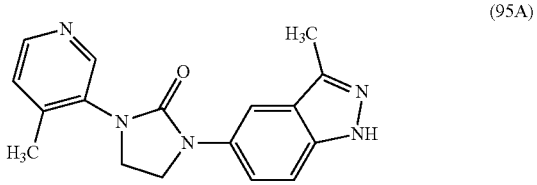

(95A)

Using the same reaction conditions as in Example 14, 1-(4-methyl-pyridin-3-yl)-imidazolidin-2-one (I-14b: 500 mg, 2.8248 mmol) was reacted with 1-(5-bromo-2-fluoro-phenyl)-ethanone (610 mg, 2.8248 mmol), 1,4-dioxane (15 mL), copper iodide (53.81 mg, 0.28248 mmol), trans-1,2-diamino cyclohexane (97.03 mg, 0.8474 mmol) and potassium phosphate (1.798 g, 8.474 mmol) to afford the crude product. Purification by column chromatography on silica gel (2% MeOH in CHCl₃) afforded 170 mg of 1-(3-acetyl-4-fluoro-phenyl)-3-(4-methyl-pyridin-3-yl)-imidazolidin-2-one (19.31% yield).

$^1$H NMR (CDCl₃, 300 MHz): δ 8.5 (d, 1H), 8.4-8.3 (m, 1H), 7.7-7.6 (m, 1H), 7.3-7.1 (m, 2H), 4.2-3.9 (m, 4H), 2.7 (d, 3H), 2.35 (s, 3H)

LCMS purity: 99.03%, m/z =314.0 (M+1)

1-(3-Acetyl-4-fluoro-phenyl)-3-(4-methyl-pyridin-3-yl)-imidazolidin-2-one (160 mg, 0.513 mmol) in hydrazine hydrate (5 mL) was taken in a reaction flask and the flask was heated to reflux and maintained for 21 hours. The reaction was monitored by TLC (10% MeOH in CHCl₃). The reaction mixture was partitioned between ethylacetate and water. The organic layer was dried over Na₂SO₄, filtered and the filtrate was concentrated. Purification by column chromatography on silica gel (3% MeOH in CHCl₃), followed by preparative HPLC afforded 22 mg of the product (14% yield).

$^1$H NMR (CDCl₃, 300 MHz): δ 8.55 (s, 1H), 8.44-8.4 (d, 1H), 7.8 (d, 1H), 7.7 (s, 1H), 7.44-7.4 (d, 1H), 7.25-7.2 (m, 1H), 4.25-4.2 (m, 2H), 4.02-3.9 (m, 2H), 2.6 (s, 3H), 2.4 (s, 3H)

LCMS purity: 98.92%, m/z =308.0 (M+1)
HPLC: 93.18%

Example 96

Preparation of N-{4-[3-(4-Methyl-pyridin-3-O-2-oxo-imidazolidin-1-yl]-pyridin-2-yl}-acetamide (96A)

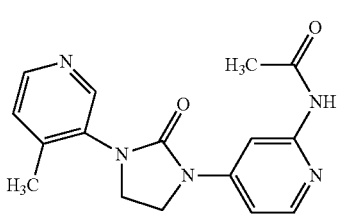

(96A)

Using the same reaction conditions as in Example 14, 1-(4-methyl-pyridin-3-yl)-imidazolidin-2-one (I-14b: 150 mg, 0.8465 mmol) was reacted with N-(4-bromo-pyridin-2-yl)-acetamide (240 mg, 1.12 mmol), 1,4-dioxane (25 mL), copper iodide (16 mg, 0.084 mmol), trans-1,2-diamino cyclohexane (29.4 mg, 0.254 mmol) and potassium phosphate (449.7 mg, 2.118 mmol) to afford the crude product. Purification by column chromatography on silica gel (5% MeOH in CHCl₃) afforded 120 mg of the product (45.5% yield).

$^1$H NMR (CDCl₃, 300 MHz): δ 8.52 (s, 1H), 8.45 (d, 1H), 8.19-8.05 (m, 2H), 8.02-7.9 (m, 2H), 7.25-7.2 (m, 1H), 4.2-4.1 (m, 2H), 4.0-3.9 (m, 2H), 2.35 (s, 3H), 2.22 (s, 3H)

LCMS purity: 98.96%, m/z =312.2 (M+1)
HPLC: 86.35%

Example 97

Preparation of 1-(4-Methoxy-thieno[3,2-c]pyridin-2-yl)-3-(4-methyl-pyridin-3-yl)-imidazolidin-2-one (97A)

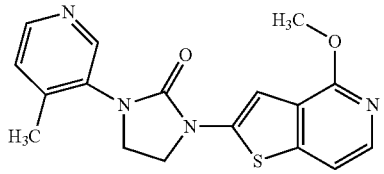

(97A)

Using the same reaction conditions as in Example 14, 1-(4-methyl-pyridin-3-yl)-imidazolidin-2-one (I-14b: 62 mg, 0.3498 mmol) was reacted with 2-bromo-4-methoxy-thieno[3,2-c]pyridine (85.4 mg, 0.3498 mmol), 1,4-dioxane (50 mL), copper iodide (6.6 mg, 0.03498 mmol), trans-1,2-diamino cyclohexane (12 mg, 0.1049 mmol) and potassium phosphate (185.6 mg, 0.8747 mmol) to afford the crude product. Purification by column chromatography on silica gel (1% MeOH in CHCl₃) afforded 50 mg of the product (40% yield).

$^1$H NMR (DMSO-D₆, 300 MHz): δ 8.59 (s, 1H), 8.42 (d, 1H), 7.88 (d, 1H), 7.5 (d, 1H), 7.39 (d, 1H), 6.72 (s, 1H), 4.25-4.15 (m, 2H), 4.1-4.04 (m, 2H), 4.0 (s, 3H), 2.3 (s, 3H)

LCMS purity: 97.46%, m/z =341.1 (M+1)
HPLC: 93.75%

Example 98

Preparation of 1-(4-Chloro-thieno[3,2-c]pyridin-2-yl)-3-(4-methyl-pyridin-3-yl)-imidazolidin-2-one (98A)

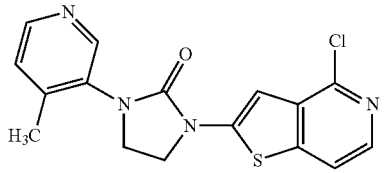

(98A)

Using the same reaction conditions as in Example 14, 1-(4-methyl-pyridin-3-yl)-imidazolidin-2-one (I-14b: 100 mg, 0.5643 mmol) was reacted with 2-bromo-4-chloro-thieno[3,2-c]pyridine (141.3 mg, 0.5643 mmol), 1,4-dioxane (20 mL), copper iodide (10.75 mg, 0.05643 mmol), trans-1, 2-diamino cyclohexane (19.38 mg, 0.1693 mmol) and potassium phosphate (299 mg, 1.4108 mmol) to afford the crude product. Purification by column chromatography on silica gel (2% MeOH in CHCl₃) afforded 43 mg of the product (22.16% yield).

¹H NMR (DMSO-D₆, 300 MHz): δ 8.7 (s, 1H), 8.55-8.49 (m, 1H), 8.1 (d, 1H), 7.98 (d, 1H), 7.56 (d, 1H), 6.75 (s, 1H), 4.3-4.2 (m, 4H), 2.38 (s, 3H)

LCMS purity: 91.81%, m/z=345.0 (M+1)
HPLC: 91.32%

Example 99

Preparation of 1-(4-Chloro-thieno[3,2-c]pyridin-3-yl)-3-(4-methyl-pyridin-3-yl)-imidazolidin-2-one (99A)

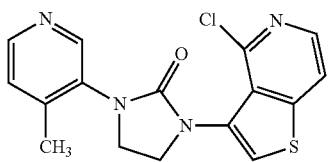

Using the same reaction conditions as in Example 14, 1-(4-methyl-pyridin-3-yl)-imidazolidin-2-one (I-14b: 100 mg, 0.5643 mmol) was reacted with 3-bromo-4-chloro-thieno[3,2-c]pyridine (141.3 mg, 0.5643 mmol), 1,4-dioxane (20 mL), copper iodide (10.75 mg, 0.05643 mmol), trans-1,2-diamino cyclohexane (19.38 mg, 0.1693 mmol) and potassium phosphate (299 mg, 1.4108 mmol) to afford the crude product. Purification by preparative HPLC afforded 10 mg of the product (10% yield).

¹H NMR (DMSO-D₆, 300 MHz): δ 8.68 (s, 1H), 8.5 (d, 1H), 8.1 (d, 1H), 7.98 (d, 1H), 7.54 (d, 1H), 6.75 (s, 1H), 4.3-4.2 (m, 2H), 4.12-4.05 (m, 2H), 2.36 (s, 3H)

LCMS purity: 98.12%, m/z =345.0 (M+1)
HPLC: 99.28%

Example 100

Preparation of 1-(4-Methyl-pyridin-3-yl)-3-(2-methyl-pyridin-4-yl)-imidazolidin-2-one (100A)

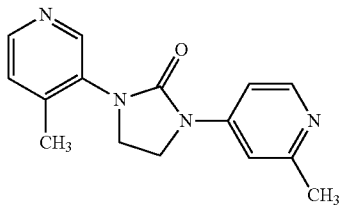

Using the same reaction conditions as in Example 14, 1-(4-methyl-pyridin-3-yl)-imidazolidin-2-one (I-14b: 100 mg, 0.5649 mmol) was reacted with 4-bromo-2-methyl-pyridine (97 mg, 0.5649 mmol), 1,4-dioxane (5 mL), copper iodide (10.76 mg, 0.05649 mmol), trans-1,2-diamino cyclohexane (19.4 mg, 0.1694 mmol) and potassium phosphate (359.58 mg, 1.694 mmol) to afford the crude product. Purification by column chromatography on silica gel (2% MeOH in CHCl₃) afforded 132 mg of the product (88.0% yield).

¹H NMR (DMSO-D₆, 300 MHz): δ 8.5-8.3 (m, 3H), 7.5-7.3 (m, 3H), 4.1-3.9 (m, 4H), 2.3 (s, 3H), 2.2 (s, 3H)

LCMS purity: 92.28%, m/z=269.0 (M+1)
HPLC: 97.29%

Example 101

Preparation of 1-(3-Methyl-benzo[d]isoxazol-5-yl)-3-(4-methyl-pyridin-3-yl)-imidazolidin-2-one (101A)

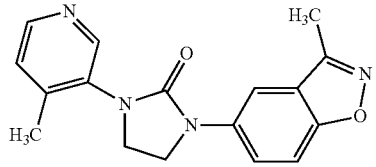

Using the same reaction conditions as in Example 14, 1-(4-methyl-pyridin-3-yl)-imidazolidin-2-one (I-14b: 0.500 g, 2.82 mmol) was reacted with 1-(5-bromo-2-fluoro-phenyl)-ethanone (0.612 g, 2.82 mmol), 1,4-dioxane (30 mL), copper iodide (53.81 mg, 0.282 mmol), trans-1,2-diamino cyclohexane (97.03 mg, 0.846 mmol) and potassium phosphate (1.79 g, 8.46 mmol) to afford the crude product. Purification by column chromatography on silica gel (2% MeOH in CHCl₃) afforded 220 mg of 1-(3-Acetyl-4-fluoro-phenyl)-3-(4-methyl-pyridin-3-yl)-imidazolidin-2-one (24.9% yield).

¹H NMR (DMSO-D₆, 300 MHz): δ 8.52 (s, 1H), 8.38 (d, 1H), 8.0-7.84 (m, 2H), 7.4-7.32 (m, 2H), 4.1-4.0 (m, 2H), 3.95-3.9 (m, 2H), 2.6 (d, 3H), 2.29 (s, 3H)

LCMS purity: 99.03%, m/z=314.0 (M+1) Hydroxylamine hydrochloride (145 mg, 2.106 mmol) in pyridine (5 mL) was added to 1-(3-acetyl-4-fluoro-phenyl)-3-(4-methyl-pyridin-3-yl)-imidazolidin-2-one (220 mg, 0.702 mmol) under nitrogen atmosphere. The resulting mixture was stirred at room temperature for 18 hours. The reaction was monitored by TLC (10% MeOH in CHCl₃). The reaction mixture was partitioned between ethylacetate and water. The organic layer was dried over Na₂SO₄ and concentrated to afford 220 mg of 1-[4-Fluoro-3-(1-hydroxyimino-ethyl)-phenyl]-3-(4-methyl-pyridin-3-yl)-imidazolidin-2-one (90% yield).

LCMS purity: 98.93%, m/z=329.0 (M+1)

1-[4-Fluoro-3-(1-hydroxyimino-ethyl)-phenyl]-3-(4-methyl-pyridin-3-yl)-imidazolidin-2-one (220 mg, 0.670 mmol) in DMF (5 mL) was added to a stirred mixture of NaH (19 mg, 0.804 mmol) in DMF (2 mL) under nitrogen atmosphere at 0° C. The resulting mixture was stirred at room temperature for 21 hours. The reaction was monitored by TLC (10% MeOH in CHCl₃). The reaction mixture was partitioned between ethylacetate and ice water. The organic layer was washed with brine solution, dried over Na₂SO₄ and concentrated. Purification by column chromatography on silica gel (1% MeOH in CHCl₃) afforded 28 mg of the product (14.5% yield).

¹H NMR (CDCl₃, 300 MHz): δ 8.6-8.5 (br s, 1H), 8.5-8.4 (br s, 1H), 7.9 (d, 1H), 7.78 (dd, 1H), 7.55 (d, 1H), 7.26-7.24 (m, 1H), 4.2-4.1 (m, 2H), 4.05-3.95 (m, 2H), 2.59 (s, 3H), 2.39 (s, 3H)

LCMS purity: 95.75%, m/z=309.0 (M+1)
HPLC: 88.61%

Example 102

Preparation of 1-(3-Methyl-1H-indazol-6-yl)-3-(4-methyl-pyridin-3-yl)-imidazolidin-2-one (102A)

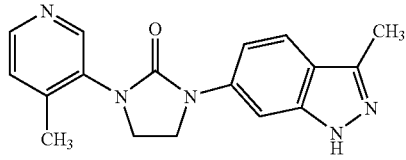

Using the same reaction conditions as in Example 14, 1-(4-methyl-pyridin-3-yl)-imidazolidin-2-one (I-14b: 500 mg, 2.8216 mmol) was reacted with 1-(4-bromo-2-fluoro-phenyl)-ethanone (679.9 mg, 3.1038 mmol), 1,4-dioxane (50 mL), copper iodide (53.6 mg, 0.28216 mmol), trans-1,2-diamino cyclohexane (97.09 mg, 0.84650 mmol) and potassium phosphate (1.49 g, 7.0541 mmol) to afford the crude product. Purification by column chromatography on silica gel (2% MeOH in $CHCl_3$) afforded 780 mg of 1-(4-acetyl-3-fluoro-phenyl)-3-(4-methyl-pyridin-3-yl)-imidazolidin-2-one (88.2% yield).

$^1$H NMR (DMSO-$D_6$, 300 MHz): δ 8.55 (s, 1H), 8.4 (d, 1H), 7.85 (t, 1H), 7.68 (dd, 1H), 7.52 (dd, 1H), 7.37 (d, 1H), 4.15-3.9 (m, 4H), 2.56 (s, 3H), 2.29 (s, 3H)

Hydrazine hydrate (10 mL) was added to 1-(4-acetyl-3-fluoro-phenyl)-3-(4-methyl-pyridin-3-yl)-imidazolidin-2-one (380 mg, 1.2128 mmol) under nitrogen atmosphere. The resulting mixture was stirred at 120° C. for 12 hours, cooled to room temperature and continued stirring for the next 12 hours. The reaction was monitored by TLC (10% MeOH in $CHCl_3$). The reaction mixture was partitioned between ethylacetate and ice water. The organic layer was washed with brine solution, dried over $Na_2SO_4$ and concentrated. Purification by column chromatography on silica gel (4% MeOH in $CHCl_3$) afforded 240 mg of the product (64.5% yield).

$^1$H NMR (DMSO-$D_6$, 300 MHz): δ 8.84 (s, 1H), 8.65-8.55 (m, 1H), 7.8-7.64 (m, 3H), 7.55-7.45 (d, 1H), 4.25-3.95 (m, 4H), 2.49 (d, 6H)

LCMS purity: 94.698%, m/z=308.2 (M+1)

HPLC: 96.12%

Example 103

Preparation of 2-Fluoro-5-[3-(4-methyl-pyridin-3-yl)-2-oxo-imidazolidin-1-yl]-benzonitrile (103A)

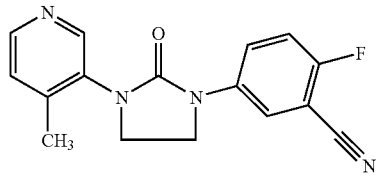

(103A)

Using the same reaction conditions as in Example 14, 1-(4-methyl-pyridin-3-yl)-imidazolidin-2-one (I-14b: 100 mg, 0.5643 mmol) was reacted with 5-bromo-2-fluoro-benzonitrile (124 mg, 0.6199 mmol), 1,4-dioxane (20 mL), copper iodide (10.7 mg, 0.056 mmol), trans-1,2-diamino cyclohexane (19.4 mg, 0.169 mmol) and potassium phosphate (300 mg, 1.413 mmol) to afford the crude product. Purification by column chromatography on silica gel (2% MeOH in $CHCl_3$) afforded 110 mg of the product (65.7% yield).

$^1$H NMR (DMSO-$D_6$, 300 MHz): δ 8.6-8.5 (br s, 1H), 8.4 (s, 1H), 8.1-8.0 (m, 2H), 7.6-7.5 (t, 1H), 7.4-7.3 (m, 1H), 4.1-3.9 (m, 4H), 2.3 (s, 3H)

LCMS purity: 98.73%, m/z=297.2 (M+1)

HPLC: 97.3%

Example 104

Preparation of 1-(2-Methyl-imidazo[1,2-a]pyridin-6-O-3-(4-methyl-pyridin-3-yl)-imidazolidin-2-one (104A)

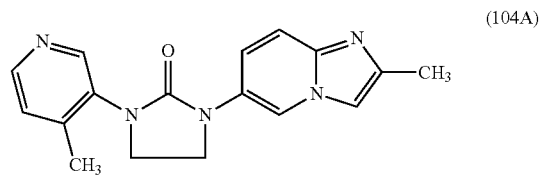

(104A)

Using the same reaction conditions as in Example 14, 1-(4-methyl-pyridin-3-yl)-imidazolidin-2-one (I-14b: 118 mg, 0.6633 mmol) was reacted with 6-bromo-2-methyl-imidazo[1,2-a]pyridine (140 mg, 0.6633 mmol), 1,4-dioxane (10 mL), copper iodide (14 mg), trans-1,2-diamino cyclohexane (28 mg) and potassium phosphate (422 mg, 1.9899 mmol) to afford the crude product. Purification by column chromatography on silica gel (10% MeOH in DCM), followed by preparative HPLC afforded 13 mg of the product (6.4% yield).

$^1$H NMR (DMSO-$D_6$, 300 MHz): δ 8.6 (d, 2H), 8.4 (d, 1H), 7.75-7.65 (m, 2H), 7.5 (d, 1H), 7.36 (d, 1H), 4.1-3.9 (m, 4H), 2.4-2.2 (d, 6H), LCMS purity: 99.71%, m/z=308.1 (M+1)

HPLC: 98.04%

Example 105

Preparation of 1-(2-Methyl-benzothiazol-6-yl)-3-(4-methyl-pyridin-3-yl)-imidazolidin-2-one (105A)

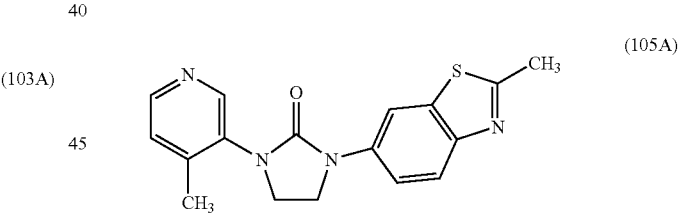

(105A)

Using the same reaction conditions as in Example 14, 1-(4-methyl-pyridin-3-yl)-imidazolidin-2-one (I-14b: 100 mg, 0.5643 mmol) was reacted with 6-iodo-2-methyl-benzothiazole (154 mg, 0.5598 mmol), 1,4-dioxane (20 mL), copper iodide (10.7 mg, 0.056 mmol), trans-1,2-diamino cyclohexane (19.4 mg, 0.169 mmol) and potassium phosphate (300 mg, 1.413 mmol) to afford the crude product. Purification by column chromatography on silica gel (5% MeOH in $CHCl_3$) afforded 115 mg of the product (62.8% yield).

$^1$H NMR ($CDCl_3$, 300 MHz): δ 8.54 (s, 1H), 8.42 (d, 1H), 8.24 (s, 1H), 7.9 (d, 1H), 7.56 (d, 1H), 7.26-7.2 (m, 1H), 4.2-3.9 (m, 4H), 2.82 (s, 3H), 2.35 (s, 3H)

LCMS purity: 96.39%, m/z =324.8 (M+1)

HPLC: 96.16%

Example 106

Preparation of 3-[3-(4-Methyl-pyridin-3-yl)-2-oxo-imidazolidin-1-yl]-benzonitrile (106A)

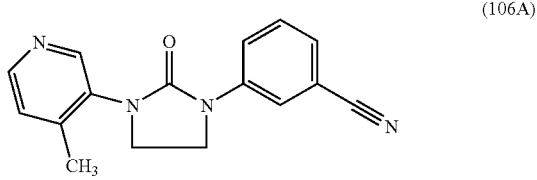
(106A)

Using the same reaction conditions as in Example 14, 1-(4-methyl-pyridin-3-yl)-imidazolidin-2-one (I-14b: 100 mg, 0.5643 mmol) was reacted with 3-bromo-benzonitrile (115 mg, 0.6317 mmol), 1,4-dioxane (20 mL), copper iodide (10.7 mg, 0.0564 mmol), trans-1,2-diamino cyclohexane (19.4 mg, 0.169 mmol) and potassium phosphate (300 mg, 1.413 mmol) to afford the crude product. Purification by column chromatography on silica gel (2% MeOH in CHCl$_3$), followed by preparative HPLC afforded 80 mg of the product (49% yield).

$^1$H NMR (DMSO-d$_6$, 300 MHz): S 8.75 (s, 1H), 8.55 (s, 1H), 8.1-7.9 (m, 2H), 7.7-7.5 (m, 3H), 4.2-4.05 (m, 4H), 2.58 (s, 3H)

LCMS purity: 99.71%, m/z =279.0 (M+1)
HPLC: 95.64%

Example 107

Preparation of 1-(1H-Indol-3-yl)-3-(4-methyl-pyridin-3-yl)-imidazolidin-2-one (107A)

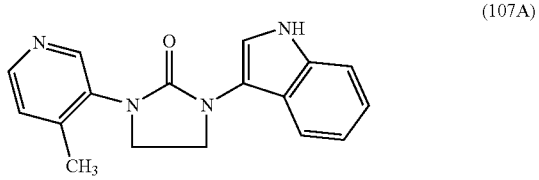
(107A)

Using the same reaction conditions as in Example 14, 1-(4-methyl-pyridin-3-yl)-imidazolidin-2-one (I-14b: 150 mg, 0.00084 mol) was reacted with 3-bromo-1-(toluene-4-sulfonyl)-1H-indole (292 mg, 0.00084 mol), 1,4-dioxane (20 mL), copper iodide (0.015 g, 0.000084 mol), trans-1,2-diamino cyclohexane (0.028 g, 0.00025 mol) and potassium phosphate (356 mg, 0.00168 mol) to afford the crude product. Purification by column chromatography on silica gel (2% MeOH in CHCl$_3$), followed by preparative HPLC afforded 110 mg of 1-(4-Methyl-pyridin-3-yl)-3-[1-(toluene-4-sulfonyl)-1H-indol-3-yl]-imidazolidin-2-one (33.66% yield).

LCMS purity: 92.68%, m/z=446.9 (M+1) 10% NaOH solution (10 mL) was added to a solution of 1-(4-methyl-pyridin-3-yl)-3-[1-(toluene-4-sulfonyl)-1H-indol-3-yl]-imidazolidin-2-one (110 mg, 0.0002 mol) in ethanol (10 mL) and the resulting mixture was stirred at 90° C. for 1 hour. The reaction was monitored by TLC (10% MeOH in CHCl$_3$). The reaction mixture was partitioned between ethylacetate and ice water. The organic layer was washed with brine solution, dried over Na$_2$SO$_4$ and concentrated. Purification by column chromatography on silica gel (2% MeOH in CHCl$_3$) afforded 50 mg of the product (86.2% yield).

$^1$H NMR (DMSO-D$_6$, 300 MHz): δ 11.1 (s, 1H), 8.55 (s, 1H), 8.4-8.3 (m, 1H), 7.64 (d, 1H), 7.5-7.3 (m, 3H), 7.2-6.95 (m, 2H), 4.1-3.9 (m, 4H), 2.35 (s, 3H)

LCMS purity: 96.36%, m/z=292.8 (M+1)
HPLC: 88.07%

Example 108

Preparation of 1-(1H-Benzoimidazol-5-yl)-3-(4-methyl-pyridin-3-yl)-imidazolidin-2-one (108A)

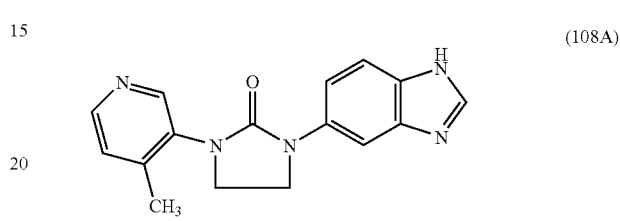
(108A)

Using the same reaction conditions as in Example 14, 1-(4-methyl-pyridin-3-yl)-imidazolidin-2-one (I-14b: 150 mg, 0.8474 mmol) was reacted with 5-bromo-1-(2-trimethylsilanyl-ethoxymethyl)-1H-benzoimidazole (332 mg, 1.0152 mmol), 1,4-dioxane (15 mL), copper iodide (16 mg, 0.0842 mmol), trans-1,2-diamino cyclohexane (28 mg, 0.2456 mmol) and potassium phosphate (538 mg, 2.5377 mmol) to afford the crude product. Purification by column chromatography on silica gel (1% MeOH in CHCl$_3$) afforded 270 mg of 1-(4-Methyl-pyridin-3-yl)-3-[1-(2-trimethylsilanyl-ethoxymethyl)-1H-benzoimidazol-5-yl]-imidazolidin-2-one (75.41% yield).

LCMS purity: 98.46%, m/z =424.1 (M+1)

1-(4-Methyl-pyridin-3-yl)-3-[1-(2-trimethylsilanyl-ethoxymethyl)-1H-benzoimidazol-5-yl]-imidazolidin-2-one (260 mg, 0.6138 mmol) in 1,4-dioxane hydrochloride (15 mL) was taken in a reaction flask and the flask was stirred at room temperature for 12 hours. The reaction was monitored by TLC (10% MeOH in CHCl$_3$). The reaction mixture was concentrated under reduced pressure and the concentrate was washed with diethyl ether and hexane to afford 26 mg of the product (46.8% yield).

$^1$H NMR (DMSO-D$_6$, 300 MHz): δ 8.6-8.55 (br s, 1H), 8.45-8.35 (m, 1H), 8.25-8.15 (br s, 1H), 7.85-7.8 (br s, 1H), 7.65-7.5 (m, 2H), 7.4-7.35 (m, 1H), 4.2-3.9 (m, 4H), 2.3 (s, 3H)

LCMS purity: 99.71%, m/z =294.0 (M+1)
HPLC: 93.74%

Example 109

Preparation of 1-Benzo[b]thiophen-3-yl-3-(4-methyl-pyridin-3-yl)-imidazolidin-2-one (109A)

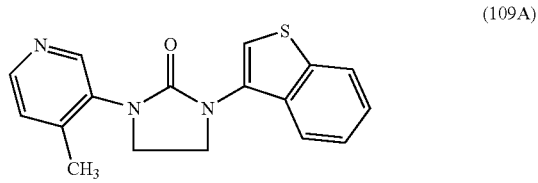
(109A)

Using the same reaction conditions as in Example 14, 1-(4-methyl-pyridin-3-yl)-imidazolidin-2-one (I-14b: 150 mg, 0.8465 mmol) was reacted with 3-bromo-benzo[b]thiophene (216.3 mg, 1.0158 mmol), 1,4-dioxane (50 mL), copper iodide (10.7 mg, 0.0865 mmol), trans-1,2-diamino cyclohexane (29 mg, 0.2539 mmol) and potassium phosphate (449.1 mg, 2.1162 mmol) to afford the crude product. Purification by column chromatography on silica gel (2% MeOH in CHCl$_3$) afforded 95 mg of the product (36.3% yield).

$^1$H NMR (DMSO-d$_6$, 300 MHz): δ 8.65-8.55 s, 1H), 8.45-8.3 (br s, 1H), 8.05-7.8 (m, 2H), 7.69 (s, 1H), 7.5-7.3 (m, 3H), 4.15-3.9 (m, 4H), 2.35 (s, 3H)

LCMS purity: 93.71%, m/z =310.0 (M+1)
HPLC: 96.65%

Example 110

Preparation of 1-(4-Methoxy-thieno[3,2-c]pyridin-3-yl)-3-(4-methyl-pyridin-3-yl)-imidazolidin-2-one (110A)

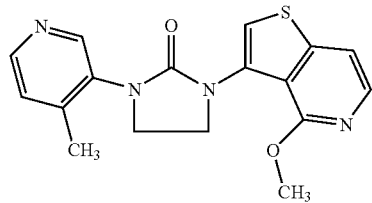

(110A)

Using the same reaction conditions as in Example 14, 1-(4-methyl-pyridin-3-yl)-imidazolidin-2-one (I-14b: 65 mg, 0.3668 mmol) was reacted with 3-bromo-4-methoxy-thieno[3,2-c]pyridine (98.4 mg, 0.4034 mmol), 1,4-dioxane (20 mL), copper iodide (6.9 mg, 0.03668 mmol), trans-1,2-diamino cyclohexane (12.6 mg, 0.1100 mmol) and potassium phosphate (194.6 mg, 0.91704 mmol) to afford the crude product. Purification by column chromatography on silica gel (2% MeOH in CHCl$_3$) afforded 50 mg of the product (40.3% yield).

$^1$H NMR (DMSO-d$_5$, 300 MHz): δ 8.65-8.3 (m, 2H), 8.05 (d, 1H), 7.8 (s, 1H), 7.65 (d, 1H), 7.45-7.4 (br s, 1H), 4.1-3.9 (m, 7H), 2.36 (s, 3H)

LCMS purity: 99.04%, m/z=340.9 (M+1)
HPLC: 95.61

Example 111

Preparation of 1-(3-Methyl-benzo[d]isoxazol-6-yl)-3-(4-methyl-pyridin-3-yl)-imidazolidin-2-one (111A)

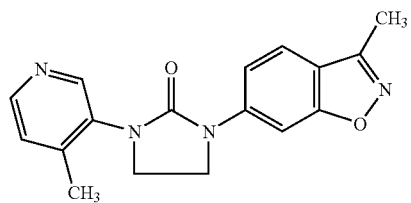

(111A)

Step 1: Preparation of Intermediate 1-(4-Acetyl-3-fluoro-phenyl)-3-(4-methyl-pyridin-3-yl)-imidazolidin-2-one (111A)

Using the same reaction conditions as in Example 14, 1-(4-methyl-pyridin-3-yl)-imidazolidin-2-one (I-14b: 500 mg, 2.8216 mmol) was reacted with 1-(4-bromo-2-fluoro-phenyl)-ethanone (679.9 mg, 3.1038 mmol), 1,4-dioxane (50 mL), copper iodide (53.6 mg, 0.28216 mmol), trans-1,2-diamino cyclohexane (97.09 mg, 0.84650 mmol) and potassium phosphate (1.49 g, 7.0541 mmol) to afford the crude product. Purification by column chromatography on silica gel (2% MeOH in CHCl$_3$) afforded 780 mg of 1-(4-acetyl-3-fluoro-phenyl)-3-(4-methyl-pyridin-3-yl)-imidazolidin-2-one (111a: 88.2% yield).

$^1$H NMR (DMSO-D$_6$, 300 MHz): δ 8.54 (s, 1H), 8.4 (d, 1H), 7.84 (t, 1H), 7.68 (dd, 1H), 7.5 (dd, 1H), 7.34 (d, 1H), 4.15-3.9 (m, 4H), 2.55 (s, 3H), 2.28 (s, 3H)

Step 2: Preparation of Intermediate 1-[3-Fluoro-4-(1-hydroxyimino-ethyl)-phenyl]-3-(4-methyl-pyridin-3-yl)-imidazolidin-2-one (111 h)

NaOH (72.7 mg, 1.8193 mmol) in water (5 mL) was added dropwise to a stirred solution of 1-(4-acetyl-3-fluoro-phenyl)-3-(4-methyl-pyridin-3-yl)-imidazolidin-2-one (I-111a: 380 mg, 1.2128 mmol) and hydroxylamine hydrochloride in ethanol (10 mL) over a period of 5 minutes. The resulting mixture was stirred at room temperature for 4 hours. The reaction was monitored by TLC (10% MeOH in CHCl$_3$). Ice was added to the reaction mixture to yield a precipitate which was collected and dried under reduced pressure to afford 350 mg of 1-[3-Fluoro-4-(1-hydroxyimino-ethyl)-phenyl]-3-(4-methyl-pyridin-3-yl)-imidazolidin-2-one (I-111b: 87.9% yield).

$^1$H NMR (DMSO-D$_6$, 300 MHz): δ 11.3 (s, 1H), 8.52 (s, 1H), 8.4 (d, 1H), 7.6 (dd, 1H), 7.54-7.3 (m, 3H), 4.1-3.9 (m, 4H), 2.28 (s, 3H), 2.12 (s, 3H)

Final Step: Preparation of 1-(3-Methyl-benzo[d]isoxazol-6-yl)-3-(4-methyl-pyridin-3-yl)-imidazolidin-2-one (111A)

NaH (32.8 mg, 1.3705 mmol) and DMF (4 mL) was added to 1-[3-fluoro-4-(1-hydroxyimino-ethyl)-phenyl]-3-(4-methyl-pyridin-3-yl)-imidazolidin-2-one (111b: 150 mg, 0.4568 mmol). The resulting mixture was microwaved at 50° C. for 1 hour. The reaction was monitored by TLC (10% MeOH in DCM). The reaction mixture was partitioned between ice water and ethylacetate. The organic layer was washed with water, brine solution, dried over Na$_2$SO$_4$ and concentrated under reduced pressure. Purification by column chromatography on silica gel (5% MeOH in CHCl$_3$) afforded 15 mg of the product (10.7% yield).

$^1$H NMR (CD$_3$OD, 300 MHz): δ 8.6-8.32 (m, 2H), 7.9-7.6 (m, 3H), 7.4 (s, 1H), 4.3-4.2 (m, 2H), 4.1-3.98 (m, 2H), 2.6 (s, 3H), 2.4 (s, 3H)

LCMS purity: 97.90%, m/z =309.0 (M+1)
HPLC: 83.77%

Example 112

Preparation of 2-Chloro-4-[3-(4-methyl-pyridin-3-yl)-2-oxo-imidazolidin-1-yl]-benzonitrile (112A)

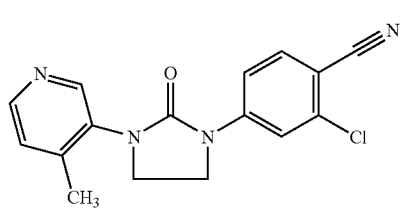

(112A)

Using the same reaction conditions as in Example 14, 1-(4-methyl-pyridin-3-yl)-imidazolidin-2-one (I-14b: 150 mg, 0.8465 mmol) was reacted with 2-chloro-4-iodo-benzonitrile (245.3 mg, 0.9311 mmol), 1,4-dioxane (20 mL), copper iodide (16.1 mg, 0.08465 mmol), trans-1,2-diamino cyclohexane (12.6 mg, 0.1100 mmol) and potassium phosphate (30.6 mL, 0.254 mmol) to afford the crude product which was purified by column chromatography on silica gel (2% MeOH in CHCl$_3$). The residue was washed with hexane and dried to afford 85 mg of the product (32% yield).

$^1$H NMR (CDCl$_3$, 300 MHz): δ 8.52-8.4 (m, 2H), 7.85 (s, 1H), 7.62 (s, 2H), 7.3-7.2 (m, 1H), 4.12-3.9 (m, 4H), 2.32 (s, 3H)

LCMS purity: 99.54%, m/z =312.8 (M+1)
HPLC: 93.79%

Example 113

Preparation of 1-Benzo[d]isoxazol-5-yl-3-(4-methyl-pyridin-3-yl)-imidazolidin-2-one (113A)

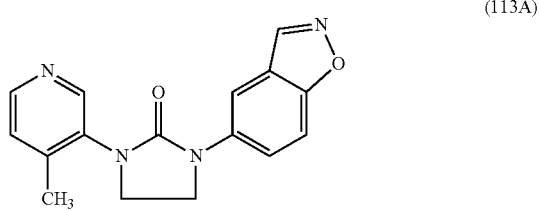

(113A)

Step 1: Preparation of Intermediate 2-Fluoro-5-[3-(4-methyl-pyridin-3-yl)-2-oxo-imidazolidin-1-yl]-benzaldehyde (I-113a)

Using the same reaction conditions as in Example 14, 1-(4-methyl-pyridin-3-yl)-imidazolidin-2-one (I-14b: 200 mg, 1.12 mmol) was reacted with 5-bromo-2-fluoro-benzaldehyde (272 mg, 1.34 mmol), 1,4-dioxane (20 mL), copper iodide (18 mg, 0.098 mmol), trans-1,2-diamino cyclohexane (0.05 mL, 0.294 mmol) and potassium phosphate (520 mg, 2.54 mmol) to afford the crude product which was purified by column chromatography on silica gel (2-3% MeOH in CHCl$_3$). The residue was washed with DCM and hexane in dry ice and dried to afford 235 mg of 2-Fluoro-5-[3-(4-methyl-pyridin-3-yl)-2-oxo-imidazolidin-1-yl]-benzaldehyde (70.35% yield).

$^1$H NMR (CDCl$_3$, 300 MHz): δ 10.38 (s, 1H), 8.6-8.3 (m, 3H), 7.6 (q, 1H), 7.3-7.25 (m, 2H), 4.12-3.9 (m, 4H), 2.32 (s, 3H)

LCMS purity: 98.49%, m/z=299.9 (M+1)

Step 2: Preparation of Intermediate 2-Fluoro-5-[3-(4-methyl-pyridin-3-yl)-2-oxo-imidazolidin-1-yl]-benzaldehyde oxime (I-113b)

2-Fluoro-5-[3-(4-methyl-pyridin-3-yl)-2-oxo-imidazolidin-1-yl]-benzaldehyde (I-113a: 230 mg, 0.769 mmol), hydroxylamine hydrochloride (160 mg, 2.307 mmol) and pyridine (5 mL) were taken in a reaction flask and the flask was stirred at room temperature for 18 hours under nitrogen atmosphere. The reaction was monitored by TLC (10% MeOH in CHCl$_3$). The reaction mixture was partitioned between ice water and ethylacetate. The organic layer was dried over Na$_2$SO$_4$ and concentrated. The concentrate was washed with diethyl ether and decanted to afford 170 mg of 2-Fluoro-5-[3-(4-methyl-pyridin-3-yl)-2-oxo-imidazolidin-1-yl]-benzaldehyde oxime (70.8% yield).

$^1$H NMR (CDCl$_3$, 300 MHz): δ 8.88-8.32 (m, 4H), 7.9-7.72 (m, 2H), 7.32-7.02 (m, 2H), 4.1-3.89 (m, 4H), 2.35 (s, 3H)

LCMS purity: 99.53%, m/z = 314.9 (M+1)

Final Step: Preparation of 1-Benzo[d]isoxazol-5-yl-3-(4-methyl-pyridin-3-yl)-imidazolidin-2-one (113A)

2-Fluoro-5-[3-(4-methyl-pyridin-3-yl)-2-oxo-imidazolidin-1-yl]-benzaldehyde oxime (I-113b: 160 mg, 0.509 mmol) in dry DMF (2 mL) was added dropwise to a stirred mixture of NaH (72 mg, 1.52 mmol) in DMF (1 mL) at 0° C. The resulting mixture was stirred at room temperature for 70 hours. The reaction was monitored by TLC (10% MeOH in CHCl$_3$). The reaction mixture was partitioned between ice water and ethylacetate. The aqueous layer was distilled to afford the solid residue which was dissolved 1:1 DCM:MeOH. The crude product was purified by column chromatography on silica gel (4-5% MeOH in CHCl$_3$). The residue was washed with hexane and dried to afford 105 mg of the product (70.4% yield).

$^1$H NMR (CD$_3$OD, 300 MHz): δ 8.58 (s, 1H), 8.38 (d, 1H), 7.76-7.68 (m, 2H), 7.42 (d, 1H), 7.0-6.92 (m, 1H), 4.1-3.9 (m, 4H), 2.41 (s, 3H)

LCMS purity: 97.14%, m/z=295.1 (M+1)
HPLC: 95.66%

Example 114

Preparation of 1-(1-Methyl-1H-indazol-5-yl)-3-(4-methyl-pyridin-3-yl)-imidazolidin-2-one (114A)

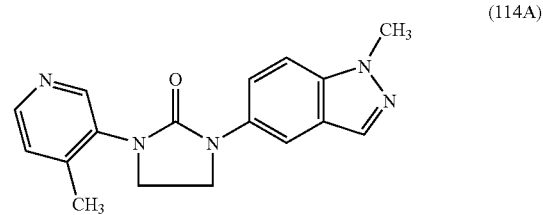

(114A)

Using the same reaction conditions as in Example 14, 1-(4-methyl-pyridin-3-yl)-imidazolidin-2-one (I-14b: 100 mg, 0.5649 mmol) was reacted with 5-bromo-1-methyl-1H-indazole (142 mg, 0.6794 mmol), 1,4-dioxane (15 mL), copper iodide (10 mg, 0.0526 mmol), trans-1,2-diamino cyclohexane (19 mg, 0.1666 mmol) and potassium phosphate (36 mg, 1.698 mmol) to afford the crude product. Purification by column chromatography on silica gel (2% MeOH in CHCl$_3$) afforded 57 mg of the product (32.94% yield).

$^1$H NMR (CDCl$_3$, 300 MHz): δ 8.52 (s, 1H), 8.4 (d, 1H), 7.94 (m, 2H), 7.62 (s, 1H), 7.4 (d, 1H), 7.26-7.2 (d, 1H), 4.2-3.8 (m, 7H), 2.4 (s, 3H)

LCMS purity: 96.62%, m/z =308.1 (M+1)
HPLC: 97.44%

Example 115

Preparation of 1-(1-Methyl-1H-indol-3-yl)-3-(4-methyl-pyridin-3-yl)-imidazolidin-2-one Trifluoroacetic acid (115A)

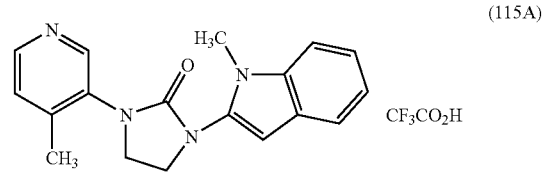

(115A)

Using the same reaction conditions as in Example 14, 1-(4-methyl-pyridin-3-yl)-imidazolidin-2-one (I-14b: 150 mg, 0.00084 mol) was reacted with 3-bromo-1-methyl-1H-indole (174 mg, 0.00084 mol), 1,4-dioxane (20 mL), copper iodide (15 mg, 0.000084 mol), trans-1,2-diamino cyclohexane (28 mg, 0.00025 mol) and potassium phosphate (356 mg, 0.00168 mol) to afford the crude product. Purification by column chromatography on silica gel (2-3% MeOH in CHCl$_3$), followed by preparative HPLC afforded 23 mg of the product (9% yield).

$^1$H NMR (CD$_3$OD$_3$, 300 MHz): δ 8.9-8.8 (br s, 1H), 8.6-8.5 (br s, 1H), 7.9-7.82 (m, 1H), 7.65 (d, 1H), 7.44-7.3 (m, 2H), 7.22 (t, 1H), 7.08 (t, 1H), 4.2-4.05 (m, 4H), 3.8 (s, 3H), 2.62 (s, 3H)

LCMS purity: 97.54%, m/z =307.0 (M+1)
HPLC: 97.65%

Example 116

Preparation of 1-(1-Methyl-1H-benzoimidazol-5-yl)-3-(4-methyl-pyridin-3-yl)-trifluoroacetic Acid (116A)

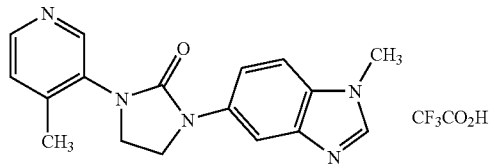

(116A)

Using the same reaction conditions as in Example 14, 1-(4-methyl-pyridin-3-yl)-imidazolidin-2-one (I-14b: 150 mg, 0.847 mmol) was reacted with 5-bromo-1-methyl-1H-benzoimidazole (214 mg, 1.016 mmol), 1,4-dioxane (25 mL), copper iodide (14 mg, 0.071 mmol), trans-1,2-diamino cyclohexane (24 mg, 0.213 mmol) and potassium phosphate (375 mg, 1.77 mmol) to afford the crude product. Purification by column chromatography on silica gel (2% MeOH in CHCl$_3$), followed by preparative HPLC afforded 25 mg of the product (9.6% yield).

$^1$H NMR (CDCl$_3$, 300 MHz): δ 8.9-8.8 (m, 2H), 8.52-8.35 (m, 2H), 7.82 (s, 1H), 7.61 (m, 2H), 4.25-4.12 (m, 2H), 4.15 (s, 5H), 2.5 (s, 3H)

LCMS purity: 89.78%, m/z=308.1 (M+1)
HPLC: 86.56%

Example 117

Preparation of 5-[3-(4-Methyl-pyridin-3-yl)-2-oxo-imidazolidin-1-yl]-1,2-dihydro-indazol-3-one (174)

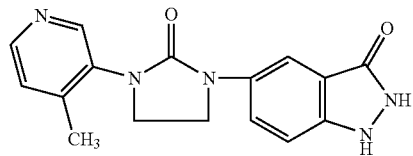

(117A)

Step 1: Preparation of Intermediate 2-Fluoro-5-[3-(4-methyl-pyridin-3-yl)-2-oxo-imidazolidin-1-yl]-benzoic acid methyl ester (I-117a)

Using the same reaction conditions as in Example 14, 1-(4-methyl-pyridin-3-yl)-imidazolidin-2-one (I-14b: 315 mg, 1.78 mmol) was reacted with 5-bromo-2-fluoro-benzoic acid methyl ester (500 mg, 2.14 mmol), 1,4-dioxane (30 mL), copper iodide (34 mg, 0.178 mmol), trans-1,2-diamino cyclohexane (0.08 mL, 0.534 mmol) and potassium phosphate (935 mg, 4.45 mmol) to afford 520 mg of 2-Fluoro-5-[3-(4-methyl-pyridin-3-yl)-2-oxo-imidazolidin-1-yl]-benzoic acid methyl ester (88.8% yield).

$^1$H NMR (CDCl$_3$, 300 MHz): δ 8.55-8.4 (m, 2H), 8.1-7.82 (m, 2H), 7.3-7.1 (m, 2H), 4.1-3.9 (m, 7H), 2.35 (s, 3H)

Final Step: Preparation of 5-[3-(4-Methyl-pyridin-3-yl)-2-oxo-imidazolidin-1-yl]-1,2-dihydro-indazol-3-one (117A)

2-Fluoro-5-[3-(4-methyl-pyridin-3-yl)-2-oxo-imidazolidin-1-yl]-benzoic acid methyl ester (I-117a: 510 mg, 1.55 mmol) and hydrazine hydrate were taken in a reaction flask and the flask was heated to 120° C. for 18 hours with stirring. The reaction was monitored by TLC (10% MeOH in CHCl$_3$). The reaction mixture was partitioned between ice water and ethylacetate. The aqueous layer was concentrated to afford the solid residue which was dissolved in 1:1 DCM: MeOH and filtered. The filtrate was concentrated and purified by column chromatography on silica gel (10-15% MeOH in CHCl$_3$). The residue was washed with DCM and dried to afford 180 mg of the product (37.6% yield).

$^1$H NMR (DMSO-D$_6$, 300 MHz): δ 11.2 (s, 1H), 8.55 (s, 1H), 8.46 (d, 1H), 7.86 (d, 1H), 7.6 (s, 1H), 7.39-7.28 (m, 2H), 4.1-3.89 (m, 4H), 2.3 (s, 3H)

LCMS purity: 86.23%, m/z =310.1 (M+1)
HPLC: 93.9%

Example 118

Preparation of 1-(3-Amino-1H-indazol-5-yl)-3-(4-methyl-pyridin-3-yl)-imidazolidin-2-one (118A)

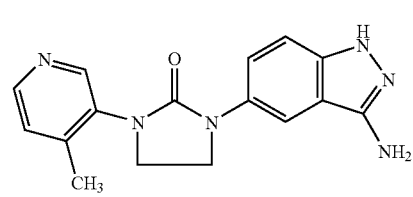

(118A)

Hydrazine hydrate (5 mL) was added to solution of 2-fluoro-5-[3-(4-methyl-pyridin-3-yl)-2-oxo-imidazolidin-1-yl]-benzonitrile (103A: 265 mg) in 2-methoxymethanol (5 mL). The resulting mixture was heated to 170° C. and maintained for 20 hours. The reaction was monitored by TLC (20% MeOH in CHCl$_3$). The reaction mixture was partitioned between ice water and DCM. The organic layer was dried over Na$_2$SO$_4$ and concentrated. Purification by column chromatography on silica gel (10% MeOH in CHCl$_3$) afforded 125 mg of the product (45.3% yield).

$^1$H NMR (DMSO-D$_6$, 300 MHz): δ 11.28 (s, 1H), 8.55 (s, 1H), 8.4-8.32 (d, 1H), 7.75-7.62 (m, 2H), 7.4-7.2 (m, 2H), 5.5-5.2 (br s, 2H), 4.1-3.9 (m, 4H), 2.32 (s, 3H)

LCMS purity: 97.92%, m/z =308.8 (M+1)
HPLC: 94.4%

Example 119

Preparation of 1-Imidazo[1,2-a]pyridin-3-yl-3-(4-methyl-pyridin-3-yl)-imidazolidin-2-One (119A)

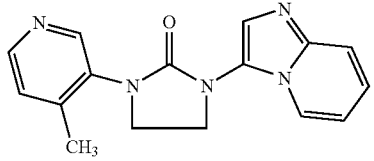
(119A)

Using the same reaction conditions as in Example 14, 1-(4-methyl-pyridin-3-yl)-imidazolidin-2-one (I-14b: 250 mg, 1.4108 mmol) was reacted with 3-iodo-imidazo[1,2-a]pyridine (344 mg, 1.4108 mmol), 1,4-dioxane (10 mL), copper iodide (34 mg), trans-1,2-diamino cyclohexane (68 mg) and potassium phosphate (898 mg, 4.2325 mmol) to afford the crude product. Purification by column chromatography on silica gel (10% MeOH in CHCl$_3$) afforded 82 mg of the product (19.81% yield).

$^1$H NMR (DMSO-D$_6$, 300 MHz): δ 8.62 (s, 1H), 8.42-8.3 (m, 2H), 7.66-7.58 (m, 2H), 7.4-7.26 (m, 2H), 7.02 (t, 1H), 4.05 (s, 4H), 2.38 (s, 3H)

LCMS purity: 98.51%, m/z=294.1 (M+1)

HPLC: 90.42%

Example 120

Preparation of 1-(4-Methyl-pyridin-3-yl)-3-thieno[3,2-c]pyridin-2-yl-imidazolidin-2-one (120A)

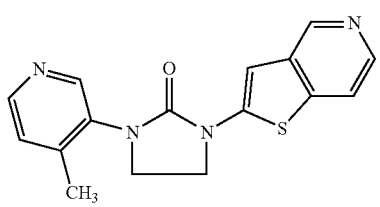
(120A)

10% Pd-C (10 mg) was added to a solution of 1-(4-chloro-thieno[3,2-c]pyridin-2-yl)-3-(4-methyl-pyridin-3-yl)-imidazolidin-2-one (98A: 80 mg, 0.232 mmol) in methanol (10 mL) under nitrogen atmosphere. The resulting mixture was hydrogenated at 30 PSI (2.04 atm) for 12 hours at room temperature. The reaction was monitored by TLC (10% MeOH in CHCl$_3$). The reaction mixture was filtered through celite bed, washed with methanol and the filtrate was concentrated under reduced pressure to afford the crude product. Purification by preparative TLC afforded 10 mg of the product (14% yield).

$^1$H NMR (CD$_3$OD, 300 MHz): δ 8.85-8.75 (br s, 1H), 8.45 (s, 1H), 8.3 (d, 1H), 8.2-8.1 (m, 1H), 7.9 (d, 1H), 7.35 (d, 1H), 6.8 (s, 1H), 4.25-4.15 (m, 2H), 4.1-4.0 (m, 2H), 2.3 (s, 3H)

LCMS purity: 97.15%, m/z=311.0 (M+1)

HPLC: 93.24%

Example 121

Preparation of 1-(1H-Indazol-6-yl)-3-(4-methyl-pyridin-3-O-imidazolidin-2-one (121A)

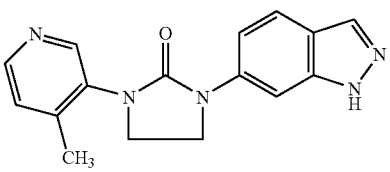
(121A)

Step 1: Preparation of Intermediate 2-Fluoro-4-[3-(4-methyl-pyridin-3-yl)-2-oxo-imidazolidin-1-yl]-benzaldehyde (I-121a)

Using the same reaction conditions as in Example 14, 1-(4-methyl-pyridin-3-yl)-imidazolidin-2-one (I-14b: 300 mg, 1.694 mmol) was reacted with 4-bromo-2-fluoro-benzaldehyde (403 mg, 2.118 mmol), 1,4-dioxane (25 mL), copper iodide (32.186 mg, 0.1694 mmol), trans-1,2-diamino cyclohexane (72.16 mg, 0.5082 mmol) and potassium phosphate (1.077 g, 5.082 mmol) to afford the crude product. Purification by column chromatography on silica gel (1.5% MeOH in CHCl$_3$) afforded 300 mg of 2-Fluoro-4-[3-(4-methyl-pyridin-3-yl)-2-oxo-imidazolidin-1-yl]-benzaldehyde (59.05% yield).

$^1$H NMR (CDCl$_3$, 300 MHz): δ 10.25 (s, 1H), 8.7-8.4 (m, 2H), 7.9 (t, 1H), 7.7 (d, 1H), 7.4-7.2 (m, 2H), 4.2-3.9 (m, 4H), 2.35 (s, 3H)

Step 2: Preparation of Intermediate 2-Fluoro-4-[3-(4-methyl-pyridin-3-yl)-2-oxo-imidazolidin-1-yl]-benzaldehyde O-methyl-oxime (121b)

O-Methyl-hydroxylamine (84 mg, 1.003 mmol) and K$_2$CO$_3$ (207 mg, 1.5 mmol) were added to a solution of 2-fluoro-4-[3-(4-methyl-pyridin-3-yl)-2-oxo-imidazolidin-1-yl]-benzaldehyde-(I-121a: 300 mg, 1.003 mmol) in dimethoxyethane (10 mL). The resulting mixture was heated to 40° C. for 2 hours. The reaction was monitored by TLC (5% MeOH in CHCl$_3$). The reaction mixture was filtered, washed with CHCl$_3$ and the filtrate was concentrated under reduced pressure to afford 30 mg of crude 2-Fluoro-4-[3-(4-methyl-pyridin-3-yl)-2-oxo-imidazolidin-1-yl]-benzaldehyde O-methyl-oxime, which was used in the next step without further purification.

$^1$H NMR (CDCl$_3$, 300 MHz): δ 8.5 (s, 2H), 8.25 (s, 1H), 7.8 (t, 1H), 7.6-7.5 (m, 1H), 7.3-7.2 (m, 3H), 4.1-3.9 (m, 7H), 2.35 (s, 3H)

Final Step: Preparation of 1-(1H-Indazol-6-yl)-3-(4-methyl-pyridin-3-yl)-imidazolidin-2-one (121A)

Hydrazine hydrate (5 mL) was added to solution of 2-fluoro-4-[3-(4-methyl-pyridin-3-yl)-2-oxo-imidazolidin-1-yl]-benzaldehyde O-methyl-oxime (I-121b: 350 mg, 0.917 mmol) in 2-methoxy methanol (10 mL). The resulting mixture was heated to 200° C. and maintained for 2 days. The reaction was monitored by TLC (5% MeOH in CHCl$_3$). The reaction mixture was cooled to room temperature and concentrated. The crude product was purified by column chromatography on silica gel (4% MeOH in CHCl₃), washed with ether and dried to afford 105 mg of the product (39.17% yield).

¹H NMR (CD₃OD, 300 MHz): δ 8.45 (s, 1H), 8.29 (d, 1H), 7.9 (s, 1H), 7.7-7.6 (m, 2H), 7.45-7.3 (m, 2H), 4.2-4.1 (m, 2H), 4.0-3.9 (m, 2H), 2.32 (s, 3H)

LCMS purity: 99.18%, m/z =294.0 (M+1)
HPLC: 94.38%

Example 122

Preparation of 1-(3H-Imidazo[4,5-b]pyridin-6-yl)-3-(4-methyl-pyridin-3-yl)-imidazolidin-2-one Trifluoroacetic Acid (122A)

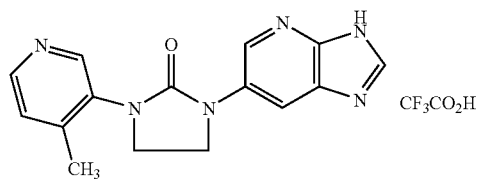

(122A)

Step 1: Preparation of Intermediate-(4-Methyl-pyridin-3-yl)-3-[1-(2-trimethylsilanyl-ethoxymethyl)-1H-pyrazolo[3,4-b]pyridin-5-yl]-imidazolidin-2-one (I-122a)

Using the same reaction conditions as in Example 18, 1-(4-methyl-pyridin-3-yl)-imidazolidin-2-one (I-14b: 0.108 g, 0.0006 mol) was reacted with 5-bromo-1-(2-trimethylsilanyl-ethoxymethyl)-1H-pyrazolo[3,4-b]pyridine (0.2 g, 0.0006 mol), 1,4-dioxane (20 mL), copper iodide (6.011 g, 0.00006 mol), trans-1,2-diamino cyclohexane (0.020 g, 0.00018 mol) and potassium phosphate (0.254 g, 0.0012 mol) to afford the crude product. Purification by column chromatography on silica gel (15% MeOH in CHCl₃) afforded 172 mg of 1-(4-Methyl-pyridin-3-yl)-3-[1-(2-trimethylsilanyl-ethoxymethyl)-1H-pyrazolo[3,4-b]pyridin-5-yl]-imidazolidin-2-one (67.71% yield).

Final Step: Preparation of 1-(3H-Imidazo[4,5-b]pyridin-6-yl)-3-(4-methyl-pyridin-3-yl)-imidazolidin-2-one trifluoroacetic acid (122A)

Dioxane HCl (5 mL) was added to 1-(4-methyl-pyridin-3-yl)-3-[1-(2-trimethylsilanyl-ethoxymethyl)-1H-pyrazolo[3,4-b]pyridin-5-yl]-imidazolidin-2-one (I-122a: 172 mg) at 0° C. The resulting mixture was stirred at room temperature for 2 hours. The reaction was monitored by TLC (10% MeOH in CHCl₃). Purification by preparative HPLC afforded 38 mg of the product (32% yield).

¹H NMR (CD₃OD, 300 MHz): δ 8.6 (s, 1H), 8.45 (s, 1H), 8.3-8.2 (m, 3H), 7.35 (d, 1H), 4.2-4.1 (m, 2H), 4.0-3.9 (m, 2H), 2.32 (s, 3H)

LCMS purity: 99.19%, m/z =295.0 (M+1)
HPLC: 95.78%

Example 123

Preparation of 1-(3-Amino-1H-indazol-6-yl)-3-(4-methyl-pyridin-3-yl)-imidazolidin-2-one (123A)

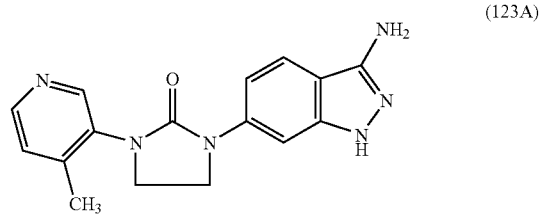

(123A)

Step 1: Preparation of Intermediate 2-Fluoro-4-[3-(4-methyl-pyridin-3-yl)-2-oxo-imidazolidin-1-yl]-benzonitrile (I-123a)

Using the same reaction conditions as in Example 14, 1-(4-methyl-pyridin-3-yl)-imidazolidin-2-one (I-14b: 300 mg, 1.693 mmol) was reacted with 4-bromo-2-fluoro-benzonitrile (372 mg, 1.86 mmol), 1,4-dioxane (50 mL), copper iodide (32.2 mg, 0.016 mmol), trans-1,2-diamino cyclohexane (61 mL, 0.5079 mmol) and potassium phosphate (900 mg, 4.23 mmol) to afford the crude product. Purification by column chromatography on silica gel (2% MeOH in CHCl₃) afforded 163 mg of 2-Fluoro-4-[3-(4-methyl-pyridin-3-yl)-2-oxo-imidazolidin-1-yl]-benzonitrile (32.5% yield).

LCMS purity: 97.23%, m/z =297.0 (M+1)

Final Step: Preparation of 1-(3-Amino-1H-indazol-6-yl)-3-(4-methyl-pyridin-3-yl)-imidazolidin-2-one (123A)

Hydrazine hydrate (5 mL) was added to solution of 2-fluoro-4-[3-(4-methyl-pyridin-3-yl)-2-oxo-imidazolidin-1-yl]-benzonitrile (I-123a: 163 mg) in 2-methoxymethanol (10 mL). The resulting mixture was heated to 170° C. and maintained for 22 hours. The reaction was monitored by TLC (10% MeOH in CHCl₃). The reaction mixture was partitioned between ice water and ethylacetate. The organic layer was washed with brine solution, dried over Na₂SO₄ and concentrated. Purification by preparative HPLC afforded 30 mg of the product (17.6% yield).

¹H NMR (DMSO-d₆, 300 MHz): ε 11.2 (s, 1H), 8.54 (s, 1H), 8.38 (d, 1H), 7.62 (d, 1H), 7.44 (s, 1H), 7.36 (d, 1H), 7.24 (d, 1H), 5.3 (s, 2H), 4.15-3.85 (m, 4H), 2.28 (s, 3H)

LCMS purity: 97.44%, m/z =308.9 (M+1)
HPLC: 95.39%

Example 124

Preparation of 1-Benzothiazol-6-yl-3-(4-methoxy-pyridin-3-yl)-imidazolidin-2-one (124A)

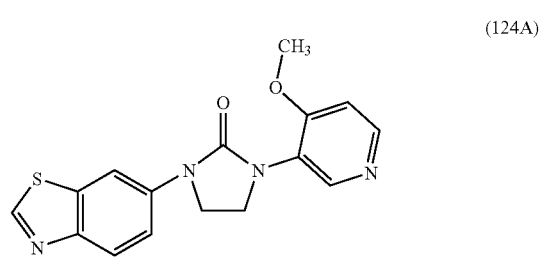

(124A)

1-Benzothiazol-6-yl-3-(4-chloro-pyridin-3-yl)-imidazolidin-2-one (84A: 50 mg, 0.1515 mmol) was added dropwise to a solution of sodium methoxide (0.122 g, 2.259 mmol) in 1,4-dioxane (15 mL) over a period of 5 minutes. The resulting mixture was refluxed for 10 hours. The reaction was monitored by TLC (10% MeOH in CHCl$_3$). The reaction mixture was partitioned between ice water and ethylacetate. The organic layer was dried over Na$_2$SO$_4$ and concentrated. Purification by preparative HPLC afforded 16 mg of the product (31.66% yield).

$^1$H NMR (CDCl$_3$, 300 MHz): δ 8.9 (s, 1H), 8.58 (s, 1H), 8.46 (d, 1H), 8.39 (s, 1H), 8.1 (d, 1H), 7.7 (dd, 1H), 6.92 (d, 1H), 4.18-4.09 (m, 2H), 4.0-3.9 (m, 5H)

LCMS purity: 99.16%, m/z=326.9 (M+1)
HPLC: 91.89%

Example 125

Preparation of 1-Benzothiazol-6-yl-3-(4-difluoromethyl-pyridin-3-yl)-imidazolidin-2-one (125A)

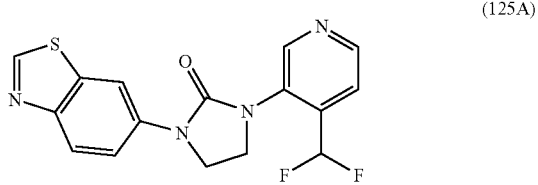

(125A)

Using the same reaction conditions as in Example 14, 1-benzothiazol-6-yl-imidazolidin-2-one (I-84b: 75 mg, 0.3173 mmol) was reacted with 3-bromo-4-difluoromethyl-pyridine (60 mg, 0.2884 mmol), 1,4-dioxane (5 mL), copper iodide (7.5 mg), trans-1,2-diamino cyclohexane (15 mg) and potassium phosphate (122 mg, 0.5769 mmol) to afford the crude product. Purification by column chromatography on silica gel (2% MeOH in CHCl$_3$), followed by preparative HPLC afforded 2 mg of the product (2% yield).

$^1$H NMR (CDCl$_3$, 300 MHz): δ 8.92 (s, 1H), 8.68 (s, 2H), 8.36-8.32 (d, 1H), 8.16-8.12 (d, 1H), 7.72-7.58 (m, 2H), 7.24-6.8 (t, 1H), 4.24-4.04 (m, 4H)

LCMS purity: 95.49%, m/z=347 (M+1)
HPLC: 93.66%

Example 126

Preparation of 1-Benzothiazol-6-yl-3-(4-hydroxymethyl-pyridin-3-yl)-imidazolidin-2-one (126A)

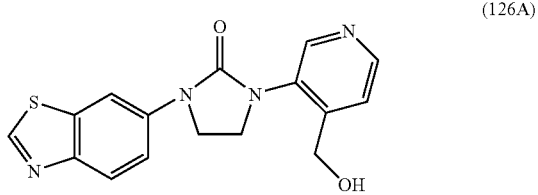

(126A)

Step 1: Preparation of Intermediate 3-(3-Benzothiazol-6-yl-2-oxo-imidazolidin-1-β-pyridine-4-carbaldehyde (I-126a)

Using the same reaction conditions as in Example 14, 1-benzothiazol-6-yl-imidazolidin-2-one (I-84b: 588.7 mg, 2.688 mmol) was reacted with 3-bromo-pyridine-4-carbaldehyde (500 mg, 2.688 mmol), 1,4-dioxane (10 mL), copper iodide (51.2 mg, 0.2688 mmol), trans-1,2-diamino cyclohexane (92.33 mg, 0.8064 mmol) and potassium phosphate (1.711 g, 8.064 mmol) to afford the crude product. Purification by column chromatography on silica gel (2% MeOH in CHCl$_3$) afforded 250 mg of 3-(3-Benzothiazol-6-yl-2-oxo-imidazolidin-1-yl)-pyridine-4-carbaldehyde (28.9% yield).

$^1$H NMR (DMSO-D$_6$, 300 MHz): δ 9.94 (s, 1H), 9.3 (s, 1H), 8.85 (s, 1H), 8.64 (d, 1H), 8.32 (d, 1H), 8.12-8.08 (d, 1H), 7.7 (dd, 1H), 7.66 (d, 1H), 4.32-4.16 (m, 4H)

Final Step: Preparation of 1-Benzothiazol-6-yl-3-(4-hydroxymethyl-pyridin-3-yl)-imidazolidin-2-one (126A)

NaBH$_4$ (82 mg, 2.1604 mmol) was added to a solution of 3-(3-benzothiazol-6-yl-2-oxo-imidazolidin-1-yl)-pyridine-4-carbaldehyde (I-126a: 140 mg, 0.4320 mmol) in MeOH (15 mL) and DCM (5 mL) at 0° C. The resulting mixture was stirred for 10 minutes. The reaction was monitored by TLC (10% MeOH in CHCl$_3$). The reaction mixture was partitioned between water and DCM. The organic layer was washed with water and dried under reduced pressure to afford 110 mg of the product (78.01% yield).

$^1$H NMR (DMSO-D$_6$, 300 MHz): δ 9.3 (s, 1H), 8.62 (s, 1H), 8.54 (d, 1H), 8.32 (s, 1H), 8.15-7.95 (m, 2H), 7.6 (d, 1H), 5.48 (t, 1H), 4.6 (d, 2H), 4.2-3.98 (m, 4H)

LCMS purity: 88.87%, m/z =327.1 (M+1)
HPLC: 94.07%

Example 127

Preparation of 1-Benzothiazol-6-yl-3-(6-methyl-pyridin-3-yl)-imidazolidin-2-one (127A)

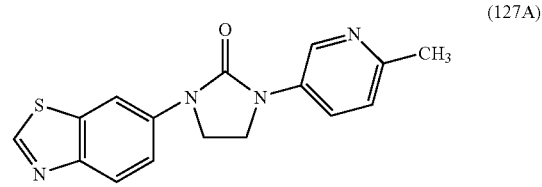

(127A)

Using the same reaction conditions as in Example 14, 1-benzothiazol-6-yl-imidazolidin-2-one (I-84b: 150 mg, 0.685 mmol) was reacted with 5-bromo-2-methyl-pyridine (140.5 mg, 0.822 mmol), 1,4-dioxane (10 mL), copper iodide (12.92 mg, 0.068 mmol), trans-1,2-diamino cyclohexane (23 mg, 0.205 mmol) and potassium phosphate (435 mg, 2.055 mmol) to afford the crude product. Purification by column chromatography on silica gel (2% MeOH in CHCl$_3$) afforded 110 mg of the product (51.80% yield).

$^1$H NMR (DMSO-D$_6$, 300 MHz): δ 9.3 (s, 1H), 8.7 (s, 1H), 8.3 (s, 1H), 8.1-7.9 (m, 3H), 7.3-7.2 (m, 1H), 4.1-4.0 (m, 4H), 2.5 (s, 3H)

LCMS purity: 91.9%, m/z=311.1 (M+1)
HPLC: 92.14%

Example 128

Preparation of 1-Benzothiazol-6-yl-3-(4-trifluoromethyl-pyridin-3-yl)-imidazolidin-2-one (128A)

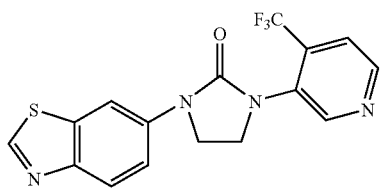

(128A)

Using the same reaction conditions as in Example 14, 1-benzothiazol-6-yl-imidazolidin-2-one (I-84b: 150 mg, 0.684 mmol) was reacted with 3-bromo-4-trifluoromethyl-pyridine (185.75 mg, 0.822 mmol), 1,4-dioxane (10 mL), copper iodide (12.99 mg, 0.0684 mmol), trans-1,2-diamino cyclohexane (23.37 mg, 0.205 mmol) and potassium phosphate (435 mg, 2.052 mmol) to afford the crude product. Purification by column chromatography on silica gel (1% MeOH in CHCl$_3$), followed by preparative HPLC afforded 7 mg of the product (12.04% yield).

$^1$H NMR (CDCl$_3$, 300 MHz): δ 8.92 (s, 1H), 8.82-8.79 (m, 2H), 8.38 (s, 1H), 8.12 (d, 1H), 7.7-7.62 (m, 2H), 4.18 (t, 2H), 3.96 (t, 2H)

LCMS purity: 85.069%, m/z=365.1 (M+1)

HPLC: 92.93%

Example 129

Preparation of 3-(3-Benzothiazol-6-yl-2-oxo-imidazolidin-1-O-isonicotinonitrile (129A)

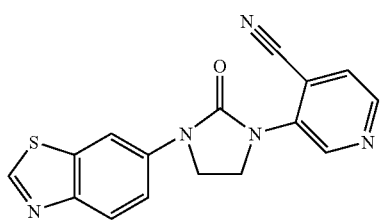

(129A)

Using the same reaction conditions as in Example 14, 1-benzothiazol-6-yl-imidazolidin-2-one (I-84b: 120 mg, 0.5472 mmol) was reacted with 3-bromo-isonicotinonitrile (100 mg, 0.5472 mmol), 1,4-dioxane (10 mL), copper iodide (12 mg), trans-1,2-diamino cyclohexane (24 mg) and potassium phosphate (349 mg, 1.6418 mmol) to afford the crude product. Purification by column chromatography on silica gel (2% MeOH in CHCl$_3$) afforded 47 mg of the product (26.70% yield).

$^1$H NMR (DMSO-D$_6$, 300 MHz): δ 9.3 (s, 1H), 8.98 (s, 1H), 8.65 (d, 1H), 8.35 (s, 1H), 8.12-7.9 (m, 3H), 4.4-4.1 (m, 4H)

LCMS purity: 95.40%, m/z =322 (M+1)

HPLC: 98.74%

Example 130

Preparation of 1-(4-Methyl-pyridin-3-yl)-3-naphthalen-2-yl-tetrahydro-pyrimidin-2-one (130A)

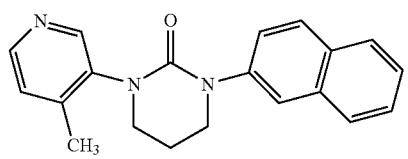

(130A)

Step 1: Preparation of Intermediate 1-(3-chloro-propyl)-3-(4-methyl-pyridin-3-yl)-urea (I-130a)

1-Chloro-3-isocyanato-propane (1.6 g, 13.87 mmol) was added dropwise to a stirred solution of 4-methyl-pyridin-3-ylamine (1 g, 9.25 mmol) in toluene (15 mL) at 0° C. The reaction mixture was stirred at room temperature for 18 hours. The reaction was monitored by TLC (100% ethylacetate). The reaction mixture was filtered, washed with toluene and dried under reduced pressure to afford 2.12 g (99.5% yield) of 1-(3-chloro-propyl)-3-(4-methyl-pyridin-3-yl)-urea.

LCMS: 94.28%, m/z=228.1 (M+1)

Step 2: Preparation of Intermediate 1-(4-methyl-pyridin-3-yl)-tetrahydro-pyrimidin-2-one (I-130b)

1-(3-Chloro-propyl)-3-(4-methyl-pyridin-3-yl)-urea (I-130a: 2 g, 9.25 mmol) in dry DMF (15 mL) was added to a stirred mixture of sodium hydride (330 mg, 13.87 mmol) in THF (30 mL) at 0° C. The reaction was stirred at room temperature for 1 hour. The reaction was monitored by TLC (100% ethylacetate). The reaction mixture was quenched with MeOH at 0° C., concentrated under reduced pressure and partitioned between ice water and chloroform. The organic layer was washed with brine solution, dried over Na$_2$SO$_4$ and concentrated under reduced pressure to afford 1.7 g (96.5% yield) of 1-(4-methyl-pyridin-3-yl)-tetrahydro-pyrimidin-2-one.

$^1$H NMR (CDCl$_3$, 300 MHz): δ 8.44-8.36 (m, 2H), 7.19 (d, 1H), 5.1-5.0 (br s, 1H), 3.72-3.64 (m, 1H), 3.52-3.4 (m, 3H), 2.29 (s, 3H), 2.2-2.1 (m, 2H)

Final Step: Preparation of 1-(4-Methyl-pyridin-3-yl)-3-naphthalen-2-yl-tetrahydro-pyrimidin-2-one (130A)

Using the same reaction conditions as in Example 14, 1-(4-methyl-pyridin-3-yl)-tetrahydro-pyrimidin-2-one (I-130b: 150 mg, 0.785 mmol) was reacted with 2-bromo-naphthalene (195 mg, 0.942 mmol), 1,4-dioxane (20 mL), copper iodide (15 mg, 0.078 mmol), trans-1,2-diamino cyclohexane (0.03 mL, 0.235 mmol) and potassium phosphate (415 mg, 1.96 mmol) to afford the crude product. Purification by column chromatography on silica gel (1% MeOH in CHCl$_3$), followed by recrystallization using DCM and hexane afforded 65 mg of the product (26.2% yield).

$^1$H NMR (CDCl$_3$, 300 MHz): δ 8.5 (s, 1H), 8.39 (d, 1H), 7.85-7.7 (m, 4H), 7.6-7.4 (m, 3H), 7.18 (d, 1H), 4.1-3.8 (m, 3H), 3.69-3.58 (m, 1H), 2.4-2.3 (m, 5H)

LCMS purity: 99.72%, m/z=318.1 (M+1)

HPLC: 98.65%

Example 131

Preparation of 1-m-Tolyl-3-(4-trifluoromethyl-pyridin-3-yl)-imidazolidin-2-one (131A)

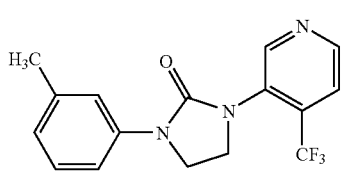

(131A)

Step 1: Preparation of Intermediate 1-(2-chloroethyl)-3-m-tolyl-urea (I-131a)

1-Chloro-2-isocyanato-ethane (2.36 g, 0.02239 mmol) was added dropwise to a stirred solution of m-tolylamine (2 g, 0.01866 mmol) in toluene (50 mL) over a period of 30 minutes at 0° C. The reaction mixture was stirred at room temperature for 12 hours. The reaction was monitored by TLC (5% MeOH in DCM). The reaction mixture was filtered, washed with toluene and dried under reduced pressure to afford 3.8 g (97% yield) of 1-(2-chloro-ethyl)-3-m-tolyl-urea.

$^1$H NMR (DMSO-D$_6$, 300 MHz): δ 8.56 (s, 1H), 7.23 (s, 1H), 7.2-7.05 (m, 2H), 6.72 (d, 1H), 6.36 (t, 1H), 3.7-3.6 (m, 2H), 3.45-3.38 (m, 2H), 2.23 (s, 3H)

Step 2: Preparation of Intermediate 1-m tolyl imidazolidin 2 one (I-131b)

1-(2-Chloro-ethyl)-3-m-tolyl-urea (I-131a: 4 g, 18.86 mmol) in dry DMF (70 mL) was added to a stirred mixture of sodium hydride (1.358 g, 28.30 mmol) in THF (70 mL) at 0° C. The reaction was stirred at room temperature for 1 hour. The reaction was monitored by TLC (100% ethylacetate). The reaction mixture was quenched with MeOH at 0° C., concentrated under reduced pressure and partitioned between ice water and chloroform. The organic layer was washed with brine solution, dried over Na$_2$SO$_4$, and concentrated under reduced pressure to afford 2.7 g (81.34% yield) of 1-m-tolyl-imidazolidin-2-one.

$^1$H NMR (DMSO-D$_6$, 300 MHz): δ 7.4-7.3 (m, 2H), 7.18 (t, 1H), 6.95-6.89 (br s, 1H), 6.8 (d, 1H), 3.85-3.78 (m, 2H), 3.44-3.36 (m, 2H), 2.26 (s, 3H)

LCMS purity: 96.44%, m/z=177.2 (M+1)

Final Step: Preparation of 1-m-Tolyl-3-(4-trifluoromethyl-pyridin-3-yl)-imidazolidin-2-one (131A)

Using the same reaction conditions as in Example 14, 1-m-tolyl-imidazolidin-2-one (I-131b: 150 mg, 0.8522 mmol) was reacted with 3-bromo-4-trifluoromethyl-pyridine (160 mg, 0.8522 mmol), 1,4-dioxane (5 mL), copper iodide (16.23 mg, 0.08522 mmol), trans-1,2-diamino cyclohexane (29.27 mg, 0.2552 mmol) and potassium phosphate (542.56 mg, 2.556 mmol) to afford the crude product. Purification by preparative HPLC afforded 94 mg of the product (34.43% yield).

$^1$H NMR (CDCl$_3$, 300 MHz): δ 8.82-8.75 (br s, 1H), 7.64 (d, 1H), 7.46 (s, 1H), 7.4-7.2 (m, 3H), 6.95 (d, 1H), 4.15-3.85 (m, 4H), 2.36 (s, 3H)

LCMS purity: 97.94%, m/z=321.7 (M+1)
HPLC: 97.47%

Example 132

Preparation of 1-(2-Methyl-2H-indazol-5-yl)-3-(4-methyl-pyridin-3-yl)-imidazolidin-2-one (132A)

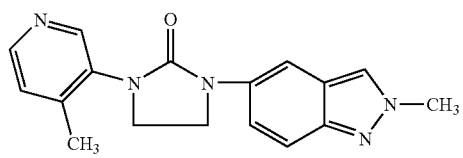

(132A)

Using the same reaction conditions as in Example 14, 1-(4-methyl-pyridin-3-yl)-imidazolidin-2-one (I-14b: 100 mg, 0.564 mmol) was reacted with 5-bromo-2-methyl-2H-indazole (120 mg, 0.5741 mmol), 1,4-dioxane (15 mL), copper iodide (10 mg, 0.056 mmol), trans-1,2-diamino cyclohexane (19 mg, 0.166 mmol) and potassium phosphate (360 mg, 1.698 mmol) to afford the crude product. Purification by preparative HPLC afforded 3.6 mg of the product (6.228% yield).

$^1$H NMR (CD$_3$OD, 300 MHz): δ 8.5-8.46 (br s, 1H), 8.43-8.32 (m, 1H), 8.15 (s, 1H), 7.82-7.54 (m, 3H), 7.4 (d, 1H), 4.3-4.1 (m, 5H), 4.05-3.92 (m, 2H), 2.4 (s, 3H)

LCMS purity: 96.38%, m/z=308.1 (M+1)
HPLC: 96.18%

Example 133

Preparation of 1-(4-Methyl-pyridin-3-yl)-3-naphthalen-1-O-imidazolidin-2-one (133A)

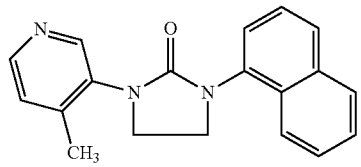

(133A)

Using the same reaction conditions as in Example 14, 1-(4-methyl-pyridin-3-yl)-imidazolidin-2-one (I-14b: 150 mg, 0.8465 mmol) was reacted with 1-bromo-naphthalene (118 mL, 0.8465 mmol), 1,4-dioxane (10 mL), copper iodide (18 mg), trans-1,2-diamino cyclohexane (36 mg) and potassium phosphate (539 mg, 2.5395 mmol) to afford the crude product. Purification by column chromatography on silica gel (2% MeOH in DCM) afforded 162 mg of the product (63.28% yield).

$^1$H NMR (DMSO-D$_6$, 300 MHz): δ 8.76-8.28 (m, 2H), 8.2-7.8 (m, 3H), 7.76-7.24 (m, 5H), 4.2-3.92 (br s, 4H), 2.35 (s, 3H)

LCMS purity: 98.99%, m/z=303.9 (M+1)
HPLC: 98.34%

Example 134

Preparation of 1-(1-Methyl-1H-indol-5-yl)-3-(4-methyl-pyridin-3-yl)-imidazolidin-2-one (134A)

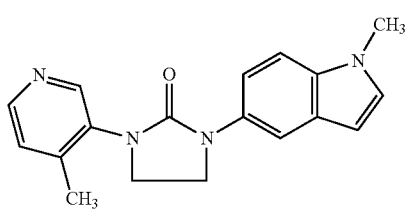

(134A)

Using the same reaction conditions as in Example 14, 1-(4-methyl-pyridin-3-yl)-imidazolidin-2-one (I-14b: 150 mg, 0.847 mmol) was reacted with 5-bromo-1-methyl-1H-indole (215 mL, 1.016 mmol), 1,4-dioxane (20 mL), copper iodide (15 mg, 0.084 mmol), trans-1,2-diamino cyclohexane (0.03 mL, 0.254 mmol) and potassium carbonate (230 mg, 1.69 mmol) to afford the crude product. Purification by column chromatography on silica gel (2% MeOH in $CHCl_3$), followed by recrystallization using DCM and hexane afforded 55 mg of the product (27% yield).

$^1$H NMR ($CDCl_3$, 300 MHz): δ 8.53 (s, 1H), 8.38 (d, 1H), 7.7-7.55 (m, 2H), 7.4-7.15 (m, 2H), 7.1-7.01 (m, 1H), 6.5-6.45 (br s, 1H), 4.2-4.05 (m, 2H), 4.0-3.9 (m, 2H), 3.78 (s, 3H), 2.38 (s, 3H)

LCMS purity: 93.43%, m/z=307.1 (M+1)
HPLC: 87.91%

Example 135

Preparation of 6-[3-(4-Methyl-pyridin-3-yl)-2-oxo-imidazolidin-1-yl]-1,2-dihydro-indazol-3-one (135A)

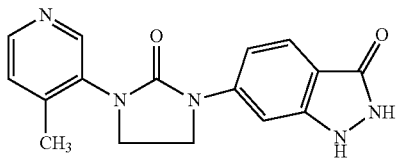

(135A)

Step 1: Preparation of Intermediate 2-fluoro-4-[3-(4-methyl-pyridin-3-yl)-2-oxo-imidazolidin-1-yl]-benzoic acid methyl ester (I-135a)

Using the same reaction conditions as in Example 15, 1-(4-methyl-pyridin-3-yl)-imidazolidin-2-one (I-14b: 295 mg, 1.65 mmol) was reacted with 4-bromo-2-fluoro-benzoic acid methyl ester (350 mg, 1.5 mmol), 1,4-dioxane (25 mL), copper iodide (32 mg, 0.165 mmol), trans-1,2-diamino cyclohexane (70 mg, 0.495 mmol) and potassium phosphate (875 mg, 4.12 mmol). The resulting mixture was refluxed for 18 hours. The reaction workup afforded 350 mg of 2-fluoro-4-[3-(4-methyl-pyridin-3-yl)-2-oxo-imidazolidin-1-yl]-benzoic acid methyl ester (68.7% yield).

$^1$H NMR ($CDCl_3$, 300 MHz): δ 8.78-8.26 (m, 2H), 8.1-7.82 (m, 1H), 7.55 (d, 1H), 7.48-7.12 (m, 2H), 4.3-3.8 (m, 7H), 2.32 (s, 3H)

LCMS purity: 97.47%, m/z=330.1 (M+1)

Final Step: Preparation of 6-[3-(4-Methyl-pyridin-3-yl)-2-oxo-imidazolidin-1-yl]-1,2-dihydro-indazol-3-one (135A)

Hydrazine hydrate (10 mL) was added to 2-fluoro-4-[3-(4-methyl-pyridin-3-yl)-2-oxo-imidazolidin-1-yl]-benzoic acid methyl ester (I-135a: 350 mg, 1.06 mmol) and the resulting mixture was heated to 120° C. for 18 hours. The reaction was monitored by TLC (10% MeOH in $CHCl_3$). The reaction mixture was partitioned between ice water and ethylacetate. The aqueous layer was concentrated to afford the crude product. Purification by column chromatography on silica gel (10% MeOH in $CHCl_3$), followed by preparative HPLC afforded 135 mg of the product (41.2% yield).

$^1$H NMR (DMSO-$D_6$, 300 MHz): δ 11.2-10.8 (br s, 1H), 10.7-10.4 (br s, 1H), 8.58-8.3 (m, 2H), 7.62-7.42 (m, 2H), 7.41-7.22 (m, 2H), 4.2-3.82 (m, 4H), 2.28 (s, 3H)

LCMS purity: 99.15%, m/z=310.0 (M+1)
HPLC: 97.14%

Example 136

Preparation of 1-(4-Methyl-pyridin-3-yl)-3-thieno[3,2-c]pyridin-3-yl-imidazolidin-2-one (136A)

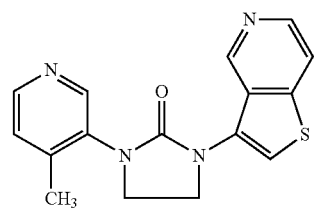

(136A)

Step I. Preparation of Intermediate 1-(4-Chloro-thieno[3,2-c]pyridin-3-yl)-3-(4-methyl-pyridin-3-yl)-imidazolidin-2-one (I-136a)

Using the same reaction conditions as in Example 14, 1-(4-methyl-pyridin-3-yl)-imidazolidin-2-one (I-14b: 321.4 mg, 1.8142 mmol) was reacted with 3-bromo-4-chloro-thieno[3,2-c]pyridine (500 mg, 1.9956 mmol), 1,4-dioxane (50 mL), copper iodide (34.4 mg, 0.1845 mmol), trans-1,2-diamino cyclohexane (62.3 mg, 0.5434 mmol) and potassium phosphate (961.3 mg, 4.528 mmol) to afford the crude product. Purification by column chromatography on silica gel (2% MeOH in $CHCl_3$) afforded 220 mg of 1-(4-Chloro-thieno[3,2-c]pyridin-3-yl)-3-(4-methyl-pyridin-3-yl)-imidazolidin-2-one (35.2% yield).

$^1$H NMR ($CDCl_3$, 300 MHz): δ 8.55 (s, 1H), 8.46-8.2 (dd, 2H), 7.8-7.6 (m, 1H), 7.3-7.2 (m, 2H), 4.2-4.0 (m, 4H), 2.4 (s, 3H)

Final Step: Preparation of 1-(4-Methyl-pyridin-3-yl)-3-thieno[3,2-c]pyridin-3-yl-imidazolidin-2-one (136A)

Activated Zinc (417 mg, 6.380 mmol) was added to a stirred solution of 1-(4-chloro-thieno[3,2-c]pyridin-3-yl)-3-(4-methyl-pyridin-3-yl)-imidazolidin-2-one (I-136a: 220 mg, 0.6380 mmol) in acetic acid (10 mL). The resulting mixture was stirred at room temperature for 2 days. The reaction was monitored by TLC (10% MeOH in DCM). The reaction mixture was filtered and the filtrate was concentrated under reduced pressure. Aqueous NH₃ solution was added to the concentrate and extracted with DCM. The organic layer was dried over Na₂SO₄ and concentrated under reduced pressure to afford the crude product. Purification by column chromatography on silica gel (5% MeOH in DCM) afforded 80 mg of the product (40.6% yield).

$^1$H NMR (DMSO-D₆, 300 MHz): δ 9.15 (s, 1H), 8.8-7.91 (m, 4H), 7.68 (s, 1H), 7.48-7.02 (m, 1H), 4.24-3.92 (m, 4H), 2.3 (s, 3H)

LCMS purity: 98.96%, m/z=310.9 (M+1)
HPLC: 95.37%

Example: 137

Preparation of 1-(5-Chloro-1-methyl-1H-indol-3-yl)-3-(4-methyl-pyridin-3-yl)-imidazolidin-2-one (137A)

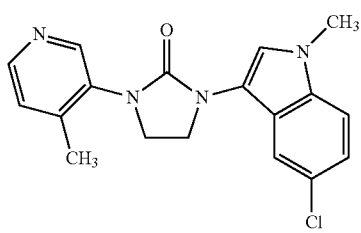

(137A)

Step 1: Preparation of Intermediate 3-Bromo-5-chloro-1-methyl-1H-indole (I-137a)

K₂CO₃ (1.39 g, 10.08 mmol) was added to a stirred solution of 3-bromo-5-chloro-1H-indole (775 mg, 3.36 mmol) in DMF (7.5 mL) and the resulting mixture was stirred for 30 minutes. This was followed by the addition of methyl iodide (572.5 mg, 4.03 mmol) at 0-5° C. and the stirring was continued for a further 2 hours at room temperature. The reaction was monitored by TLC (10% ethylacetate in hexane). The reaction mixture was partitioned between ice water and DCM. The organic layer was concentrated to afford the crude product. Purification by column chromatography on silica gel (5% ethylacetate in hexane) afforded 530 mg of 3-Bromo-5-chloro-1-methyl-1H-indole (65% yield).

$^1$H NMR (DMSO-D₆, 300 MHz): δ 7.94-7.2 (m, 4H), 3.8 (s, 3H)

Final Step: Preparation of 1-(5-Chloro-1-methyl-1H-indol-3-yl)-3-(4-methyl-pyridin-3-yl)-imidazolidin-2-one (137A)

Using the same reaction conditions as in Example 15, 1-(4-methyl-pyridin-3-yl)-imidazolidin-2-one (I-114b: 150 mg, 0.8465 mmol) was reacted with 3-bromo-5-chloro-1-methyl-1H-indole (I-137a: 226.2 mg, 0.9311 mmol), 1,4-dioxane (20 mL), copper iodide (16.1 mg, 0.8465 mmol), trans-1,2-diamino cyclohexane (30.6 mL, 0.255 mmol) and potassium phosphate (441 mg, 2.077 mmol). The resulting mixture was heated to reflux for 16 hours. The reaction workup afforded 170 mg of 1-(5-Chloro-1-methyl-1H-indol-3-yl)-3-(4-methyl-pyridin-3-yl)-imidazolidin-2-one (58.9% yield).

$^1$H NMR (DMSO-D₆, 300 MHz): δ 8.68-8.18 (m, 2H), 7.7 (s, 1H), 7.6-7.08 (m, 4H), 4.1-3.9 (br s, 4H), 3.78 (s, 3H), 2.3 (s, 3H)

LCMS purity: 100%, m/z=340.8 (M+1)
HPLC: 96.1%

Example 138

Preparation of 1-Indan-5-yl-3-(4-methyl-pyridin-3-yl)-imidazolidin-2-one (1384)

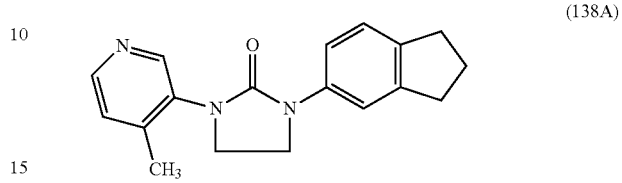

(138A)

Using the same reaction conditions as in Example 14, 1-(4-methyl-pyridin-3-yl)-imidazolidin-2-one (I-14b: 150 mg, 0.847 mmol) was reacted with 5-bromo-indan (248 mg, 1.0163 mmol), 1,4-dioxane (10 mL), copper iodide (0.0161 g, 0.0842 mmol), trans-1,2-diamino cyclohexane (0.028 g, 0.245 mmol) and potassium phosphate (538 mg, 2.537 mmol) to afford the crude product. Purification by column chromatography on silica gel (1% MeOH in CHCl₃) afforded 45 mg of the product (20% yield).

$^1$H NMR (CDCl₃, 300 MHz): δ 8.8-8.2 (m, 2H), 7.7-7.0 (m, 4H), 4.15-3.8 (m, 4H), 3.15-2.65 (m, 4H), 2.34 (s, 3H), 2.2-1.8 (m, 2H)

LCMS purity: 85.44%, m/z=294.1 (M+1)
HPLC: 91.46%

Example 139

Preparation of 1-Benzo[b]thiophen-5-yl-3-(4-methyl-pyridin-3-yl)-1,3-dihydro-imidazol-2-one (139A)

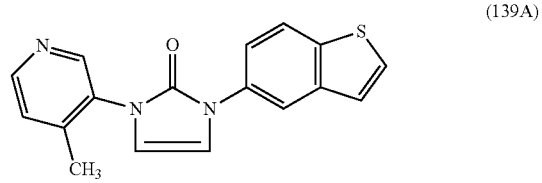

(139A)

Using the same reaction conditions as in Example 14, 1-(4-methyl-pyridin-3-yl)-imidazolidin-2-one (I-14b: 500 mg, 2.825 mmol) was reacted with 5-bromo-benzo[b]thiophene (661.86 mg, 3.12 mmol), 1,4-dioxane (20 mL), copper iodide (53.81 g, 0.2825 mmol), trans-1,2-diamino cyclohexane (97.03 g, 0.8475 mmol) and potassium phosphate (1.796 g, 8.475 mmol) to afford the crude product. Purification by column chromatography on silica gel (1.2% MeOH in CHCl₃), followed by preparative HPLC afforded 40 mg of the product (4.61% yield).

$^1$H NMR (CD₃OD, 300 MHz): δ 7.4-7.1 (m, 2H), 7.02-6.65 (m, 2H), 6.54-6.1 (m, 4H), 6.0-5.5 (m, 2H), 1.12 (s, 3H)

LCMS purity: 95.27%, m/z=308.0 (M+1)
HPLC: 97.39%

Example 140

Preparation of 2-Fluoro-4-[3-(4-methyl-pyridin-3-yl)-2-oxo-imidazolidin-1-yl]-benzonitrile (140A)

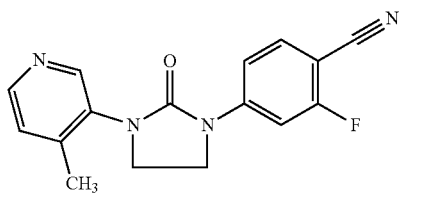
(140A)

The title compound was prepared in a manner analogous to the procedures described for Example (I-123a).

$^1$H NMR (DMSO-D$_6$, 300 MHz): δ 8.55 (s, 1H), 8.42 (d, 1H), 8.0-7.74 (m, 2H), 7.7-7.52 (m, 1H), 7.38 (d, 1H), 4.18-3.9 (m, 4H), 2.29 (s, 3H)
LCMS purity: 96.96%, m/z=297.1 (M+1)
HPLC: 97.49%

Example 141

Preparation of 1-(1H-Benzotriazol-5-yl)-3-(4-methyl-pyridin-3-yl)-imidazolidin-2-one Hydrochloride (141A)

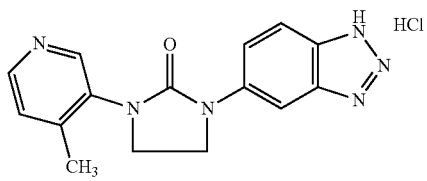
(141A)

Step 1: Preparation of Intermediate 1-(4-Methyl-pyridin-3-yl)-3-yl)-(2-trimethylsilanyl-ethoxymethyl)-1H-benzotriazol-5-yl)-imidazolidin-2-one (I-141a)

Using the same reaction conditions as in Example 14, 1-(4-methyl-pyridin-3-yl)-imidazolidin-2-one (I-14b: 175 mg, 0.9875 mmol) was reacted with 5-bromo-1-(2-trimethylsilanyl-ethoxymethyl)-1H-benzotriazole (353 mg, 1.08634 mmol), 1,4-dioxane (50 mL), copper iodide (80.76 mg, 0.09875 mmol), trans-1,2-diamino cyclohexane (33.9 mg, 0.2962 mmol) and potassium phosphate (524 mg, 2.4689 mmol) to afford the crude product. Purification by column chromatography on silica gel (2% MeOH in CHCl$_3$) afforded 350 mg of 1-(4-Methyl-pyridin-3-yl)-3-[1-(2-trimethylsilanyl-ethoxymethyl)-1H-benzotriazol-5-yl]-imidazolidin-2-one (79% yield).

$^1$H NMR (CDCl$_3$, 300 MHz): δ 8.66-8.25 (m, 2H), 8.2-7.6 (m, 2H), 7.2-7.4 (m, 2H), 6.15-5.8 (d, 2H), 4.35-3.9 (m, 4H), 3.7-3.4 (m, 2H), 2.4 (s, 3H), 1.05-0.7 (m, 2H), 0.2-0.2 (m, 9H)

Final Step: Preparation of 1-(1H-Benzotriazol-5-yl)-3-(4-methyl-pyridin-3-yl)-imidazolidin-2-one Hydrochloride (141A)

Dioxane HCl (10 ml) was added to 1-(4-methyl-pyridin-3-yl)-3-[1-(2-trimethylsilanyl-ethoxymethyl)-1H-benzotriazol-5-yl]-imidazolidin-2-one (I-141a: 350 mg, 0.78125 mmol) and the resulting mixture was stirred room temperature for 12 hours. The reaction was monitored by TLC (10% MeOH in DCM). The reaction mixture was concentrated and washed with ether. The solid formed was collected and dried under reduced pressure to afford 230 mg of the product (89.4% yield).

$^1$H NMR (DMSO-D$_6$, 300 MHz): δ 9.02 (s, 1H), 8.84-8.6 (m, 1H), 8.2-7.8 (m, 4H), 4.3-4.0 (m, 4H), 2.35 (s, 3H)
LCMS purity: 84.98%, m/z=295.1 (M+1)
HPLC: 95.17%

Example 142

Preparation of 1-Benzothiazol-6-yl-3-(4-methyl-pyridin-3-yl)-1,3-dihydro-imidazol-2-one (142A)

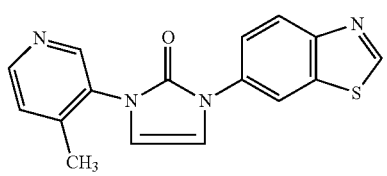
(142A)

Step 1: Preparation of Intermediate 1-Benzothiazol-6-yl-3-(2,2-dimethoxy-ethyl)-urea (I-142a)

TEA (185 mL, 1.3315 mmol) and triphosgene (138 mg, 0.4660 mmol) were added to a solution of benzothiazol-6-ylamine (200 mg, 1.3315 mmol) in THF (20 mL) at 0° C. The resulting mixture was stirred at room temperature for 3 hours. This was followed by the addition of 2,2-dimethoxy-ethylamine (173 mL, 1.5978 mmol) in THF and TEA (185 mL, 1.3315 mmol) and the stirring was continued for a further 18 hours at room temperature. The reaction was monitored by TLC (50% ethylacetate in hexane). The reaction mixture was concentrated and the concentrate was partitioned between ethylacetate and water. The organic layer was washed with water, brine solution, dried over Na$_2$SO$_4$ and concentrated. Purification by column chromatography on silica gel (100% ethylacetate) afforded 300 mg of 1-Benzothiazol-6-yl-3-(2,2-dimethoxy-ethyl)-urea (80.21% yield).

$^1$H NMR (DMSO-D$_6$, 300 MHz): δ 9.2 (s, 1H), 8.85 (s, 1H), 8.3 (s, 1H), 7.95 (d, 1H), 7.4 (d, 1H), 6.3 (s, 1H), 4.6-4.2 (m, 1H), 3.4-3.1 (m, 8H)
LCMS purity: 98.37%, m/z=282.0 (M+1)

Step 2: Preparation of Intermediate 1-Benzothiazol-6-yl-1,3-dihydro-imidazol-2-one (I-142b)

1N H$_2$SO$_4$ (2 mL) was added to 1-benzothiazol-6-yl-3-(2,2-dimethoxy-ethyl)-urea (I-142a: 300 mg) and the resulting mixture was stirred at 0° C. for 30 minutes. The reaction mixture was heated to 50° C. for 2 hours. The reaction was monitored by TLC (10% MeOH in CHCl$_3$). The reaction mixture was cooled to 0° C. and basified with 10% KOH solution. The precipitate was collected, washed with water and dried under reduced pressure to afford 170 mg of 1-Benzothiazol-6-yl-1,3-dihydro-imidazol-2-one (73.59% yield).

$^1$H NMR (DMSO-D$_6$, 300 MHz): δ 10.6-10.1 (br s, 1H), 9.35 (br s, 1H), 8.5 (s, 1H), 8.2-7.7 (m, 2H), 7.0 (s, 1H), 6.6 (s, 1H)
LCMS purity: 93.78%, m/z=217.9 (M+1)
HPLC: 94.03%

Final Step: Preparation of 1-Benzothiazol-6-yl-3-(4-methyl-pyridin-3-yl)-1,3-dihydro-imidazol-2-one (142A)

Using the same reaction conditions as in Example 14, 1-benzothiazol-6-yl-1,3-dihydro-imidazol-2-one (I-142b: 170 mg, 0.7834 mmol) was reacted with 3-iodo-4-methyl-pyridine (172 mg, 0.7834 mmol), 1,4-dioxane (10 mL), copper iodide (17 mg), trans-1,2-diamino cyclohexane (34 mg) and potassium phosphate (499 mg, 2.3502 mmol) to afford the crude product. Purification by column chromatography on silica gel (2-3% MeOH in CHCl$_3$), followed by preparative HPLC afforded 16 mg of the product (6.63% yield).

$^1$H NMR (DMSO-D$_6$, 300 MHz): δ 9.42 (s, 1H), 8.67-8.45 (d, 2H), 8.25-8.14 (d, 1H), 8.05-7.94 (m, 1H), 7.55-7.32 (m, 2H), 7.18-7.05 (d, 1H), 2.34 (s, 3H)

LCMS purity: 97.90%, m/z=308.9 (M+1)
HPLC: 97.01%

Example 143

Preparation of 1-(3-Amino-1-methyl-1H-indazol-6-yl)-3-(4-methyl-pyridin-3-yl)-imidazolidin-2-one (143A)

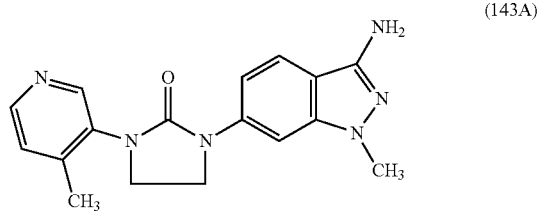

(143A)

Methyl hydrazine (10 mL) was added to a stirred solution of 2-fluoro-4-[3-(4-methyl-pyridin-3-yl)-2-oxo-imidazolidin-1-yl]-benzonitrile (I-123a: 240 mg, 0.80998 mmol) in 2-methoxy ethanol (20 mL). The resulting mixture was stirred at 170° C. for 12 hours. The reaction was monitored by TLC (10% MeOH in CHCl$_3$). The reaction mixture was cooled to room temperature and concentrated. Ice was added to the concentrate and the precipitate formed was collected and dried under reduced pressure to afford 180 mg of the product (69.2% yield).

$^1$H NMR (DMSO-D$_6$, 300 MHz): δ 8.8-8.1 (d, 2H), 7.8-7.15 (m, 4H), 5.35 (s, 2H), 4.4-3.8 (m, 4H), 3.6 (s, 3H), 2.35 (s, 3H)

LCMS purity: 99.42%, m/z=323.1 (M+1)
HPLC: 95.08%

Example 144

Preparation of 1-(1H-Indol-6-yl)-3-(4-methyl-pyridin-3-yl)-imidazolidin-2-one (144A)

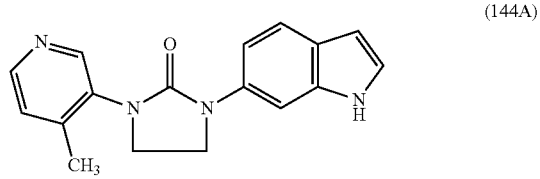

(144A)

Step 1: Preparation of Intermediate-(4-Methyl-pyridin-3-yl)-3-[1-(toluene-4-sulfonyl)-1H-indol-6-yl]-imidazolidin-2-one (I-144a)

Using the same reaction conditions as in Example 14, 1-(4-methyl-pyridin-3-yl)-imidazolidin-2-one (I-14b: 130 mg, 0.00073 mol) was reacted with 6-bromo-1-(toluene-4-sulfonyl)-1H-indole (200 mg, 0.00073 mol), 1,4-dioxane (20 mL), copper iodide (13 mg, 0.000073 mol), trans-1,2-diamino cyclohexane (26 mg, 0.00021 mol) and potassium phosphate (309 mg, 0.00146 mol) to afford the crude product. Purification by column chromatography on silica gel (2% MeOH in CHCl$_3$) afforded 94 mg of 1-(4-Methyl-pyridin-3-yl)-3-[1-(toluene-4-sulfonyl)-1H-indol-6]-imidazolidin-2-one (30.12% yield).

$^1$H NMR (CDCl$_3$, 300 MHz): δ 8.7-8.3 (m, 2H), 8.16 (s, 1H), 7.95-7.7 (m, 2H), 7.68-7.4 (m, 2H), 7.36-7.12 (m, 4H), 6.7-6.5 (s, 1H), 4.3-3.8 (m, 4H), 2.4 (s, 3H), 2.3 (s, 3H)

LCMS purity: 81.93%, m/z=447.1 (M+1)

Final Step: Preparation of 1-(1H-Indol-6-yl)-3-(4-methyl-pyridin-3-yl)-imidazolidin-2-one (144A)

10% NaOH solution (10 mL) was added to a solution of 1-(4-methyl-pyridin-3-yl)-3-[1-(toluene-4-sulfonyl)-1H-indol-6-yl]-imidazolidin-2-one (I-144a: 94 mg) in ethanol (10 mL). The resulting mixture was heated to reflux at 90° C. for 1 hour. The reaction was monitored by TLC (10% MeOH in CHCl$_3$). The reaction mixture was concentrated and partitioned between ethylacetate and water. The organic layer was washed with water, brine solution, dried and concentrated. Purification by column chromatography on silica gel (2% MeOH in DCM) afforded 29 mg of the product (47.54% yield).

$^1$H NMR (CD$_3$OD, 300 MHz): δ 8.7-8.2 (m, 2H), 7.9-7.0 (m, 5H), 6.4 (s, 1H), 4.3-3.8 (m, 4H), 2.4 (s, 3H)

LCMS purity: 75.15%, m/z=293.0 (M+1)
HPLC: 85.90%

Example 145

Preparation of 1-(3-Chloro-imidazo[1,2-a]pyridin-7-yl)-3-(4-methyl-pyridin-3-yl)-imidazolidin-2-one (145A)

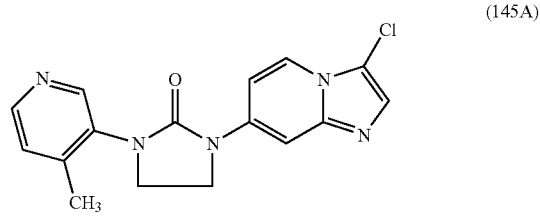

(145A)

Using the same reaction conditions as in Example 14, 1-(4-methyl-pyridin-3-yl)-imidazolidin-2-one (I-14b: 165 mg, 0.932 mmol) was reacted with 7-bromo-3-chloro-imidazo[1,2-a]pyridine (278 mg, 1.21 mmol), 1,4-dioxane (6 mL), copper iodide (17.71 mg, 0.093 mmol), trans-1,2-diamino cyclohexane (32.01 mg, 0.279 mmol) and potassium phosphate (493.96 mg, 2.33 mmol) to afford the crude product. Purification by column chromatography on silica gel (2% MeOH in CHCl$_3$), followed by preparative HPLC afforded 20 mg of the product (6.57% yield).

$^1$H NMR (CDCl$_3$, 300 MHz): δ 9.1-8.9 (m, 2H), 8.6-8.3 (m, 2H), 8.0-7.6 (m, 3H), 4.4-4.1 (m, 4H), 2.6 (s, 3H)

LCMS purity: 83.31%, m/z=328.0 (M+1)
HPLC: 89.12%

Example 146

Preparation of 1-Methyl-3-[3-(4-methyl-pyridin-3-yl)-2-oxo-imidazolidin-1-yl]-1H-indole-4-carbonitrile (146A)

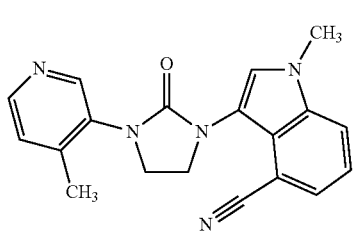
(146A)

Step 1: Preparation of Intermediate 3-Bromo-1H-indole-4-carbonitrile (I-146a)

Bromine in DMF (0.796 g, 4.975 mmol) was added to a stirred solution of 1H-indole-4-carbonitrile (700 mg, 4.9295 mmol) in DMF (15 mL) at room temperature. The resulting mixture was stirred at room temperature for 2 hours. The reaction was monitored by TLC (10% ethylacetate in hexane). The reaction mixture was poured into ice water containing 0.5% ammonia and 0.5% sodium metabisulphite. The precipitate was collected, washed with cold water and dried to afford 850 mg of 3-Bromo-1H-indole-4-carbonitrile (78.41% yield).

$^1$H NMR (DMSO-D$_6$, 300 MHz): δ 12.1 (s, 1H), 8.02-7.49 (m, 3H), 7.42-7.2 (m, 1H)

Step 2: Preparation of Intermediate 3-Bromo-1-methyl-1H-indole-4-carbonitrile (I-146b)

3-Bromo-1H-indole-4-carbonitrile (I-146a: 500 mg, 2.272 mmol) was added dropwise to a stirred mixture of NaH (0.218 g, 9.0833 mmol) in dry DMF (15 mL) at 0° C. over a period of 10 minutes. This was followed by the addition of methyl iodide and the resulting mixture was stirred at 0° C. for 2 hours. The reaction was monitored by TLC (10% ethylacetate in hexane). The reaction mixture was quenched with ice water; the precipitate formed was collected and dried to afford 0.400 g of the crude product.

$^1$H NMR (CDCl$_3$, 300 MHz): δ 7.8-7.0 (m, 4H), 3.82 (s, 3H)

Final Step: Preparation of Intermediate 1-Methyl-3-[3-(4-methyl-pyridin-3-yl)-2-oxo-imidazolidin-1-yl]-1H-indole-4-carbonitrile (146A)

Using the same reaction conditions as in Example 14, 1-(4-methyl-pyridin-3-yl)-imidazolidin-2-one (I-14b: 110 mg, 0.621 mmol) was reacted with 3-bromo-1-methyl-1H-indole-4-carbonitrile (I-146b: 175 mg, 0.744 mmol), 1,4-dioxane (15 mL), copper iodide (11 mg, 0.0573 mmol), trans-1,2-diamino cyclohexane (21 mg, 0.1843 mmol) and potassium carbonate (171 mg, 1.239 mmol) to afford the crude product. Purification by column chromatography on silica gel (3% MeOH in CHCl$_3$) afforded 49 mg of 1-Methyl-3-[3-(4-methyl-pyridin-3-yl)-2-oxo-imidazolidin-1-yl]-1H-indole-4-carbonitrile (23.90% yield).

$^1$H NMR (CDCl$_3$, 300 MHz): δ 8.6 (s, 1H), 8.5-8.3 (m, 1H), 7.7-7.1 (m, 4H), 4.18-3.95 (m, 4H), 3.85 (s, 3H), 2.45 (s, 3H)

LCMS purity: 99.70%, m/z=331.9 (M+1)
HPLC: 95.81%

Example 147

Preparation of 1-Hydroxymethyl-3,3-dimethyl-5-[3-(4-methyl-pyridin-3-yl)-2-oxo-imidazolidin-1-yl]-1,3-dihydro-indol-2-one (147A)

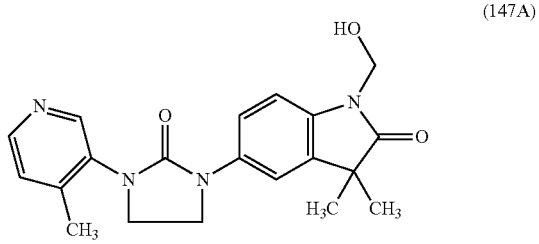
(147A)

Step 1: Preparation of Intermediate 3,3-Dimethyl-5-[3-(4-methyl-pyridin-3-yl)-2-oxo-imidazolidin-1-yl]-1-(2-trimethylsilanyl-ethoxymethyl)-1,3-dihydro-indol-2-one (147a)

Using the same reaction conditions as in Example 14, 1-(4-methyl-pyridin-3-yl)-imidazolidin-2-one (I-14b: 0.123 g, 0.0007 mol) was reacted with 5-iodo-3,3-dimethyl-1-(2-trimethylsilanyl-ethoxymethyl)-1,3-dihydro-indol-2-one (0.29 g, 0.0007 mol), 1,4-dioxane (20 mL), copper iodide (0.013 g, 0.00007 mol), trans-1,2-diamino cyclohexane (0.028 g, 0.00025 mol) and potassium phosphate (356 mg, 0.00168 mol) to afford the crude product. Purification by column chromatography on silica gel (80% ethylacetate in hexane) afforded 170 mg of 3,3-Dimethyl-5-[3-(4-methyl-pyridin-3-yl)-2-oxo-imidazolidin-1-yl]-1-(2-trimethylsilanyl-ethoxymethyl)-1,3-dihydro-indol-2-one (52.14% yield).

$^1$H NMR (CDCl$_3$, 300 MHz): δ 8.6-8.4 (m, 2H), 7.5-7.0 (m, 4H), 5.2 (s, 2H), 4.2-3.9 (m, 4H), 3.6-3.4 (m, 2H), 2.3 (s, 3H), 1.4 (s, 6H), 1.1-0.7 (m, 2H), 0.2-0.2 (s, 9H)

LCMS purity: 88.56%, m/z=467.2 (M+1)

Final Step: Preparation of 1-Hydroxymethyl-3,3-dimethyl-5-[3-(4-methyl-pyridin-3-yl)-2-oxo-imidazolidin-1-yl]-1,3-dihydro-indol-2-one (147A)

Dioxane HCl (4 mL) was added to 3,3-dimethyl-5-[3-(4-methyl-pyridin-3-yl)-2-oxo-imidazolidin-1-yl]-1-(2-trimethylsilanyl-ethoxymethyl)-1,3-dihydro-indol-2-one (I-147a: 50 mg) and the resulting mixture was stirred room temperature for 1 hour. The reaction was monitored by TLC (10% MeOH in CHCl$_3$). The reaction mixture was basified with bicarbonate solution and extracted with DCM. The organic layer was concentrated; the concentrate was recrystallized with DCM and hexane and dried to afford 37 mg of the product (94.87% yield).

$^1$H NMR (CD$_3$OD, 300 MHz): δ 8.7-8.3 (m, 2H), 7.7-7.1 (m, 4H), 5.2 (s, 2H), 4.3-3.9 (m, 4H), 2.4 (s, 3H), 1.4 (s, 6H)

LCMS purity: 79.51%, m/z=367.1 (M+1)
HPLC: 82.25%

Example 148

Preparation of 1-(4-Methyl-pyridin-3-yl)-3-(2-trifluoromethyl-pyridin-4-yl)-imidazolidin-2-one (163A)

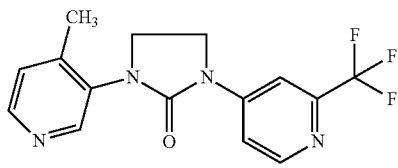

(148A)

Using the same reaction conditions as in Example 15, 1-(4-methyl-pyridin-3-yl)-imidazolidin-2-one (I-14b: 150 mg, 0.847 mmol) was reacted with 4-bromo-2-trifluoromethyl-pyridine (229 mg, 1.017 mmol), 1,4-dioxane (10 mL), copper iodide (16.13 mg, 0.0847 mmol), trans-1,2-diamino cyclohexane (29.09 mg, 0.254 mmol) and potassium phosphate (44.89 mg, 2.117 mmol). The resulting mixture was heated to 120° C. for 6 hours. The reaction workup afforded 200 mg of the product (73.52% yield).

$^1$H NMR (DMSO-D$_6$, 300 MHz): δ 8.8-8.5 (m, 2H), 8.5-8.35 (m, 1H), 8.35-8.1 (br s, 1H), 7.8-7.6 (m, 1H), 7.5-7.25 (m, 1H), 4.3-3.8 (m, 4H), 2.3 (s, 3H)

LCMS purity: 98.05%, m/z=323.0 (M+1)
HPLC: 98.13%

Example 149

Preparation of 1-Benzothiazol-6-yl-3-(4-dimethoxymethyl-pyridin-3-yl)-imidazolidin-2-one (149A)

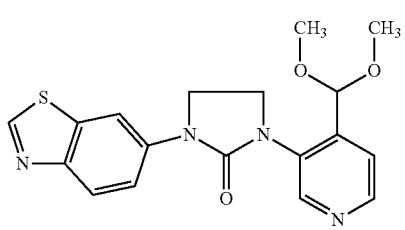

(149A)

Step 1: Preparation of Intermediate 3-Bromo-4-dimethoxymethyl-pyridine (I-149a)

PTSA (834 mg, 4.384 mmol) was added to a solution of 3-bromo-pyridine-4-carbaldehyde (600 mg, 3.2256 mmol) in methanol (20 mL). The resulting mixture was heated to reflux for 4 hours. The reaction was monitored by TLC (20% ethylacetate in hexane). The reaction mixture was concentrated and basified with NaHCO$_3$ solution. The reaction mixture was partitioned between water and DCM. The organic layer was washed with brine solution, dried over Na$_7$SO$_4$, filtered and the filtrate was concentrated to afford 700 mg of 3-Bromo-4-dimethoxymethyl-pyridine (93.5% yield).

$^1$H NMR (CDCl$_3$, 300 MHz): δ 8.8-8.4 (m, 2H), 7.5 (s, 1H), 5.5 (s, 1H), 3.4 (s, 6H)

Final Step Preparation of 1-Benzothiazol-6-yl-3-(4-dimethoxymethyl-pyridin-3-yl)-imidazolidin-2-one (149A)

Using the same reaction conditions as in Example 14, 1-benzothiazol-6-yl-imidazolidin-2-one (I-84b: 590 mg, 2.7 mmol) was reacted with 3-bromo-4-dimethoxymethyl-pyridine (I-149a: 690 mg, 2.97 mmol), 1,4-dioxane (50 mL), copper iodide (51.46 mg, 0.27 mmol), trans-1,2-diamino cyclohexane (93 mg, 0.81 mmol) and potassium phosphate (1.72 g, 8.1 mmol) to afford the crude product. Purification by column chromatography on silica gel (1% MeOH in CHCl$_3$) afforded 510 mg of the product (51.2% yield).

$^1$H NMR (DMSO-D$_6$, 300 MHz): δ 9.28 (s, 1H), 8.8-8.5 (m, 2H), 8.3 (s, 1H), 8.18-7.82 (m, 2H), 7.68-7.42 (br s, 1H), 5.6 (s, 1H), 4.25-3.85 (m, 4H), 3.3 (s, 6H)

LCMS purity: 98.35%, m/z=371.2 (M+1)
HPLC: 96.82%

Example 150

Preparation of N-[3-(3-Benzothiazol-6-yl-2-oxo-imidazolidin-1-yl)-pyridin-4-yl]-acetamide (150A)

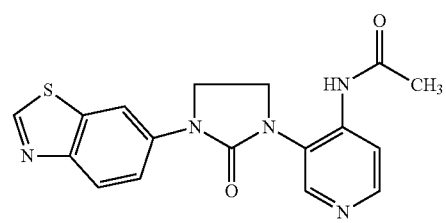

(150A)

Using the same reaction conditions as in Example 14, 1-benzothiazol-6-yl-imidazolidin-2-one (I-84b: 200 mg, 0.912 mmol) was reacted with N-(3-iodo-pyridin-4-yl)-acetamide (262 mg, 1.003 mmol), 1,4-dioxane (10 mL), copper iodide (17.3 mg, 0.09 mmol), trans-1,2-diamino cyclohexane (31.4 mg, 0.273 mmol) and potassium phosphate (581 mg, 2.73 mmol) to afford the crude product. Purification by column chromatography on silica gel (2% MeOH in CHCl$_3$) afforded 75 mg of the product (23.36% yield).

$^1$H NMR (DMSO-D$_6$, 300 MHz): δ 9.75 (s, 1H), 9.28 (s, 1H), 8.55 (s, 1H), 8.45-7.9 (m, 5H), 4.3-4.0 (m, 2H), 3.95-3.8 (m, 2H), 2.2 (s, 3H)

LCMS purity: 78.28%, m/z=354.0 (M+1)
HPLC: 90.16%

Example 151

Preparation of 1-Benzothiazol-6-yl-3-(5-chloro-4-methyl-pyridin-3-yl)-imidazolidin-2-one (151A)

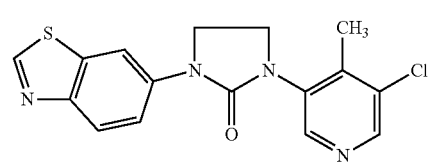

(151A)

Using the same reaction conditions as in Example 14, 1-benzothiazol-6-yl-imidazolidin-2-one (I-84b: 100 mg, 0.456 mmol) was reacted with 3-bromo-5-chloro-4-methylpyridine (94 mg, 0.456 mmol), 1,4-dioxane (5 mL), copper iodide (8.68 mg, 0.0456 mmol), trans-1,2-diamino cyclohexane (15.66 mg, 0.1368 mmol) and potassium phosphate (290.38 mg, 1.368 mmol) to afford the crude product. Purification by preparative HPLC afforded 52 mg of the product (34.21% yield).

$^1$H NMR (CD$_3$OD, 300 MHz): δ 9.15 (s, 1H), 8.5 (s, 1H), 8.32 (s, 1H), 8.15-7.8 (m, 2H), 4.31-4.2 (m, 2H), 4.1-3.98 (m, 2H), 2.41 (s, 3H)

LCMS purity: 99.33%, m/z=344.9 (M+1)
HPLC: 97.28%

Example 152

Preparation of 1-(4-Amino-pyridin-3-yl)-3-benzothiazol-6-yl-imidazolidin-2-one Hydrochloride Salt (152A)

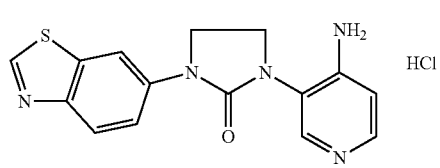

(152A)

6N HCl (3 mL) was added to a solution of N-[3-(3-benzothiazol-6-yl-2-oxo-imidazolidin-1-yl)-pyridin-4-yl]-acetamide (150A: 70 mg, 0.198 mmol) in ethanol (3 mL) and the resulting mixture was refluxed at 65° C. overnight. The reaction was monitored by TLC (10% MeOH in CHCl$_3$). The reaction mixture was concentrated and the concentrate was washed with diethyl ether and dried to afford 20 mg of the product (29.02% yield).

$^1$H NMR (CD$_3$OD, 300 MHz): δ 9.6 (s, 1H), 8.6-8.3 (m, 2H), 8.1 (s, 3H), 7.1-6.9 (m, 1H), 4.4-4.2 (m, 2H), 4.05-3.85 (m, 2H)

LCMS purity: 98.71%, m/z=312.1 (M+1)
HPLC: 95.01%

Example 153

Preparation of 1-(benzo[d]thiazol-6-yl)-3-(4-methyl-5-(trifluoromethyl)pyridin-3-yl)imidazolidin-2-one, Trifluoroacetic Acid Salt (153A)

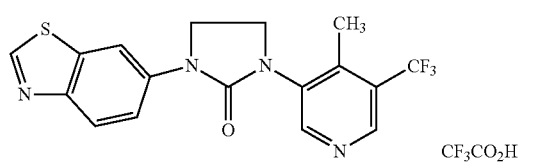

(153A)

Preparation of Starting Material
3-Bromo-4-methyl-5-trifluoromethyl-pyridine (SM-153a)

Butyl Lithium (1.9 mL, 3.044 mmol) was added to a solution of DIPA (335.7 mg, 3.318 mmol) in THF (6 mL) at -78° C. The reaction mixture was stirred at -10° C. for 10 minutes. This was followed by the addition of 3-bromo-5-trifluoromethyl-pyridine (500 mg, 2.212 mmol) in THF (3 mL) at -100° C. The reaction mixture was stirred for a further 15 minutes at -90° C. and was followed by the addition of methyl iodide (557.0 mg, 3.924 mmol) in THF (2 mL) at -78° C. with stirring over a period of 30 minutes. The reaction was monitored by TLC (5% ethylacetate in hexane). The reaction mixture was quenched with aqueous NaHCO$_3$ solution and extracted with ethylacetate (100 mL). The organic layer was dried over Na$_2$SO$_4$ and concentrated. Purification by column chromatography on silica gel (2% ethylacetate in hexane) afforded 95 mg of the product (17.92% yield).

LCMS: m/z=239.8 (M+1)

Final Step: Preparation of 14-benzo[d]thiazol-6-yl)-3-(4-methyl-5-(trifluoromethyl)pyridin-3-yl)imidazolidin-2-one, Trifluoroacetic Acid Salt (153A)

Using the same reaction conditions as described in example 14, 1-benzothiazol-6-yl-imidazolidin-2-one (I-84b: 80 mg, 0.365 mmol) was reacted with 3-bromo-4-methyl-5-trifluoromethyl-pyridine (SM-153a: 90 mg, 0.365 mmol), 1,4-dioxane (5 mL), copper iodide (6.95 mg, 0.0365 mmol), trans-1,2-diamino cyclohexane (12.5 mg, 0.1095 mmol) and potassium phosphate (232.4 mg, 1.095 mmol) to afford the crude product. Purification by preparative HPLC afforded 5 mg of the product (3.6% yield).

$^1$H NMR (CDCl$_3$, 300 MHz): δ 9.05-8.65 (m, 3H), 8.35 (s, 1H), 8.25-8.05 (m, 1H), 7.78-7.58 (m, 1H), 4.32-4.12 (m, 2H), 4.12-3.91 (m, 2H), 2.49 (s, 3H)

LCMS purity: 100%, m/z=378.9 (M+1)
HPLC: 93.5%

Example 154

Preparation of 1-(isothiazol-4-yl)-3-(4 ethylpyridin-3-yl)imidazolidin-2-one (154A)

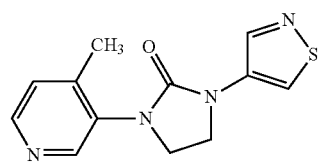

(154A)

Using the same reaction conditions as described in example 14, 1-(4-methyl-pyridin-3-yl)-imidazolidin-2-one (I-14b: 150 mg, 0.847 mmol) was reacted with 4-bromo-isothiazole (166 mg, 1.016 mmol), 1,4-dioxane (15 mL), copper iodide (16.09 mg, 0.0847 mmol), trans-1,2-diamino cyclohexane (29 mg, 0.254 mmol) and potassium phosphate (540 mg, 2.541 mmol) to afford the crude product. Purification by column chromatography on silica gel (2% MeOH in CHCl$_3$) afforded 120 mg of the product (54.54% yield).

$^1$H NMR (CDCl$_3$, 300 MHz): δ 8.82 (s, 1H), 8.65-8.25 (m, 3H), 7.4-7.1 (m, 1H), 4.20-3.95 (m, 4H), 2.19 (s, 3H)

LCMS purity: 97.95%, m/z=261.0 (M+1)
HPLC: 96.08%

Example 155

Preparation of 1-(4-Methylpyridin-3-yl)-3-(5-(trifluoromethyl)thiophen-2-yl)-imidazolidin-2-one (155A)

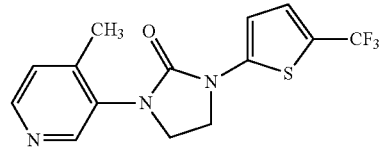

(155A)

Using the same reaction conditions as described in example 14, 1-(4-methyl-pyridin-3-yl)-imidazolidin-2-one (I-14b: 100 mg, 0.5643 mmol) was reacted with 2-bromo-5-trifluoromethyl-thiophene (136.9 mg, 0.5925 mmol), 1,4-dioxane (10 mL), copper iodide (10.75 mg, 0.0564 mmol), trans-1,2-diamino cyclohexane (20.4 mL, 0.1693 mmol) and potassium phosphate (360 mg, 1.693 mmol) to afford the crude product. Purification by column chromatography on silica gel (2% MeOH in CHCl$_3$) afforded 120 mg of the product (65% yield).

$^1$H NMR (DMSO-D$_6$, 300 MHz): δ 8.66-8.3 (m, 2H), 7.65-7.23 (m, 2H), 6.55 (d, 1H), 4.24-3.90 (m, 4H), 2.26 (s, 3H)

LCMS purity: 96.35%, m/z=327.9 (M+1)
HPLC: 95.04%

Example 156

Preparation of 1-(benzo[d]thiazol-6-yl)-3-(4-(2-hydroxypropan-2-yl)pyridin-3-yl)imidazolidin-2-one (156A)

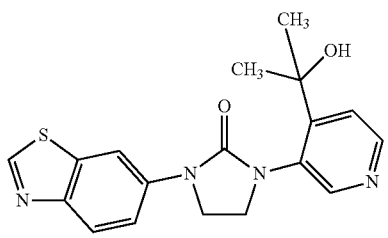

(156A)

Preparation of Starting Material 2-(3-Bromo-pyridin-4-O-propan-2-ol (SM-156a)

Butyl Lithium (10.28 mL, 16.455 mmol) was added to a solution of DIPA (2.66 mL, 18.98 mmol) in THF (25 mL) at -78° C. The reaction mixture was stirred at -10° C. for 10 minutes, followed by the addition of 3-bromo-pyridine (500 mg, 2.212 mmol) in THF (10 mL) at -100° C. The reaction mixture was stirred for a further 15 minutes at -90° C. and was followed by the addition of acetone (1.675 mL, 22.78 mmol) in THF (10 mL) at -78° C. with stirring over a period of 1 hour. The reaction was monitored by TLC (5% ethylacetate in hexane). The reaction mixture was quenched with aqueous NaHCO$_3$ solution and extracted with ethylacetate. The organic layer was dried over Na$_2$SO$_4$ and concentrated. Purification by column chromatography on silica gel (15% ethylacetate in hexane) afforded 200 mg of 2-(3-bromo-pyridin-4-yl)-propan-2-ol (11% yield).

$^1$H NMR (CDCl$_3$, 300 MHz): δ 8.7 (s, 1H), 8.5 (d, 1H), 7.65 (d, 1H), 1.7 (s, 6H)

LCMS purity: 89.57%, m/z=215.9 (M+1)

Final Step: Preparation of 1-(benzo[d]thiazol-6-yl)-3-(4-(2-hydroxypropan-2-yl)pyridin-3-yl)imidazolidin-2-one (156A)

Using the same reaction conditions as described in example 14, 1-benzothiazol-6-yl-imidazolidin-2-one (I-84b: 125 mg, 0.57 mmol) was reacted with 2-(3-bromo-pyridin-4-yl)-propan-2-ol (SM-156a: 122.7 mg, 0.57 mmol), 1,4-dioxane (5 mL), copper iodide (10.85 mg, 0.057 mmol), trans-1, 2-diamino cyclohexane (19.57 mg, 0.171 mmol) and potassium phosphate (362.9 mg, 1.71 mmol) to afford the crude product. Purification by preparative HPLC afforded 38 mg of the product (19% yield).

$^1$H NMR (CDCl$_3$, 300 MHz): δ 8.68 (s, 1H), 8.50-8.32 (m, 2H), 7.86 (d, 1H), 7.18-7.02 (m, 2H), 6.82 (dd, 1H), 4.55-4.42 (m, 1H), 4.32 (t, 2H), 3.7-3.6 (m, 2H), 1.74-1.58 (m, 6H)

LCMS purity: 97.84%, m/z=354.9 (M+1)
HPLC: 95.61%

Example 157

Preparation of 1-(4-Methylpyridin-3-yl)-3-(4-methylthieno[3,2-e]pyridin-2-yl)imidazolidin-2-one (157A)

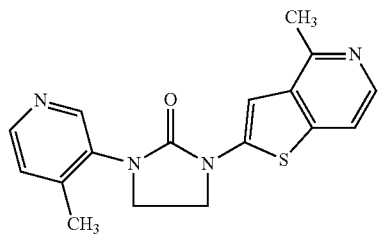

(157A)

Tetrakis (triphenylphosphine) palladium (33 mg, 0.0288 mmol) was added to potassium carbonate (120 mg, 0.8649 mmol) previously purged with argon (30 minutes). The reaction mixture was purged with argon for 15 minutes, followed by the addition of 1-(4-chloro-thieno[3,2-c]pyridin-2-yl)-3-(4-methyl-pyridin-3-yl)-imidazolidin-2-one (98A: 100 mg, 0.2883 mmol) and methyl boronic acid (21 mg, 0.3459 mmol). The reaction mixture was heated to reflux for 6 hours. The reaction was monitored by TLC (10% MeOH in CHCl$_3$). The reaction mixture was concentrated to afford the crude product. Purification by column chromatography on silica gel (3-4% MeOH in CHCl$_3$), followed by preparative HPLC afforded 10 mg of the product (16.39% yield).

$^1$H NMR (CDCl$_3$, 300 MHz): δ 8.7-8.35 (m, 2H), 8.35-8.2 (d, 1H), 7.5 (d, 1H), 6.58 (s, 1H), 4.4-3.9 (m, 4H), 2.79 (s, 3H), 2.36 (s, 3H)

LCMS purity: 96.01%, m/z=324.9 (M+1)
HPLC: 96.32%

Example 158

Preparation of 1-(benzo[d]thiazol-6-yl)-3-(4-(1-hydroxyethyl)pyridin-3-yl)imidazolidin-2-one (158A)

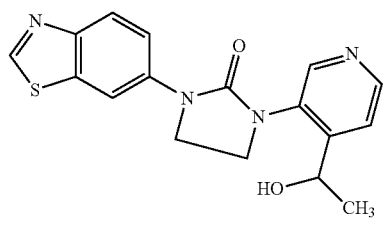

(158A)

Using the same reaction conditions as described in example 14, 1-benzothiazol-6-yl-imidazolidin-2-one (I-84b: 150 mg, 0.6849 mmol) was reacted with 1-(3-bromo-pyridin-4-yl)-ethanol (137.6 mg, 0.6849 mmol), 1,4-dioxane (5 mL), copper iodide (13.04 mg, 0.06849 mmol), trans-1,2-diamino cyclohexane (23.52 mg, 0.205 mmol) and potassium phosphate (435.1 mg, 2.05 mmol) to afford the crude product. Purification by column chromatography on silica gel (2% MeOH in CHCl$_3$), followed by preparative HPLC afforded 9 mg of the product (3.9% yield).

$^1$H NMR (CDCl$_3$, 300 MHz): δ 8.92 (s, 1H), 8.65-8.54 (m, 2H), 8.32 (d, 1H), 8.15 (d, 1H), 7.70-7.62 (dd, 1H), 7.6 (d, 1H), 5.10-4.96 (m, 1H), 4.30-4.12 (m, 3H), 4.02-3.85 (m, 1H), 3.75-3.66 (br s, 1H), 1.60-1.45 (d, 3H)

LCMS purity: 98.20%, m/z=340.9 (M+1)

HPLC: 91.15%

Example 159

Preparation of 1-(benzo[d]thiazol-6-yl)-3-(4-ethylpyridin-3-yl)imidazolidin-2-one (159A)

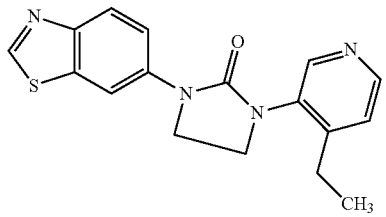

(159A)

Using the same reaction conditions as described in example 14, 1-benzothiazol-6-yl-imidazolidin-2-one (I-84b: 600 mg, 2.739 mmol) was reacted with 3-bromo-4-ethylpyridine (512 mg, 2.739 mmol), 1,4-dioxane (10 mL), copper iodide (52 mg, 0.2739 mmol), trans-1,2-diamino cyclohexane (94.08 mg, 0.82 mmol) and potassium phosphate (1.74 mg, 8.2 mmol) to afford the crude product. Purification by column chromatography on silica gel (2% MeOH in CHCl$_3$), followed by preparative HPLC afforded 30 mg of the product (3.75% yield).

$^1$H NMR (CD$_3$OD, 300 MHz): δ 9.15 (s, 1H), 8.60-8.35 (m, 3H), 8.15-7.95 (m, 1H), 7.95-7.70 (m, 1H), 7.5 (d, 1H), 4.3-3.9 (m, 4H), 2.85-2.65 (q, 2H), 1.4-1.2 (t, 3H)

LCMS purity: 99.77%, m/z=325.1 (M+1)

HPLC: 95.03%

Example 160

Preparation of 1-(4-methylpyridin-3-yl)-3-(3-(trifluoromethyl)-1H-indazol-6-yl)imidazolidin-2-one (160A)

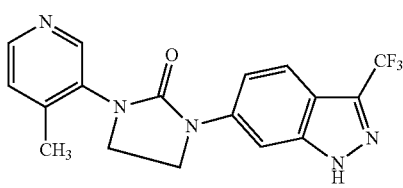

(160A)

Step 1: Preparation of Intermediate 1-[3-Fluoro-4-(2,2,2-trifluoro-1-hydroxy-ethyl)-phenyl]-3-(4-methyl-pyridin-3-yl)-imidazolidin-2-one (I-160a)

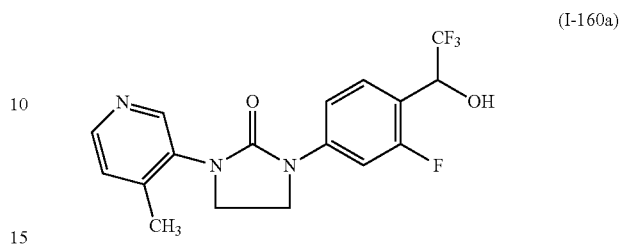

(I-160a)

A 0.5M solution of trimethyl-trifluoromethyl-silane in THF (6.68 mL, 3.344 mmol) and K$_2$CO$_3$ (250 mg, 10.82 mmol) was added to 2-fluoro-4-[3-(4-methyl-pyridin-3-yl)-2-oxo-imidazolidin-1-yl]-benzaldehyde (I-121a: 400 mg, 1.337 mmol) in dry DMF (5 mL) under nitrogen atmosphere. The resulting mixture was stirred at room temperature overnight. The reaction was monitored by thin layer chromatography (5% MeOH in CHCl$_3$). The reaction mixture was quenched with brine solution and the THF layer was concentrated. The aqueous layer was extracted with chloroform. The organic layer was dried over Na$_2$SO$_4$ and concentrated to get the crude product. Purification by column chromatography on silica gel (2.5% MeOH in CHCl$_3$), followed by hexane wash, afforded 325 mg of the product (65.92% yield).

$^1$H NMR (CDCl$_3$, 300 MHz): δ 8.56-8.00 (m, 2H), 7.75-7.45 (m, 2H), 7.36-7.08 (m, 2H), 5.38 (q, 1H), 4.55-4.24 (br s, 1H), 4.20-3.76 (m, 4H), 2.32 (s, 3H)

Step 2: Preparation of Intermediate 1-[3-Fluoro-4-(2,2,2-trifluoro-acetyl)-phenyl methyl-pyridin-3-yl]-imidazolidin-2-one (I-160b)

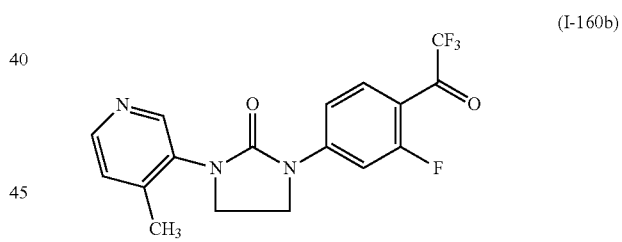

(I-160b)

MnO$_2$ (536 mg, 6.165 mmol) was added to 1-[3-fluoro-4-(2,2,2-trifluoro-1-hydroxy-ethyl)-phenyl]-3-(4-methyl-pyridin-3-yl)-imidazolidin-2-one (I-160a: 325 mg, 0.880 mmol) in DCM (20 mL) under nitrogen atmosphere. The resulting suspension was stirred at 50° C. overnight. The reaction was monitored by TLC (5% MeOH in DCM). The reaction mixture was cooled to room temperature and filtered through celite pad. The filtrate was washed with CHCl$_3$, dried over Na$_2$SO$_4$ and concentrated. The concentrate was washed with hexane and dried to afford 240 mg of the product (74.53% yield).

$^1$H NMR (DMSO-D$_6$, 300 MHz): δ 8.8-8.2 (m, 2H), 7.98 (t, 1H), 7.86-7.50 (m, 2H), 7.46-7.25 (m, 1H), 4.40-3.75 (m, 4H), 2.28 (s, 3H).

Final Step: Preparation of 1-(4-methylpyridin-3-yl)-3-(3-(trifluoromethyl)-1H-indazol-6-yl)imidazolidin-2-one (160A)

Acetic acid (0.1 mL, 1.36 mmol) and 1M hydrazine in THF (4 mL, 2.72 mmol) were added to 1-[3-fluoro-4-(2,2,2-trifluoro-acetyl)-phenyl]-3-(4-methyl-pyridin-3-yl)-imidazolidin-2-one (I-160b: 100 mg, 0.272 mmol) in dry THF (2 mL). The resulting mixture was stirred at 150° C. overnight. The reaction was monitored by TLC (5% MeOH in CHCl$_3$). The reaction mixture was partitioned between water and chloroform. The organic layer was dried over Na$_2$SO$_4$ and concentrated. Purification by column chromatography on silica gel (4% MeOH in CHCl$_3$), followed by preparative HPLC afforded 23 mg of the product (23.46% yield).

$^1$H NMR (CD$_3$OD, 300 MHz): δ 8.57-8.48 (br s, 1H), 8.37 (d, 1H), 7.86-7.70 (m, 2H), 7.70-7.60 (m, 1H), 7.42 (d, 1H), 4.34-4.12 (m, 2H), 4.12-3.90 (m, 2H), 2.41 (s, 3H).

LCMS purity: 96.14%, m/z=362.0 (M+1)
HPLC: 94.33%

Example 161

Preparation of 1-(3-cyclopropyl-1-1H-indazol-6-yl)-3-(4-methylpyridin-3-yl)imidazolidin-2-one (161A)

(161A)

Step 1: Preparation of Intermediate 1-[4-(Cyclopropyl-hydroxy-methyl)-3-fluoro-phenyl]-3-(4-methyl-pyridin-3-yl)-imidazolidin-2-one (I-161a)

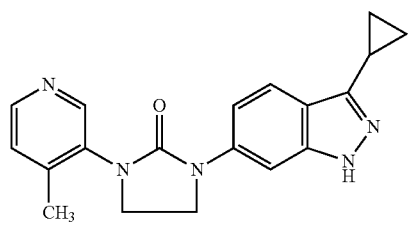

(I-121a)

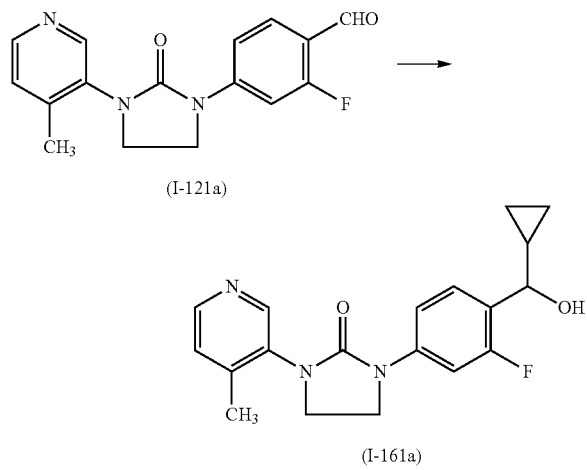

(I-161a)

A 0.5M solution of cyclopropyl magnesium bromide in THF (2.4 mL, 1.170 mmol) was added dropwise to 2-fluoro-4-[3-(4-methyl-pyridin-3-yl)-2-oxo-imidazolidin-1-yl]-benzaldehyde (I-121a: 175 mg, 0.585 mmol) in dry THF (10 mL) at 0° C. under nitrogen atmosphere. The resulting mixture was stirred at room temperature for 3 hours. The reaction was monitored by TLC (5% MeOH in CHCl$_3$). The reaction mixture was quenched with aqueous NH$_4$Cl solution and the THF layer was concentrated. The aqueous layer was extracted with ethylacetate. The organic layer was dried over Na$_2$SO$_4$ and concentrated to afford the crude product. Purification by column chromatography on silica gel (3% MeOH in CHCl$_3$), followed by hexane wash, afforded 200 mg of the product (99.41% yield).

$^1$H NMR (DMSO-D$_6$, 300 MHz): δ 8.72-8.28 (m, 2H), 7.70-7.48 (m, 2H), 7.42-7.25 (m, 2H), 5.30 (d, 1H), 4.48-4.20 (m, 1H), 4.18-3.82 (m, 4H), 2.32 (s, 3H), 1.2-1.0 (m, 1H), 0.7-0.1 (m, 4H)

LCMS purity: 97.58%, m/z=342.3 (M+1)

Step 2: Preparation of Intermediate 1-(4-Cyclopropanecarbonyl-3-fluoro-phenyl)-3-(4-methyl-pyridin-3-yl)-imidazolidin-2-one (I-161b)

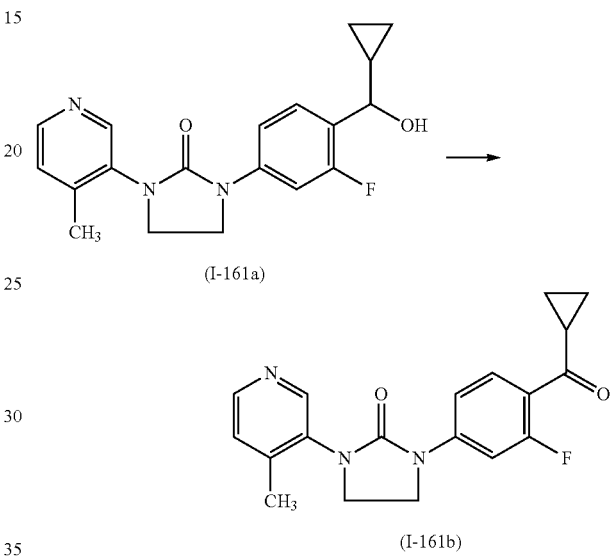

MnO$_2$ (357 mg, 41.055 mmol) was added to 1-[4-(cyclopropyl-hydroxy-methyl)-3-fluoro-phenyl]-3-(4-methyl-pyridin-3-yl)-imidazolidin-2-one (I-161a: 200 mg, 8.586 mmol) in DCM (20 mL) under nitrogen atmosphere and worked up in a manner similar to what has been described previously for example 160 (Step 2) to afford 175 mg of the product (60.13% yield).

$^1$H NMR (DMSO-D$_6$, 300 MHz): δ 8.56 (s, 1H), 8.41 (d, 1H), 7.82 (t, 1H), 7.76-7.65 (m, 1H), 7.60-7.47 (m, 1H), 7.37 (d, 1H), 4.22-3.82 (m, 4H), 2.80-2.60 (m, 1H), 2.29 (s, 3H), 1.18-0.93 (m, 4H)

LCMS purity: 98.34%, m/z=339.7 (M+1)

Final Step: Preparation of 1-(3-Cyclopropyl-1H-indazol-6-yl)-3-(4-methylpyridin-3-yl)imidazolidin-2-one (161A)

1-(4-Cyclopropanecarbonyl-3-fluoro-phenyl)-3-(4-methyl-pyridin-3-yl)-imidazolidin-2-one (I-161b: 175 mg, 0.516 mmol) in hydrazine hydrate solution (10 mL) was taken in a reaction flask. The flask was refluxed at 120° C. overnight. The reaction was monitored by TLC (5% MeOH in CHCl$_3$). The reaction mixture was cooled to room temperature and partitioned between ice water and chloroform. The organic layer was dried over Na$_2$SO$_4$ and concentrated. Purification by column chromatography on silica gel (4% MeOH in CHCl$_3$), followed by hexane and ether wash, afforded 55 mg of the product (31.97% yield).

$^1$H NMR (DMSO-D$_6$, 300 MHz): δ 12.42 (s, 1H), 8.55 (s, 1H), 8.39 (d, 1H), 7.85-7.28 (m, 4H), 4.28-3.80 (m, 4H), 2.6-2.1 (m, 4H), 1.04-0.80 (m, 4H)

LCMS purity: 100.00%, m/z=333.8 (M+1)
HPLC: 94.27%

Example 162

Preparation of 1-(4-methylpyridin-3-yl)-3-(quinolin-7-yl)imidazolidin-2-one (162A)

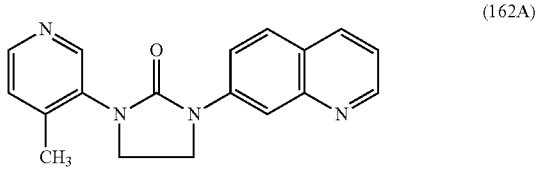

(162A)

Using the same reaction conditions as described in example 14, 1-(4-methyl-pyridin-3-yl)-imidazolidin-2-one (I-14b: 116 mg, 0.6554 mmol) was reacted with 7-bromoquinoline (150 mg, 0.72098 mmol), 1,4-dioxane (50 mL), copper iodide (12.4 mg, 0.06554 mmol), trans-1,2-diamino cyclohexane (22.5 mg, 0.19638 mmol) and potassium phosphate (347.3 g, 1.6365 mmol) to afford the crude product. Purification by column chromatography on silica gel (2% MeOH in CHCl$_3$) afforded 130 mg of the product (65.3% yield).

$^1$H NMR (DMSO-D$_6$, 300 MHz): δ 8.95-8.76 (m, 1H), 8.6 (s, 1H), 8.48-8.22 (m, 3H), 8.06-7.82 (m, 2H), 7.50-7.32 (m, 2H), 4.32-4.12 (m, 2H), 4.10-3.90 (m, 2H), 2.31 (s, 3H)

LCMS purity: 99.57%, m/z=305.0 (M+1)
HPLC: 93.16%

Example 163

Preparation of 3-Benzothiazol-6-yl-4,4-dimethyl-1-(4-methyl-pyridin-3-yl)-imidazolidin-2-one (163A)

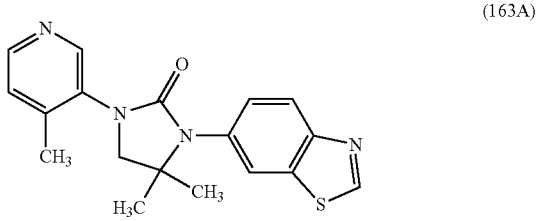

(163A)

Preparation of Starting Material 1-Chloro-2-isocyanato-2-methyl-propane

SOCl$_2$ (5.22 g, 44.23 mmol) was added dropwise to a stirred solution of 3-chloro-2,2-dimethyl-propionic acid (5 g, 36.76 mmol) in DCM (50 mL) at 0° C. over a period of 5 mins. This was followed by the addition of DMF (0.1 mL) and the resulting mixture was heated to 60° C. for 3 hours. The reaction was monitored by TLC (5% MeOH in CHCl$_3$). The reaction mixture was concentrated and the crude product (6 g) was used in the next step without further purification.

Sodium azide (4.64 g, 71.38 mmol) was added to a solution of 3-chloro-2,2-dimethyl-propionyl chloride (6 g, 35.71 mmol) in 1,4-dioxane (15 mL) and water (15 mL). The resulting mixture was stirred at room temperature for 2 hours. The reaction was monitored by TLC (5% ethylacetate in hexane). The reaction mixture was extracted with diethyl ether and the organic layer was dried over Na$_2$SO$_4$ to afford 3.5 g of the product (61.40% yield).

1-Chloro-2-isocyanato-2-methyl-propane (3.5 g, 20 mmol) in toluene (35 mL) was taken a reaction flask and flask was heated to 85° C. for 1.30 hour. The reaction was monitored by TLC (5% ethylacetate in hexane). The crude product (3 g) was used in the next step without further purification.

Preparation of Intermediate 1-(2-Chloro-1,1-dimethyl-ethyl)-3-(4-methyl-pyridin-3-yl)-urea (I-163a)

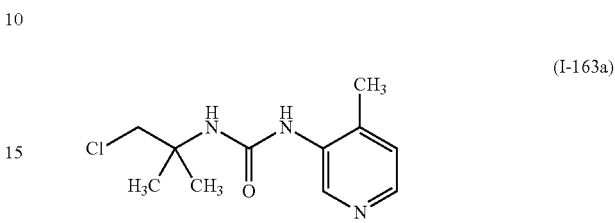

(I-163a)

4-Methyl-pyridin-3-ylamine (1.98 g, 18.33 mmol) was added to solution of 1-chloro-2-isocyanato-2-methyl-propane (3 g, 20.40 mmol) in toluene (30 mL). The resulting mixture was stirred at room temperature for 3 days. The reaction was monitored by TLC (5% MeOH in CHCl$_3$). The reaction mixture was filtered and the residue was dried to afford 4.3 g of the product (87.75% yield).

$^1$H NMR (CDCl$_3$, 300 MHz): δ 8.70 (s, 1H), 8.3 (s, 1H), 7.12 (s, 1H), 6.39 (s, 1H), 4.9 (s, 1H), 3.87 (s, 2H), 2.30 (s, 3H), 1.4 (s, 6H)

LCMS purity: 76.36%, m/z=242.0 (M+1)

Preparation of Intermediate 4,4-Dimethyl-1-(4-methyl-pyridin-3-yl)-imidazolidin-2-one (I-163b)

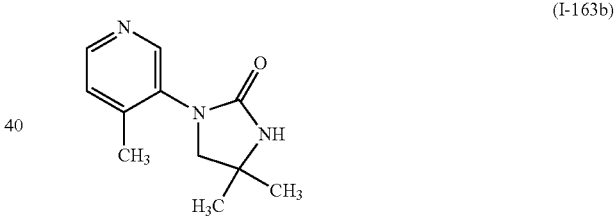

(I-163b)

1-(2-Chloro-1,1-dimethyl-ethyl)-3-(4-methyl-pyridin-3-yl)-urea (I-163a: 1 g, 4.149 mmol) in dry THF (5 mL) was added dropwise to a stirred mixture of NaH (298 mg, 6.208 mmol) in dry THF (10 mL) under argon atmosphere over a period of 10 minutes at 0° C. The resulting reaction mixture was stirred for 2 hours. The reaction was monitored by TLC (5% MeOH in CHCl$_3$). The reaction mixture was partitioned between water and ethylacetate. The organic layer was dried over Na$_2$SO$_4$ and concentrated to afford 800 mg of the product (94.33% yield).

$^1$H NMR (DMSO, 300 MHz): δ 8.4 (s, 1H), 8.3 (d, 1H), 7.30 (d, 1H), 7.0 (s, 1H), 3.53 (s, 2H), 2.22 (s, 3H), 1.3 (s, 6H)

LCMS purity: 100%, m/z=205.7 (M+1)

Final Step: Preparation of 3-Benzothiazol-6-yl-4,4-dimethyl-1-(4-methyl-pyridin-3-yl)-imidazolidin-2-one (163A)

Using the same reaction conditions as described in example 14, 4,4-dimethyl-1-(4-methyl-pyridin-3-yl)-imidazolidin-2-one (I-163b: 150 mg, 0.731 mmol) was reacted with 6-iodo-benzothiazole (248 mg, 0.950 mmol), 1,4-dioxane (10 mL), copper iodide (13 mg, 0.0682 mmol), trans-1,2-diamino cyclohexane (31 mg, 0.218 mmol) and potassium phosphate (387 mg, 1.825 mmol) to afford the crude product. Purification by column chromatography on silica gel (1% MeOH in CHCl$_3$) afforded 30 mg of the product (12.14% yield).

$^1$H NMR (CD$_3$OD, 300 MHz): δ 9.32 (s, 1H), 8.51 (s, 1H), 8.35 (d, 1H), 8.0-8.2 (m, 2H), 7.60 (d, 1H), 7.40 (d, 1H), 3.90 (s, 2H), 2.45 (s, 3H), 1.5 (s, 6H)

LCMS purity: 94.09%, m/z=339.1 (M+1)
HPLC: 89.11%

Example 164

Preparation of 1-Benzothiazol-6-yl-4,4-dimethyl-3-pyridin-3-yl-imidazolidin-2-one (164A)

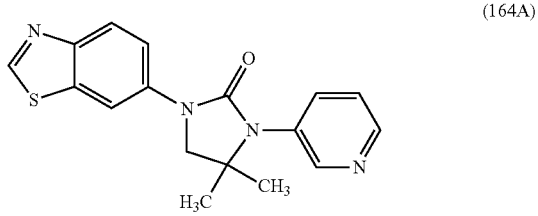

(164A)

Preparation of Intermediate 1-Benzothiazol-6-yl-3-(2-chloro-1,1-dimethyl-ethyl)-urea (I-164a)

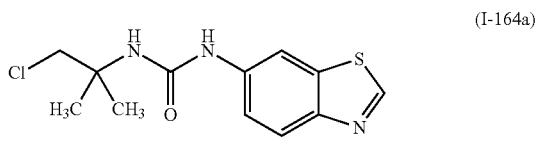

(I-164a)

Benzothiazol-6-ylamine (1.8 g, 12.00 mmol) was added portion wise to solution of 1-chloro-2-isocyanato-2-methyl-propane (2 g, 13.60 mmol) in toluene (20 mL) over a period of 5 minutes. The resulting mixture was stirred at room temperature for 2½ days. The reaction was monitored by TLC (5% MeOH in CHCl$_3$). The reaction mixture was concentrated and extracted with ethylacetate. The organic layer was dried over Na$_2$SO$_4$ and concentrated. Purification by column chromatography on silica gel (1% MeOH in CHCl$_3$) afforded 630 mg of the product (16.57% yield).

$^1$H NMR (CDCl$_3$, 300 MHz): δ 8.85 (s, 1H), 8.23 (d, 1H), 8.0 (d, 1H), 7.20-7.15 (dd, 1H), 7.03 (s, 1H), 5.10 (s, 1H), 3.89 (s, 2H), 1.49 (s, 6H)

LCMS purity: 98.84%, m/z=283.9 (M+1)

Preparation of Intermediate 1-Benzothiazol-6-yl-4,4-dimethyl-imidazolidin-2-one (I-64b)

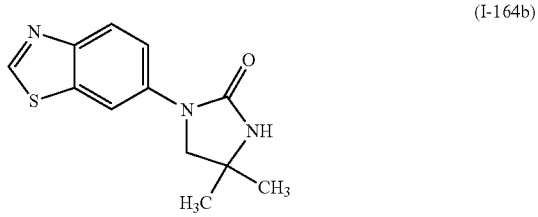

(I-164b)

1-Benzothiazol-6-yl-3-(2-chloro-1,1-dimethyl-ethyl)-urea (I-164a: 620 mg, 2.18 mmol) in dry THF (5 mL) was added dropwise to a stirred mixture of NaH (78 mg, 3.25 mmol) in dry THF (5 mL) under argon atmosphere over a period of 10 mins at 0° C. The resulting reaction mixture was stirred at room temperature for 45 minutes. The reaction was monitored by TLC (5% MeOH in CHCl$_3$). The reaction mixture was partitioned between chilled water and ethylacetate. The organic layer was dried over Na$_2$SO$_4$ and concentrated to afford 410 mg of the product (77.35% yield).

$^1$H NMR (CDCl$_3$, 300 MHz): δ 8.90 (s, 1H), 8.31 (d, 1H), 8.09 (d, 1H), 7.69-7.58 (dd, 1H), 5.0 (br s, 1H), 3.73 (s, 2H), 1.49 (s, 6H)

LCMS purity: 99.16%, m/z=247.8 (M+1)

Final Step: Preparation of 1-Benzothiazol-6-yl-4,4-dimethyl-3-pyridin-3-yl-imidazolidin-2-one (164A)

Using the same reaction conditions as described in example 14, 1-benzothiazol-6-yl-4,4-dimethyl-imidazolidin-2-one (I-164b: 100 mg, 0.4048 mmol) was reacted with 3-bromo-pyridine (83 mg, 0.525 mmol), 1,4-dioxane (10 mL), copper iodide (7 mg, 0.036 mmol), trans-1,2-diamino cyclohexane (17 mg, 0.119 mmol) and potassium phosphate (214 mg, 1.009 mmol) to afford the crude product. Purification by column chromatography on silica gel (1% MeOH in CHCl$_3$) afforded 15 mg of the product (11.45% yield).

$^1$H NMR (CDCl$_3$, 300 MHz): δ 8.90 (s, 1H), 8.7-8.5 (br s, 2H), 8.35 (d, 1H), 8.12 (d, 1H), 7.77-7.60 (m, 2H), 7.5-7.4 (m, 1H), 3.9 (s, 2H), 1.49 (s, 6H)

LCMS purity: 100%, m/z=325.1 (M+1)
HPLC: 95.40%

Example 165

Preparation of 1-Benzothiazol-6-yl-4,4-dimethyl-3-(4-methyl-pyridin-3-yl)-imidazolidin-2-one (165A)

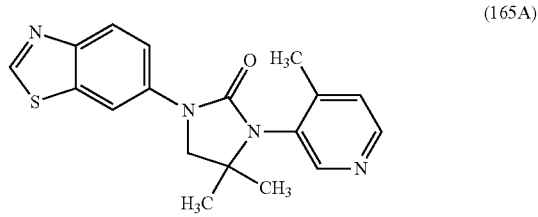

(165A)

Using the same reaction conditions as described in example 14, 1-benzothiazol-6-yl-4,4-dimethyl-imidazolidin-2-one (I-164b: 100 mg, 0.4048 mmol) was reacted with 3-iodo-4-methyl-pyridine (115 mg, 0.525 mmol), 1,4-dioxane (10 mL), copper iodide (7 mg, 0.0368 mmol), trans-1,2-diamino cyclohexane (18 mg, 0.1197 mmol) and potassium phosphate (214 mg, 1.0094 mmol) to afford the crude product. Purification by column chromatography on silica gel (1% MeOH in CHCl$_3$) afforded 6 mg of the product (4.8% yield).

$^1$H NMR (CDCl$_3$, 300 MHz): δ 8.30 (d, 1H), 8.15 (d, 1H), 7.7-7.6 (dd, 1H), 3.8 (s, 2H), 2.72 (s, 3H), 1.49 (s, 6H)

LCMS purity: 94.22%, m/z=339.1 (M+1)
HPLC: 86.98%

Example 166

Preparation of 3-Benzothiazol-6-yl-4-methyl-1-(4-methyl-pyridin-3-yl)-imidazolidin-2-one (166A)

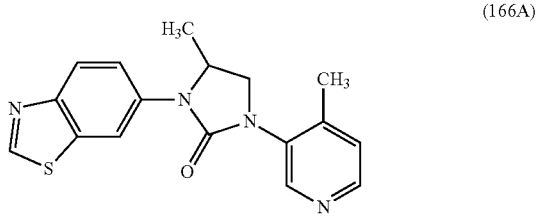
(166A)

Preparation of Intermediate 3-(Benzothiazol-6-ylamino)-butyric acid (I-166a)

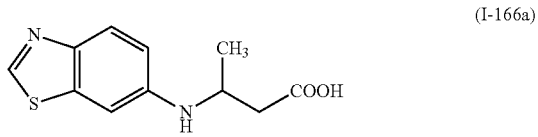
(I-166a)

3-Amino-butyric acid ethyl ester (2 g, 15.27 mmol), 6-iodo-benzothiazole (3.98 g, 15.27 mmol) and potassium carbonate (5.27 g, 38.18 mmol) were dissolved in DMF (50 mL) and the reaction mixture was purged with argon for 10 minutes. This was followed by the addition of copper iodide (290 mg, 1.527 mmol) and the resulting mixture was heated to 110° C. overnight. The reaction was monitored by TLC (10% MeOH in $CHCl_3$) which showed the presence of starting material. The reaction mixture was heated to 120° C. for a further 24 hours. The reaction mixture was concentrated and adjusted the pH to 5 using acetic acid. The reaction mixture was partitioned between water and ethylacetate. The organic layer was dried over $Na_2SO_4$ and concentrated. Purification by column chromatography on silica gel (1% MeOH in $CHCl_3$) afforded 800 mg of the product (22.22% yield).

$^1$H NMR (DMSO, 300 MHz): δ 12.2 (s, 1H), 8.9 (s, 1H), 7.75 (d, 1H), 7.15 (d, 1H), 6.85 (dd, 1H), 5.90-5.80 (m, 1H), 3.90-3.80 (m, 1H), 2.60-2.50 (m, 1H), 2.25-2.35 (m, 1H), 1.20 (d, 3H)

LCMS purity: 61.65%, m/z=237.0 (M+1)

Preparation of Intermediate 1-Benzothiazol-6-yl-5-methyl-imidazolidin-2-one (I-166b)

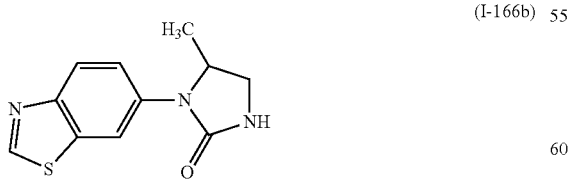
(I-166b)

Triethylamine (1.129 g, 11.18 mmol) was added to a mixture of 3-(benzothiazol-6-ylamino)-butyric acid (I-166a: 800 mg, 3.39 mmol) in toluene (30 mL) and the reaction mixture was purged with argon for 10 minutes. This was followed by the addition of DPPA (2.796 g, 10.17 mmol) and the resulting mixture was heated to 100° C. overnight. The reaction was monitored by TLC (10% MeOH in $CHCl_3$) which showed the presence of starting material. The reaction mixture was heated to 120° C. for the next 24 hours. The reaction mixture was partitioned between water and ethylacetate. The organic layer was dried over $Na_2SO_4$ and concentrated. Purification by column chromatography on silica gel (2% MeOH in $CHCl_3$) afforded 600 mg of the product (75.95% yield).

$^1$H NMR (DMSO, 300 MHz): δ 9.25 (s, 1H), 8.22 (d, 1H), 8.0 (d, 1H), 7.7 (dd, 1H), 7.0 (s, 1H), 4.6-4.5 (m, 1H), 3.6 (t, 1H), 3.0 (m, 1H), 1.2 (d, 3H)

LCMS purity: 81.90%, m/z=234.0 (M+1)

Final Step: Preparation of 3-Benzothiazol-6-yl-4-methyl-1-(4-methyl-pyridin-3-yl)-imidazolidin-2-one (166A)

Using the same reaction conditions as described in example 14, 1-benzothiazol-6-yl-5-methyl-imidazolidin-2-one (I-166b: 150 mg, 0.644 mmol) was reacted with 3-iodo-4-methyl-pyridine (140.99 mg, 0.644 mmol), 1,4-dioxane (10 mL), copper iodide (12.27 mg, 0.0644 mmol), trans-1,2-diamino cyclohexane (27.43 mg, 0.193 mmol) and potassium phosphate (341 mg, 1.61 mmol) to afford the crude product. Purification by column chromatography on silica gel (1.5% MeOH in DCM) afforded 50 mg of the product (24.15% yield).

$^1$H NMR ($CDCl_3$, 300 MHz): δ 8.95 (s, 1H), 8.55 (s, 1H), 8.43 (d, 1H), 8.26 (d, 1H), 8.15 (d, 1H), 7.55 (dd, 1H), 7.25 (d, 1H), 4.7-4.6 (m, 1H), 4.2-4.1 (m, 1H), 3.6-3.5 (m, 1H), 2.4 (s, 3H), 1.5 (d, 3H)

LCMS purity: 95.66%, m/z=325.0 (M+1)
HPLC: 96.32%

Example 167

Preparation of 1-Benzothiazol-6-yl-4-methyl-3-(4-methyl-pyridin-3-yl)-imidazolidin-2-one (167A)

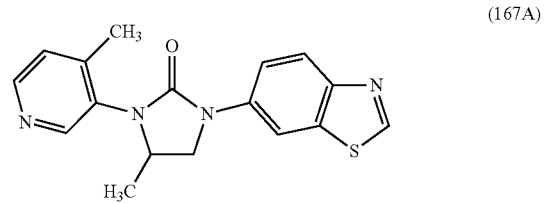
(167A)

Step 1: Synthesis of Intermediate 3-(Benzothiazol-6-ylamino)-2-methyl-propionic Acid (I-167a)

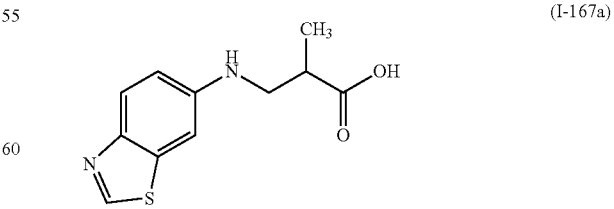
(I-167a)

2-Methyl-acrylic acid (0.63 g, 0.00732 mol) and Benzene-1,4-diol (0.029 g, 0.000266 mol) were added to a stirred solution of Benzothiazol-6-ylamine (1 g, 0.00665 mol) in toluene (6 mL) under nitrogen atmosphere. The resulting reaction mass was heated at 70° C. for 72 hours and further at 100° C. for 48 hours. The reaction was monitored by TLC (5% methanol in chloroform). The reaction mixture was cooled to room temperature and partitioned between water and ethyl acetate. The organic layer was washed with brine solution, dried over Na₂SO₄ and concentrated to afford the crude product. Purification by column chromatography on silica gel (0.75% methanol in chloroform) afforded 0.43 g of the product (26.87% yield).

¹H NMR (300 MHz, DMSO): δ 12.25 (s, 1H), 8.9 (s, 1H), 7.75 (d, 1H), 7.15 (s, 1H), 6.85 (d, 1H), 6.20-6.05 (bs, 1H), 3.45-3.3 (m, 1H), 3.15-3.0 (m, 1H), 2.7 (q, 1H), 1.15 (d, 3H)

LCMS: 100%, m/z=237.3 (M+1)

Step 2: Synthesis of Intermediate 1-Benzothiazol-6-yl-4-methyl-imidazolidin-2-one (I-167b)

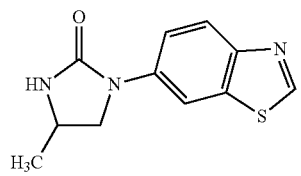

(I-167b)

3-(Benzothiazol-6-ylamino)-2-methyl-propionic acid (I-167a: 500 mg, 2.118 mmol) was refluxed with triethylamine (1 mL, 6.989 mmol), DPPA (1.75 g, 6.35 mmol) and toluene (10 mL) at 120° C. in a sealed tube to afford the crude product. The reaction was monitored by TLC (5% methanol in chloroform). Purification by column chromatography on silica gel (2% methanol in chloroform) afforded 350 mg of the product (71.42% yield).

¹H NMR (300 MHz, DMSO): δ 9.25(s, 1H), 8.25 (d, 1H), 8.0 (d, 1H), 7.9-7.8 (dd, 1H), 7.28 (s, 1H), 4.05 (t, 1H), 3.9-3.8 (m, 1H), 3.55-3.45 (m, 1H), 1.2 (d, 3H)

LCMS: 100%, m/z=233.8 (M+H)

Final Step: Synthesis of 1-Benzothiazol-6-yl-4-methyl-3-(4-methyl-pyridin-3-yl)-imidazolidin-2-one (167A)

Using the same reaction conditions and work up as described in Example 1, step-3,1-benzothiazol-6-yl-4-methyl-imidazolidin-2-one (I-167b: 150 mg, 0.643 mmol) was refluxed with 3-iodo-4-methyl-pyridine (155 mg, 0.708 mmol), copper iodide (12.21 mg, 0.0643 mmol), N,N'-dimethyl-cyclohexane-1,2-diamine (27.39 mg, 0.192 mmol), potassium phosphate (341.5 mg, 1.607 mmol) and 1,4-dioxane (5 mL) at 120° C. for 12 hours to afford the crude product. The reaction was monitored by TLC (10% MeOH in chloroform). Purification by column chromatography on silica gel (3% methanol in chloroform) followed by preparative HPLC afforded 34 mg of the product (16.66% yield).

¹H NMR (300 MHz, CDCl₃): δ 8.9 (s, 1H), 8.5-8.4 (bs, 2H), 8.35 (d, 1H), 8.1 (d, 1H), 7.65 (dd, 1H) 7.26 (s, 1H), 4.45-4.2 (m, 2H), 3.75 (t, 1H), 2.35 (s, 3H), 1.34 (d, 3H).

LCMS: 98.01%, m/z=325 (M+1)

HPLC: 96.28%

Example 168

Preparation of 1-Benzothiazol-6-yl-4-ethyl-3-(4-methyl-pyridin-3-yl)-1,3-dihydro-imidazol-2-one (168A)

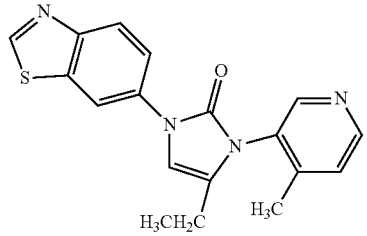

(168A)

Step 1: Synthesis of Intermediate 1-(Benzothiazol-6-ylamino)-butan-2-one (I-168a)

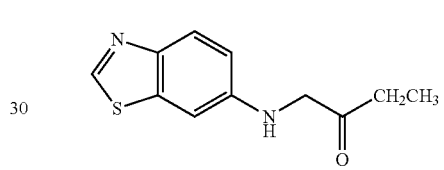

(I-168a)

Sodium acetate (300 mg, 3.66 mmol) and 1-bromo-butan-2-one (0.373 mL, 3.66 mmol) were added to a stirred solution of benzothiazol-6-ylamine (500 mg, 3.328 mmol) in methanol (10 mL) under nitrogen atmosphere. The resulting reaction mass was stirred at room temperature for 24 hours. The reaction was monitored by TLC (20% ethyl acetate in hexane). The reaction mixture was filtered and the solid collected was dried under reduced pressure to afford 250 mg of the product (32% yield).

¹H NMR (DMSO-d₅, 300 MHz) δ: 8.9 (s, 1H), 7.8 (d, 1H), 7.1 (d, 1H), 6.9 (m, 1H), 6.3 (t, 1H), 4.1 (d, 2H), 2.5 (q, 2H), 1.0 (t, 3H)

LCMS: 50.40%, m/z=221.0 (M+1).

Step-2: Synthesis of Intermediate 1-Benzothiazol-6-yl-3-(4-methyl-pyridin-3-yl-(2-oxo-butyl)-urea (I-168b)

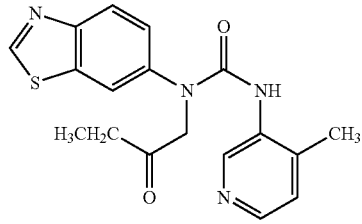

(I-168b)

(4-Methyl-pyridin-3-yl)-carbamic acid phenyl ester (165 mg, 0.727 mmol) and 1-(benzothiazol-6-ylamino)-butan-2-one (I-168a: 160 mg, 0.727 mmol) in toluene (10 mL) were refluxed at 120° C. under nitrogen atmosphere for 48 hours. The reaction was monitored by TLC (5% MeOH in chloroform). The reaction mixture was concentrated under reduced pressure and partitioned between water and chloroform. The organic layer was washed with brine solution, dried over $Na_2SO_4$ and concentrated to afford the crude product. Purification by column chromatography on silica gel (2% methanol in chloroform) afforded 185 mg of the product (71.98% yield).

LCMS: 99.81%, m/z=355.2 (M+1)

Final Step: Synthesis of 1-Benzothiazol-6-yl-4-ethyl-3-(4-methyl-pyridin-3-yl)-1,3-dihydro-imidazol-2-one (168A)

1-Benzothiazol-6-yl-3-(4-methyl-pyridin-3-yl)-1-(2-oxo-butyl)-urea (I-168b: 185 mg, 0.522 mmol) in toluene (15 mL) was refluxed at 120° C. for 20 hours. The reaction was monitored by TLC (5% MeOH in chloroform). The reaction mixture was concentrated under reduced pressure and the crude residue was purified by column chromatography on silica gel (2.5% methanol in chloroform) to afford 50 mg of the product (28.57% yield).

$^1$H NMR (300 MHz, $CDCl_3$): δ 9.0 (s, 1H), 8.58-8.45 (m, 3H), 8.2 (d, 1H) 7.75 (dd, 1H), 7.34 (d, 1H), 6.6 (s, 1H), 2.4-2.1 (m, 5H), 1.1 (t, 3H).

LCMS: 100%, m/z=337 (M+1)
HPLC: 98.76%

Example 169

Preparation of 1-Benzothiazol-6-yl-4-ethyl-3-pyridin-3-yl-1,3-dihydro-imidazol-2-one (169A)

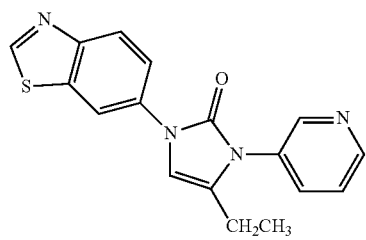

(169A)

Triethylamine (0.2 mL, 1.219 mmol) and DPPA (0.3 mL, 1.219 mmol) were added to a solution of nicotinic acid (150 mg, 1.219 mmol) in toluene (12 mL) under nitrogen atmosphere and stirred at room temperature for 1.5 hours. The reaction mixture was allowed to reflux at 70° C. for 1.5 hours. The reaction was monitored by TLC (5% MeOH in DCM). This was followed by the addition of 1-(benzothiazol-6-ylamino)-butan-2-one (I-168a: 241 mg, 1.097 mmol) at room temperature. The resulting reaction mass was heated at 100° C. overnight. The reaction mixture was cooled to room temperature, concentrated under reduced pressure and the crude residue was partitioned between water and DCM. The organic layer was washed with water, brine solution, dried over $Na_2SO_4$ and concentrated to afford the crude product. Purification by column chromatography on silica gel (1.5% methanol in chloroform) followed by preparative HPLC afforded 5 mg of the product (1.5% yield).

$^1$H NMR (300 MHz, $CDCl_3$): δ 9.0 (s, 1H), 8.7-8.6 (m, 2H), 8.44 (d, 1H), 8.2 (d, 1H), 7.85-7.68 (m, 2H), 7.5-7.44 (m, 1H), 6.55 (s, 1H), 2.46-2.35 (q, 2H), 1.15 (t, 3H).

LCMS: 90.98%, m/z=323.1 (M+1)
HPLC: 94.09%

Example 170

Preparation of 1-benzothiazol-6-yl-3-pyridin-3-yl-4-trifluoromethyl-imidazolidin-2-one (170A)

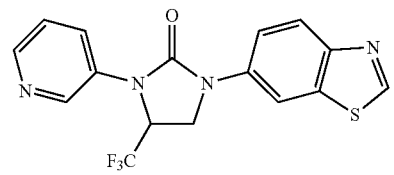

(170A)

Step-1: Synthesis of Intermediate 2-(Benzothiazol-6-ylaminomethyl)-3,3,3-trifluoro-propionic Acid (I-170a)

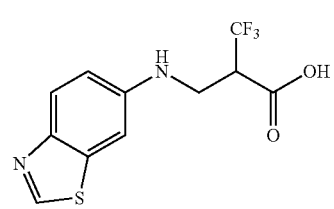

(I-170a)

Benzothiazol-6-ylamine (1 g, 6.66 mmol) was reacted with 2-trifluoromethyl-acrylic acid (1.39 g, 9.99 mmol), benzene-1,4-diol (51.3 mg, 0.46 mmol) and toluene (10 mL) to afford the crude product. Purification by column chromatography on silica gel (30% ethyl acetate in hexane) afforded 380 mg of the product (19.67% yield).

$^1$H NMR (300 MHz, DMSO-$d_6$): δ 13.8-13.0 (bs, 1H), 8.95 (s, 1H), 7.8 (d, 1H), 7.2 (d, 1H), 6.95-6.85 (dd, 1H), 3.75-3.50 (m, 3H)

LCMS: 100%, m/z=291.1 (M+1)

Step-2: Synthesis of Intermediate 1-Benzothiazol-6-yl-4-trifluoromethyl-imidazolidin-2-one (I-170b)

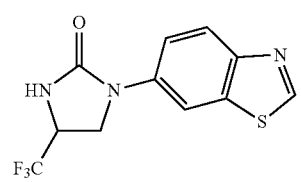

(I-170b)

2-(Benzothiazol-6-ylaminomethyl)-3,3,3-trifluoro-propionic acid (I-170a: 380 mg, 1.3 mmol) was refluxed with triethyl amine (433.29 mg, 4.29 mmol), DPPA (1.08 g, 3.9 mmol) and toluene (8 mL) at 110° C. for 72 hours to afford the crude product. Purification by column chromatography on silica gel (1.5% methanol in chloroform) afforded 40 mg of the product (10.72% yield).

$^1$H NMR (300 MHz, $CDCl_3$): δ 8.93 (s, 1H), 8.3 (d, 1H), 8.1 (d, 1H), 7.61 (dd, 1H), 5.68-5.58 (bs, 1H), 4.42-4.22 (m, 2H), 4.12-4.04 (m, 1H)

129

Final Step: Synthesis of 1-Benzothiazol-6-yl-3-pyridin-3-yl-4-trifluoromethyl-imidazolidin-2-one (170A)

Using the same reaction conditions and work up as described in example 1, step-3,1-Benzothiazol-6-yl-4-trifluoromethyl-imidazolidin-2-one (I-170b: 50 mg, 0.174 mmol) was refluxed with 3-Bromo-pyridine (33 mg, 0.209 mmol), copper iodide (3.3 mg, 0.0174 mmol), Cyclohexane-1,2-diamine (6 mg, 0.0522 mmol), potassium phosphate (110 mg, 0.522 mmol) and 1,4-Dioxane (2 mL) at 120° C. for 12 hours to afford the crude product. Purification by column chromatography on silica gel (2% methanol in chloroform) followed by n-pentane washing afforded 15 mg of the product (23.8% yield).

$^1$H NMR (300 MHz, CDCl$_3$): δ 8.95(s, 1H), 8.92-8.4 (m, 2H), 8.35 (d, 1H), 8.15 (d, 1H), 7.95 (d, 1H), 7.7 (dd, 1H), 7.5-7.35 (bs, 1H), 5.1-4.9 (m, 1H), 4.4 (t, 1H), 4.25 (dd, 1H).

LCMS: 98.0%, m/z=364.7 (M+1)

HPLC: 90.04%

Example 171

Preparation of 1-Benzothiazol-6-yl-3-(4-methyl-pyridin-3-yl)-1,3-dihydro-benzoimidazol-2-one (171A)

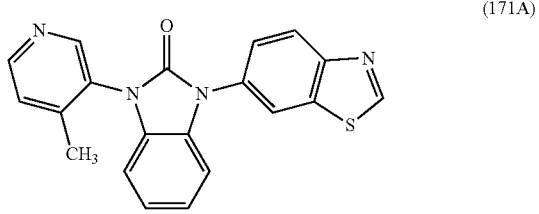

(171A)

Step-1: Synthesis of Intermediate (4-Methyl-pyridin-3-yl)-(2-nitro-phenyl)-amine (I-171a)

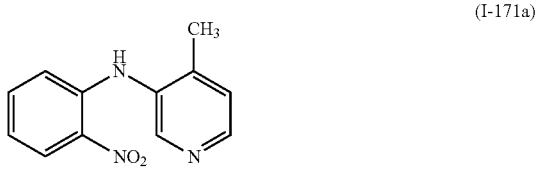

(I-171a)

1M LiHMDS solution (9.25 mL, 9.25 mmol) in THF was added drop wise to a cooled solution of 4-Methyl-pyridin-3-ylamine (1 g, 9.25 mmol) in THF (10 mL) at 0° C. under nitrogen atmosphere. The resulting mixture was added drop wise to a solution of 1-fluoro-2-nitro-benzene (0.98 mL, 9.25 mmol) in THF at 0° C. The resulting reaction mass was stirred at room temperature overnight. The reaction was monitored by TLC (50% ethyl acetate in hexane). The reaction mixture was diluted with ethyl acetate and concentrated under reduced pressure. The crude residue was purified by column chromatography on silica gel (50% ethyl acetate in hexane) to afford 600 mg of the product (28.32% yield).

130

$^1$H NMR (300 MHz, CDCl$_3$): δ 9.3 (s, 1H), 8.55 (s, 1H), 8.45 (d, 1H), 8.25 (d, 1H), 7.40-7.25 (m, 2H), 6.85-6.75 (m, 2H), 2.3 (s, 3H)

Step-2: Synthesis of Intermediate N-(4-Methyl-pyridin-3-yl)-benzene-1,2-diamine (I-171b)

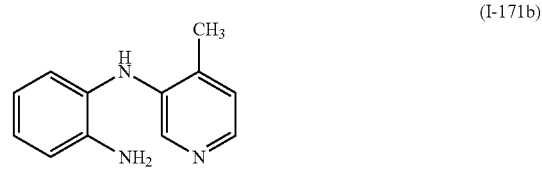

(I-171b)

10% Pd/C (100 mg) was charged portion wise to a solution of (4-methyl-pyridin-3-yl)-(2-nitro-phenyl)-amine (I-171a: 600 mg, 2.62 mmol) in methanol (15 mL) under nitrogen atmosphere. The resulting mixture was stirred at room temperature under hydrogen atmosphere for 2 hours. The reaction was monitored by TLC (80% ethyl acetate in hexane). The reaction mixture was filtered and the filtrate was concentrated under reduced pressure to afford 525 mg of the product (98.91% yield).

$^1$H NMR (300 MHz, DMSO): δ 7.82 (s, 1H), 7.6 (s, 1H), 7.08 (d, 1H), 6.9-6.7 (m, 3H), 6.65-6.50 (m, 2H), 5.0-4.7 (bs, 2H), 2.2 (s, 3H)

Step-3: Synthesis of Intermediate 1-(4-Methyl-pyridin-3-yl)-1,3-dihydro-benzoimidazol-2-one (1471c)

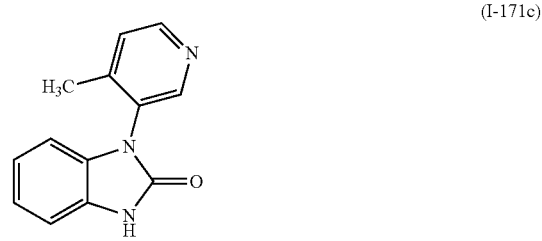

(I-171c)

Triethylamine (0.76 mL, 5.276 mmol) was added to a solution of N-(4-Methyl-pyridin-3-yl)-benzene-1,2-diamine (525 mg, 2.638 mmol) in THF (10 mL) under nitrogen atmosphere. This was followed by the drop wise addition of triphosgene (313 mg, 1.055 mmol) in THF (10 mL) at 0° C. The resulting suspension was stirred at room temperature for 1.5 hours. The reaction was monitored by TLC (50% ethyl acetate in hexane). The reaction mixture was quenched with ice and partitioned between water and ethyl acetate. The organic layer was washed with water, brine solution, dried over Na$_2$SO$_4$ and concentrated to afford the crude product. Purification by column chromatography on silica gel (50% ethyl acetate in hexane) afforded 270 mg of the product (46.37% yield).

$^1$H NMR (300 MHz, CDCl$_3$): δ 8.9 (s, 1H), 8.15-8.05 (m, 2H), 7.80-7.65 (m, 3H), 6.7 (dd, 1H), 5.8 (dd, 1H), 1.9 (s, 3H)

Final Step: Synthesis of 1-Benzothiazol-6-yl-3-(4-methyl-pyridin-3-yl)-1,3-dihydro-benzoimidazol-2-one (171A)

Using the same reaction conditions and work up as described in Example 1, step-3,1-(4-methyl-pyridin-3-yl)-1, 3-dihydro-benzoimidazol-2-one (I-171c: 120 mg, 0.53 mmol) was refluxed with 6-Iodo-benzothiazole (167 mg, 0.639 mmol), copper iodide (10.13 mg, 0.0533 mmol), N,N'-Dimethyl-cyclohexane-1,2-diamine (22.7 mg, 0.159 mmol), potassium phosphate (339 mg, 0.015 mmol) and 1,4-Dioxane (5 mL) at 120° C. for 12 hours to afford the crude product. Purification by column chromatography on silica gel (1% methanol in chloroform) followed by hexane washing afforded 20 mg of the product (10.5% yield).

$^1$H NMR (300 MHz, DMSO): δ 9.55(s, 1H), 8.7-8.6 (m, 2H), 8.54 (s, 1H), 8.3 (d, 1H), 7.85 (dd, 1H), 7.6 (d, 1H), 7.3-7.1 (m, 3H), 6.9-6.8 (m, 1H), 2.2 (s, 3H).

LCMS: 97.32%, m/z=359.1(M+1)

HPLC: 95.78%

Example 172

Preparation of 1-Benzothiazol-6-yl-4-methyl-3-(4-methyl-pyridin-3-yl)-imidazolidin-2-one (172A)

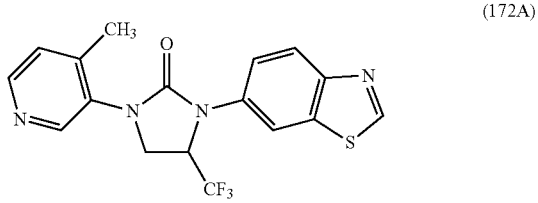

Step-1: Synthesis of Intermediate 3-(Benzothiazol-6-ylamino)-4,4,4-trifluoro-butyric acid (I-172a)

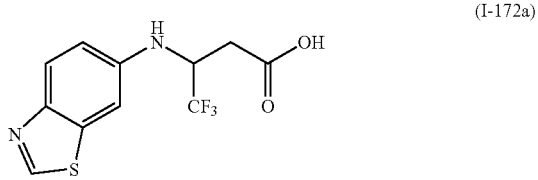

Benzothiazol-6-ylamine (1 g, 0.006 mol) was reacted with 4,4,4-trifluoro-but-2-enoic acid (1.39 g, 0.009 mol), benzene-1,4-diol (0.05 g, 0.00046 mol) and toluene (50 mL) to afford the crude product. Purification by column chromatography on silica gel (15% ethyl acetate in hexane) afforded 1.02 g of the product (53.68% yield).

$^1$H NMR (300 MHz, DMSO-D$_6$): δ 12.6 (bs, 1H), 9.0 (s, 1H), 7.9 (d, 1H), 7.5 (d, 1H), 7.0 (dd, 1H), 6.6 (d, 1H), 4.8-4.6 (m, 1H), 2.9 (dd, 1H), 2.7-2.55 (m, 1H)

Step-2: Synthesis of Intermediate 1-Benzothiazol-6-yl-5-trifluoromethyl-imidazolidin-2-one (I-1726)

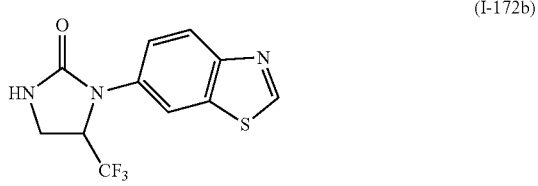

3-(Benzothiazol-6-ylamino)-4,4,4-trifluoro-butyric acid (I-172a: 1 g, 0.003 mol) was refluxed with triethyl amine (0.4 g, 0.0041 mol), DPPA (1.1 g, 0.004 mol) and toluene (510 mL) at 120° C. to afford the crude product. The reaction was monitored by TLC (80% ethyl acetate in hexane). Purification by column chromatography on silica gel (40% ethyl acetate in hexane) afforded 0.62 g of the product (63.2% yield).

$^1$H NMR (300 MHz, DMSO-D$_6$): δ 9.4(s, 1H), 8.3 (d, 1H), 8.1 (d, 1H), 7.7 (dd, 1H), 7.5 (s, 1H), 5.65-5.5 (m, 1H), 3.85 (t, 1H), 3.5 (dd, 1H)

LCMS: 100.0%, (m/z)=288.2 (M+1)

Final Step: Synthesis of 1-Benzothiazol-6-yl-4-methyl-3-(4-methyl-pyridin-3-yl)-imidazolidin-2-one (172A)

Using the same reaction conditions and work up as described in Example 1, step-3,1-benzothiazol-6-yl-5-trifluoromethyl-imidazolidin-2-one (I-172b: 0.15 g, 0.0005 mol) was refluxed with 3-Iodo-4-methyl-pyridine (0.168 g, 0.0007 mol), copper iodide (0.01 g, 0.00005 mol), N,N'-Dimethyl-cyclohexane-1,2-diamine (0.01 g, 0.000015 mol), potassium phosphate (0.3 g, 0.001 mol) and 1,4-dioxane (20 mL) at 120° C. for 12 hours to afford the crude product. The reaction was monitored by TLC (100% ethyl acetate). Purification by column chromatography on silica gel (2% methanol in DCM) afforded 75 mg of the product (39.47% yield).

$^1$H NMR (300 MHz, CDCl$_3$): δ 9.04 (s, 1H), 8.82-8.6 (bs, 1H), 8.5-8.3 (bs, 1H), 8.28-8.12 (m, 3H), 7.52 (dd, 1H), 7.4-7.28 (bs, 1H), 5.05-4.9 (m, 1H), 4.35 (t, 1H), 3.96 (dd, 1H), 2.4 (s, 3H).

LCMS: 98.43%, m/z=378.7 (M+1)

HPLC: 96.49%

Example 173

Preparation of 3-Benzothiazol-6-yl-1-pyridin-3-yl-4-trifluoromethyl-imidazolidin-2-one (173A)

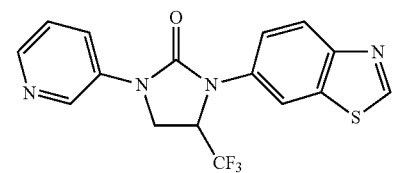

Using the same reaction conditions and work up as described in Example 1, step-3,1-benzothiazol-6-yl-5-trifluoromethyl-imidazolidin-2-one (I-172b: 0.1 g, 0.0004 mol) was refluxed with 3-bromo-pyridine (0.085 g, 0.0005 mol), copper iodide (0.0076 g, 0.00004 mol), N,N'-dimethyl-cyclohexane-1,2-diamine (0.017 g, 0.00012 mol), potassium phosphate (0.22 g, 0.0012 mol) and 1,4-dioxane (20 mL) at 120° C. for 12 hours to afford the crude product. The reaction was monitored by TLC (100% ethyl acetate). Purification by column chromatography on silica gel (2% methanol in DCM) afforded 54 mg of the product (45.2% yield).

$^1$H NMR (300 MHz, CDCl$_3$): δ 9.04 (s, 1H), 8.82-8.6 (bs, 1H), 8.5-8.36 (bs, 1H), 8.28-8.12 (m, 3H), 7.52 (dd, 1H), 7.4-7.28 (bs, 1H), 5.05-4.9 (m, 1H), 4.35 (t, 1H), 4.1 (dd, 1H).

LCMS: 99.42%, m/z=364.7 (M+1)

HPLC: 96.05%

Example 174

Preparation of 1-Benzothiazol-6-yl-3-(4-methyl-pyridin-3-yl)-4-trifluoromethyl-imidazolidin-2-one (174A)

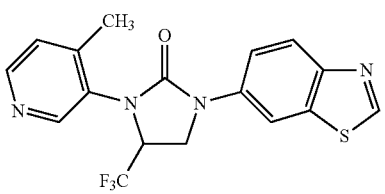

(174A)

1-Benzothiazol-6-yl-4-trifluoromethyl-imidazolidin-2-one (I-170b: 100 mg, 0.348 mmol) was reacted with 3-iodo-4-methyl-pyridine (83.9 mg, 0.383 mmol), Pd$_2$(dba)$_3$ (15.9 mg, 0.0174 mmol), Xantphos (30.2 mg, 0.0528 mmol), cesium carbonate (170 mg, 0.152 mmol) and 1,4-dioxane (10 mL) to afford the crude product. Purification by column chromatography on silica gel (2% methanol in chloroform) followed by preparative HPLC afforded 10 mg of the product (7.5% yield).

$^1$H NMR (300 MHz, CD$_3$OD): δ 9.2-9.05 (bs, 1H), 8.74-8.58 (bs, 1H), 8.34 (d, 1H), 8.1-8.03 (m, 1H), 7.96-7.7 (m, 2H), 4.65-4.1 (m, 3H), 2.86 (s, 3H).

LCMS: 95.13%, m/z=379 (M+1)

HPLC: 76.33%

Example 175

Preparation of 1-Benzothiazol-6-yl-4,5-dimethyl-3-(4-methyl-pyridin-3-yl)-imidazolidin-2-one (175A)

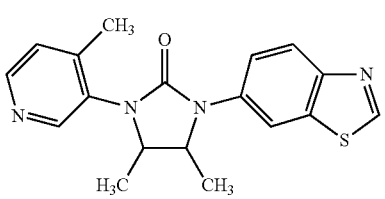

(175A)

Step-1: Synthesis of Intermediate 3-(Benzothiazol-6-ylamino)-2-methyl-butyric acid (I-175a)

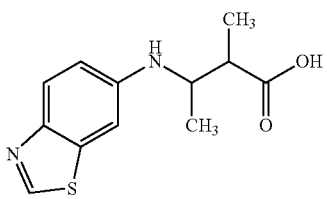

(I-175a)

Benzothiazol-6-ylamine (1 g, 6.667 mmol) was reacted with 2-methyl-but-2-enoic acid (1 g, 9.99 mmol), benzene-1,4-diol (51.38 mg, 0.467 mmol) and toluene (6 mL) to afford the crude product. Purification by column chromatography on silica gel (50% ethyl acetate in hexane) afforded 100 mg of the product (6.02% yield).

LCMS: 59.05%, m/z=251 (M+1)

Step-2: Synthesis of Intermediate 1-Benzothiazol-6-yl-4,5-dimethyl-imidazolidin-2-one (I-175b)

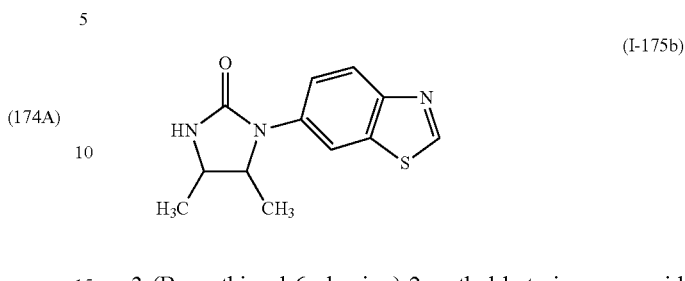

(I-175b)

3-(Benzothiazol-6-ylamino)-2-methyl-butyric acid (I-175a: 100 mg, 0.4 mmol) was refluxed with triethyl amine (0.067 mL, 0.48 mmol), DPPA (0.107 mLg, 6.35 mmol) and toluene (3 mL) at 120° C. in a sealed tube to afford the crude product. The reaction was monitored by TLC (80% ethyl acetate in hexane). Purification by column chromatography on silica gel (40% ethyl acetate in hexane) afforded 50 mg of the product (50.6% yield).

LCMS: 79.64%, m/z=248 (M+1)

Final Step: Synthesis of 1-Benzothiazol-6-yl-4,5-dimethyl-3-(4-methyl-pyridin-3-yl)-imidazolidin-2-one (175A)

Using the same reaction conditions and work up as described in Example 1, step-3, 1-benzothiazol-6-yl-4,5-dimethyl-imidazolidin-2-one (I-175b: 50 mg, 0.202 mmol) was refluxed with 3-iodo-4-methyl-pyridine (44.33 mg, 0.202 mmol), copper iodide (3.85 mg, 0.0202 mmol), N,N-dimethyl-cyclohexane-1,2-diamine (0.0095 mL, 0.061 mmol), potassium phosphate (107.2 mg, 0.506 mmol) and 1,4-dioxane (5 mL) at 120° C. for 16 hours to afford the crude product. The reaction was monitored by TLC (100% ethyl acetate). Purification by column chromatography on silica gel (60% ethyl acetate in hexane) followed by preparative HPLC afforded 6 mg of the product (8.76% yield).

$^1$H NMR (300 MHz, CDCl$_3$): δ 8.95 (s, 1H), 8.5-8.4 (m, 2H), 8.16-8.1 (m, 2H), 7.59-7.5 (dd, 1H), 7.25 (s, 1H), 4.2-4.1 (m, 1H), 3.92-3.82 (m, 1H), 2.35 (s, 3H), 1.46 (d, 3H), 1.3 (d, 3H).

LCMS: 100.00%, m/z=339 (M+1)

HPLC: 95.46%

Example 176

Preparation of 1-Benzothiazol-6-yl-3-(4-pyrrolidin-1-ylmethyl-pyridin-3-yl)-imidazolidin-2-one (176A)

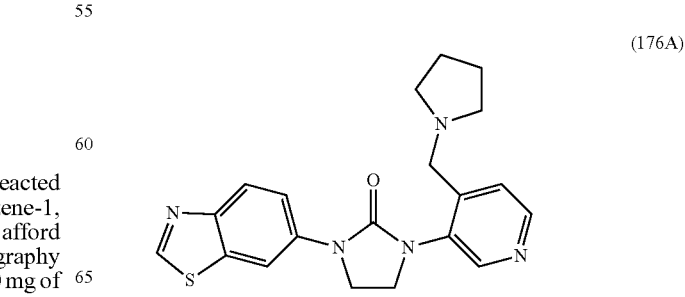

(176A)

Step I. Synthesis of Intermediate 3-Bromo-4-pyrrolidin-1-ylmethyl-pyridine (I-176a)

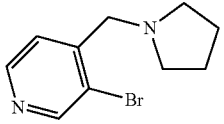
(I-176a)

Acetic acid (0.1 mL) was added to a stirred solution of 3-bromo-pyridine-4-carbaldehyde (220 mg, 1.18 mmol) and pyrrolidine (0.11 mL, 1.34 mmol) in DCE (15 mL) under nitrogen atmosphere and stirred at room temperature for 2 hours. This was followed by addition of NaBH(OAc)$_3$ (342 mg, 1.612 mmol) at 0° C. over a period of 10 minutes. The resulting reaction mass was stirred for 12 hours at room temperature. The reaction was monitored by TLC (30% ethyl acetate in hexane). The reaction mixture was washed with NaHCO$_3$ solution and extracted using ethyl acetate. The organic layer was dried over Na$_2$SO$_4$ and concentrated to afford 275 mg of the product (98.2% yield).

$^1$H NMR (300 MHz, CDCl$_3$): δ 8.63 (s, 1H), 8.46 (dd, 1H), 7.49 (d, 1H), 7.27 (d, 1H), 3.72 (s, 2H), 2.6 (m, 4H), 1.84 (m, 4H)

Final Step: Synthesis of 1-Benzothiazol-6-yl-3-(4-pyrrolidin-1-ylmethyl-pyridin-3-yl)-imidazolidin-2-one (176A)

Using the same reaction conditions and work up as described in Example 1, step-3, 3-bromo-4-pyrrolidin-1-ylmethyl-pyridine (I-176a: 290 mg, 1.205 mmol) was refluxed with 1-benzothiazol-6-yl-imidazolidin-2-one (I-84b: 220 mg, 1.004 mmol), copper iodide (19 mg, 0.1004 mmol), N,N'-Dimethyl-cyclohexane-1,2-diamine (42.7 mg, 0.301 mmol), potassium phosphate (640 mg, 3.012 mmol) and 1,4-dioxane (15 mL) at 120° C. for 12 hours to afford the crude product. The reaction was monitored by TLC (5% MeOH in DCM). Purification by column chromatography on silica gel (5% MeOH in chloroform) followed by preparative HPLC afforded 72 mg of the product (18.9% yield).

$^1$H NMR (300 MHz, CDCl$_3$): δ 8.9 (s, 1H), 8.6-8.5 (m, 2H), 8.38 (d, 1H), 8.12 (d, 1H), 7.7 (dd, 1H) 7.54 (d, 1H), 4.2-3.95 (m, 4H), 3.7 (s, 2H), 2.5 (bs, 4H), 1.8 (m, 4H).

LCMS: 98.39%, m/z=380.1 (M+1)
HPLC: 99.11%

Example 177

Preparation of 1-benzothiazol-6-yl-3-(4-morpholin-4-ylmethyl-pyridin-3-yl)-imidazolidin-2-one (177A)

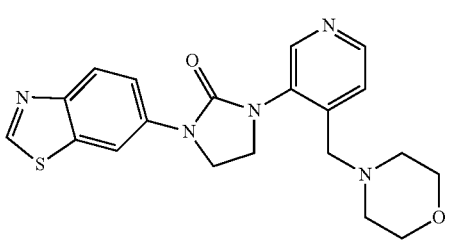
(177A)

Step 1: Synthesis of Intermediate 1-Benzothiazol-6-yl-3-(4-dimethoxymethyl-pyridin-3-yl)-imidazolidin-2-one (I-177a)

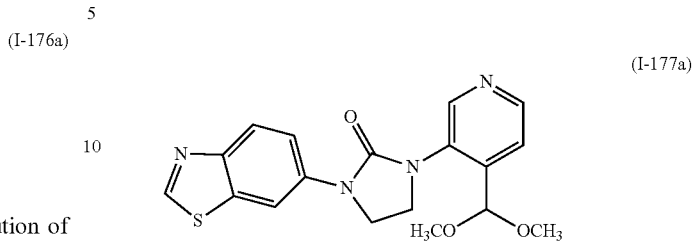
(I-177a)

Using the same reaction conditions and work up as described in Example 1, step-3, 1-benzothiazol-6-yl-imidazolidin-2-one (I-84b: 515 mg, 2.35 mmol) was refluxed with 3-bromo-4-dimethoxymethyl-pyridine (600 mg, 2.584 mmol), copper iodide (44.7 mg, 0.2312 mmol), N,N'-dimethyl-cyclohexane-1,2-diamine (80.8 mg, 0.7405 mmol), potassium phosphate (1.4 g, 7.046 mmol) and 1,4-dioxane (20 mL) at 110° C. for 12 hours to afford the crude product. The reaction was monitored by TLC (10% MeOH in chloroform). Purification by column chromatography on silica gel (2% methanol in chloroform) afforded 460 mg of the product (52.9% yield).

$^1$H NMR (400 MHz, CDCl$_3$): δ 8.9 (s, 1H), 8.6 (bs, 2H), 8.4 (d, 1H), 8.14-8.1 (d, 1H), 7.7 (dd, 1H), 7.64-7.6 (bs, 1H), 5.7 (s, 1H), 4.2-4.12 (m, 2H), 4.0-3.95 (m, 2H), 3.35 (s, 6H)

Step 2: Synthesis of 3-(3-Benzothiazol-6-yl-2-oxo-imidazolidin-1-yl)-pyridine-4-carbaldehyde (I-177b)

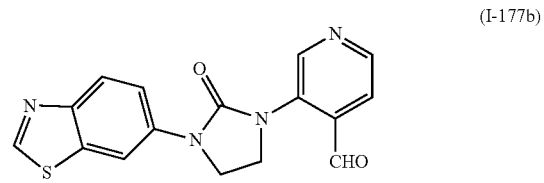
(I-177b)

PTSA (2.2 g, 11.672 mmol) was added to a stirred solution of 1-benzothiazol-6-yl-3-(4-dimethoxymethyl-pyridin-3-yl)-imidazolidin-2-one (I-177a: 460 mg, 1.2418 mmol) in acetone (20 mL) and water (20 mL). The resulting reaction mass was stirred for 48 hours at room temperature. The reaction was monitored by TLC (5% methanol in chloroform). The reaction mixture was concentrated, the residue was diluted with ice-water, basified with saturated NaHCO$_3$ solution and extracted using ethyl acetate. The aqueous layer was filtered and the solid collected was dried under reduced pressure. The solid was dissolved in methanol and chloroform, dried over Na$_2$SO$_4$ and concentrated under reduced pressure to afford 400 mg of the product (99.5% yield).

$^1$H NMR (300 MHz, DMSO): δ 9.9 (s, 1H), 9.3 (s, 1H), 8.9 (s, 1H), 8.62 (d, 1H), 8.3 (d, 1H), 8.1 (d, 1H), 7.9 (dd, 1H), 7.65 (d, 1H), 4.3-4.15 (m, 4H)

Final Step: Synthesis of 1-Benzothiazol-6-yl-3-(4-morpholin-4-ylmethyl-pyridin-3-yl)-imidazolidin-2-one (177A)

Morpholine (0.032 mL, 0.3699 mmol) was added to a stirred solution of 3-(3-Benzothiazol-6-yl-2-oxo-imidazolidin-1-yl)-pyridine-4-carbaldehyde (I-177b: 100 mg, 0.3082 mmol) in acetic acid (2 mL) and stirred at room temperature for 4 hours. This was followed by the addition of NaBH (OAc)₃ (98 mg, 0.4624 mmol). The resulting reaction mass was stirred at room temperature for 24 hours. The reaction was monitored by TLC (10% methanol in chloroform). The reaction mixture was concentrated under reduced pressure, added ice, basified using saturated NaHCO₃ solution and extracted using ethyl acetate. The organic layer was washed with water, brine solution, dried over Na₂SO₄ and concentrated. Purification by column chromatography on silica gel (2% methanol in chloroform) followed by preparative HPLC afforded 25 mg of the product (20.6% yield).

¹H NMR (400 MHz, CDCl₃): δ 8.9 (s, 1H), 8.58-8.5 (m, 2H), 8.34 (d, 1H), 8.12 (d, 1H) 7.7 (dd, 1H), 7.54 (d, 1H), 4.2-4.14 (m, 2H), 4.04 (m, 2H), 3.7 (t, 4H), 3.6 (s, 2H), 2.44 (t, 4H).

LCMS: 99.10%, m/z=396.1 (M+1)
HPLC: 95.64%

Example 178

Preparation of 1-Benzothiazol-6-yl-3-(4-cyclopropylaminomethyl-pyridin-3-yl)-imidazolidin-2-one (178A)

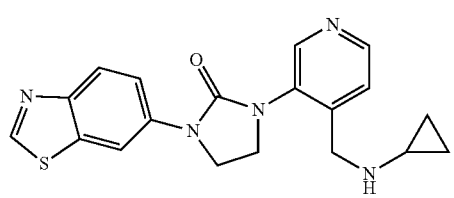

(178A)

3-(3-Benzothiazol-6-yl-2-oxo-imidazolidin-1-yl)-pyridine-4-carbaldehyde (I-177b: 100 mg, 0.3083 mmol) was reacted with NaBH(OAc)₃ (98 mg, 0.4624 mmol), Cyclopropylamine (0.032 mL, 0.462 mmol) and acetic acid (5 mL) at room temperature for 12 hours to afford the crude product. The reaction was monitored by TLC (5% methanol in chloroform). Purification by column chromatography on silica gel (2% methanol in chloroform) followed by preparative HPLC afforded 13 mg of the product (11.6% yield).

¹H NMR (400 MHz, CDCl₃): δ 8.9 (s, 1H), 8.6-8.5 (m, 2H), 8.35 (s, 1H), 8.1 (d, 1H), 7.7 (dd, 1H) 7.5 (d, 1H), 4.2 (m, 2H), 4.05 (m, 2H), 3.9 (s, 2H), 2.25-2.15 (m, 1H), 0.5-0.3 (m, 4H).

LCMS: 98.17%, m/z=366.1 (M+1)
HPLC: 93.36%

Example 179

Preparation of 1-Benzothiazol-6-yl-3-(6-fluoro-4-methyl-pyridin-3-yl)-imidazolidin-2-one (179A)

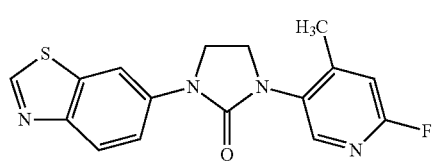

(179A)

1-Benzothiazol-6-yl-imidazolidin-2-one (I-84b: 150 mg, 0.6849 mmol) was reacted with 5-bromo-2-fluoro-4-methyl-pyridine (130 mg, 0.6849 mmol), 1,4-dioxane (5 mL), copper iodide (13 mg, 0.06849 mmol), trans -N,N'-dimethyl-cyclohexane-1,2-diamine (32.3 mL, 0.2054 mmol) and potassium phosphate (362.9 mg, 1.7122 mmol) to afford the crude product. Purification by column chromatography on silica gel (60% ethylacetate in hexane) afforded 65 mg of the product (28.9% yield).

¹H NMR (400 MHz, CDCl₃): δ 8.9 (s, 1H), 8.34 (d, 1H), 8.16-8.1 (m, 2H), 7.68 (dd, 1H), 6.9 (d, 1H), 4.16 (m, 2H), 3.95 (m, 2H), 2.4 (s, 3H).

LCMS: 98.93%, m/z=328.9 (M+1)
HPLC: 98.02%

Example 180

Preparation of 1-Benzothiazol-6-yl-3-[4-(2-morpholin-4-O-ethoxy)-pyridin-3-yl]imidazolidin-2-one (180A)

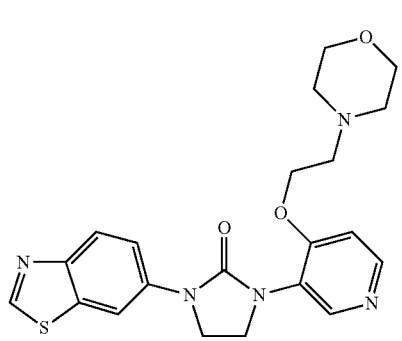

(180A)

Step 1: Preparation of Intermediate 1-Benzothiazol-6-yl-3-(4-chloro-pyridin-3-yl)-imidazolidin-2-one (I-180a)

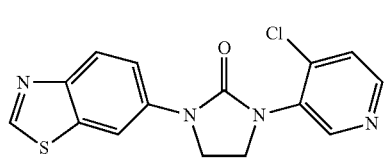

(I-180a)

Using the same reaction conditions and work up as described in Example 1, step-3,1-benzothiazol-6-yl-imidazolidin-2-one (I-84b: 800 mg, 3.653 mmol) was refluxed with 3-bromo-4-chloro-pyridine (879 mg, 4.566 mmol), copper iodide (70 mg, 0.365 mmol), cyclohexane-1,2-diamine (125 mg, 1.0958 mmol), potassium phosphate (2.32 g, 10.958 mmol) and 1,4-Dioxane (50 mL) at 110° C. for 12 hours to afford the crude product. The reaction was monitored by TLC (10% MeOH in chloroform). Purification by column chromatography on silica gel (1.5% methanol in chloroform) afforded 715 mg of the product (60% yield).

¹H NMR (400 MHz, CDCl₃): δ 8.9 (s, 1H), 8.7 (s, 1H), 8.48 (d, 1H), 8.38 (d, 1H), 8.12 (d, 1H), 7.68 (dd, 1H), 7.46 (d, 1H), 4.22-4.14 (m, 2H), 4.06-4.0 (m, 2H).

LCMS: 96.70%, m/z=331 (M+1)
HPLC: 95.64%.

Final Step: Synthesis of 1-Benzothiazol-6-yl-3-[4-(2-morpholin-4-yl-ethoxy)-pyridin-3-yl]-imidazolidin-2-one (180A)

1-Benzothiazol-6-yl-3-(4-chloro-pyridin-3-yl)-imidazolidin-2-one (I-180a: 100 mg, 0.3023 mmol) was refluxed with 2-morpholin-4-yl-ethanol (60 mg, 0.4534 mmol), potassium hydroxide (68 mg, 1.2092 mmol), potassium carbonate (42 mg, 0.3023 mmol), 18-crown-ether (8 mg, 0.0302 mmol) and toluene (3 mL) at 120° C. to afford the crude product. The reaction was monitored by TLC (10% MeOH in chloroform). Purification by column chromatography on silica gel (3.5% methanol in chloroform) followed by hexane wash and ether wash afforded 8.5 mg of the product (6.6% yield).

$^1$H NMR (400 MHz, CDCl$_3$): δ 8.9 (s, 1H), 8.65 (s, 1H), 8.54 (d, 1H), 8.3 (s, 1H), 8.1 (d, 1H) 7.7 (d, 1H), 6.95 (d, 1H), 4.24 (t, 2H), 4.32-3.94 (m, 4H), 3.64 (t, 4H), 2.82 (t, 2H), 2.58-2.48 (m, 4H)

LCMS: 94.37%, m/z=426 (M+1)
HPLC: 91.83%

Example 181

Preparation of 1-Benzothiazol-6-yl-3-[4-(1-methyl-pyrrolidin-2-ylmethoxy)-pyridin-3-yl]-imidazolidin-2-one (181A)

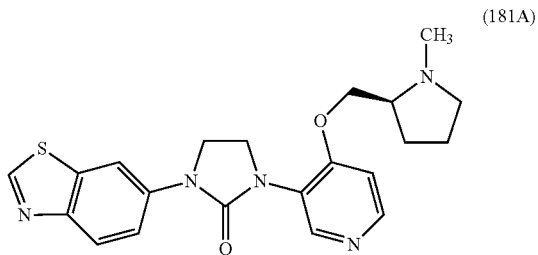

(181A)

1-Benzothiazol-6-yl-3-(4-chloro-pyridin-3-yl)-imidazolidin-2-one (I-180a: 100 mg, 0.3023 mmol) was added to a stirred mixture of KOH (68 mg, 1.2092 mmol), K$_2$CO$_3$ (42 mg, 0.3023 mmol) and toluene (3 mL) and the reaction mixture was stirred at RT for 5 mins. This was followed by the addition of (1-methyl-pyrrolidin-2-yl)-methanol (52 mg, 0.4534 mmol) and 18 crown ether (8 mg, 0.0302 mmol) and the resulting mixture was refluxed for 24 hrs. The reaction was monitored by TLC (10% MeOH in CHCl$_3$). The reaction mixture was concentrated and the concentrate was partitioned between ethylacetate and water. The organic layer was washed with water, brine, dried over Na$_2$SO$_4$ and concentrated. Purification by preparative HPLC afforded 6 mg of the product (5% yield).

$^1$H NMR (300 MHz, CDCl$_3$): δ 8.9 (s, 1H), 8.55 (s, 1H), 8.45 (d, 1H), 8.35 (d, 1H), 8.1 (d, 1H) 7.7 (dd, 1H), 6.9 (d, 1H), 4.2-3.9 (m, 7H), 3.1 (t, 1H), 2.7 (bs, 1H), 2.45 (s, 3H), 2.35-2.2 (m, 1H), 2.05-1.95 (m, 1H), 1.85-1.7 (m, 2H).

LCMS: 100%, m/z (M+1)
HPLC: 96.12%

Example 182

Preparation of 1-Benzothiazol-6-yl-3-{4-[(5-methyl-1H-pyrazol-3-ylamino)-methyl]-pyridin-3-yl}-imidazolidin-2-one (182A)

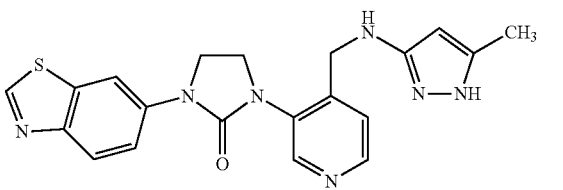

(182A)

3-(3-benzothiazol-6-yl-2-oxo-imidazolidin-1-yl)-pyridine-4-carbaldehyde (I-177b: 100 mg, 0.308 mmol) was reacted with NaBH(OAc)$_3$ (131 mg, 0.616 mmol), 5-methyl-1H-pyrazol-3-ylamine (40 mg, 0.370 mmol) and acetic acid (10 mL) to afford the crude product. Purification by column chromatography on silica gel (5% MeOH in CHCl$_3$), followed by preparative HPLC afforded 4 mg of the product (7.7% yield).

$^1$H NMR (400 MHz, CD$_3$OD): δ 9.18 (s, 1H), 8.64 (s, 1H), 8.5 (d, 1H), 8.32 (d, 1H), 8.06 (d, 1H), 7.9 (dd, 1H), 7.6 (d, 1H), 5.5 (s, 1H), 4.5 (s, 2H), 4.3-4.05 (m, 4H), 2.15 (s, 3H).

LCMS: 100%, m/z=405.9 (M+1)
HPLC: 80.60%

Example 183

Preparation of 1-Benzothiazol-6-yl-3-(3H-imidazo[4,5-b]pyridin-6-yl)-imidazolidin-2-one (183A)

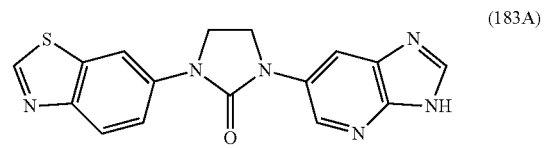

(183A)

Step 1: Synthesis of Intermediate 6-Bromo-3-(2-trimethylsilanyl-ethoxymethyl)-3H-imidazo[4,5-b]pyridine (I-183a)

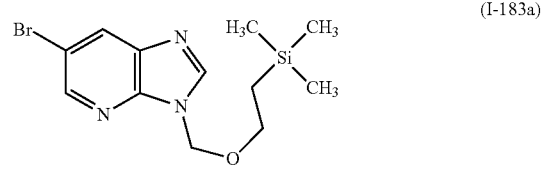

(I-183a)

(2-Chloromethoxy-ethyl)-trimethyl-silane (508.6 mg, 3.0456 mmol), catalytic amount of benzyl triethyl-ammonium chloride and NaOH (203.04 mg, 5.076 mmol) were added to a solution of 6-bromo-3H-imidazo[4,5-b]pyridine (500 mg, 2.538 mmol) in DCM (10 mL) at 0° C. The resulting mixture was stirred room temperature for 6 hours. The reaction was monitored by TLC (80% ethylacetate in hexane). The reaction mixture was partitioned between DCM and water. The organic layer was washed with water, brine, dried over Na$_2$SO$_4$ and concentrated. Purification by column chromatography on silica gel (20% ethylacetate in hexane) afforded 120 mg of the product (14.4% yield).

$^1$H NMR (400 MHz, CDCl$_3$): 8.48 (d, 1H), 8.25 (d, 1H), 8.2 (s, 1H), 5.65 (s, 2H), 3.7-3.5 (t, 2H), 1.0-0.9 (t, 2H), -0.09-0.00 (m, 9H).

Step 2: Synthesis of Intermediate 1-Benzothiazol-6-yl-3-[3-(2-trimethylsilanyl-ethoxy)-3H-imidazo[4,5-b]pyridin-6-yl]-imidazolidin-2-one (I-183b)

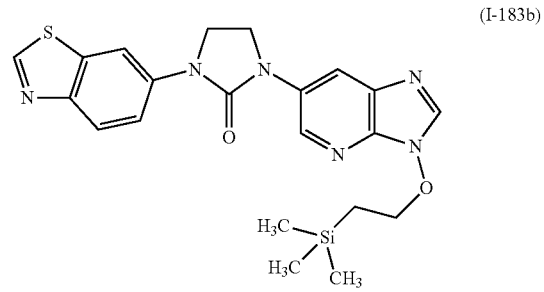

(I-183b)

1-Benzothiazol-6-yl-imidazolidin-2-one (I-84b: 80.3 mg, 0.3669 mmol) was reacted with 6-bromo-3-(2-trimethylsilanyl-ethoxymethyl)-3H-imidazo[4,5-b]pyridine (I-183a: 120 mg, 0.3669 mmol), 1,4-dioxane (5 mL), copper iodide (6.9 mg, 0.03669 mmol), trans N,N'-dimethyl-cyclohexane-1,2-diamine (17.3 mL, 0.1100 mmol) and potassium phosphate (194.4 mg, 0.9172 mmol) to afford the crude product. Purification by column chromatography on silica gel (2% MeOH in DCM) afforded 100 mg of the product (58.4% yield).

$^1$H NMR (400 MHz, CDCl$_3$): δ 9.0-8.8 (m, 2H), 8.5-8.1 (m, 4H), 7.7 (d, 1H), 5.7 (bs, 2H), 4.2 (bs, 4H), 3.6 (t, 2H), 0.95 (t, 2H), -0.09-0.00 (m, 9H).

Final Step: Synthesis of 1-Benzothiazol-6-yl-3-(3H-imidazo[4,5-b]pyridin-6-yl)-imidazolidin-2-one (183A)

1,4-Dioxane HCl (5 ml) was added to 1-benzothiazol-6-yl-3-[3-(2-trimethylsilanyl-ethoxy)-3H-imidazo[4,5-b]pyridin-6-yl]-imidazolidin-2-one (I-183b: 100 mg, 0.2145 mmol) and the resulting mixture was stirred room temperature for 6 hours. The reaction was monitored by TLC (10% MeOH in DCM). The reaction mixture was concentrated and washed with diethyl ether. Purification by preparative HPLC afforded 20 mg of the product (25.4% yield).

$^1$H NMR (400 MHz, DMSO-D$_6$): δ 13.2 (s, 0.5H), 12.6 (s, 0.5H), 9.3 (s, 1H), 8.7 (dd, 1H), 8.44 (s, 1H), 8.36 (s, 1H), 8.3 (dd, 1H), 8.1 (d, 1H), 8.0 (dd, 1H), 4.2 (s, 4H).

LCMS: 75.25%, m/z=337 (M+1)

HPLC: 95.02%

Example 184

Synthesis of 1-Benzothiazol-6-yl-3-[4-(1-methyl-piperidin-4-ylmethoxy)-pyridin-3-yl]-imidazolidin-2-one (184A)

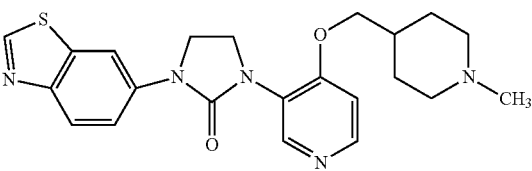

(184)

1-Benzothiazol-6-yl-3-(4-chloro-pyridin-3-yl)-imidazolidin-2-one (I-180a: 150 mg, 0.4534 mmol) was reacted with (1-methyl-piperidin-4-yl)-methanol (88 mg, 0.6801 mmol), KOH (101 mg, 1.8138 mmol), K$_2$CO$_3$ (63 mg, 0.4534 mmol) and toluene (6 mL) to afford crude product. Purification by column chromatography on silica gel (10% MeOH in CHCl$_3$), followed by preparative HPLC afforded 10 mg of the product (5% yield).

$^1$H NMR (400 MHz, CDCl$_3$): δ 8.9 (s, 1H), 8.55 (s, 1H), 8.45 (d, 1H), 8.35 (d, 1H), 8.1 (d, 1H), 7.7 (dd, 1H), 6.9 (d, 1H), 4.15 (m, 2H), 4.0-3.9 (m, 4H), 2.9 (d, 2H), 2.3 (s, 3H), 2.0-1.75 (m, 5H), 1.5 (t, 2H).

LCMS: 100%, m/z=424.2 (M+1)

HPLC: 98.88%

Example 185

Preparation of 3-(3-Benzothiazol-6-yl-2-oxo-imidazolidin-1-yl)-isonicotinamide (185A)

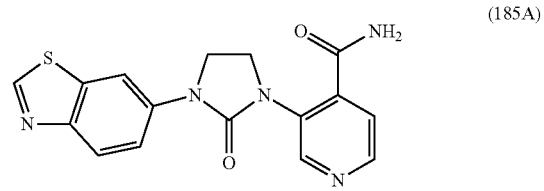

(185A)

Step 1: Synthesis of 3-(3-Benzothiazol-6-yl-2-oxo-imidazolidin-1-yl)-isonicotinic Acid Ethyl Ester (I-185a)

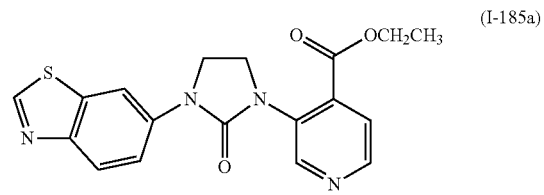

(I-185a)

1-Benzothiazol-6-yl-imidazolidin-2-one (I-84b: 0.25 g, 1.1 mmol) was reacted with 3-bromo-isonicotinic acid ethyl ester (0.28 g, 1.2 mmol), 1,4-dioxane (30 mL), copper iodide (0.065 g, 0.3 mmol), trans N,N'-dimethyl-cyclohexane-1,2-diamine (0.048 g, 0.3 mmol) and potassium phosphate (0.81 g, 2.8 mmol) to afford the crude product. Purification by column chromatography on silica gel (100% CHCl$_3$) afforded 160 mg of the product (38.2% yield).

LC-MS (m/z), 61.53%, 369.0 (m+1)

Final Step: Synthesis of 3-(3-Benzothiazol-6-yl-2-oxo-imidazolidin-1-yl)-isonicotinamide (185A)

3-(3-Benzothiazol-6-yl-2-oxo-imidazolidin-1-yl)-isonicotinic acid ethyl ester (I-185a: 0.16 g, 0.4 mmol) in methanolic ammonia (20 mL) was taken in a reaction flask and the flask was heated to 40° C. overnight. The reaction was monitored by TLC (10% MeOH in CHCl$_3$). The reaction mixture was cooled to room temperature and concentrated. The concentrate was partitioned between DCM and water. The organic layer was washed with water, brine, dried over Na$_2$SO$_4$ and concentrated. Purification by column chromatography on silica gel (10% MeOH in CHCl$_3$) afforded 40 mg of the product (28.57% yield).

$^1$H NMR (400 MHz, DMSOd$_6$): δ 9.3 (s, 1H), 8.7 (s, 1H), 8.55 (d, 1H), 8.3 (d, 1H), 8.1-7.9 (m, 3H) 7.6 (s, 1H), 7.5 (d, 1H), 4.1 (s, 4H).

LCMS: 100%, m/z=339.9 (M+1)

HPLC: 88.41%

Example 186

Preparation of 1-Benzothiazol-6-yl-3-imidazo[1,2-a]pyrazin-5-yl-imidazolidin-2-one (186A)

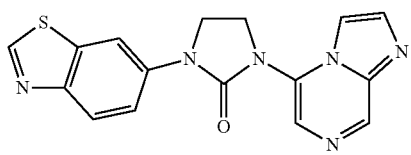
(186)

Synthesis of Intermediate 5-Chloro-imidazo[1,2-a]pyrazine (I-186a)

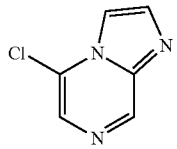
(I-186a)

NaHCO₃ (4.215 g, 50.1736 mmol) and IPA (40 mL) were added to a mixture of 2-bromo-1,1-dimethoxy-ethane (6.37 mL, 10.8066 mmol), 40% HBr (475 mL, 2.3157 mmol) and 2 drops of water previously refluxed for 1 hr. The reaction mixture was stirred for 5 mins and filtered. To the filtrate was added 6-chloro-pyrazin-2-ylamine (1 g, 7.7190 mmol) and the resulting mixture was refluxed for overnight. The reaction was monitored by TLC (50% ethylacetate in hexane). The reaction mixture was neutralized with Na₂CO₃ and partitioned between ethylacetate and water. The organic layer was washed with water, brine, dried over Na₂SO₄ and concentrated. Purification by column chromatography on silica gel (1-2% MeOH in CHCl₃) afforded 300 mg of the product (25.31% yield).

¹H NMR (400 MHz, CDCl₃): δ 9.05 (s, 1H), 7.98 (s, 1H), 7.92-7.85 (m, 2H).

LCMS: 97.85%, m/z=154.0 (M+1)

Final Step: Synthesis of 1-Benzothiazol-6-yl-3-imidazo[1,2-a]pyrazin-5-yl-imidazolidin-2-one (186A)

1-benzothiazol-6-yl-imidazolidin-2-one (I-84b: 240 mg, 1.0945 mmol) was reacted with 5-chloro-imidazo[1,2-a]pyrazine (I-186a: 202 mg, 1.3135 mmol), 1,4-dioxane (3 mL), copper iodide (24 mg), trans N,N'-dimethyl-cyclohexane-1,2-diamine (48 mg) and potassium phosphate (581 mg, 2.7364 mmol) to afford the crude product. Purification by column chromatography on silica gel (2% MeOH in CHCl₃), followed by preparative HPLC afforded 13 mg of the product (3.53% yield).

¹H NMR (300 MHz, CDCl₃): δ 8.9 (s, 1H), 8.54 (d, 1H), 8.1 (d, 1H), 7.95 (d, 1H), 7.85 (d, 1H) 7.75-7.7 (m, 3H), 4.5 (t, 2H), 4.1 (t, 2H).

LCMS: 100%, m/z=337 (M+1)

HPLC: 91.78%

Example 187

Preparation of 1-Benzothiazol-6-yl-3-(1H-pyrrolo[2,3-b]pyridin-5-yl)-imidazolidin-2-one (187A)

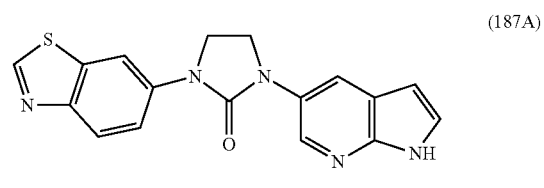
(187A)

Step 1: Synthesis of 5-Bromo-1-(2-trimethylsilanyl-ethoxymethyl)-1H-pyrrolo[2,3-b]pyridine (I-187a)

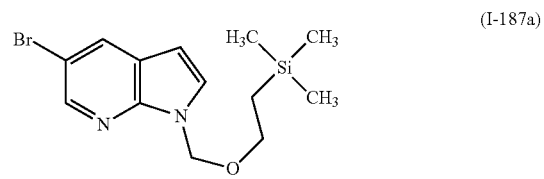
(I-187a)

5-bromo-1H-pyrrolo[2,3-b]pyridine (0.3 g, 1.6 mmol) was reacted with (2-chloromethoxy-ethyl)-trimethyl-silane (0.35 g, 2.1 mmol), catalytic amount of benzyl triethyl-ammonium chloride and NaOH (0.2 g, 5.2 mmol) and DCM (20 mL) to afford the crude product. Purification by column chromatography on silica gel (20% ethylacetate in hexane) afforded 0.32 g of the product (64.2% yield).

¹H NMR (400 MHz, CDCl₃) δ: 8.36 (d, 1H), 8.03 (d, 1H), 7.36 (d, 1H), 6.46 (d, 1H), 5.6 (s, 2H), 3.5 (t, 2H), 0.9 (t, 2H), -0.95 (m, 9H)

Step 2: Synthesis of Intermediate 1-(benzothiazol-6-yl)-3-(1-((2-(trimethylsilyl)-ethoxy)methyl)-1H-pyrrolo[2,3-b]pyridin-5-yl)imidazolidin-2-one (I-187b)

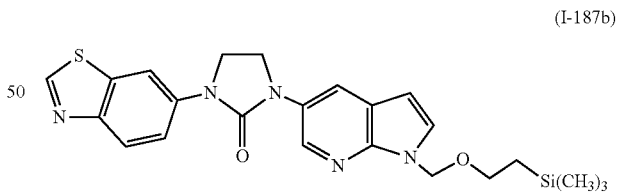
(I-187b)

1-Benzothiazol-6-yl-imidazolidin-2-one (I-84b: 0.2 g, 0.9 mmol) was reacted with 5-bromo-1-(2-trimethylsilanyl-ethoxymethyl)-1H-pyrrolo[2,3-b]pyridine (I-187a: 0.32 g, 1.0 mmol), 1,4-dioxane (15 mL), copper iodide (0.052 g, 0.2 mmol), trans N,N'-dimethyl-cyclohexane-1,2-diamine (0.038 g, 0.27 mmol) and potassium phosphate (0.65 g, 2.2 mmol) to afford the crude product. Purification by column chromatography on silica gel (1.5% methanol in DCM) afforded 0.22 g of the product (52.3% yield).

¹H NMR (400 MHz, CDCl₃) δ: 8.9 (s, 1H), 8.48 (d, 1H), 8.38 (d, 1H), 8.24 (d, 1H), 8.1 (d, 1H), 7.7 (dd, 1H), 7.37 (d, 1H), 6.5 (s, 1H), 5.7 (s, 2H), 4.1 (s, 4H), 3.55 (t, 2H), 0.9 (t, 2H), -0.95 (s, 9H)

Final Step: Synthesis of 1-Benzothiazol-6-yl-3-(1H-pyrrolo[2,3-b]pyridin-5-yl)-imidazolidin-2-one (187A)

1,4-Dioxane HCl (10 ml) was added to 1-(benzothiazol-6-yl)-3-(1-((2-(trimethylsilyl)-ethoxy)methyl)-1H-pyrrolo[2,3-b]pyridin-5-yl)imidazolidin-2-one (I-187b: 0.07 g, 0.19 mmol) and the resulting mixture was heated to 110° C. for 2 days. The reaction was monitored by TLC (20% MeOH in CHCl$_3$). The reaction mixture was basified with Na$_2$CO$_3$ solution (pH~8), cooled to room temperature, concentrated and the concentrate was washed with diethyl ether. Purification by preparative HPLC afforded 1.7 mg of the product (25.6% yield).

$^1$H NMR (300 MHz, CDCl$_3$): δ 8.9 (s, 1H), 8.5 (s, 1H), 8.4 (d, 1H), 8.3 (s, 1H), 8.1 (d, 1H) 7.7 (dd, 1H), 7.35 (t, 1H), 6.55 (m, 1H), 4.2 (s, 4H).

LCMS: 97.14%, m/z=336 (M+1)
HPLC: 87.78%

Example 188

Synthesis of 3-Benzothiazol-6-yl-3'-methyl-4,5-dihydro-3H,3'H-[1,4]biimidazolyl-2-one (179A)

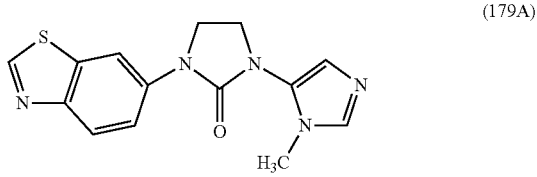

(179A)

1-Benzothiazol-6-yl-imidazolidin-2-one (I-84b: 150 mg, 0.6849 mmol) was reacted with 5-bromo-1-methyl-1H-imidazole (121.3 mg, 0.753 mmol), 1,4-dioxane (5 mL), copper iodide (12.99 mg, 0.0684 mmol), trans N,N'-dimethyl-cyclohexane-1,2-diamine (29.176 mg, 0.205 mmol) and potassium phosphate (435.01 mg, 2.05 mmol) to afford the crude product. Purification by column chromatography on silica gel (2% MeOH in CHCl$_3$) afforded 85 mg of the product (41.64% yield).

$^1$H NMR (300 MHz, CDCl$_3$): δ 8.9 (s, 1H), 8.35 (d, 1H), 8.1 (d, 1H), 7.7 (dd, 1H), 7.5-7.4 (brs, 1H), 7.0 (brs, 1H), 4.1 (t, 2H), 3.9 (t, 2H), 3.6 (s, 3H).

LCMS: 100%, m/z=299.8 (M+1)
HPLC: 98.52%

Example 189

Preparation of 1-Benzothiazol-6-yl-3-(4-methyl-5-trifluoromethyl-pyridin-3-yl)-imidazolidin-2-one Trifluoro-acetic Acid (189A)

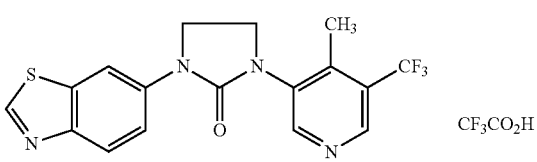

(189A)

Step 1: Synthesis of 3-Bromo-4-methyl-5-trifluoromethyl-pyridine (I-189a)

(I-189a)

n-Butyl Lithium (1.9 mL, 3.044 mmol) was added to a solution of DIPA (335.7 mg, 3.318 mmol) in THF (6 mL) at -78° C. The reaction mixture was stirred at -10° C. for 10 minutes. This was followed by the addition of 3-bromo-5-trifluoromethyl-pyridine (500 mg, 2.212 mmol) in THF (3 mL) at -100° C. The reaction mixture was stirred for a further 15 minutes at -90° C. and was followed by the addition of methyl iodide (557.0 mg, 3.924 mmol) in THF (2 mL) at -78° C. with stirring over a period of 30 minutes. The reaction was monitored by TLC (5% ethyl acetate in hexane). The reaction mixture was quenched with aqueous NaHCO$_3$ solution and extracted with ethyl acetate (100 mL). The organic layer was dried over Na$_2$SO$_4$ and concentrated. Purification by column chromatography on silica gel (2% ethylacetate in hexane) afforded 95 mg of the product (17.92% yield). LCMS: m/z=239.8 (M+1)

Final Step: Synthesis of 1-Benzothiazol-6-yl-3-(4-methyl-5-trifluoromethyl-pyridin-3-yl)-imidazolidin-2-one Trifluoro-acetic Acid (189A)

1-Benzothiazol-6-yl-imidazolidin-2-one (I-84b: 80 mg, 0.365 mmol) was reacted with 3-bromo-4-methyl-5-trifluoromethyl-pyridine (I-189a: 90 mg, 0.365 mmol), 1,4-dioxane (5 mL), copper iodide (6.95 mg, 0.0365 mmol), trans-1,2-diamino cyclohexane (12.5 mg, 0.1095 mmol) and potassium phosphate (232.4 mg, 1.095 mmol) to afford the crude product. Purification by preparative HPLC afforded 5ing of the product (3.6% yield).

$^1$H NMR (CDCl$_3$, 300 MHz): δ 9.05-8.65 (m, 3H), 8.35 (s, 1H), 8.25-8.05 (m, 1H), 7.78-7.58 (m, 1H), 4.32-4.12 (m, 2H), 4.12-3.91 (m, 2H), 2.49 (s, 3H)

LCMS purity: 100%, m/z=378.9 (M+1)
HPLC: 93.5%

Example 190

Preparation of 1-Isothiazol-4-yl-3-(4-methyl-pyridin-3-yl)-imidazolidin-2-one (190A)

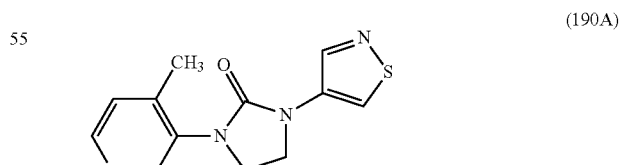

(190A)

1-(4-Methyl-pyridin-3-yl)-imidazolidin-2-one (I-14b: 150 mg, 0.847 mmol) was reacted with 4-bromo-isothiazole (166 mg, 1.016 mmol), 1,4-dioxane (15 mL), copper iodide (16.09 mg, 0.0847 mmol), trans-1,2-diamino cyclohexane (29 mg, 0.254 mmol) and potassium phosphate (540 mg, 2.541 mmol) to afford the crude product. Purification by column chromatography on silica gel (2% MeOH in CHCl₃) afforded 120 mg of the product (54.54% yield).

¹H NMR (CDCl₃, 300 MHz): δ 8.82 (s, 1H), 8.65-8.25 (m, 3H), 7.4-7.1 (m, 1H), 4.20-3.95 (m, 4H), 2.19 (s, 3H)

LCMS purity: 97.95%, m/z=261.0 (M+1)

HPLC: 96.08%

Example 191

Preparation of 1-Benzothiazol-6-yl-3-pyridin-2-yl-imidazolidin-2-one (191A)

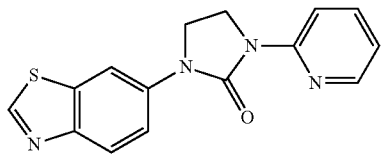

(191A)

1-Benzothiazol-6-yl-imidazolidin-2-one (I-84b: 150 mg, 0.6904 mmol) was reacted with 2-bromo-pyridine (99 mL, 1.0356 mmol), 1,4-dioxane (10 mL), copper iodide (16 mg), trans-1,2-diamino cyclohexane (32 mg) and potassium phosphate (440 mg, 2.0713 mmol) to afford the crude product. Purification by column chromatography on silica gel (10% ethylacetate in hexane), followed by preparative HPLC afforded 37 mg of the product (18.13% yield).

¹H NMR (DMSO-D₆, 300 MHz): δ 9.3 (s, 1H), 8.5-8.3 (m, 2H), 8.25 (d, 1H), 8.18-8.02 (m, 1H), 8.02-7.9 (m, 1H), 7.88-7.70 (m, 1H), 7.18-7.00 (m, 1H), 4.2-4.0 (m, 4H)

LCMS purity: 97.44%, m/z=297.1 (M+1)

HPLC: 95.28%

Example 192

Preparation of 1-(4-Methyl-pyridin-3-yl)-3-(5-trifluoromethyl-thiophen-2-yl)-imidazolidin-2-one (192A)

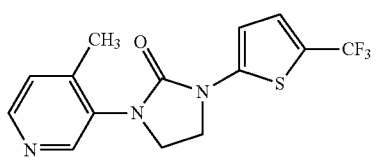

(192A)

1-(4-methyl-pyridin-3-yl)-imidazolidin-2-one (I-14b: 100 mg, 0.5643 mmol) was reacted with 2-bromo-5-trifluoromethyl-thiophene (136.9 mg, 0.5925 mmol), 1,4-dioxane (10 mL), copper iodide (10.75 mg, 0.0564 mmol), trans-1,2-diamino cyclohexane (20.4 mL, 0.1693 mmol) and potassium phosphate (360 mg, 1.693 mmol) to afford the crude product. Purification by column chromatography on silica gel (2% MeOH in CHCl₃) afforded 120 mg of the product (65% yield).

¹H NMR (DMSO-D₆, 300 MHz): δ 8.66-8.3 (m, 2H), 7.65-7.23 (m, 2H), 6.55 (d, 1H), 4.24-3.90 (m, 4H), 2.26 (s, 3H)

LCMS purity: 96.35%, m/z=327.9 (M+1)

HPLC: 95.04%

Example 193

Preparation of 1-Benzothiazol-6-yl-3-[4-(1-hydroxy-1-methyl-ethyl)-pyridin-3-yl]-imidazolidin-2-one (193A)

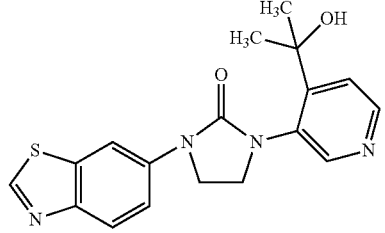

(193A)

Step 1: Synthesis of Intermediate 2-(3-Bromo-pyridin-4-yl)-propan-2-ol (I-193a)

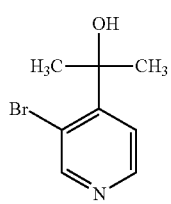

(I-193a)

n-Butyl Lithium (10.28 mL, 16.455 mmol) was added to a solution of DIPA (2.66 mL, 18.98 mmol) in THF (25 mL) at -78° C. The reaction mixture was stirred at -10° C. for 10 mins, followed by the addition of 3-bromo-pyridine (500 mg, 2.212 mmol) in THF (10 mL) at -100° C. The reaction mixture was stirred for a further 15 minutes at -90° C. and was followed by the addition of acetone (1.675 mL, 22.78 mmol) in THF (10 mL) at -78° C. with stirring over a period of 1 hr. The reaction was monitored by TLC (5% ethylacetate in hexane). The reaction mixture was quenched with aqueous NaHCO₃ solution and extracted with ethylacetate. The organic layer was dried over Na₂SO₄ and concentrated. Purification by column chromatography on silica gel (15% ethylacetate in hexane) afforded 200 mg of the product (11% yield).

¹H NMR (CDCl₃, 300 MHz): δ 8.7 (s, 1H), 8.5 (d, 1H), 7.65 (d, 1H), 1.7 (s, 6H)

LCMS purity: 89.57%, m/z=215.9 (M+1)

Final Step: Synthesis of 1-Benzothiazol-6-yl-3-[4-(1-hydroxy-1-methyl-ethyl)-pyridin-3-yl]-imidazolidin-2-one (193A)

1-benzothiazol-6-yl-imidazolidin-2-one (I-84b: 125 mg, 0.57 mmol) was reacted with 2-(3-bromo-pyridin-4-yl)-propan-2-ol (122.7 mg, 0.57 mmol), 1,4-dioxane (5 mL), copper iodide (10.85 mg, 0.057 mmol), trans-1,2-diamino cyclohexane (19.57 mg, 0.171 mmol) and potassium phosphate (362.9 mg, 1.71 mmol) to afford the crude product. Purification by preparative HPLC afforded 38 mg of the product (19% yield).

¹H NMR (CDCl₃, 300 MHz): δ 8.68 (s, 1H), 8.50-8.32 (m, 2H), 7.86 (d, 1H), 7.18-7.02 (m, 2H), 6.82 (dd, 1H), 4.55-4.42 (m, 1H), 4.32 (t, 2H), 3.7-3.6 (m, 2H), 1.74-1.58 (m, 6H)

LCMS purity: 97.84%, m/z=354.9 (M+1)

HPLC: 95.61%

Example 194

Preparation of 1-(4-Methyl-pyridin-3-(4-methyl-thieno[3,2-c]pyridin-2-yl)-imidazolidin-2-one (194A)

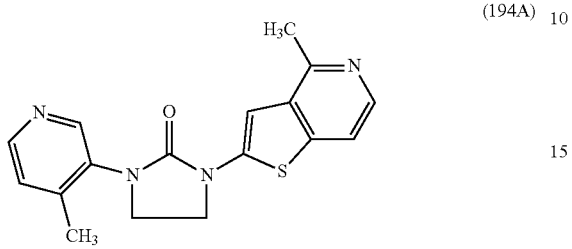
(194A)

Tetrakis (triphenylphosphine) palladium (33 mg, 0.0288 mmol) was added to potassium carbonate (120 mg, 0.8649 mmol) previously purged with argon (30 minutes). The reaction mixture was purged with argon for 15 minutes, followed by the addition of 1-(4-chloro-thieno[3,2-c]pyridin-2-yl)-3-(4-methyl-pyridin-3-yl)-imidazolidin-2-one (98A: 100 mg, 0.2883 mmol) and methyl boronic acid (21 mg, 0.3459 mmol). The reaction mixture was heated to reflux for 6 hours. The reaction was monitored by TLC (10% MeOH in CHCl$_3$). The reaction mixture was concentrated to afford the crude product. Purification by column chromatography on silica gel (3-4% MeOH in CHCl$_3$), followed by preparative HPLC afforded 10 mg of the product (16.39% yield).

$^1$H NMR (CDCl$_3$, 300 MHz): δ 8.7-8.35 (m, 2H), 8.35-8.2 (d, 1H), 7.5 (d, 1H), 6.58 (s, 1H), 4.4-3.9 (m, 4H), 2.79 (s, 3H), 2.36 (s, 3H)

LCMS purity: 96.01%, m/z=324.9 (M+1)
HPLC: 96.32%

Example 195

Preparation of 1-Benzothiazol-6-yl-3-[4-(1-hydroxy-ethyl)-pyridin-3-yl]-imidazolidin-2-one (195A)

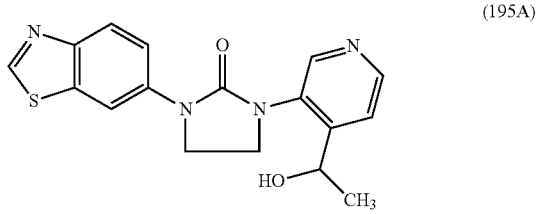
(195A)

1-Benzothiazol-6-yl-imidazolidin-2-one (I-84b: 150 mg, 0.6849 mmol) was reacted with 1-(3-bromo-pyridin-4-yl)-ethanol (137.6 mg, 0.6849 mmol), 1,4-dioxane (5 mL), copper iodide (13.04 mg, 0.06849 mmol), trans-1,2-diamino cyclohexane (23.52 mg, 0.205 mmol) and potassium phosphate (435.1 mg, 2.05 mmol) to afford the crude product. Purification by column chromatography on silica gel (2% MeOH in CHCl$_3$), followed by preparative HPLC afforded 9 mg of the product (3.9% yield).

$^1$H NMR (CDCl$_3$, 300 MHz): δ 8.92 (s, 1H), 8.65-8.54 (m, 2H), 8.32 (d, 1H), 8.15 (d, 1H), 7.70-7.62 (dd, 1H), 7.6 (d, 1H), 5.10-4.96 (m, 1H), 4.30-4.12 (m, 3H), 4.02-3.85 (m, 1H), 3.75-3.66 (br s, 1H), 1.60-1.45 (d, 3H)

LCMS purity: 98.20%, m/z=340.9 (M+1)
HPLC: 91.15%

Example 196

Synthesis of 1-Benzothiazol-6-yl-3-(4-ethyl-pyridin-3-yl)-imidazolidin-2-one (196A)

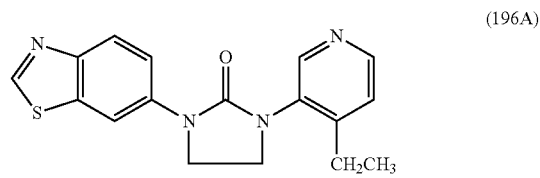
(196A)

1-Benzothiazol-6-yl-imidazolidin-2-one (I-84b: 600 mg, 2.739 mmol) was reacted with 3-bromo-4-ethyl-pyridine (512 mg, 2.739 mmol), 1,4-dioxane (10 mL), copper iodide (52 mg, 0.2739 mmol), trans-1,2-diamino cyclohexane (94.08 mg, 0.82 mmol) and potassium phosphate (1.74 mg, 8.2 mmol) to afford the crude product. Purification by column chromatography on silica gel (2% MeOH in CHCl$_3$), followed by preparative HPLC afforded 30 mg of the product (3.75% yield).

$^1$H NMR (CD$_3$OD, 300 MHz): δ 9.15 (s, 1H), 8.60-8.35 (m, 3H), 8.15-7.95 (m, 1H), 7.95-7.70 (m, 1H), 7.5 (d, 1H), 4.3-3.9 (m, 4H), 2.85-2.65 (q, 2H), 1.4-1.2 (t, 3H)

LCMS purity: 99.77%, m/z=325.1 (M+1)
HPLC: 95.03%

Example 197

Preparation of 1-(4-Methyl-pyridin-3-yl)-3-(3-trifluoromethyl-1H-indazol-6-yl)-imidazolidin-2-one (197A)

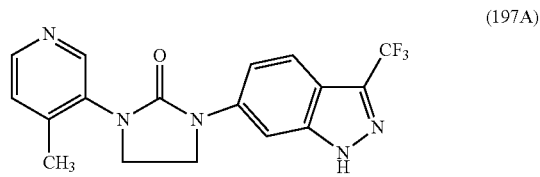
(197A)

Step 1: Synthesis of 1-[3-Fluoro-4-(2,2,2-trifluoro-1-hydroxy-ethyl)-phenyl]-3-(4-methyl-pyridin-3-yl)-imidazolidin-2-one (I-197a)

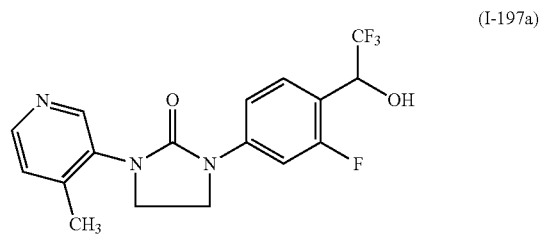
(I-197a)

0.5M solution of trimethyl-trifluoromethyl-silane in THF (6.68 mL, 3.344 mmol) and K₂CO₃ (250 mg, 10.82 mmol) were added to 2-fluoro-4-[3-(4-methyl-pyridin-3-yl)-2-oxo-imidazolidin-1-yl]-benzaldehyde (I-121a: 400 mg, 1.337 mmol) in dry DMF (5 mL) under nitrogen atmosphere. The resulting mixture was stirred at room temperature overnight. The reaction was monitored by TLC (5% MeOH in CHCl₃). The reaction mixture was quenched with brine solution and the THF layer was concentrated. The aqueous layer was extracted with chloroform. The organic layer was dried over Na₂SO₄ and concentrated to get the crude product. Purification by column chromatography on silica gel (2.5% MeOH in CHCl₃), followed by hexane wash, afforded 325 mg of the product (65.92% yield).

¹H NMR (CDCl₃, 300 MHz): δ 8.56-8.00 (m, 2H), 7.75-7.45 (m, 2H), 7.36-7.08 (m, 2H), 5.38 (q, 1H), 4.55-4.24 (br s, 1H), 4.20-3.76 (m, 4H), 2.32 (s, 3H)

Step 2: Synthesis of 1-[3-Fluoro-4-(2,2,2-trifluoro-acetyl)-phenyl]-3-(4-methyl-pyridin-3-yl)-imidazolidin-2-one (I-197b)

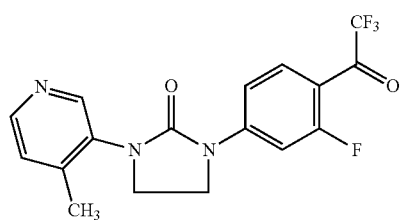

(I-197b)

MnO₂ (536 mg, 6.165 mmol) was added to 1-[3-fluoro-4-(2,2,2-trifluoro-1-hydroxy-ethyl)-phenyl]-3-(4-methyl-pyridin-3-yl)-imidazolidin-2-one (I-197a: 325 mg, 0.880 mmol) in DCM (20 mL) under nitrogen atmosphere. The resulting suspension was stirred at 50° C. overnight. The reaction was monitored by TLC (5% MeOH in DCM). The reaction mixture was cooled to room temperature and filtered through celite pad. The filtrate was washed with CHCl₃, dried over Na₂SO₄ and concentrated. The concentrate was washed with hexane and dried to afford 240 mg of the product (74.53% yield).

¹H NMR (DMSO-D₆, 300 MHz): δ 8.8-8.2 (m, 2H), 7.98 (t, 1H), 7.86-7.50 (m, 2H), 7.46-7.25 (m, 1H), 4.40-3.75 (m, 4H), 2.28 (s, 3H)

Final Step: Synthesis of 1-(4-Methyl-pyridin-3-yl)-3-(3-trifluoromethyl-1H-indazol-6-yl)-imidazolidin-2-one (197A)

Acetic acid (0.1 mL, 1.36 mmol) and 1M hydrazine in THF (4 mL, 2.72 mmol) were added to 1-[3-fluoro-4-(2,2,2-trifluoro-acetyl)-phenyl]-3-(4-methyl-pyridin-3-yl)-imidazolidin-2-one (I-197b: 100 mg, 0.272 mmol) in dry THF (2 mL). The resulting mixture was stirred at 150° C. overnight. The reaction was monitored by TLC (5% MeOH in CHCl₃). The reaction mixture was partitioned between water and chloroform. The organic layer was dried over Na₂SO₄ and concentrated. Purification by column chromatography on silica gel (4% MeOH in CHCl₃), followed by preparative HPLC afforded 23 mg of the product (23.46% yield).

¹H NMR (CD₃OD, 300 MHz): δ 8.57-8.48 (br s, 1H), 8.37 (d, 1H), 7.86-7.70 (m, 2H), 7.70-7.60 (m, 1H), 7.42 (d, 1H), 4.34-4.12 (m, 2H), 4.12-3.90 (m, 2H), 2.41 (s, 3H)

LCMS purity: 96.14%, m/z=362.0 (M+1)
HPLC: 94.33%

Example 198

Preparation of 1-(3-Cyclopropyl-1H-indazol-6-yl)-3-(4-methyl-pyridin-3-yl)-imidazolidin-2-one (198A)

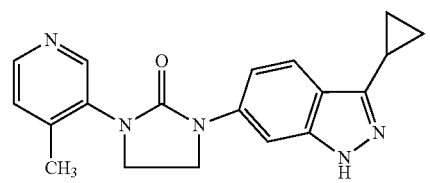

(198A)

Step I. Synthesis of 1-[4-(Cyclopropyl-hydroxy-methyl)-3-fluoro-phenyl]-3-(4-methyl-pyridin-3-yl)-imidazolidin-2-one (I-198a)

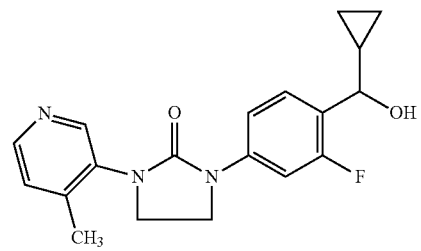

(I-198a)

0.5M solution of cyclopropyl magnesium bromide in THF (2.4 mL, 1.170 mmol) was added dropwise to 2-fluoro-4-[3-(4-methyl-pyridin-3-yl)-2-oxo-imidazolidin-1-yl]-benzaldehyde (I-121a: 175 mg, 0.585 mmol) in dry THF (10 mL) at 0° C. under nitrogen atmosphere. The resulting mixture was stirred at room temperature for 3 hours. The reaction was monitored by TLC (5% MeOH in CHCl₃). The reaction mixture was quenched with aqueous NH₄Cl solution and the THF layer was concentrated. The aqueous layer was extracted with ethylacetate. The organic layer was dried over Na₂SO₄ and concentrated to afford the crude product. Purification by column chromatography on silica gel (3% MeOH in CHCl₃), followed by hexane wash, afforded 200 mg of the product (99.41% yield).

¹H NMR (DMSO-D₆, 300 MHz): δ 8.72-8.28 (m, 2H), 7.70-7.48 (m, 2H), 7.42-7.25 (m, 2H), 5.30 (d, 1H), 4.48-4.20 (m, 1H), 4.18-3.82 (m, 4H), 2.32 (s, 3H), 1.2-1.0 (m, 1H), 0.7-0.1 (m, 4H)

LCMS purity: 97.58%, m/z=342.3 (M+1)

Step 2: Synthesis of 1-(4-Cyclopropanecarbonyl-3-fluoro-phenyl)-3-(4-methyl-pyridin-3-yl)-imidazolidin-2-one (I-198b)

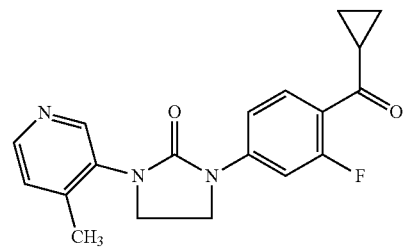

(I-198b)

MnO$_2$ (357 mg, 41.055 mmol) was added to 1-[4-(cyclopropyl-hydroxy-methyl)-3-fluoro-phenyl]-3-(4-methyl-pyridin-3-yl)-imidazolidin-2-one (I-198a: 200 mg, 8.586 mmol) in DCM (20 mL) under nitrogen atmosphere and worked up in a manner similar to what was described for Example 197 to afford 175 mg of the product (60.13% yield).

$^1$H NMR (DMSO-D$_6$, 300 MHz): δ 8.56 (s, 1H), 8.41 (d, 1H), 7.82 (t, 1H), 7.76-7.65 (m, 1H), 7.60-7.47 (m, 1H), 7.37 (d, 1H), 4.22-3.82 (m, 4H), 2.80-2.60 (m, 1H), 2.29 (s, 3H), 1.18-0.93 (m, 4H)

LCMS purity: 98.34%, m/z=339.7 (M+1)

Final Step: Synthesis of 1-(3-Cyclopropyl-1H-indazol-6-yl)-3-(4-methyl-pyridin-3-yl)-imidazolidin-2-one (198A)

1-(4-Cyclopropanecarbonyl-3-fluoro-phenyl)-3-(4-methyl-pyridin-3-yl)-imidazolidin-2-one (I-198b: 175 mg, 0.516 mmol) in hydrazine hydrate solution (10 mL) was taken in a reaction flask. The flask was refluxed at 120° C. overnight. The reaction was monitored by TLC (5% MeOH in CHCl$_3$). The reaction mixture was cooled to room temperature and partitioned between ice water and chloroform. The organic layer was dried over Na$_2$SO$_4$ and concentrated. Purification by column chromatography on silica gel (4% MeOH in CHCl$_3$), followed by hexane and ether wash, afforded 55 mg of the product (31.97% yield).

$^1$H NMR (DMSO-D$_6$, 300 MHz): δ 12.42 (s, 1H), 8.55 (s, 1H), 8.39 (d, 1H), 7.85-7.28 (m, 4H), 4.28-3.80 (m, 4H), 2.6-2.1 (m, 4H), 1.04-0.80 (m, 4H)

LCMS purity: 100.00%, m/z=333.8 (M+1)

HPLC: 94.27%

Example 199

Preparation of 1-(4-Methyl-pyridin-3-yl)-3-quinolin-7-yl-imidazolidin-2-one (199A)

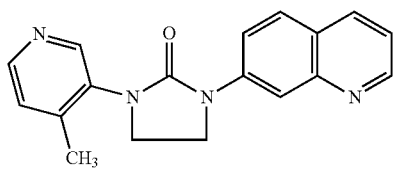

(199A)

1-(4-Methyl-pyridin-3-yl)-imidazolidin-2-one (I-14b: 116 mg, 0.6554 mmol) was reacted with 7-bromo-quinoline (150 mg, 0.72098 mmol), 1,4-dioxane (50 mL), copper iodide (12.4 mg, 0.06554 mmol), trans-1,2-diamino cyclohexane (22.5 mg, 0.19638 mmol) and potassium phosphate (347.3 g, 1.6365 mmol) to afford the crude product. Purification by column chromatography on silica gel (2% MeOH in CHCl$_3$) afforded 130 mg of the product (65.3% yield).

$^1$H NMR (DMSO-D$_6$, 300 MHz): δ 8.95-8.76 (m, 1H), 8.6 (s, 1H), 8.48-8.22 (m, 3H), 8.06-7.82 (m, 2H), 7.50-7.32 (m, 2H), 4.32-4.12 (m, 2H), 4.10-3.90 (m, 2H), 2.31 (s, 3H)

LCMS purity: 99.57%, m/z=305.0 (M+1)

HPLC: 93.16%

Example 200

Synthesis of 3-Benzothiazol-6-yl-4,4-dimethyl-1-(4-methyl-pyridin-3-yl)-imidazolidin-2-one (200A)

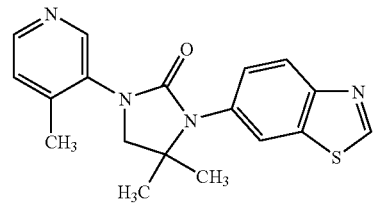

(200A)

Step 1: Synthesis of Intermediate 3-Chloro-2,2-dimethyl-propionyl chloride (I-200a)

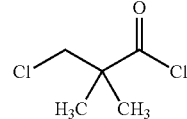

(I-200a)

SOCl$_2$ (5.22 g, 44.23 mmol) was added dropwise to a stirred solution of 3-chloro-2,2-dimethyl-propionic acid (5 g, 36.76 mmol) in DCM (50 mL) at 0° C. over a period of 5 mins. This was followed by the addition of DMF (0.1 mL) and the resulting mixture was heated to 60° C. for 3 hours. The reaction was monitored by TLC (5% MeOH in CHCl$_3$). The reaction mixture was concentrated and the crude product (6 g) was used in the next step without further purification.

Step 2: Synthesis of Intermediate 3-Chloro-2,2-dimethyl-propionyl azide (I-200b)

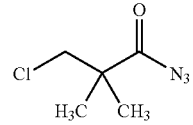

(I-200b)

Sodium azide (4.64 g, 71.38 mmol) was added to a solution of 3-chloro-2,2-dimethyl-propionyl chloride (I-200a: 6 g, 35.71 mmol) in 1,4-dioxane (15 mL) and water (15 mL). The resulting mixture was stirred at room temperature for 2 hours. The reaction was monitored by TLC (5% ethylacetate in hexane). The reaction mixture was extracted with diethyl ether and the organic layer was dried over Na$_2$SO$_4$ to afford 3.5 g of the product (61.40% yield).

Step 3: Synthesis of 1-Chloro-2-isocyanato-2-methyl-propane (I-200c)

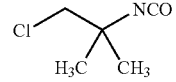

(I-200c)

1-Chloro-2-isocyanato-2-methyl-propane (I-200b: 3.5 g, 20 mmol) in toluene (35 mL) was taken a reaction flask and flask was heated to 85° C. for 1.30 hr. The reaction was monitored by TLC (5% ethylacetate in hexane). The crude product (3 μm) was used in the next step without further purification.

Step 4: Synthesis of 1-(2-Chloro-1,1-dimethyl-ethyl)-3-(4-methyl-pyridin-3-yl)-urea (I-200d)

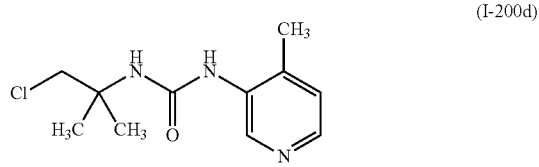

(I-200d)

4-Methyl-pyridin-3-ylamine (1.98 g, 18.33 mmol) was added to solution of 1-chloro-2-isocyanato-2-methyl-propane (I-200c: 3 g, 20.40 mmol) in toluene (30 mL). The resulting mixture was stirred at room temperature for 3 days. The reaction was monitored by TLC (5% MeOH in $CHCl_3$). The reaction mixture was filtered and the residue was dried to afford 4.3 g of the product (87.75% yield).
$^1$H NMR ($CDCl_3$, 300 MHz): δ 8.70 (s, 1H), 8.3 (s, 1H), 7.12 (s, 1H), 6.39 (s, 1H), 4.9 (s, 1H), 3.87 (s, 2H), 2.30 (s, 3H), 1.4 (s, 6H)
LCMS purity: 76.36%, m/z=242.0 (M+1)

Step 5: Synthesis of intermediate 4,4-Dimethyl-1-(4-methyl-pyridin-3-yl)-imidazolidin-2-one (I-200e)

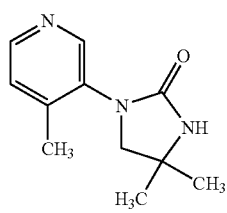

(I-200e)

1-(2-Chloro-1,1-dimethyl-ethyl)-3-(4-methyl-pyridin-3-yl)-urea (I-200d: 1 g, 4.149 mmol) in dry THF (5 mL) was added dropwise to a stirred mixture of NaH (298 mg, 6.208 mmol) in dry THF (10 mL) under argon atmosphere over a period of 10 minutes at 0° C. The resulting reaction mixture was stirred for 2 hrs. The reaction was monitored by TLC (5% MeOH in $CHCl_3$). The reaction mixture was partitioned between water and ethylacetate. The organic layer was dried over $Na_2SO_4$ and concentrated to afford 800 mg of the product (94.33% yield).
$^1$H NMR (DMSO, 300 MHz): δ 8.4 (s, 1H), 8.3 (d, 1H), 7.30 (d, 1H), 7.0 (s, 1H), 3.53 (s, 2H), 2.22 (s, 3H), 1.3 (s, 6H)
LCMS purity: 100%, m/z=205.7 (M+1)

Final Step: Synthesis of 3-Benzothiazol-6-yl-4,4-dimethyl-1-(4-methyl-pyridin-3-yl)-imidazolidin-2-one (200A)

4,4-Dimethyl-1-(4-methyl-pyridin-3-yl)-imidazolidin-2-one (I-163b: 150 mg, 0.731 mmol) was reacted with 6-iodo-benzothiazole (I-200e: 248 mg, 0.950 mmol), 1,4-dioxane (10 mL), copper iodide (13 mg, 0.0682 mmol), trans-1,2-diamino cyclohexane (31 mg, 0.218 mmol) and potassium phosphate (387 mg, 1.825 mmol) to afford the crude product. Purification by column chromatography on silica gel (1% MeOH in $CHCl_3$) afforded 30 mg of the product (12.14% yield).
$^1$H NMR ($CD_3OD$, 300 MHz): δ 9.32 (s, 1H), 8.51 (s, 1H), 8.35 (d, 1H), 8.0-8.2 (m, 2H), 7.60 (d, 1H), 7.40 (d, 1H), 3.90 (s, 2H), 2.45 (s, 3H), 1.5 (s, 6H)
LCMS purity: 94.09%, m/z=339.1 (M+1)
HPLC: 89.11%

Example 201

Preparation of 1-Benzothiazol-6-yl-4,4-dimethyl-3-pyridin-3-yl-imidazolidin-2-one (201A)

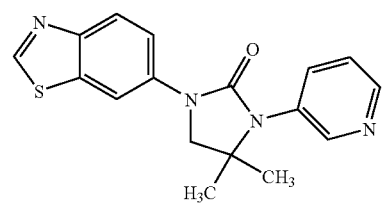

(201A)

Step 1: Synthesis of Intermediate 1-Benzothiazol-6-yl-3-(2-chloro-1,1-dimethyl-ethyl)-urea (I-201a)

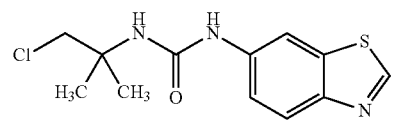

(I-201a)

Benzothiazol-6-ylamine (1.8 g, 12.00 mmol) was added portion wise to solution of 1-chloro-2-isocyanato-2-methyl-propane (2 g, 13.60 mmol) in toluene (20 mL) over a period of 5 minutes. The resulting mixture was stirred at room temperature for 2½ days. The reaction was monitored by TLC (5% MeOH in $CHCl_3$). The reaction mixture was concentrated and extracted with ethylacetate. The organic layer was dried over $Na_2SO_4$ and concentrated. Purification by column chromatography on silica gel (1% MeOH in $CHCl_3$) afforded 630 mg of the product (16.57% yield).
$^1$H NMR ($CDCl_3$, 300 MHz): δ 8.85 (s, 1H), 8.23 (d, 1H), 8.0 (d, 1H), 7.20-7.15 (dd, 1H), 7.03 (s, 1H), 5.10 (s, 1H), 3.89 (s, 2H), 1.49 (s, 6H)
LCMS purity: 98.84%, m/z=283.9 (M+1)

Step 2: Synthesis of intermediate 1-Benzothiazol-6-yl-4,4-dimethyl-imidazolidin-2-one (I-201 h)

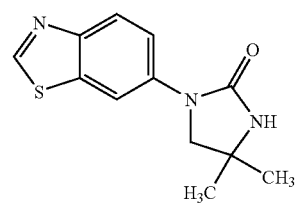

(I-201b)

1-Benzothiazol-6-yl-3-(2-chloro-1,1-dimethyl-ethyl)-urea (I-201a: 620 mg, 2.18 mmol) in dry THF (5 mL) was added dropwise to a stirred mixture of NaH (78 mg, 3.25 mmol) in dry THF (5 mL) under argon atmosphere over a period of 10 minutes at 0° C. The resulting reaction mixture was stirred at room temperature for 45 minutes. The reaction was monitored by TLC (5% MeOH in CHCl$_3$). The reaction mixture was partitioned between chilled water and ethylacetate. The organic layer was dried over Na$_2$SO$_4$ and concentrated to afford 410 mg of the product (77.35% yield).

$^1$H NMR (CDCl$_3$, 300 MHz): δ 8.90 (s, 1H), 8.31 (d, 1H), 8.09 (d, 1H), 7.69-7.58 (dd, 1H), 5.0 (br s, 1H), 3.73 (s, 2H), 1.49 (s, 6H)

LCMS purity: 99.16%, m/z=247.8 (M+1)

Final Step: Synthesis of 1-Benzothiazol-6-yl-4,4-dimethyl-3-pyridin-3-yl-imidazolidin-2-one (201A)

1-Benzothiazol-6-yl-4,4-dimethyl-imidazolidin-2-one (I-201b: 100 mg, 0.4048 mmol) was reacted with 3-bromopyridine (83 mg, 0.525 mmol), 1,4-dioxane (10 mL), copper iodide (7 mg, 0.036 mmol), trans-1,2-diamino cyclohexane (17 mg, 0.119 mmol) and potassium phosphate (214 mg, 1.009 mmol) to afford the crude product.

Purification by column chromatography on silica gel (1% MeOH in CHCl$_3$) afforded 15 mg of the product (11.45% yield).

$^1$H NMR (CDCl$_3$, 300 MHz): δ 8.90 (s, 1H), 8.7-8.5 (br s, 2H), 8.35 (d, 1H), 8.12 (d, 1H), 7.77-7.60 (m, 2H), 7.5-7.4 (m, 1H), 3.9 (s, 2H), 1.49 (s, 6H)

LCMS purity: 100%, m/z=325.1 (M+1)

HPLC: 95.40%

Example 202

Preparation of 1-Benzothiazol-6-yl-4,4-dimethyl-3-(4-methyl-pyridin-3-yl)-imidazolidin-2-one (202A)

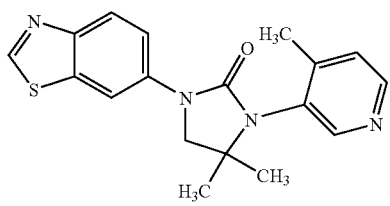

(202A)

1-Benzothiazol-6-yl-4,4-dimethyl-imidazolidin-2-one (I-201b: 100 mg, 0.4048 mmol) was reacted with 3-iodo-4-methyl-pyridine (115 mg, 0.525 mmol), 1,4-dioxane (10 mL), copper iodide (7 mg, 0.0368 mmol), trans-1,2-diamino cyclohexane (18 mg, 0.1197 mmol) and potassium phosphate (214 mg, 1.0094 mmol) to afford the crude product. Purification by column chromatography on silica gel (1% MeOH in CHCl$_3$) afforded 6 mg of the product (4.8% yield).

$^1$H NMR (CDCl$_3$, 300 MHz): δ 8.30 (d, 1H), 8.15 (d, 1H), 7.7-7.6 (dd, 1H), 3.8 (s, 2H), 2.72 (s, 3H), 1.49 (s, 6H)

LCMS purity: 94.22%, m/z=339.1 (M+1)

HPLC: 86.98%

Example 203

Synthesis of 3-Benzothiazol-6-yl-4-methyl-1-(4-methyl-pyridin-3-yl)-imidazolidin-2-one (203A)

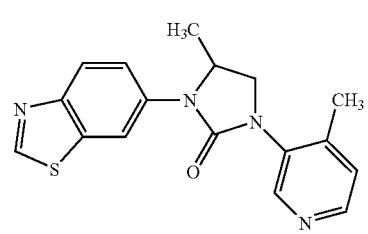

(203A)

Step 1: Synthesis of intermediate 3-(Benzothiazol-6-ylamino)-butyric Acid (I-203a)

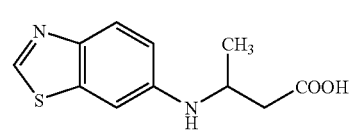

(I-203a)

3-Amino-butyric acid ethyl ester (2 g, 15.27 mmol), 6-iodo-benzothiazole (3.98 g, 15.27 mmol) and potassium carbonate (5.27 g, 38.18 mmol) were dissolved in DMF (50 mL) and the reaction mixture was purged with argon for 10 minutes. This was followed by the addition of copper iodide (290 mg, 1.527 mmol) and the resulting mixture was heated to 110° C. overnight. The reaction was monitored by TLC (10% MeOH in CHCl$_3$) which showed the presence of starting material. The reaction mixture was heated to 120° C. for a further 24 hours. The reaction mixture was concentrated and adjusted the pH to 5 using acetic acid. The reaction mixture was partitioned between water and ethylacetate. The organic layer was dried over Na$_2$SO$_4$ and concentrated. Purification by column chromatography on silica gel (1% MeOH in CHCl$_3$) afforded 800 mg of the product (22.22% yield).

$^1$H NMR (DMSO, 300 MHz): δ 12.2 (s, 1H), 8.9 (s, 1H), 7.75 (d, 1H), 7.15 (d, 1H), 6.85 (dd, 1H), 5.90-5.80 (m, 1H), 3.90-3.80 (m, 1H), 2.60-2.50 (m, 1H), 2.25-2.35 (m, 1H), 1.20 (d, 3H)

LCMS purity: 61.65%, m/z=237.0 (M+1)

Step 2: Synthesis of 1-Benzothiazol-6-yl-5-methyl-imidazolidin-2-one (I-203b)

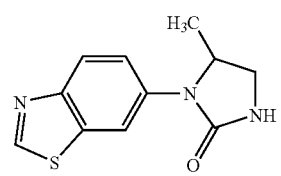

(I-203b)

Triethylamine (1.129 g, 11.18 mmol) was added to a mixture of 3-(benzothiazol-6-ylamino)-butyric acid (I-203a: 800 mg, 3.39 mmol) in toluene (30 mL) and the reaction mixture was purged with argon for 10 minutes. This was followed by the addition of DPPA (2.796 g, 10.17 mmol) and the resulting mixture was heated to 100° C. overnight.

The reaction was monitored by TLC (10% MeOH in CHCl$_3$) which showed the presence of starting material. The reaction mixture was heated to 120° C. for the next 24 hours. The reaction mixture was partitioned between water and ethylacetate. The organic layer was dried over Na$_2$SO$_4$ and concentrated. Purification by column chromatography on silica gel (2% MeOH in CHCl$_3$) afforded 600 mg of the product (75.95% yield).

$^1$H NMR (DMSO, 300 MHz): δ 9.25 (s, 1H), 8.22 (d, 1H), 8.0 (d, 1H), 7.7 (dd, 1H), 7.0 (s, 1H), 4.6-4.5 (m, 1H), 3.6 (t, 1H), 3.0 (m, 1H), 1.2 (d, 3H)

LCMS purity: 81.90%, m/z=234.0 (M+1)

Final Step: Synthesis of 3-Benzothiazol-6-yl-4-methyl-1-(4-methyl-pyridin-3-yl)-imidazolidin-2-one (203A)

1-Benzothiazol-6-yl-5-methyl-imidazolidin-2-one (I-203b: 150 mg, 0.644 mmol) was reacted with 3-iodo-4-methyl-pyridine (140.99 mg, 0.644 mmol), 1,4-dioxane (10 mL), copper iodide (12.27 mg, 0.0644 mmol), trans-1,2-diamino cyclohexane (27.43 mg, 0.193 mmol) and potassium phosphate (341 mg, 1.61 mmol) to afford the crude product. Purification by column chromatography on silica gel (1.5% MeOH in DCM) afforded 50 mg of the product (24.15% yield).

$^1$H NMR (CDCl$_3$, 300 MHz): δ 8.95 (s, 1H), 8.55 (s, 1H), 8.43 (d, 1H), 8.26 (d, 1H), 8.15 (d, 1H), 7.55 (dd, 1H), 7.25 (d, 1H), 4.7-4.6 (m, 1H), 4.2-4.1 (m, 1H), 3.6-3.5 (m, 1H), 2.4 (s, 3H), 1.5 (d, 3H)

LCMS purity: 95.66%, m/z=325.0 (M+1)
HPLC: 96.32%

Pharmacological Testing

The abbreviations listed below and used in the preparations below have the corresponding meanings.

| | |
|---|---|
| CYP | Cytochrome P450 |
| CPM | Counts per minute |
| Cyt b5 | Cytochrome b5 |
| DMSO | Dimethyl sulfoxide |
| DHEA | Dehydroepiandrosterone |
| NADPH | Nicotinamide adenine dinucleotide phosphate |

Human and Rat-Cytochrome P450, 17-20 Lyase

1) Cytochrome P450, 17-20 lyase (CYP17-lyase) assay development using recombinant human CYP17 enzyme and 17-α-hydroxy pregnenolone [21-3H] as the substrate.

Cytochrome P450,17-α-Hydroxylase, 17-20 lyase (CYP17) is a multi functional enzyme that plays a key role in the biosynthesis of steroid hormones. It catalyses both conventional hydroxylation and also the carbon-carbon bond cleavage reactions (Peter Lee-Robichaud et al, Biochem. J, (1997) 321, 857-63). In the hydroxylation reaction, it converts progesterone and pregnenolone to the corresponding hydroxylated products 17-α-hydroxy progesterone and 17-α-hydroxy pregnenolone. In the lyase reaction, it catalyzes the conversion of these hydroxylated substrates to Androstenedione and Dehydroepiandrosterone (DHEA) respectively. In the Cyp17 lyase assay described here, the conversion of 17-α-hydroxy pregnenolone to Dehydroepiandrosterone and acetic acid is being monitored.

The hydroxylation and cleavage activities are catalyzed sequentially at the common active site of Cyp17 and proceed through transfer of two electrons from NADPH via its redox partner, cytochrome P450 reductase (CPR). The reaction mechanism for each activity is thought to involve formation of distinct iron-oxygen complexes. Cytochromeb5 selectively stimulates the lyase activity and has no significant effect on its hydroxylase activity. Lyase activity is stimulated by cytochrome b5 up to 10-fold in reconstituted assays with insignificant stimulation of the hydroxylase activity (M K Akthar et al, *Journal of Endocrinology* (2005) 187, 267-274 and Katagiri M et al, *Biophysical Research Communications* (1982) 108, 379-384).

Assay method was adopted from a published protocol with some modifications to suit our requirements (Dmitry N Grigoryev et al, *Analytical Biochemistry*, (1999) 267, 319-330). The conversion of 17-α-hydroxy pregnenolone to Dehydroepiandrosterone is accompanied by the release of acetic acid. In the Cyp17 lyase assay, 17-α-hydroxy pregnenolone labeled with tritium (3H) at position 21 is used as the substrate. Chloroform extraction removes the radioactive steroids and acetic acid is taken into aqueous layer. The tritiated acetic acid released in the assay thus extracted is quantified to determine the enzyme activity.

Initial buffer conditions were, 50 mM Phosphate buffer, pH 7.5 was used as the starting buffer for Cyp17 lyase activity based on the data published in U.S. patent publication No. US2004/0198773 A1. This buffer was found to be suitable for regular Cyp17 lyase assay. Human Cyp 17 gene was cloned and expressed in Adenoviral expression system in A549 cell lines. The purified cell membrane preparations were used as the source for Human CYP17 enzyme. Total protein concentration: 8 mg/mL. To identify the appropriate concentration of the enzyme required for the assay, concentration dependent enzyme activity was determined at a substrate (17-α-hydroxypregnenolone [21-3H]) concentration of 0.5 µM (Vincent C. O, Nijar, et al., *J Med Chem*, (1998) 41, 902-912). The protein activity was found to be in the linear range up to 20 µg, the highest concentration tested. Based on the enzyme concentration curve and stock concentration, 15 µg was selected for the assay. At this protein concentration, the S/N ratio was 30, with a good signal window (CPM$_{Pos.Ctrl}$-CPM$_{Blank}$=1650)

K$_m$ (Michaelis Menton constant) is a measure of the binding affinity of substrate to the enzyme. 17-α-hydroxy pregnenolone [21-3H] is a substrate for 17, 20 lyase enzyme. K$_m$ for this substrate was determined by monitoring the tritiated acetic acid release as a function of substrate concentration. Concentration of 17-α-hydroxy-pregnenolone [21-3H] was varied from 0.03125 µM to 1 µM. For the K$_m$ determination, the data was fit to a hyperbolic equation (Graphpad Prism® software IV). The K$_m$ was estimated as 0.25 µM, close to the reported value. (Dmitry N. Grigoryev et al, *Analytical Biochemistry* (1999) 267, 319-330)

For routine screening, the assay was set up with 16 µg of enzyme in 50 µL reaction volume. 17α-hydroxy pregnenolone [21-3H] was added to a final concentration of 0.25 µM. NADPH is used at a final concentration of 4.2 mM. Total reaction volume was made up to 50 µL with 50 mM Phosphate buffer pH 7.5. The reaction mixture was incubated at room temperature for 90 minutes with gentle shaking. The reaction was stopped by the addition of 100 µL of buffer. 500 µL of 5% freshly prepared activated charcoal was added to the solution and mixed well by vortexing. The samples were centrifuged at 17568×g for 5 minutes. (14000 rpm). The supernatant was carefully transferred to fresh tube and 1.3 mL of scintillation fluid was added, mixed by vortexing.

The radioactivity was measured in a 1450 MicroBeta Tri-Lux™ scintillation counter from Wallac-Perkin Elmer®, USA. The measurements were carried out in 2.0 mL Eppendorforf™ tubes. Each tube was counted for 1 minute. The amount of tritiated acetic acid released is proportional to the lyase activity. Percent lyase activity in presence of inhibitor was calculated using the formula given below.

$$\% \text{ Lyase activity} = \frac{CPM_{sample} - CPM_{blank}}{CPM_{Pos.\ Ctrl} - CPM_{Blank}} \times 100$$

Sample: Enzyme reaction in presence of inhibitor.
Positive control: Enzyme reaction without inhibitor but containing DMSO at 1% final concentration.
Blank-Contains all reagents except enzyme.

% Inhibition=100%-% Lyase activity

For IC$_{50}$ determination, the % inhibition was plotted as a function of inhibitor concentration. The data was fitted to sigmoidal equation using Graphpad Prism® software IV to generate IC$_{50}$ values.

Dose-response studies by standard compounds Abiraterone and Ketoconazole were carried out as part of assay optimization.

For the rat CYP 17 Lyase Model:

The same procedure described above was used but using rat testes microsomes as the source and with a substrate concentration of 0.5 μM.

The results for the compounds tested from the Examples above using the assay above are listed in Table 1 below.

TABLE 1

| Example No. | Final compounds | Lyase IC 50 nM Human/Rat | rCYP17 Lyase % Inh @ 100 nM |
|---|---|---|---|
| 1A | 1-Naphthalen-2-yl-3-pyridin-3-yl-imidazolidin-2-one | 34 nM/35 nM | 84% |
| 2A | 1-(1-Ethyl-1H-indol-5-yl)-3-pyridin-3-yl-imidazolidin-2-one | —/— | 23% |
| 3A | 1-(6-Methoxy-naphthalen-2-yl)-3-pyridin-3-yl-imidazolidin-2-one | —/— | 31% |
| 4A | 1-Benzothiazol-6-yl-3-pyridin-3-yl-imidazolidin-2-one | 77 nM/— | 59% |
| 5A | 1-Ethyl-6-(2-oxo-3-pyridin-3-yl-imidazolidin-1-yl)-3,4-dihydro-1H-quinolin-2-one | —/— | 51% |
| 6A | 1-(5-Fluoro-3-methyl-benzo[b]thiophen-2-yl)-3-pyridin-3-yl-imidazolidin-2-one | —/157 nM | 51% |
| 7A | 1-Benzo[b]thiophen-5-yl-3-pyridin-3-yl-imidazolidin-2-one | —/16 nM | 87% |
| 8A | 1-Pyridin-3-yl-3-quinolin-6-yl-imidazolidin-2-one | —/— | 48% |
| 9A | 1-Benzothiazol-5-yl-3-pyridin-3-yl-imidazolidin-2-one | —/— | 18% |
| 10A | 1-Naphthalen-2-yl-3-pyridin-3-yl-tetrahydro-pyrimidin-2-one | —/— | 11% |
| 11A | 1-(2-Chloro-4-methyl-quinolin-6-yl)-3-pyridin-3-yl-imidazolidin-2-one | —/97 nM | 59% |
| 12A | 1-(1-Hydroxyimino-indan-5-yl)-3-pyridin-3-yl-imidazolidin-2-one | —/— | 17% |
| 13A | 1-Benzo[b]thiophen-5-yl-3-pyridin-3-yl-tetrahydro-pyrimidin-2-one | —/— | 9% |
| 14A | 1-(4-Methyl-pyridin-3-yl)-3-naphthalen-2-yl-imidazolidin-2-one | 17 nM/2 nM | 102% |
| 15A | 1-(4-Methyl-pyridin-3-yl)-3-(5-methyl-thiophen-2-yl)-imidazolidin-2-one | 10 nM/— | — |
| 16A | 1-Benzothiazol-6-yl-3-(4-methyl-pyridin-3-yl)-imidazolidin-2-one | 6 nM/5 nM | 94% |

TABLE 1-continued

| Example No. | Final compounds | Lyase IC 50 nM Human/Rat | rCYP17 Lyase % Inh @ 100 nM |
|---|---|---|---|
| 17A | 1-Ethyl-6-[3-(4-methyl-pyridin-3-yl)-2-oxo-imidazolidin-1-yl]-3,4-dihydro-1H-quinolin-2-one | —/21 nM | 83% |
| 18A | 1-(4-Fluoro-phenyl)-3-(4-methyl-pyridin-3-yl)-imidazolidin-2-one | 76 nM/12 nM | 88% |
| 19A | 1-Biphenyl-4-yl-3-(4-methyl-pyridin-3-yl)-imidazolidin-2-one | —/11 nM | 91% |
| 20A | 1-Ethyl-4-methyl-6-[3-(4-methyl-pyridin-3-yl)-2-oxo-imidazolidin-1-yl]-1H-quinolin-2-one | —/56 nM | 69% |
| 21A | 1-(2-Chloro-4-methyl-quinolin-6-yl)-3-(4-methyl-pyridin-3-yl)-imidazolidin-2-one | —/5 nM | 98% |
| 22A | 4-Methyl-6-[3-(4-methyl-pyridin-3-yl)-2-oxo-imidazolidin-1-yl]-1H-quinolin-2-one | —/24 nM | 85% |
| 23A | 1-(4-Methyl-pyridin-3-yl)-3-quinolin-2-yl-imidazolidin-2-one | —/20 nM | 85% |
| 24A | 1-(4-Methyl-pyridin-3-yl)-3-quinolin-3-yl-imidazolidin-2-one | 72 nM/— | 98% |
| 25A | 1-(6-Methoxy-naphthalen-2-yl)-3-(4-methyl-pyridin-3-yl)-imidazolidin-2-one | —/— | 89% |
| 26A | 1-Benzo[b]thiophen-2-yl-3-(4-methyl-pyridin-3-yl)-imidazolidin-2-one | 15 nM/— | 100% |
| 27A | 1-Benzo[b]thiophen-5-yl-3-(4-methyl-pyridin-3-yl)-imidazolidin-2-one | 24 nM/— | 101% |
| 28A | 1-(1H-Indazol-5-yl)-3-(4-methyl-pyridin-3-yl)-imidazolidin-2-one | 4 nM/52 nM | 61% |
| 29A | 1-(3-Methyl-benzofuran-5-yl)-3-(4-methyl-pyridin-3-yl)-imidazolidin-2-one | 3 nM/— | 98% |
| 30A | 1-(6-Fluoro-pyridin-3-yl)-3-(4-methyl-pyridin-3-yl)-imidazolidin-2-one | —/— | 76% |
| 31A | 1-(4-Methyl-pyridin-3-yl)-3-thiophen-3-yl-imidazolidin-2-one | 108 nM/— | 74% |
| 32A | 1-(5-Methoxy-pyridin-3-yl)-3-(4-methyl-pyridin-3-yl)-imidazolidin-2-one | —/— | 73% |
| 33A | 1-(5-Fluoro-3-methyl-benzo[b]thiophen-2-yl)-3-(4-methyl-pyridin-3-yl)-imidazolidin-2-one | —/— | — |
| 34A | 1-(2-Chloro-pyrimidin-5-yl)-3-(4-methyl-pyridin-3-yl)-imidazolidin-2-one | —/— | — |
| 35A | 1-(4-Methyl-pyridin-3-yl)-3-(1H-pyrazol-4-yl)-imidazolidin-2-one | —/— | — |
| 36A | 1-(4-Methyl-pyridin-3-yl)-3-thiazol-2-yl-imidazolidin-2-one | —/— | — |
| 37A | 1-(4-Methoxy-phenyl)-3-(4-methyl-pyridin-3-yl)-imidazolidin-2-one | —/— | — |
| 38A | 1-(4-Chloro-phenyl)-3-(4-methyl-pyridin-3-yl)-imidazolidin-2-one | 70 nM/— | — |
| 39A | 4-[3-(4-Methyl-pyridin-3-yl)-2-oxo-imidazolidin-1-yl]-benzonitrile | —/— | — |
| 40A | 1-Benzooxazol-2-yl-3-(4-methyl-pyridin-3-yl)-imidazolidin-2-one | —/— | — |
| 41A | 1-(5-Chloro-thiophen-2-yl)-3-(4-methyl-pyridin-3-yl)-imidazolidin-2-one | 10 nM/3 nM | — |

TABLE 1-continued

| Example No. | Final compounds | Lyase IC 50 nM Human/Rat | rCYP17 Lyase % Inh @ 100 nM |
|---|---|---|---|
| 42A | 1-(4-Methyl-pyridin-3-yl)-3-thiophen-2-yl-imidazolidin-2-one | —/— | — |
| 43A | 1-(6-Hydroxy-pyridin-3-yl)-3-(4-methyl-pyridin-3-yl)-imidazolidin-2-one | —/— | — |
| 44A | N-Methyl-4-[3-(4-methyl-pyridin-3-yl)-2-oxo-imidazolidin-1-yl]-benzamide | —/— | — |
| 45A | 1-(3,4-Difluoro-phenyl)-3-(4-methyl-pyridin-3-yl)-imidazolidin-2-one | 27 nM/— | — |
| 46A | 1-(3-Chloro-4-fluoro-phenyl)-3-(4-methyl-pyridin-3-yl)-imidazolidin-2-one | 10 nM/— | — |
| 47A | 1-Benzothiazol-2-yl-3-(4-methyl-pyridin-3-yl)-imidazolidin-2-one | —/— | — |
| 48A | 1-(1H-Indol-5-yl)-3-(4-methyl-pyridin-3-yl)-imidazolidin-2-one | —/— | — |
| 49A | 1-(2,3-Dihydro-benzo[1,4]dioxin-6-yl)-3-(4-methyl-pyridin-3-yl)-imidazolidin-2-one | 30 nM/— | — |
| 50A | 1-(4-Methyl-pyridin-3-yl)-3-(4-trifluoromethyl-phenyl)-imidazolidin-2-one | 51 nM/— | — |
| 51A | 1-(2,3-Dihydro-benzofuran-5-yl)-3-(4-methyl-pyridin-3-yl)-imidazolidin-2-one | 14 nM/— | — |
| 52A | 1-(4-Methyl-pyridin-3-yl)-3-quinolin-6-yl-imidazolidin-2-one | 96 nM/5 nM | 97% |
| 53A | 1-(3-Fluoro-4-methoxy-phenyl)-3-(4-methyl-pyridin-3-yl)-imidazolidin-2-one | 136 nM/— | — |
| 54A | 1-(4-Chloro-3-fluoro-phenyl)-3-(4-methyl-pyridin-3-yl)-imidazolidin-2-one | 15 nM/— | — |
| 55A | 1-(4-Methyl-pyridin-3-yl)-3-m-tolyl-imidazolidin-2-one | 9 nM/7 nM | — |
| 56A | 1-(3-Methoxy-phenyl)-3-(4-methyl-pyridin-3-yl)-imidazolidin-2-one | 25 nM/— | — |
| 57A | 1-(4-Methyl-pyridin-3-yl)-3-(4,5,6,7-tetrahydro-thieno[2,3-c]pyridin-2-yl)-imidazolidin-2-one | —/— | — |
| 58A | 1-(2-Chloro-pyridin-4-yl)-3-(4-methyl-pyridin-3-yl)-imidazolidin-2-one | 27 nM/— | — |
| 59A | 1-(4-Fluoro-3-methyl-phenyl)-3-(4-methyl-pyridin-3-yl)-imidazolidin-2-one | 17 nM/— | — |
| 60A | 1-(5-Chloro-2-fluoro-phenyl)-3-(4-methyl-pyridin-3-yl)-imidazolidin-2-one | —/— | — |
| 61A | 1-(2,4-Difluoro-phenyl)-3-(4-methyl-pyridin-3-yl)-imidazolidin-2-one | —/— | — |
| 62A | 1-Benzothiazol-5-yl-3-(4-methyl-pyridin-3-yl)-imidazolidin-2-one | 426 nM/— | — |
| 63A | 6-[3-(4-Methyl-pyridin-3-yl)-2-oxo-imidazolidin-1-yl]-3,4-dihydro-1H-quinolin-2-one | —/— | — |
| 64A | 1-(2,2-Difluoro-benzo[1,3]dioxol-5-yl)-3-(4-methyl-pyridin-3-yl)-imidazolidin-2-one | 35 nM/— | — |
| 65A | 7-[3-(4-Methyl-pyridin-3-yl)-2-oxo-imidazolidin-1-yl]-3,4-dihydro-1H-quinolin-2-one | —/— | — |
| 66A | N-{3-[3-(4-Methyl-pyridin-3-yl)-2-oxo-imidazolidin-1-yl]-phenyl}-acetamide | —/— | — |
| 67A | 1-(4-Methyl-pyridin-3-yl)-3-(3-methyl-thiophen-2-yl)-imidazolidin-2-one | —/— | — |
| 68A | 1-(4-Methyl-pyridin-3-yl)-3-(2-methyl-quinolin-6-yl)-imidazolidin-2-one | —/— | — |
| 69A | 1-(4-Methyl-pyridin-3-yl)-3-phenyl-imidazolidin-2-one | 34 nM/— | — |
| 70A | 1-(4-Methyl-pyridin-3-yl)-3-(3-trifluoromethyl-phenyl)-imidazolidin-2-one | 6.5 nM/2 nM | — |
| 71A | 1-(1-Isopropyl-1H-pyrazol-4-yl)-3-(4-methyl-pyridin-3-yl)-imidazolidin-2-one | —/— | — |
| 72A | 1-(2-Methoxy-pyridin-4-yl)-3-(4-methyl-pyridin-3-yl)-imidazolidin-2-one | 9.4 nM/10 nM | — |
| 73A | 1-Imidazo[1,2-a]pyridin-7-yl-3-(4-methyl-pyridin-3-yl)-imidazolidin-2-one | 109 nM/— | — |
| 74A | 1-(4-Fluoro-3-methoxy-phenyl)-3-(4-methyl-pyridin-3-yl)-imidazolidin-2-one | 76 nM/— | — |
| 75A | N-{5-[3-(4-Methyl-pyridin-3-yl)-2-oxo-imidazolidin-1-yl]-pyridin-2-yl}-acetamide | >10 μM | — |
| 76A | 1-(2-Amino-pyridin-4-yl)-3-(4-methyl-pyridin-3-yl)-imidazolidin-2-one | 192 nM/— | — |
| 77A | 1-(4-Methyl-pyridin-3-yl)-3-quinoxalin-6-yl-imidazolidin-2-one | 195 nM/— | — |
| 78A | 1-(5-Difluoromethyl-thiophen-3-yl)-3-(4-methyl-pyridin-3-yl)-imidazolidin-2-one, trifluoro-acetic acid | 9.3 nM/— | — |
| 79A | 1-Naphthalen-2-yl-3-(5-trifluoromethyl-pyridin-3-yl)-imidazolidin-2-one | —/— | 3.6% |
| 80A | 1-(5-Chloro-pyridin-3-yl)-3-naphthalen-2-yl-imidazolidin-2-one | —/— | 57% |
| 81A | 1-(5-Fluoro-pyridin-3-yl)-3-naphthalen-2-yl-imidazolidin-2-one | —/— | 82% |
| 82A | 1-(5-Methoxy-pyridin-3-yl)-3-naphthalen-2-yl-imidazolidin-2-one | —/— | — |
| 83A | 5-(3-Naphthalen-2-yl-2-oxo-imidazolidin-1-yl)-nicotinic acid methyl ester | —/— | — |
| 84A | 1-Benzothiazol-6-yl-3-(4-chloro-pyridin-3-yl)-imidazolidin-2-one | 85 nM/— | — |
| 85A | 1-(4-Methyl-pyridin-3-yl)-3-(2-pyrrolidin-1-yl-pyridin-4-yl)-imidazolidin-2-one | 1,263 nM/— | — |
| 86A | 1-(3-Chloro-2-fluoro-phenyl)-3-(4-methyl-pyridin-3-yl)-imidazolidin-2-one | 1,200 nM/— | — |
| 87A | 1-(4'-Fluoro-biphenyl-4-yl)-3-(4-methyl-pyridin-3-yl)-imidazolidin-2-one | 255 nM/— | — |
| 88A | 1-(3-Chloro-phenyl)-3-(4-methyl-pyridin-3-yl)-imidazolidin-2-one | 12 nM/— | — |
| 89A | 1-(4-Chloro-2-methyl-phenyl)-3-(4-methyl-pyridin-3-yl)-imidazolidin-2-one | 326 nM/— | — |
| 90A | 1-(4-Fluoro-3-trifluoromethyl-phenyl)-3-(4-methyl-pyridin-3-yl)-imidazolidin-2-one | 5 nM/— | — |
| 91A | 1-(3-Difluoromethyl-4-fluoro-phenyl)-3-(4-methyl-pyridin-3-yl)-imidazolidin-2-one | 4.3 nM/— | — |

TABLE 1-continued

| Example No. | Final compounds | Lyase IC 50 nM Human/Rat | rCYP17 Lyase % Inh @ 100 nM |
|---|---|---|---|
| 91B | 1-(3-Difluoromethyl-4-fluoro-phenyl)-3-(4-methyl-pyridin-3-yl)-1,3-dihydro-imidazol-2-one | 22 nM/— | — |
| 92A | 1-(4-Methyl-pyridin-3-yl)-3-(5-methyl-thiophen-3-yl)-1,3-dihydro-imidazol-2-one | 21 nM/— | — |
| 92B | 1-(4-Methyl-pyridin-3-yl)-3-(5-methyl-thiophen-3-yl)-imidazolidin-2-one | 12 nM/— | — |
| 93A | 1-(2-Methyl-benzooxazol-5-yl)-3-(4-methyl-pyridin-3-yl)-imidazolidin-2-one | >10 μM/— | — |
| 94A | 1-Imidazo[1,2-a]pyridin-6-yl-3-(4-methyl-pyridin-3-yl)-imidazolidin-2-one | 110 nM/— | — |
| 95A | 1-(3-Methyl-1H-indazol-5-yl)-3-(4-methyl-pyridin-3-yl)-imidazolidin-2-one | 119 nM/— | — |
| 96A | N-{4-[3-(4-Methyl-pyridin-3-yl)-2-oxo-imidazolidin-1-yl]-pyridin-2-yl}-acetamide | >10 μM/— | — |
| 97A | 1-(4-Methoxy-thieno[3,2-c]pyridin-2-yl)-3-(4-methyl-pyridin-3-yl)-imidazolidin-2-one | 356 nM/— | — |
| 98A | 1-(4-Chloro-thieno[3,2-c]pyridin-2-yl)-3-(4-methyl-pyridin-3-yl)-imidazolidin-2-one | 18 nM/— | — |
| 99A | 1-(4-Chloro-thieno[3,2-c]pyridin-3-yl)-3-(4-methyl-pyridin-3-yl)-imidazolidin-2-one | 22 nM/— | — |
| 100A | 1-(4-Methyl-pyridin-3-yl)-3-(2-methyl-pyridin-4-yl)-imidazolidin-2-one | 46 nM/— | — |
| 101A | 1-(3-Methyl-benzo[d]isoxazol-5-yl)-3-(4-methyl-pyridin-3-yl)-imidazolidin-2-one | 46 nM/— | — |
| 102A | 1-(3-Methyl-1H-indazol-6-yl)-3-(4-methyl-pyridin-3-yl)-imidazolidin-2-one, trifluoroacetic acid | 7.5 nM/5 nM | — |
| 103A | 2-Fluoro-5-[3-(4-methyl-pyridin-3-yl)-2-oxo-imidazolidin-1-yl]-benzonitrile | 19 nM/— | — |
| 104A | 1-(2-Methyl-imidazo[1,2-a]pyridin-6-yl)-3-(4-methyl-pyridin-3-yl)-imidazolidin-2-one | 1,991 nM/— | — |
| 105A | 1-(2-Methyl-benzothiazol-6-yl)-3-(4-methyl-pyridin-3-yl)-imidazolidin-2-one | 1,469 nM/— | — |
| 106A | 3-[3-(4-Methyl-pyridin-3-yl)-2-oxo-imidazolidin-1-yl]-benzonitrile, trifluoroacetic acid | 35 nM/— | — |
| 107A | 1-(1H-Indol-3-yl)-3-(4-methyl-pyridin-3-yl)-imidazolidin-2-one | 334 nM/— | — |
| 108A | 1-(1H-Benzoimidazol-5-yl)-3-(4-methyl-pyridin-3-yl)-imidazolidin-2-one | 363 nM/— | — |
| 109A | 1-Benzo[b]thiophen-3-yl-3-(4-methyl-pyridin-3-yl)-imidazolidin-2-one | 158 nM/— | — |
| 110A | 1-(4-Methoxy-thieno[3,2-c]pyridin-3-yl)-3-(4-methyl-pyridin-3-yl)-imidazolidin-2-one | >10 μM/— | — |
| 111A | 1-(3-Methyl-benzo[d]isoxazol-6-yl)-3-(4-methyl-pyridin-3-yl)-imidazolidin-2-one | 106 nM/— | — |
| 112A | 2-Chloro-4-[3-(4-methyl-pyridin-3-yl)-2-oxo-imidazolidin-1-yl]-benzonitrile | 28 nM/— | — |
| 113A | 1-Benzo[d]isoxazol-5-yl-3-(4-methyl-pyridin-3-yl)-imidazolidin-2-one | 230 nM/— | — |
| 114A | 1-(1-Methyl-1H-indazol-5-yl)-3-(4-methyl-pyridin-3-yl)-imidazolidin-2-one | 24 nM/— | — |
| 115A | 1-(1-Methyl-1H-indol-3-yl)-3-(4-methyl-pyridin-3-yl)-imidazolidin-2-one, trifluoroacetic acid | 173 nM/— | — |
| 116A | 1-(1-Methyl-1H-benzoimidazol-5-yl)-3-(4-methyl-pyridin-3-yl)-imidazolidin-2-one, trifluoroacetic acid | >10 μM/— | — |
| 117A | 5-[3-(4-Methyl-pyridin-3-yl)-2-oxo-imidazolidin-1-yl]-1,2-dihydro-indazol-3-one | 94 nM/— | — |
| 118A | 1-(3-Amino-1H-indazol-5-yl)-3-(4-methyl-pyridin-3-yl)-imidazolidin-2-one | 17 nM/— | — |
| 119A | 1-Imidazo[1,2-a]pyridin-3-yl-3-(4-methyl-pyridin-3-yl)-imidazolidin-2-one | 3,198 nM/— | — |
| 120A | 1-(4-Methyl-pyridin-3-yl)-3-thieno[3,2-c]pyridin-2-yl-imidazolidin-2-one | 4 μM/— | — |
| 121A | 1-(1H-Indazol-6-yl)-3-(4-methyl-pyridin-3-yl)-imidazolidin-2-one | 2.5 nM/— | — |
| 122A | 1-(3H-Imidazo[4,5-b]pyridin-6-yl)-3-(4-methyl-pyridin-3-yl)-imidazolidin-2-one, trifluoroacetic acid | 383 nM/— | — |
| 123A | 1-(3-Amino-1H-indazol-6-yl)-3-(4-methyl-pyridin-3-yl)-imidazolidin-2-one | 10 nM/— | — |
| 124A | 1-Benzothiazol-6-yl-3-(4-methoxy-pyridin-3-yl)-imidazolidin-2-one | 23 nM/12 nM | — |
| 125A | 1-Benzothiazol-6-yl-3-(4-difluoromethyl-pyridin-3-yl)-imidazolidin-2-one | 17 nM/— | — |
| 126A | 1-Benzothiazol-6-yl-3-(4-hydroxymethyl-pyridin-3-yl)-imidazolidin-2-one | 25 nM/— | — |
| 127A | 1-Benzothiazol-6-yl-3-(6-methyl-pyridin-3-yl)-imidazolidin-2-one | >10 μM/— | — |
| 128A | 1-Benzothiazol-6-yl-3-(4-trifluoromethyl-pyridin-3-yl)-imidazolidin-2-one | 44 nM/— | — |
| 129A | 3-(3-Benzothiazol-6-yl-2-oxo-imidazolidin-1-yl)-isonicotinonitrile | 202 nM/— | — |
| 130A | 1-(4-Methyl-pyridin-3-yl)-3-naphthalen-2-yl-imidazolidin-2-one | >10 μM/— | — |
| 131A | 1-m-Tolyl-3-(4-trifluoromethyl-pyridin-3-yl)-imidazolidin-2-one | 103 nM/— | — |
| 132A | 1-(2-Methyl-2H-indazol-5-yl)-3-(4-methyl-pyridin-3-yl)-imidazolidin-2-one | >10 μM | — |
| 133A | 1-(4-Methyl-pyridin-3-yl)-3-naphthalen-1-yl-imidazolidin-2-one | 1,970 nM/— | — |
| 134A | 1-(1-Methyl-1H-indol-5-yl)-3-(4-methyl-pyridin-3-yl)-imidazolidin-2-one | 950 nM/— | — |
| 135A | 6-[3-(4-Methyl-pyridin-3-yl)-2-oxo-imidazolidin-1-yl]-1,2-dihydro-indazol-3-one | 15.9 nM/— | — |
| 136A | 1-(4-Methyl-pyridin-3-yl)-3-thieno[3,2-c]pyridin-3-yl-imidazolidin-2-one | 500 nM/— | — |
| 137A | 1-(5-Chloro-1-methyl-1H-indol-3-yl)-3-(4-methyl-pyridin-3-yl)-imidazolidin-2-one | 1,554 nM/— | — |
| 138A | 1-Indan-5-yl-3-(4-methyl-pyridin-3-yl)-imidazolidin-2-one | 13 nM/— | — |

TABLE 1-continued

| Example No. | Final compounds | Lyase IC 50 nM Human/Rat | rCYP17 Lyase % Inh @ 100 nM |
|---|---|---|---|
| 139A | 1-Benzo[b]thiophen-5-yl-3-(4-methyl-pyridin-3-yl)-1,3-dihydro-imidazol-2-one | 83 nM/— | — |
| 140A | 2-Fluoro-4-[3-(4-methyl-pyridin-3-yl)-2-oxo-imidazolidin-1-yl]-benzonitrile | 97 nM/— | — |
| 141A | 1-(1H-Benzotriazol-5-yl)-3-(4-methyl-pyridin-3-yl)-imidazolidin-2-one, hydrochloride | 13 nM/— | — |
| 142A | 1-Benzothiazol-6-yl-3-(4-methyl-pyridin-3-yl)-1,3-dihydro-imidazol-2-one | 21 nM/— | — |
| 143A | 1-(3-Amino-1-methyl-1H-indazol-6-yl)-3-(4-methyl-pyridin-3-yl)-imidazolidin-2-one | 116 nM/— | — |
| 144A | 1-(1H-Indol-6-yl)-3-(4-methyl-pyridin-3-yl)-imidazolidin-2-one | 174 nM/— | — |
| 145A | 1-(3-Chloro-imidazo[1,2-a]pyridin-7-yl)-3-(4-methyl-pyridin-3-yl)-imidazolidin-2-one | 31 nM/— | — |
| 146A | 1-Methyl-3-[3-(4-methyl-pyridin-3-yl)-2-oxo-imidazolidin-1-yl]-1H-indole-4-carbonitrile | >10 µM | — |
| 147A | 1-Hydroxymethyl-3,3-dimethyl-5-[3-(4-methyl-pyridin-3-yl)-2-oxo-imidazolidin-1-yl]-1,3-dihydro-indol-2-one | 346 nM/— | — |
| 148A | 1-(4-Methyl-pyridin-3-yl)-3-(2-trifluoromethyl-pyridin-4-yl)-imidazolidin-2-one | 25 nM/— | — |
| 149A | 1-Benzothiazol-6-yl-3-(4-dimethoxymethyl-pyridin-3-yl)-imidazolidin-2-one | 37 nM/— | — |
| 150A | N-[3-(3-Benzothiazol-6-yl-2-oxo-imidazolidin-1-yl)-pyridin-4-yl]-acetamide | 496 nM/— | — |
| 151A | 1-Benzothiazol-6-yl-3-(5-chloro-4-methyl-pyridin-3-yl)-imidazolidin-2-one | 13.3 nM/— | — |
| 152A | 1-(4-Amino-pyridin-3-yl)-3-benzothiazol-6-yl-imidazolidin-2-one hydrochloride | 7 nM/— | — |
| 153A | 1-(benzo[d]thiazol-6-yl)-3-(4-methyl-5-(trifluoromethyl)pyridin-3-yl)imidazolidin-2-one, trifluoroacetic acid salt | 280 nM | — |
| 154A | 1-(isothiazol-4-yl)-3-(4-methylpyridin-3-yl)imidazolidin-2-one | 89 nM | — |
| 155A | 1-(4-methylpyridin-3-yl)-3-(5-(trifluoromethyl)thiophen-2-yl)imidazolidin-2-one | 2.7 nM | — |
| 156A | 1-(benzo[d]thiazol-6-yl)-3-(4-(2-hydroxypropan-2-yl)pyridin-3-yl)imidazolidin-2-one | >10 µM | — |
| 157A | 1-(4-methylpyridin-3-yl)-3-(4-methylthieno[3,2-c]pyridin-2-yl)imidazolidin-2-one | 21 nM | — |
| 158A | 1-(benzo[d]thiazol-6-yl)-3-(4-(1-hydroxyethyl)pyridin-3-yl)imidazolidin-2-one | 38 nM | — |
| 159A | 1-(benzo[d]thiazol-6-yl)-3-(4-ethylpyridin-3-yl)imidazolidin-2-one | 3.4 nM | — |
| 160A | 1-(4-methylpyridin-3-yl)-3-(3-(trifluoromethyl)-1H-indazol-6-yl)imidazolidin-2-one | 34 nM | — |
| 161A | 1-3-cyclopropyl-1H-indazol-6-yl)-3-(4-methylpyridin-3-yl)imidazolidin-2-one | 82 nM | — |
| 162A | 1-(4-methylpyridin-3-yl)-3-(quinolin-7-yl)imidazolidin-2-one | 317 nM | — |
| 163A | 3-Benzothiazol-6-yl-4,4-dimethyl-1-(4-methyl-pyridin-3-yl)-imidazolidin-2-one | >10 µM | — |
| 164A | 1-Benzothiazol-6-yl-4,4-dimethyl-3-pyridin-3-yl-imidazolidin-2-one | 70 nM/— | — |
| 165A | 1-Benzothiazol-6-yl-4,4-dimethyl-3-(4-methyl-pyridin-3-yl)-imidazolidin-2-one | 1,153 nM/— | — |
| 166A | 3-Benzothiazol-6-yl-4-methyl-1-(4-methyl-pyridin-3-yl)-imidazolidin-2-one | 32 nM/— | — |
| 167A | 1-Benzothiazol-6-yl-4-methyl-3-(4-methyl-pyridin-3-yl)-imidazolidin-2-one | 38 nM/— | — |
| 168A | 1-Benzothiazol-6-yl-4-ethyl-3-(4-methyl-pyridin-3-yl)-1,3-dihydro-imidazol-2-one | 384 nM/— | — |
| 169A | 1-Benzothiazol-6-yl-4-ethyl-3-pyridin-3-yl-1,3-dihydro-imidazol-2-one | —/— | — |
| 170A | 1-Benzothiazol-6-yl-3-pyridin-3-yl-4-trifluoromethyl-imidazolidin-2-one | —/— | — |
| 171A | 1-Benzothiazol-6-yl-3-(4-methyl-pyridin-3-yl)-1,3-dihydro-benzoimidazol-2-one | —/— | — |
| 172A | 1-Benzothiazol-6-yl-4-methyl-3-(4-methyl-pyridin-3-yl)-imidazolidin-2-one | 326 nM/— | — |
| 173A | 3-Benzothiazol-6-yl-1-pyridin-3-yl-4-trifluoromethyl-imidazolidin-2-one | —/— | — |
| 174A | 1-Benzothiazol-6-yl-3-(4-methyl-pyridin-3-yl)-4-trifluoromethyl-imidazolidin-2-one | —/— | — |
| 175A | 1-Benzothiazol-6-yl-4,5-dimethyl-3-(4-methyl-pyridin-3-yl)-imidazolidin-2-one | 85 nM/— | — |
| 176A | 1-Benzothiazol-6-yl-3-(4-pyrrolidin-1-ylmethyl-pyridin-3-yl)-imidazolidin-2-one | 39 nM/— | — |
| 177A | 1-Benzothiazol-6-yl-3-(4-morpholin-4-ylmethyl-pyridin-3-yl)-imidazolidin-2-one | 32 nM/— | — |
| 178A | 1-Benzothiazol-6-yl-3-(4-cyclopropylaminomethyl-pyridin-3-yl)-imidazolidin-2-one | 19 nM/— | — |
| 179A | 1-Benzothiazol-6-yl-3-(6-fluoro-4-methyl-pyridin-3-yl)-imidazolidin-2-one | —/— | — |
| 180A | 1-Benzothiazol-6-yl-3-[4-(2-morpholin-4-yl-ethoxy)-pyridin-3-yl]-imidazolidin-2-one | —/— | — |
| 181A | 1-Benzothiazol-6-yl-3-[4-(1-methyl-pyrrolidin-2-ylmethoxy)-pyridin-3-yl]-imidazolidin-2-one | 3064 nM/— | — |
| 182A | 1-Benzothiazol-6-yl-3-{4-[(5-methyl-1H-pyrazol-3-ylamino)-methyl]-pyridin-3-yl}-imidazolidin-2-one | 27 nM/— | — |
| 183A | 1-Benzothiazol-6-yl-3-(3H-imidazo[4,5-b]pyridin-6-yl)-imidazolidin-2-one | >10 µM/— | — |
| 184A | 1-Benzothiazol-6-yl-3-[4-(1-methyl-piperidin-4-ylmethoxy)-pyridin-3-yl]-imidazolidin-2-one | >10 µM/— | — |
| 185A | 3-(3-Benzothiazol-6-yl-2-oxo-imidazolidin-1-yl)-isonicotinamide | >10 µM/— | — |

TABLE 1-continued

| Example No. | Final compounds | Lyase IC 50 nM Human/Rat | rCYP17 Lyase % Inh @ 100 nM |
|---|---|---|---|
| 186A | 1-Benzothiazol-6-yl-3-imidazo[1,2-a]pyrazin-5-yl-imidazolidin-2-one | >10 μM/— | — |
| 187A | 1-Benzothiazol-6-yl-3-(1H-pyrrolo[2,3-b]pyridin-5-yl)-imidazolidin-2-one | >10 μM/— | — |
| 188A | 3-Benzothiazol-6-yl-3'-methyl-4,5-dihydro-3H,3'H-[1,4']biimidazolyl-2-one | 195 nM/— | — |
| 189A | 1-Benzothiazol-6-yl-3-(4-methyl-5-trifluoromethyl-pyridin-3-yl)-imidazolidin-2-one trifluoro-acetic acid | 280 nM/— | — |
| 190A | 1-Isothiazol-4-yl-3-(4-methyl-pyridin-3-yl)-imidazolidin-2-one | 89 nM/— | — |
| 191A | 1-Benzothiazol-6-yl-3-pyridin-2-yl-imidazolidin-2-one | >10 μM/— | — |
| 192A | 1-(4-Methyl-pyridin-3-yl)-3-(5-trifluoromethyl-thiophen-2-yl)-imidazolidin-2-one | 2.7 nM/— | — |
| 193A | 1-Benzothiazol-6-yl-3-[4-(1-hydroxy-1-methyl-ethyl)-pyridin-3-yl]-imidazolidin-2-one | >10 μM/— | — |
| 194A | 1-(4-Methyl-pyridin-3-yl)-3-(4-methyl-thieno[3,2-c]pyridin-2-yl)-imidazolidin-2-one | 21 nM/— | — |
| 195A | 1-Benzothiazol-6-yl-3-[4-(1-hydroxy-ethyl)-pyridin-3-yl]-imidazolidin-2-one | 38 nM/— | 8% |
| 196A | 1-Benzothiazol-6-yl-3-(4-ethyl-pyridin-3-yl)-imidazolidin-2-one | 3.4 nM/— | — |
| 197A | 1-(4-Methyl-pyridin-3-yl)-3-(3-trifluoromethyl-1H-indazol-6-yl)-imidazolidin-2-one | 34 nM/— | — |
| 198A | 1-(3-Cyclopropyl-1H-indazol-6-yl)-3-(4-methyl-pyridin-3-yl)-imidazolidin-2-one | 82 nM/— | — |
| 199A | 1-(4-Methyl-pyridin-3-yl)-3-quinolin-7-yl-imidazolidin-2-one | 317 nM/— | — |
| 200A | 3-Benzothiazol-6-yl-4,4-dimethyl-1-(4-methyl-pyridin-3-yl)-imidazolidin-2-one | >10 μM/— | — |
| 201A | 1-Benzothiazol-6-yl-4,4-dimethyl-3-pyridin-3-yl-imidazolidin-2-one | 70 nM/— | — |
| 202A | 1-Benzothiazol-6-yl-4,4-dimethyl-3-(4-methyl-pyridin-3-yl)-imidazolidin-2-one | 1153 nM/— | — |
| 203A | 3-Benzothiazol-6-yl-4-methyl-1-(4-methyl-pyridin-3-yl)-imidazolidin-2-one | 32 nM/— | — |

The compounds of present invention in free form or in salt form, exhibit valuable pharmacological properties, e.g. inhibition of CYP17 lyase, e.g. as indicated in the in vitro tests provided above and are therefore useful for therapy mediated by such inhibition. For example, the compounds of the present invention are useful in the treatment of inflammation and cancer (in particular, prostate cancer) in a mammal (preferably, a human).

Thus, as a further embodiment, the present invention provides the use of a compound of the present invention in therapy. In a further embodiment, the therapy is selected from a disease mediated by the regulation of 17α-hydroxylase/$C_{17,20}$-lyase.

In another embodiment, the invention provides a method of treating a disease which is treated by the regulation of 17α-hydroxylase/$C_{17,20}$-lyase comprising administration of a therapeutically acceptable amount of a compound of the present invention. In a further embodiment, the disease is prostate cancer.

Additional References:

Tsuneo Imai et al, "Expression and purification of Functional Human 17α-Hydroxylase/17,20-Lyase (P450c17) in *Escherichia coli*" *Journal of biological chemistry*, (1993) 268, No. 26, 19681-9

Peter Lee-Robichaud et al, "Interaction of human Cyp17 (P-450$_{17α}$, 17α-hydroxylase-17,20-lyase) with cytochrome $b_5$: importance of the orientation of the hydrophobic domain of cytochrome $b_5$." *Biochem. J*, (1997) 321, 857-63

Zuber et al, "Expression of Bovine 17-α-hydroxylase Cytochrome P-450 c-DNA in nonsteroidogenic (COSI) cells" *Science* (1986a) 234, 1258-1261.

Sakaki T, "Expression of Bovine Cytochrome P-450c17 in *Saccharomyces serevisiae*" *DNA* (1989) 8, 409-418.

Barnes et al, "Expression and enzymatic activity of recombinant cytochrome P-450 17 alpha hydroxylase in *Escherichia coli*" *Proc. Natl. Acad. Sci. U.S.A*, (1991) 88, 5597-5601.

M. K Akhtar et al, "Cytochrome b5 modulation of 17α-hydroxylaseand 17-20 lyase (Cyp17) activities in Steroidogenesis" *Journal of Endocrinology* (2005) 187, 267-274.

Vincent C. O, Nijar et al, "Novel 17-Azolys Steroids, Potent Inhibitors of Human Cytochrome 17α-Hydroxylase-$C_{17-20}$-lyase (P450$_{17α}$: Potestial agents for the treatment of Prostate cancer" *J Med Chem* (1998) 41, 902-912.

Katagiri Ni et al, "Role of Cytochrome b5 in the Cytochrome P-450 mediated C21-Steroid 17,20-lyase activity" *Biophysical Research Communications* (1982) 108, 379-384.

US Patent: US 2004/0198773 A1.

Dmitry N. Grigoryev et al, "Cytochrome P450c17-expressing *Escherichia coli* as a first-step screening system for 17 alpha-hydroxylase-C17,20-lyase inhibitors" *Analytical Biochemistry*, (1999) 267, 319-330.

Venkatesh D. Handratta et al, "Novel C-17-heteroaryl steroidal Cyp17 inhibitors/antiandrogens: synthesis, invitro biological activity, pharmacokinetics and antitumor activity in the LAP C4 human prostate cancer xenograft model" *J. Med. Chem.* (2005) 48, 2972-2984.

Ravi A Madan et al, "Abiraterone, Cougar biotechnology" *IDrugs.* (2006) 9(1), 49-55.

What is claimed is:
1. A compound of Formula (Ib)

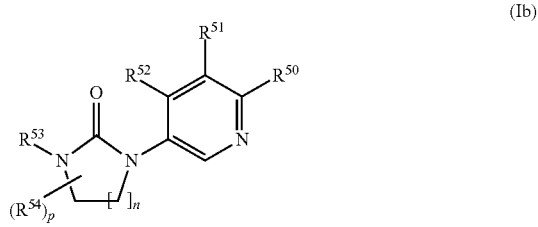

(Ib)

wherein $R^{50}$, $R^{51}$ and $R^{52}$ are each independently H, halo, -OH, -CN, $(C_1-C_4)$alkyl, halo-substituted$(C_1-C_4)$alkyl, hydroxy-substituted $(C_1-C_4)$alkyl, $-(CH_2)_r$-$O(C_1-C_4)$alkyl, $-(CH_2)_r$—$CH(O(C_1-C_4)alkyl)_2$, $-NH_2$, $-NH(C_1-C_4)$alkyl, $-N((C_1-C_4)alkyl)_2$, $-NHC(O)-(C_1-C_4)$alkyl, —$C(O)NH_2$, $-C(O)-NH(C_1-C_4)$alkyl, $-C(O)-N((C_1-C_4)alkyl)_2$, or $-C(O)-O(C_1-C_4)$alkyl;

wherein n is 1;

$R^{53}$ is (i) phenyl optionally substituted with 1 to 3 substituents selected from halo, -CN, -OH, $(C_1-C_6)$alkyl, halo-substituted $(C_1-C_6)$alkyl, $(C_1-C_6)$alkoxy, $-NH_2$, $-NH(C_1-C_4)$alkyl, $-N((C_1-C_4)alkyl)_2$, $-NHC(O)-(C_1-C_4)$alkyl, $-C(O)NH_2$, $-C(O)-NH(C_1-C_4)$alkyl, $-C(O)-N((C_1-C_4)alkyl)_2$, or a 5- to 6-membered heterocycle, (ii) biphenyl optionally substituted with 1 to 3 substituents selected from ($C_1$-$C_4$)alkyl or halo, (iii) phenyl fused to an additional phenyl, a 5- to 6-membered heteroaryl, a 5- to 6-membered partially or fully saturated cycloalkyl, or a 5- to 6-membered partially or fully saturated heterocycle, where said fused phenyl is optionally substituted with 1 to 4 substituents each independently selected from halo, -CN, ($C_1$-$C_6$)alkyl, ($C_1$-$C_6$)alkoxy, hydroxy-substituted ($C_1$-$C_4$)alkyl, halo-substituted ($C_1$-$C_4$)alkyl, cyclopropyl, oxo, -$NH_2$, -NH($C_1$-$C_4$)alkyl, -N(($C_1$-$C_4$)alkyl)$_2$, -NHC(O)-($C_1$-$C_4$)alkyl, or =N-OH, (iv) 5- to 6-membered heteroaryl optionally substituted with 1 to 3 substituents selected from halo, -CN, -OH, ($C_1$-$C_6$)alkyl, halo-substituted ($C_1$-$C_6$)alkyl, ($C_1$-$C_6$)alkoxy, -$NH_2$, -NH($C_1$-$C_4$)alkyl, -N(($C_1$-$C_4$)alkyl)$_2$, -NHC(O)-($C_1$-$C_4$)alkyl, -C(O)$NH_2$, -C(O)-NH($C_1$-$C_4$)alkyl, -C(O)-N(($C_1$-$C_4$)alkyl)$_2$, or a 5- to 6-membered heterocycle, (v) 5- to 6-membered heteroaryl fused to another 5- to 6-membered heteroaryl, phenyl, 5- to 6-membered partially or fully saturated cycloalkyl, or a 5- to 6-membered partially or fully saturated heterocycle, where said fused heteroaryl is optionally substituted with 1 to 4 substituents each independently selected from halo, -CN, ($C_1$-$C_6$)alkyl, ($C_1$-$C_6$)alkoxy, hydroxy-substituted ($C_1$-$C_4$)alkyl, halo-substituted ($C_1$-$C_4$)alkyl, cyclopropyl, oxo, -$NH_2$, -NH($C_1$-$C_4$)alkyl, -N(($C_1$-$C_4$)alkyl)$_2$, -NHC(O)-($C_1$-$C_4$)alkyl, or =N-OH;

$R^{54}$ is ($C_1$-$C_4$)alkyl, halo-substituted ($C_1$-$C_4$)alkyl, or -$CH_2$OH, or two $R^{54}$ taken together with the carbon atom(s) to which they are attached form a 3- to 6-membered fully or partially saturated carbocyclic;

p is 0, 1, 2, or 3;

with the proviso that when $R^{50}$, $R^{51}$, and $R^{52}$ are H and $R^{53}$ is phenyl, $R^{53}$ is not unsubstituted or substituted with halogen or $CF_3$, or a pharmaceutically acceptable salt thereof.

2. A compound of Formula (Ib)

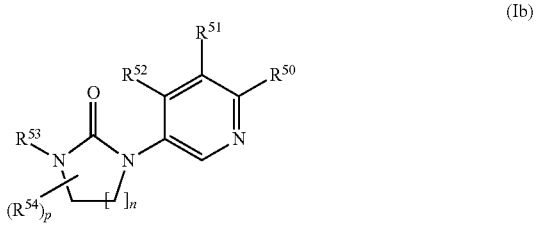

(Ib)

wherein:

n is 1;

$R^{53}$ is (i) phenyl optionally substituted with 1 to 3 substituents selected from halo, -CN, -OH, ($C_1$-$C_6$)alkyl, halo-substituted ($C_1$-$C_6$)alkyl, ($C_1$-$C_6$)alkoxy, -$NH_2$, -NH($C_1$-$C_4$)alkyl, -N(($C_1$-$C_4$)alkyl)$_2$, -NHC(O)-($C_1$-$C_4$)alkyl, -C(O)$NH_2$, -C(O)-NH($C_1$-$C_4$)alkyl, -C(O)-N(($C_1$-$C_4$)alkyl)$_2$, or a 5- to 6-membered heterocycle, (ii) biphenyl optionally substituted with 1 to 3 substituents selected from ($C_1$-$C_4$)alkyl or halo, (iii) phenyl fused to an additional phenyl, a 5- to 6-membered heteroaryl, a 5- to 6-membered partially or fully saturated cycloalkyl, or a 5- to 6-membered partially or fully saturated heterocycle, where said fused phenyl is optionally substituted with 1 to 4 substituents each independently selected from halo, -CN, ($C_1$-$C_6$)alkyl, ($C_1$-$C_6$)alkoxy, hydroxy-substituted ($C_1$-$C_4$)alkyl, halo-substituted ($C_1$-$C_4$)alkyl, cyclopropyl, oxo, -$NH_2$, -NH($C_1$-$C_4$)alkyl, -N(($C_1$-$C_4$)alkyl)$_2$, -NHC(O)-($C_1$-$C_4$)alkyl, or =N-OH, (iv) 5- to 6-membered heteroaryl optionally substituted with 1 to 3 substituents selected from halo, -CN, -OH, ($C_1$-$C_6$)alkyl, halo-substituted ($C_1$-$C_6$)alkyl, ($C_1$-$C_6$)alkoxy, -$NH_2$, -NH($C_1$-$C_4$)alkyl, -N(($C_1$-$C_4$)alkyl)$_2$, -NHC(O)-($C_1$-$C_4$)alkyl, -C(O)$NH_2$, -C(O)-NH($C_1$-$C_4$)alkyl, -C(O)-N(($C_1$-$C_4$)alkyl)$_2$, or a 5- to 6-membered heterocycle, (v) 5- to 6-membered heteroaryl fused to another 5- to 6-membered heteroaryl, phenyl, 5- to 6-membered partially or fully saturated cycloalkyl, or a 5- to 6-membered partially or fully saturated heterocycle, where said fused heteroaryl is optionally substituted with 1 to 4 substituents each independently selected from halo, -CN, ($C_1$-$C_6$)alkyl, ($C_1$-$C_6$)alkoxy, hydroxy-substituted ($C_1$-$C_4$)alkyl, halo-substituted ($C_1$-$C_4$)alkyl, cyclopropyl, oxo, -$NH_2$, -NH($C_1$-$C_4$)alkyl, -N(($C_1$-$C_4$)alkyl)$_2$, -NHC(O)-($C_1$-$C_4$)alkyl, or =N-OH;

$R^{54}$ is ($C_1$-$C_4$)alkyl, halo-substituted ($C_1$-$C_4$)alkyl, or -$CH_2$OH, or two $R^{54}$ taken together with the carbon atom(s) to which they are attached form a 3- to 6-membered fully or partially saturated carbocyclic ring;

p is 0, 1, 2, or 3;

$R^{50}$, $R^{51}$ and $R^{52}$ are each independently H, halo, -OH, -CN, ($C_1$-$C_4$)alkyl, halo-substituted ($C_1$-$C_4$)alkyl, hydroxy-substituted ($C_1$-$C_4$)alkyl, -($CH_2$)$_r$-O($C_1$-$C_4$)alkyl, -($CH_2$)$_r$—CH(O($C_1$-$C_4$)alkyl)$_2$, -$NH_2$, -NH($C_1$-$C_4$)alkyl, -N(($C_1$-$C_4$)alkyl)$_2$, -NHC(O)-($C_1$-$C_4$)alkyl, -C(O)$NH_2$, -C(O)-NH($C_1$-$C_4$)alkyl, -C(O)-N(($C_1$-$C_4$)alkyl)$_2$, or -C(O)-O($C_1$-$C_4$)alkyl;

r is 0, 1 or 2;

with the proviso that when $R^{50}$, $R^{51}$, and $R^{52}$ are H and $R^{53}$ is phenyl, $R^{53}$ is not unsubstituted or substituted with halogen or $CF_3$;

or a pharmaceutically acceptable salt thereof.

3. The compound of claim 2 wherein $R^{54}$ is -$CH_3$ or $CF_3$; or a pharmaceutically acceptable salt thereof.

4. The compound of claim 2 wherein $R^{50}$ is H or methyl; $R^{51}$ is H, halo, methyl, trifluoromethyl, methoxy, or -C(O)$OCH_3$; and $R^{52}$ is halo, -CN, methyl, ethyl, methoxy, hydroxymethyl, 1-hydroxyethyl, 2-hydroxypropan-2-yl, difluoromethyl, trifluoromethyl, dimethoxymethyl, -$NH_2$, or -NHC(O)$CH_3$; or a pharmaceutically acceptable salt thereof.

5. The compound of claim 2 wherein $R^{53}$ is (i) a phenyl optionally substituted with 1 or 2 substituents each independently selected form fluoro, chloro, cyano, methyl, difluoromethyl, trifluoromethyl, methoxy, or —C(O)NH$CH_3$;

(ii) a biphenyl optionally substituted with fluoro;

(iii) a fused phenyl selected from naphthalen-2-yl, naphthalen-1-yl, 1H-indol-5-yl, 1H-indol-6-yl, benzothiazol-5-yl, benzothiazol-6-yl, 1,2,3,4-tetrahydro-quinolin-6-yl, benzo[b]thiophen-5-yl, quinolin-6-yl, quinolin-7-yl, indan-5-yl, 1,2-dihydroquinolin-6-yl, 1H-indazol-5-yl, 1H-indazol-6-yl, benzofuran-5-yl, 2,3-dihydrobenzo[1,4]dioxin-6-yl, 2,3-dihydro-benzofuran-5-yl, benzo[1,3]dioxol-5-yl, 1,2,3,4-tetrahydroquinolin-7-yl, quinoxalin-6-yl, benzooxazol-5-yl, benzo[d]isoxazol-5-yl, benzo[d]isoxazol-6-yl, 1H-benzoimidazol-5-yl, 2,3-dihydro-1H-indazol-5-yl, 2,3-dihydro-1H-indazol-6-yl, indolin-5-yl, or 1H-benzotriazol-5-yl, where said fused phenyl is optionally substituted with 1 to 3 substituents each independently selected from fluoro, chloro, methyl, ethyl, trifluoromethyl, methoxy, oxo, -NH$_2$, =N-OH or cyclopropyl;
(iv) a 5- to 6-membered heteroaryl selected from thiophen-2-yl, thiophen-3-yl, pyridin-3-yl, pyridin-4-yl, pyrimidin-5-yl, 1H-pyrazol-4-yl, thiazol-2-yl, or isothiazol-4-yl, where said 5- to 6-membered heteroaryl is optionally substituted with 1 to 3 substituents each independently selected from fluoro, chloro, methyl, ethyl, isopropyl, hydroxy, difluoromethyl, trifluoromethyl, methoxy, -NH$_2$, -NHC(O)CH$_3$, -C(O)NHCH$_3$, or pyrrolidin-1-yl; or
(v) a fused heteroaryl selected from benzo[b]thiophen-2-yl, benzo[b]thiophen-3-yl, quinolin-2-yl, quinolin-3-yl, benzooxazol-2-yl, benzothiazol-2-yl, 4,5,6,7-tetrahydro-thieno[2,3-c]pyridin-2-yl, imidazo[1,2-a]pyridin-3-yl, imidazo[1,2-a]pyridin-6-yl, imidazo[1,2-a]pyridin-7-yl, 3H-imidazo[4,5-b]pyridin-6-yl, thieno[3,2-c]pyridin-2-yl, thieno[3,2-c]pyridin-3-yl, or 1H-indol-3-yl, where said fused heteroaryl is optionally substituted with 1 to 4 substituents each independently selected from fluoro, chloro, cyano, methyl, or methoxy;
or a pharmaceutically acceptable salt thereof.

6. The compound of claim 2 wherein R$^{53}$ is
(i) a phenyl optionally substituted with 1 to 2 substituents each independently selected from fluoro, chloro, methyl, methoxy, trifluoromethyl, difluoromethyl, or cyano;
(ii) a biphenyl;
(iii) a fused phenyl selected from naphthalen-2-yl, quinolin-6-yl, 3,4-dihydro-2-oxo-quinolin-6-yl, benzo[b]thiophen-5-yl, benzo[d]isoxazol-5-yl, 1H-indazol-6-yl, 1H-indazol-5-yl, benzothiazol-6-yl, 1,2-dihydro-3-oxo-indazol-6-yl, indan-5-yl, 1H-benzotriazol-5-yl, benzofuran-5-yl, 2,3-dihydro-benzo[1,4]dioxin-6-yl, 2,3-dihydro-benzofuran-5-yl, or benzo[1,3]dioxol-5-yl where said fused phenyl is optionally substituted with 1 to 2 substituents each independently selected from chloro, fluoro, methyl, ethyl, difluoromethyl, trifluoromethyl, cyclopropyl, cyano, or amino;
(iv) a 5- to 6-membered heteroaryl selected from isothiazol-4-yl, thiophen-2-yl, thiophen-3-yl, or pyridin-4-yl, where said isothiazol-4-yl, said thiophen-2-yl, said thiophen-3-yl, and said pyridin-4-yl are optionally substituted with fluoro, chloro, methyl, trifluoromethyl, difluoromethyl, or methoxy; or
(v) a fused heteroaryl selected from thieno[3,2-c]pyridin-2-yl, thieno[3,2-c]pyridin-3-yl, thieno[3,2-c]pyridin-2-yl, imidazo[1,2-a]pyridin-7-yl, or benzo[b]thiophen-2-yl, where said fused heteroaryl is optionally substituted with 1 to 2 substituents each independently selected from fluoro, chloro, methyl, difluoromethyl, trifluoromethyl, cyclopropyl, or amino;
or a pharmaceutically acceptable salt thereof.

7. The compound of claim 2 wherein R$^{53}$ is phenyl, 4-chloro-3-fluoro-phenyl, m-tolyl, 3-methoxy-phenyl, 3-chloro-4-fluoro-phenyl, 4-fluoro-3-methyl-phenyl, 3-trifluoromethyl-phenyl, 3-chloro-phenyl, 4-fluoro-3-trifluoromethyl-phenyl, 3-difluoromethyl-4-fluoro-phenyl, 3-cyano-4-fluorophenyl, 3-cyanophenyl, 3-chloro-4-cyanophenyl, 3,4-difluoro-phenyl, 4-trifluoromethyl-phenyl;
or a pharmaceutically acceptable salt thereof.

8. The compound of claim 2 wherein R$^{53}$ is naphthalen-2-yl, benzo[b]thiophen-5-yl, 3-methyl-benzo[d]isoxazol-5-yl, 1H-indazol-5-yl, 1-methyl-1H-indazol-5-yl, 3-amino-1H-indazol-5-yl, 1H-indazol-6-yl, 3-amino-1H-indazol-6-yl, 3-methyl-1H-indazol-6-yl, 3-trifluoromethyl-1H-indazol-6-yl, benzothiazol-6-yl, 1,2-dihydro-3-oxo-indazol-6-yl, indan-5-yl, 1H-benzotriazol-5-yl, 3-methyl-benzofuran-5-yl, 2,3-dihydro-benzo[1,4]dioxin-6-yl, 2,3-dihydro-benzofuran-5-yl, or 2,2-difluoro-benzo[1,3]dioxol-5-yl;
or a pharmaceutically acceptable salt thereof.

9. The compound of claim 8 wherein R$^{53}$ is benzothiazol-6-yl, 3-methyl-benzofuran-5-yl, 1H-indazol-6-yl, 3-methyl-1H-indazol-6-yl, or 3-trifluoromethyl-1H-indazol-6-yl;
or a pharmaceutically acceptable salt thereof.

10. The compound of claim 2 wherein R$^{53}$ is 5-methyl-thiophen-2-yl, 5-chloro-thiophen-2-yl, 5-trifluoromethyl-thiophen-2-yl, 5-difluoromethyl-thiophen-3-yl, 5-methyl-thiophen-3-yl, 2-methyl-pyridin-4-yl, 2-trifluoromethyl-pyridin-4-yl, 2-chloro-pyridin-4-yl, or 2-methoxy-pyridin-4-yl;
or a pharmaceutically acceptable salt thereof.

11. The compound of claim 2 wherein R$^{53}$ is 4-chloro-thieno[3,2-c]pyridin-2-yl, 4-chloro-thieno[3,2-c]pyridin-3-yl, thieno[3,2-c]pyridin-2-yl, 3-chloro-imidazo[1,2-a]pyridin-7-yl, benzo[b]thiophen-2-yl, or 4-methylthieno[3,2-c]pyridin-2-yl;
or a pharmaceutically acceptable salt thereof.

12. A compound selected from the group consisting of
1-Benzothiazol-6-yl-3-(4-methyl-pyridin-3-yl)-imidazolidin-2-one;
1-(2-Chloro-pyridin-4-yl)-3-(4-methyl-pyridin-3-yl)-imidazolidin-2-one;
1-(4-Chloro-thieno[3,2-c]pyridin-2-yl)-3-(4-methyl-pyridin-3-yl)-imidazolidin-2-one;
1-(1H-Indazol-6-yl)-3-(4-methyl-pyridin-3-yl)-imidazolidin-2-one;
1-(3-Methyl-1H-indazol-6-yl)-3-(4-methyl-pyridin-3-yl)-imidazolidin-2-one; and
1-Benzothiazol-6-yl-4-methyl-3-(4-methyl-pyridin-3-yl)-imidazolidin-2-one; Or a pharmaceutically acceptable salt thereof.

13. A compound selected from the group consisting of
1-Naphthalen-2-yl-3-pyridin-3-yl-imidazolidin-2-one;
1-Benzo [b]thiophen-5-yl-3-pyridin-3-yl-imidazolidin-2-one;
1-(4-Methyl-pyridin-3-yl)-3-naphthalen-2-yl-imidazolidin-2-one;
1-(4-Methyl-pyridin-3-yl)-3-(5-methyl-thiophen-2-yl)-imidazolidin-2-one;
1-Benzothiazol-6-yl-3-(4-methyl-pyridin-3-yl)-imidazolidin-2-one;
1-Benzo[b]thiophen-2-yl-3-(4-methyl-pyridin-3-yl)-imidazolidin-2-one;
1-Benzo[b]thiophen-5-yl-3-(4-methyl-pyridin-3-yl)-imidazolidin-2-one;
1-(1H-Indazol-5-yl)-3-(4-methyl-pyridin-3-yl)-imidazolidin-2-one;
1-(3-Methyl-benzofuran-5-yl)-3-(4-methyl-pyridin-3-yl)-imidazolidin-2-one;
1-(5-Chloro-thiophen-2-yl)-3-(4-methyl-pyridin-3-yl)-imidazolidin-2-one;
1-(3,4-Difluoro-phenyl)-3-(4-methyl-pyridin-3-yl)-imidazolidin-2-one;
1-(3-Chloro-4-fluoro-phenyl)-3-(4-methyl-pyridin-3-yl)-imidazolidin-2-one;
1-(2,3-Dihydro-benzo[1,4]dioxin-6-yl)-3-(4-methyl-pyridin-3-yl)-imidazolidin-2-one;
1-(2,3-Dihydro-benzofuran-5-yl)-3-(4-methyl-pyridin-3-yl)-imidazolidin-2-one;
1-(4-Chloro-3-fluoro-phenyl)-3-(4-methyl-pyridin-3-yl)-imidazolidin-2-one;
1-(4-Methyl-pyridin-3-yl)-3-m-tolyl-imidazolidin-2-one;

1-(3-Methoxy-phenyl)-3-(4-methyl-pyridin-3-yl)-imidazolidin-2-one;
1-(2-Chloro-pyridin-4-yl)-3-(4-methyl-pyridin-3-yl)-imidazolidin-2-one;
1-(4-Fluoro-3-methyl-phenyl)-3-(4-methyl-pyridin-3-yl)-imidazolidin-2-one;
1-(2,2-Difluoro-benzo[1,3]dioxol-5-yl)-3-(4-methyl-pyridin-3-yl)-imidazolidin-2-one;
1-(4-Methyl-pyridin-3-yl)-3-phenyl-imidazolidin-2-one;
1-(4-Methyl-pyridin-3-yl)-3-(3-trifluoromethyl-phenyl)-imidazolidin-2-one;
1-(2-Methoxy-pyridin-4-yl)-3-(4-methyl-pyridin-3-yl)-imidazolidin-2-one;
1-(5-Difluoromethyl-thiophen-3-yl)-3-(4-methyl-pyridin-3-yl)-imidazolidin-2-one;
1-(3-Chloro-phenyl)-3-(4-methyl-pyridin-3-yl)-imidazolidin-2-one;
1-(4-Fluoro-3-trifluoromethyl-phenyl)-3-(4-methyl-pyridin-3-yl)-imidazolidin-2-one;
1-(3-Difluoromethyl-4-fluoro-phenyl)-3-(4-methyl-pyridin-3-yl)-imidazolidin-2-one;
1-(4-Methyl-pyridin-3-yl)-3-(5-methyl-thiophen-3-yl)-imidazolidin-2-one;
1-(4-Chloro-thieno[3,2-c]pyridin-2-yl)-3-(4-methyl-pyridin-3-yl)-imidazolidin-2-one;
1-(4-Chloro-thieno[3,2-c]pyridin-2-yl)-3-(4-methyl-pyridin-3-yl)-imidazolidin-2-one;
1-(4-Methyl-pyridin-3-yl)-3-(2-methyl-pyridin-4-yl)-imidazolidin-2-one;
1-(3-Methyl-benzo[d]isoxazol-5-yl)-3-(4-methyl-pyridin-3-yl)-imidazolidin-2-one;
1-(3-Methyl-1H-indazol-6-yl)-3-(4-methyl-pyridin-3-yl)-imidazolidin-2-one;
2-Fluoro-5-[3-(4-methyl-pyridin-3-yl)-2-oxo-imidazolidin-1-yl]-benzonitrile;
3-[3-(4-Methyl-pyridin-3-yl)-2-oxo-imidazolidin-1-yl]-benzonitrile;
2-Chloro-4-[3-(4-methyl-pyridin-3-yl)-2-oxo-imidazolidin-1-yl]-benzonitrile;
1-(1-Methyl-1H-indazol-5-yl)-3-(4-methyl-pyridin-3-yl)-imidazolidin-2-one;
1-(3-Amino-1H-indazol-5-yl)-3-(4-methyl-pyridin-3-yl)-imidazolidin-2-one;
1-(4-Methyl-pyridin-3-yl)-3-thieno[3,2-c]pyridin-2-yl-imidazolidin-2-one;
1-(1H-Indazol-6-yl)-3-(4-methyl-pyridin-3-yl)-imidazolidin-2-one;
1-(3-Amino-1H-indazol-6-yl)-3-(4-methyl-pyridin-3-yl)-imidazolidin-2-one;
1-Benzothiazol-6-yl-3-(4-methoxy-pyridin-3-yl)-imidazolidin-2-one;
1-Benzothiazol-6-yl-3-(4-difluoromethyl-pyridin-3-yl)-imidazolidin-2-one;
1-Benzothiazol-6-yl-3-(4-hydroxymethyl-pyridin-3-yl)-imidazolidin-2-one;
1-Benzothiazol-6-yl-3-(4-trifluoromethyl-pyridin-3-yl)-imidazolidin-2-one;
1-Indan-5-yl-3-(4-methyl-pyridin-3-yl)-imidazolidin-2-one;
1-(1H-Benzotriazol-5-yl)-3-(4-methyl-pyridin-3-yl)-imidazolidin-2-one;
1-(3-Chloro-imidazo[1,2-a]pyridin-7-yl)-3-(4-methyl-pyridin-3-yl)-imidazolidin-2-one;
1-(4-Methyl-pyridin-3-yl)-3-(2-trifluoromethyl-pyridin-4-yl)-imidazolidin-2-one;
1-Benzothiazol-6-yl-3-(4-dimethoxymethyl-pyridin-3-yl)-imidazolidin-2-one;
1-Benzothiazol-6-yl-3-(5-chloro-4-methyl-pyridin-3-yl)-imidazolidin-2-one;
1-(4-Methylpyridin-3-yl)-3-(5-(trifluoromethyl)thiophen-2-yl)imidazolidin-2-one;
1-(4-Methylpyridin-3-yl)-3-(4-methylthieno[3,2-c]pyridin-2-yl)imidazolidin-2-one;
1-(Benzo[d]thiazol-6-yl)-3-(4-(1-hydroxyethyl)pyridin-3-yl)imidazolidin-2-one;
1-(Benzo[d]thiazol-6-yl)-3-(4-ethylpyridin-3-yl)imidazolidin-2-one;
1-(4-Methylpyridin-3-yl)-3-(3-(trifluoromethyl)-1H-indazol-6-yl)imidazolidin-2-one;
1-Benzothiazol-6-yl-4-methyl-3-(4-methyl-pyridin-3-yl)-imidazolidin-2-one;
1-Benzothiazol-6-yl-3-pyridin-3-yl-4-trifluoromethyl-imidazolidin-2-one;
1-Benzothiazol-6-yl-4-methyl-3-(4-methyl-pyridin-3-yl)-imidazolidin-2-one;
3-Benzothiazol-6-yl-1-pyridin-3-yl-4-trifluoromethyl-imidazolidin-2-one;
1-Benzothiazol-6-yl-3-(4-methyl-pyridin-3-yl)-4-trifluoromethyl-imidazolidin-2-one;
1-Benzothiazol-6-yl-4,5-dimethyl-3-(4-methyl-pyridin-3-yl)-imidazolidin-2-one;
1-Benzothiazol-6-yl-3-(4-pyrrolidin-1-ylmethyl-pyridin-3-yl)-imidazolidin-2-one;
1-Benzothiazol-6-yl-3-(4-morpholin-4-ylmethyl-pyridin-3-yl)-imidazolidin-2-one;
1-Benzothiazol-6-yl-3-(4-cyclopropylaminomethyl-pyridin-3-yl)-imidazolidin-2-one;
1-Benzothiazol-6-yl-3-(6-fluoro-4-methyl-pyridin-3-yl)-imidazolidin-2-one;
1-Benzothiazol-6-yl-3-[4-(2-morpholin-4-yl-ethoxy)-pyridin-3-yl]-imidazolidin-2-one;
1-Benzothiazol-6-yl-3-[4-(1-methyl-pyrrolidin-2-yl-methoxy)-pyridin-3-yl]-imidazolidin-2-one;
1-Benzothiazol-6-yl-3-{4-[(5-methyl-1H-pyrazol-3-ylamino)-methyl]-pyridin-3-yl}-imidazolidin-2-one;
1-Benzothiazol-6-yl-3-[4-(1-methyl-piperidin-4-yl-methoxy)-pyridin-3-yl]-imidazolidin-2-one;
3-(3-Benzothiazol-6-yl-2-oxo-imidazolidin-1-yl)-isonicotinamide;
1-Benzothiazol-6-yl-3-(4-methyl-5-trifluoromethyl-pyridin-3-yl)-imidazolidin-2-one;
1-Isothiazol-4-yl-3-(4-methyl-pyridin-3-yl)-imidazolidin-2-one;
1-(4-Methyl-pyridin-3-yl)-3-(5-trifluoromethyl-thiophen-2-yl)-imidazolidin-2-one;
1-Benzothiazol-6-yl-3-[4-(1-hydroxy-1-methyl-ethyl)-pyridin-3-yl]-imidazolidin-2-one;
1-(4-Methyl-pyridin-3-yl)-3-(4-methyl-thieno[3,2-c]pyridin-2-yl)-imidazolidin-2-one;
1-Benzothiazol-6-yl-3-[4-(1-hydroxy-ethyl)-pyridin-3-yl]-imidazolidin-2-one;
1-Benzothiazol-6-yl-3-(4-ethyl-pyridin-3-yl)-imidazolidin-2-one;
1-(4-Methyl-pyridin-3-yl)-3-(3-trifluoromethyl-1H-indazol-6-yl)-imidazolidin-2-one;
1-(3-Cyclopropyl-1H-indazol-6-yl)-3-(4-methyl-pyridin-3-yl)-imidazolidin-2-one;
1-(4-Methyl-pyridin-3-yl)-3-quinolin-7-yl-imidazolidin-2-one;
3-Benzothiazol-6-yl-4,4-dimethyl-1-(4-methyl-pyridin-3-yl)-imidazolidin-2-one;
1-Benzothiazol-6-yl-4,4-dimethyl-3-pyridin-3-yl-imidazolidin-2-one;

1-Benzothiazol-6-yl-4,4-dimethyl-3-(4-methyl-pyridin-3-yl)-imidazolidin-2-one;
3-Benzothiazol-6-yl-4-methyl-1-(4-methyl-pyridin-3-yl)-imidazolidin-2-one;
1-Benzothiazol-6-yl-4-methyl-3-(4-methyl-pyridin-3-yl)-imidazolidin-2-one;
1-Benzothiazol-6-yl-4,5-dimethyl-3-(4-methyl-pyridin-3-yl)-imidazolidin-2-one;
1-Benzothiazol-6-yl-3-(4-pyrrolidin-1-ylmethyl-pyridin-3-yl)-imidazolidin-2-one;
1-Benzothiazol-6-yl-3-(4-morpholin-4-ylmethyl-pyridin-3-yl)-imidazolidin-2-one;
1-Benzothiazol-6-yl-3-(4-cyclopropylaminomethyl-pyridin-3-yl)-imidazolidin-2-one;
1-Benzothiazol-6-yl-3-{4-[(5-methyl-1H-pyrazol-3-ylamino)-methyl]-pyridin-3-yl}-imidazolidin-2-one;
1-Benzothiazol-6-yl-4,4-dimethyl-3-pyridin-3-yl-imidazolidin-2-one; and
3-Benzothiazol-6-yl-4-methyl-1-(4-methyl-pyridin-3-yl)-imidazolidin-2-one;
or a pharmaceutically acceptable salt thereof.

14. A pharmaceutical composition comprising a compound of claim 2 or a pharmaceutically acceptable salt thereof, and a pharmaceutically acceptable carrier or excipient.

15. The pharmaceutical composition of claim 14 further comprising at least one additional pharmaceutical agent wherein said at least one additional pharmaceutical agent is an anticancer agent, chemotherapy agent, or antiproliferative compound.

16. A compound which is 1-(2-Chloro-pyridin-4-yl)-3-(4-methyl-pyridin-3-yl)-imidazolidin-2-one having the structure:

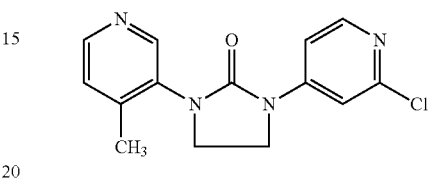

or a pharmaceutically acceptable salt thereof.

* * * * *